US008986707B2

(12) United States Patent
Neubauer et al.

(10) Patent No.: US 8,986,707 B2
(45) Date of Patent: *Mar. 24, 2015

(54) GM-NEGATIVE EHV-MUTANTS WITHOUT HETEROLOGOUS ELEMENTS

(75) Inventors: Antonie Neubauer, Munich (DE); Christina Ziegler, Munich (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/446,558

(22) Filed: Apr. 13, 2012

(65) Prior Publication Data

US 2012/0195927 A1 Aug. 2, 2012

Related U.S. Application Data

(62) Division of application No. 12/392,302, filed on Feb. 25, 2009, now Pat. No. 8,178,111, which is a division of application No. 11/550,934, filed on Oct. 19, 2006, now Pat. No. 7,524,506, which is a division of application No. 10/624,149, filed on Jul. 21, 2003, now Pat. No. 7,141,243.

(60) Provisional application No. 60/403,282, filed on Aug. 14, 2002.

(30) Foreign Application Priority Data

Jul. 19, 2002 (DE) .................................. 102 33 064
Apr. 11, 2003 (DE) .................................. 103 17 008

(51) Int. Cl.

| | |
|---|---|
| ***A61K 39/245*** | (2006.01) |
| ***C12N 7/01*** | (2006.01) |
| ***C12N 7/04*** | (2006.01) |
| ***C12N 15/00*** | (2006.01) |
| ***C07K 14/005*** | (2006.01) |
| ***C12N 7/00*** | (2006.01) |
| *A61K 39/00* | (2006.01) |

(52) U.S. Cl.

CPC ....... *C07K 14/005* (2013.01); *A61K 2039/5254* (2013.01); *C12N 2710/16022* (2013.01); *A61K 39/245* (2013.01); *C12N 7/00* (2013.01); *C12N 2710/16061* (2013.01)

USPC ................... 424/229.1; 435/235.1; 435/320.1

(58) Field of Classification Search

None

See application file for complete search history.

(56) References Cited

U.S. PATENT DOCUMENTS

| | | | |
|---|---|---|---|
| 5,084,271 | A | 1/1992 | Studdert |
| 5,674,735 | A | 10/1997 | Onions et al. |
| 5,731,188 | A | 3/1998 | Cochran et al. |
| 5,853,715 | A | 12/1998 | Macek et al. |
| 5,922,327 | A | 7/1999 | Crabb et al. |
| 6,083,511 | A | 7/2000 | Onions et al. |
| 6,187,320 | B1 | 2/2001 | Darai et al. |
| 6,193,983 | B1 | 2/2001 | Crabb et al. |
| 6,277,621 | B1 | 8/2001 | Horsburgh et al. |
| 6,387,685 | B1 | 5/2002 | Markham et al. |
| 6,703,231 | B2 | 3/2004 | Elbers et al. |
| 7,141,243 | B2 | 11/2006 | Neubauer et al. |
| 7,309,598 | B2 | 12/2007 | Elbers et al. |
| 7,524,506 | B2 | 4/2009 | Neubauer et al. |
| 8,178,111 | B2 | 5/2012 | Neubauer et al. |
| 2003/0198650 | A1 | 10/2003 | Elbers et al. |
| 2008/0160046 | A1 | 7/2008 | Elbers et al. |
| 2012/0195927 | A1 | 8/2012 | Neubauer et al. |

FOREIGN PATENT DOCUMENTS

| | | | |
|---|---|---|---|
| EP | 1129722 | A1 | 9/2001 |
| WO | 9826049 | A1 | 6/1998 |
| WO | 0008165 | A1 | 2/2000 |
| WO | 0117553 | A1 | 3/2001 |
| WO | 2001060403 | A1 | 8/2001 |
| WO | 0209750 | A2 | 2/2002 |
| WO | 2004009802 | A2 | 1/2004 |

OTHER PUBLICATIONS

Ng et al., "Predicting Deleterious Amino Acid Substitutions". Genome Research, vol. 11, No. 5, 2001, pp. 863-874.

Neubauer et al., "The Equine Herpesvirus 1 UL34 Gene Product is Involved in an Early Step in Virus Egress and Can Be Efficiently Replaced by a UL34-GFP Fusion Protein". Virology, vol. 300, 2002, pp. 189-204.

"Recombinant Herpesviruses Lacking Gene for Glycoprotein". Research Disclosure, vol. 371, No. 1, Keneth Mason Publications, Emsworth, GB, Mar. 1995, pp. 129-131.

Brune et al., "Forward with BACs—new tools for herpesvirus genomics". Trends in Genetics, vol. 16, No. 6, Jun. 2000, pp. 254-259.

Csellner et al., "EHV-1 glycoprotein D (EHV-1 gD) is required for virus entry and cell-cell fusion, and an EHHV-1 gD deletion mutant induces a protective immune response in mice". Archives of Virology, vol. 145, 2000, pp. 2371-2385.

Farrell et al., "Vaccine Potential of a gH-Negative HSV-1 Mutant". Journal of Virology, vol. 68, No. 2, Feb. 1994, pp. 927-932.

Fitzpatrick, et al., "Immunologic Relationships Between Equine Herpesvirus Type 1 (Equine Abortion Virus) and Type 4 (Equine Rhinopneumonitis Virus)". American Journal of Veterinary Research, vol. 45, No. 10, Oct. 1984, pp. 1947-1952.

(Continued)

*Primary Examiner* — Nicole Kinsey White

(74) *Attorney, Agent, or Firm* — Michael P. Morris; Joyce L. Morrison

(57) ABSTRACT

The present invention relates to the field of animal health and in particular of Equine Herpes Viruses (EHV) wherein the gene encoding the protein gM is absent, and which is free of heterologous elements. Further aspects of the invention relate to pharmaceutical compositions comprising said viruses, uses thereof, and methods for the prophylaxis and treatment of EHV infections. The invention also relates to pharmaceutical compositions comprising the combination of EHV-1 and EHV-4 viruses wherein the gene encoding the protein gM is absent and which is free of heterologous elements.

7 Claims, 10 Drawing Sheets

(56) References Cited

OTHER PUBLICATIONS

Heldens et al., "Clinical and Virological Evaluation of the Efficacy of an Inactivated EHV1 and EHV4 Whole Virus Vaccines (Duvaxyn EHV1,4). Vaccination/Challenge Experiments in Foals and Pregnant Mares". 2001, Vaccine, vol. 19, pp. 4307-4317.
Hutchinson et al., "Herpes simplex virus glycoprotein K promotes egress of virus particles". Journal of Virology, vol. 69, No. 9, Sep. 1995, pp. 5401-5413.
Hübert et al., "Alterations in the Equine Herpesvirus Type-1 (EHV-1) Strain RacH During Attenuation". Journal of Veterinary Medicine B, vol. 43, pp. 1-14, (1996).
International Search Report and Written Opinion for PCT/EP2003/07730 mailed on Mar. 2, 2004.
Marshall et al., "An equine herpesvirus-1 gene 71 deletant is attenuated and elicits a protective immune response in mice". Virology, vol. 231, No. 1, Apr. 1997, pp. 20-27.
Matsumura et al., "An Equine Herpesvirus Type 1 Recombinant with a Deletion in the gE and gI Genes is Avirulent in Young Horses". Virology, vol. 242, 1998, pp. 68-79.
Matsumura et al., "Lack of virulence of the murine fibroblast adapted strain, Kentucky A (KyA), of equine herpesvirus type 1 (EHV-1) in young horses". Veterinary Microbiology, vol. 48, 1996, pp. 353-365.
Mayr et al., "Untersuchungen zur Entwicklung eines Lebendimpfstoffes gegen die Rhinopneumonitis (Stutenabort) der Pferde". Journal of Veterinary Medicine B, vol. 15, 1968, pp. 406-418 (Abstract at p. 416).
McGregor et al., "Recent Advances in Herpesvirus Genetics Using Bacterial Artificial Chromosomes". Molecular Genetics and Metabolism, vol. 72, 2001, pp. 8-14.
Messerle et al., "Cloning and mutagenesis of a herpesvirus genome as an infectious bacterial artificial chromosome". Proceedings of the National Academy of Sciences, vol. 94, Dec. 1997, pp. 14759-14763.
Neubauer et al., "Analysis of the Contributions of the Equine Herpesvirus 1 Glycoprotein gB Homolog to Virus Entry and Direct Cell-to-Cell Spread". Virology, vol. 227, 1997, pp. 281-294.
Neubauer et al., "Equine Herpesvirus 1 Mutants Devoid of Glycoprotein B or M are Apathogenic for Mice but Induce Protection Against Challenge Infection". 1997, Virology, vol. 239, pp. 36-45.
Neubauer et al., "Mutations within the US2 and glycoprotein B genese of the equine herpesvirus 1 vaccine strain RacH do not account for its attenuation". Berliner and Muenchener Tieraerztliche Wochenschrift, vol. 112, No. 9, Sep. 1999, pp. 351-354.
O'Callaghan et al., "Equine Herpesviruses (Herpesviridae)". Encyclopedia of Virology, Academic Press, San Diego, CA, 1999, pp. 508-515.
Osterrieder et al., "Deletion of Gene 52 Encoding Glycoprotein M of Equine Herpesevirus Type 1 Strain RacH Results in Increased Immunogenicity". Veterinary Microbiology, 2001, vol. 81, pp. 219-226.
Osterrieder et al., "Synthesis and Processing of the Equine Herpesvirus 1 Glycoprotein M". 1997, Virology, vol. 232, pp. 230-239.
Osterrieder et al., "The Equine Herpesvirus 1 Gylcoprotein gp21/22a, the Herpes Simplex Virus Type 1 gM Homolog, Is Involved in Virus Penetration and Cell-to-Cell Spread of Virions". 1996, Journal of Virology, vol. 70, No. 6, pp. 4110-4115.
Osterrieder, N., "Construction and characterization of an equine herpesvirus 1 glycoprotein C negative mutant". Virus Research, vol. 59, Feb. 1999, pp. 165-177.
Rudolph et al., "Cloning of the Genomes of Equine Herpesvirus Type 1 (EHV-1) Strains KyA and RacL11 as Bacterial Artificial Chromosomes (BAC)". Journal of Veterinary Medicine B, vol. 49, Feb. 2002, pp. 31-36.
Rudolph et al., "Equine Herpesvirus Type 1 Devoid of gM and gp2 is Severely Impaired in Virus Egress but Not Direct Cell-to-Cell Spread". Virology, vol. 293, No. 2, Feb. 2002, pp. 356-367.
Schumacher et al., "Reconstitution of Marek's Disease Virus Serotype 1 (MDV-1) from DNA Cloned as a Bacterial Artificial Chromosome and Characterization of a Glycoprotein B-Negative MDV-1 Mutant". Journal of Virology, vol. 74, No. 23, Dec. 2000, pp. 11088-11098.
Seyboldt, et al., "Equine Herpesvirus 1 (EHV-1) Glycoprotein M: Effect of Deletions of Transmembrane Domains". 2000, Virology, vol. 278, pp. 477-489.
Sun et al., "The role of the gene 71 product in the life cycle of equine herpesvirus 1". Journal of General Virology, vol. 77, 1996, pp. 493-500.
Suter et al., "BAC-VAC, a novel generation of (DNA) vaccines: A bacterial artificial chromosome (BAC) containing a replication-competent, packaging-defective virus genome induces protective immunity against herpes simplex virus 1". Proceedings of the National Academy of Sciences, vol. 96, No. 22, Oct. 1999, pp. 12697-12702.
Telford et al; "The DNA Sequence of Equine Herpesvirus-1". Virology, vol. 189, 1992, pp. 304-316.
Telford, et al., "The DNA Sequence of Equine Herpesvirus-4". Journal of General Virology, vol. 79, 1998, pp. 1197-1203.

FIG. 8

| Resulting Plasmid: | 5' primer | 3' primer | Length of product (location) |
|---|---|---|---|
| **pCgM4** vector : pCDNAI/Amp | 5´gcc**tctaga**ttaacggtaa tctctgcgc3´; ***Xba*I** | 5´aa**ggatcc**atggcacgacg tggcg3´; ***Bam*HI** | 1352 bp (nt 92681-94033) |
| **pgM4R** vector: pGEM3Zf+ | 5´aat**ctgcag**gtagctacgg cctatg 3´; ***Pst*I** | 5´aa**gaattc**ccgcaatacgtc cgtcc3´; ***Eco*RI** | 3113 bp (nt 91699-94808) |
| **pgM4Del1** vector: pTZ18R | 5´cc**ggatcc**ctaccagaga cccataa3´; ***Bam*HI** | 5´aa**gaattc**ccgcaatacgtc cgtcc3´; ***Eco*RI** | 983 bp (nt 93825-94808) |
| **pgM4Del2** vector: pTZ18R | 5´aat**ctgcag**gtagctacgg cctatg 3´; ***Pst*I** | 5´ttaa**gtcgac**atttgaataga aactcg 3´; ***Sal*I** | 1017 bp (nt 91699-92714) |

SEQUENCE LISTING

<160> NUMBER OF SEQ ID NOS: 10

<210> SEQ ID NO 1
<211> LENGTH: 150223
<212> TYPE: DNA
<213> ORGANISM: Equine herpesvirus 1
<300> PUBLICATION INFORMATION:
<301> AUTHORS: Telford,E.A.; Watson, M.S.; McBride, K.; Davison, A.J.
<302> TITLE: The DNA sequence of equine herpesvirus-1
<303> JOURNAL: Journal of Virology
<304> VOLUME: 189
<305> ISSUE: 1
<306> PAGES: 304-316
<307> DATE: 1992-07
<308> DATABASE ACCESSION NUMBER: NC_001491
<309> DATABASE ENTRY DATE: 2000-08-01

<400> SEQUENCE: 1
ggccaggctc tctctcgggc gcgggcccgt gaaaaaaatt tttcggcctc gcgacggcct 60
cgaagaaaac cgtagagggg agtgggggat gggatttttt tattaggcca cgcccactgg 120
gaggccacgc ccactgggag gccacgccca ctgggaggcc acgcccactg ggaggccacg 180
cccactggga ggccacgccc actgggaggc cacgcccact gggaggccac gcccactggg 240
aggccacgcc cactgggagg ccacgcccac tgggaggcca cgcccactgg gaggccacgc 300
ccactgggag gccacgccca ctgggaggcc acgcccactc cggtgatgca gcggttatgc 360
gattgtcctc tcagcgctac agtggggctc actgctatgc tggggctcac tgctatgctg 420
gggctcactg ctatgctggg gctcactgct atgctggggc tcactgctat gctggggctc 480
actgctatgc tggggctcac tgctatgctg gggctcactg ctatgctggg gctcactgct 540
atgctggggc tcactgctat gctggggctc actgctatgc tggggctcac tgctatgctg 600
gggctcactg ctatgctggg gctcactgct atgctggggc tcactgctat gctggggctc 660
actgctatgc tggggctcac tgctatgctg gggctcactg ctatgctggg gctcactgct 720
atgctgggcc ccttgtttgt tcagcgccca atacctacca acccccggca agaagttttt 780
gtgccccttc gcgcgttcaa cccgctccgc gacattagtt gccacgcttc tgtccatcgt 840
tctgaaacac ccattgcctt gggcgttcgc acttgcattc cccggttttg ctccgcccct 900
ctagggaagt aatctaactt tactcaacca acaaccctgg gctctttaca cacagtcttt 960
taacaccatg gcaggcctgt tgtccgccat tcctctgggg gtaattaatg gctgccactc 1020
aaatcgggta tcccccactcc cctctacggt tttcttcgag gccgtcgcga ggccgaaaaa 1080
tttttttcac gggcccgcgc ccgagagaga gcctggcccc catctccccc cgcagccagc 1140

```
gtggggccca gcccactaga tttcccaact cgctgggttt cccaagcttt tttccattgg   1200
gctcctccct tttggctctg ggtatttagc ttccctccca cctctcattc cactttctcc   1260
acctgcacct tttccatctc ctctccaact cgccgccatg agacccgagg gagtttcgcg   1320
gggccgcgcc tcctctgtct ccatctccat gtgcccaccg ccgcccaatg gggcgcgccg   1380
cgcatcgctg ggctgtgcgc ccccgctgaa tagccggcct gtatgctgcg ccccgtcgag   1440
cgtctctctg agctcatcat cctcgcgaag gtccatgcct tcgctaggct cgtccagaag   1500
ctcgagcctg ccttctaccg gctccctgag atccatcacg cgggacccgg agcggcttcc   1560
gtcgaggccc ccgtcgtaca ccgccatcaa cccagagtgt ttactggaac gcggggcaga   1620
gcggccgcgg gcgtggacgg cgagcgtgat gaccgcccca ccgagttact cggaagccct   1680
gtgccaggcg ccacccgcgt acgagctcgt tcctgaactt tcttatcacc ccacccagga   1740
cccgcgcggc gtctactcgt cgcgctccga tccccaccag acctctcgaa ggagacagaa   1800
cccgatatgt atttttatta ttgttgttgc aaccatgttg ttgatactgg gactgttgct   1860
cactataacg ctcagttcgt taacaaacgg caagaaggag aaataaaacg actgtagtac   1920
cgcaaaggtt aatcgcattt atttttacat gcactccttt ccaaaccccc tgtacactat   1980
tccgatcagc accagaatct ggagcataag cagaatgatg tttattgcgg caaacttcct   2040
gcaaaaggtt ttactgtaga gccgcctttt gatgggtccc atacgaccgc tcgggtcctt   2100
gtgttgatcg cagaaaccgt cgaggtaaac ttccgatggt agtgcggccg ccccgcggtg   2160
atttctagta acgtcatcca gatgtagcac agctggactt tcagcgtatg catcggtaca   2220
gcggccagtg ggtcatcttg gtgtagtagt gggtgagtcg gtaagcacat tgcttgaggt   2280
ggcggaactt atgcgggtgt actcctcgtt ctcggagtcg ctctcatacc cgtaggggct   2340
gacgcgggcc ggaccctgcc aggccgacgg ggggaatgcg actctgccgt accacacggt   2400
ggaggggcgc gtctggcgct tctttttaaa cagctgtgac attttcttga aaaacaactg   2460
ggagagcagc tgtcttctca gagactctcg tctgggacgt ggttcaacgt tgattgtggt   2520
agggtttgag acgtgtatgc gcctcctcca cgctggatcc atgcttaaac actttggagc   2580
gagggggcgg ggtatggggg cgtatgcctg aaactcaatc tacagcgtta tgcccggggc   2640
taaaaagctg cgtcttcacg cccgaggcgc ttattgccca ctgggtacgg ggcgcgcttt   2700
tatatgtgta acgtcccacc ggtgtgacgc acgtactacg gttgttctaa atagctgtcc   2760
ccgtgattgc ctcggctgca cacatcgcct aggtttccgc cgtgcctggt gtcgagggcc   2820
cacccctgta accaacatcg atgggggcct gctgctcctc tagacgcaat cgctcgccgt   2880
cgctcgccgc cctggccgaa gaaacggagg ttgtccttcg ctgcctggcc ggaagggtag   2940
tagacctccc tggtggagat gaggtgcgaa tcgctccgga cgtcgggcgg cccgggcaga   3000
attttggcta ctttaagttt cccggcccgt cgcgctttgc ctatgttaag tttataggca   3060
gggcgtacgc gctaggaagc gggcgcaagt ttctactgta cctatccaga aactttcagg   3120
tctttggata cgaggacggt accggcctac acatgctagc caagtcccta cacgattttt   3180
taaagttcaa aggactatct gacagggacc tggtggtagt cgactcggtt gcgctgacct   3240
cgcagctgcg accacttact cttcctatac gttcgacctc ggacgtggaa acgctagttg   3300
ccgaggaggc caccaccaac tacacttcta cggaaaacct actgggccag acccagagct   3360
ccacgcaccg tccgctgggt gtaccgcttt ccaacgtaaa aacaatgggt gtgccaccca   3420
cgaaaccgag tagccaaagg cccaggggca agggggggacg ccctccagcc cgcctcaagt   3480
```

```
ctatccgaga ggagaccgta tccggcatgg caagggcccg cgaagagtgc aactctccca   3540

gcgaacacga ccgcctcacg tccgagatga cagactgcga cagcgactcg tcggtatcct   3600

ccgtcttttt ttaaataaaa agcaaaacac catatacggt ctgaatttat cgtttatttt   3660

ctcgctggcg ctctttggcc gaggttattc ccctagccac gcttaaaatt ttggcctggg   3720

cagagttggc tgcctgccaa cactctaggg aaaagggggt tttgcagtgg cagtggaaac   3780

acagtccgtt gatggtggac tcctccccgt cctcgtcgca gtcgtactgg gtggcggcgc   3840

taaacggggc gctacacacg ctatgctcgg tggccaattc ctgcatgatt ctcgggttat   3900

tgaggatgca tttgaagttg gtcaggtcgg ggagcaagat ctgcttttcc gggtccctct   3960

tctcgaacac gccgatgaaa aaggcgtgta ggcgcgtttg cagatcgcag catgctctga   4020

tggtatacgt tctggtgttc aggtaagacc tgcttctggc cggctgggag gtggtctccc   4080

acgagctcca agtcaggtca agcggcagag gcgacacaac gttgctgatg tccaccaata   4140

gccccagctt gcagtcgctg ctgtaacacc cgccgtggtt cctcccgtgg gagcctatat   4200

cccgcggctc tgcatcagat gagtgttctg cgcggtttgc cggcagcata tttacgttta   4260

gttttccacc aggctgggaa tttgctcgac tgaaggtatc aagacgcagt gtacccaacc   4320

cgacagccac cactctttaa actcccaagc gccgcccagt ttacatttta aaacacgaca   4380

aagctttgtg gaataattaa actgtattta ttgatgagta acacaaaaca agtttcctgg   4440

gaaacacact ccacagtttt tttaaaagat ttggttacag taaaagtatt tgccgtgcag   4500

gtaaaccgga acgagggtgt aggccgatac aaggctgcag gtatctgcct tgcatcgccg   4560

cttgtgcgcg tctatcgcct cgagggttcc cgccagacag gctccaggta cgtagtcggc   4620

tagaacgcgc ccgtcgggtc ccagtgcgtc cctggacaca gtttcggcgc cgctccctac   4680

agcccgagct atgcgcgcca acatcacgaa catgaaggtg ggaacacacg cgacgtcaga   4740

cagccgctgg tggtcgcaca gctctgcgag ggtagggctt cccgacgatg agaggtagca   4800

ccgcataaag ggctcaagtt tcaggcgcag gttgtccagc agggccaccg aagaagagat   4860

gatagggtct ctggtgcgca ttggtaggtt tttggtgacg atcatcttgc accaagatag   4920

ggtttcatcc gccgacgcga gcgcctctag gaggttttcg cctcgcatca ccgcgtcgcg   4980

cagagaccgc gcagcctcgg ccgcgtggga ccgcacctca aaaagcttgt acaggttaac   5040

accgtgctcg accagcgtgt cccacgtgat tctcctcgcc tccggattaa actggtccga   5100

tccgaagccg agcaccggag cccacgggga cgagttttcg gctctaaatc caccgttttt   5160

caccggcgta gttagagtct cgcgcgcccc gtgaaacatc tcaccgatgc gtgagctggt   5220

tacgcgcctg cagacatccg ctatggagct ggcggccgcc gcgttgagtc tatcccccgc   5280

ggatcgaccg ggtgtattag agccgtggtt agcgtttccc ctgcgtcggt tgcggtgaac   5340

tctggccacg ctttgcgttc tcgtcttaaa ccgccacctg tcagacggtc ctgcgccgcc   5400

atgtccagaa tctgctgagc tcgaatcgcc tccgcgttgg cccaggcgca tgtgtaccgg   5460

caggctcgac cgctttggcc agctacccgc tgactggcgc gccggcacgt tttccggctc   5520

cggcttttcc cagccacgct gttgctgctt ccagttgttg cgcctgaagg gtcgacggcg   5580

gtttctgcgc ccatggccaa acgccggccg ctcgctcttg ggtttgacg gttgcgcgcg   5640

ctgcggggac gccgagaagc tcacaacaac actctttggt gggtcgccga caacatttct   5700

aagcgctgac acggtgccaa ctgtttgcgt tggtacaaag gcgcttttgt tgaccaagcc   5760

gcgagttgcc tctgcgcatg tatcgccccc ggtgaagttg tcttcggtgt cagaccccat   5820

tatactcatt tcgtcctcca tgggctcaca gctgctcacg ctagaaagtg ccattgtctt   5880
```

```
gatacagcag agtatgtctt ccagggctct gtgtgtttag agcagcaggt gtaccaagaa   5940
aaggccaaga gtgcggacct tctcggtgac aggattttta tagagactta gaagccgcgc   6000
ccacttgctc ttaggacgag aaggactcgc ccaataagcc aatttgaata cgctgttcgt   6060
agtgcagtag aatcgacaca gcgcctatca caagtagcag atagactagt ttcccacaca   6120
ggttagccag caccgtggag cagcaactgg tacacaggcc tttcactccg tgggtggcgg   6180
gagtcggggg gtttgcgctc gagccagtct ttgggggctt ttcgtagata atagccacta   6240
tctccactat agttacagcc accacaaacc cccacgaggc gagtttaaga taaatggggt   6300
atatctgaga gcagggggtg tgaaccaagg ttacggttcc aactaccagg agtctagcca   6360
caaaatgcgt tcccacctcg agtccgatga gcgccagggc ggcgctgtgc tcgcagagaa   6420
atcctatggg gtcacgttta aaggtcctgc ttagagccac gcggcgcaga gacgcttcgc   6480
acagcagcag agcaaacttt gtgtagtgcg ttttgagcac ggtggtagca agcgtatagg   6540
tagcatagtt gaaggtgtag ccagtcggcg ataagaactc gttttggttt ctaaagggtc   6600
ccagcaagcg gcgctcttga cgcaaacaca aaaacgcaat gtagataagc cacgccccgg   6660
taatcatctg cagctgcacg ctccacaggt aagccctaca gttgcgagtg ccaaccacta   6720
ttcgcacttt gtcgtgcagc tccttcatgt tcttcaggac gtcgagcttg gactcgttta   6780
cccagttctc cctgcagacg tagtcaaatc cagacaggcc gtcgctgaat cgcttcgctc   6840
cattttctgg gtacgcatac actatagtgg agttgtatac ttcccacttg gcagcaatcc   6900
catccttaga gtctatggaa actgtagcgt acacgcaggg gttgtgcagc tgggcggtga   6960
gggtatacca gatggtaaac gcggcatagg cggtgataag gcccagtaca gataggtatg   7020
ccgttctacc accgagtaac atggcgctag ctggcctatt tggctctgtc cacctctagc   7080
gtaaaaatgg tgcacatctt attgttgccg cattttgtag caaagcactg ttgacttatg   7140
gacgcgcaga gtctgccgtg cacgtccgca cttatggaca gaaacgtacg agccagtcca   7200
cgtgccgatc gaaggtgctt ggcgcgcagg cagctgaatc cctgtgatct gtaagcgttg   7260
ccggatcggt tgatttgcat taaaatccag tcaggcttgg taacgacggt gtgtacccca   7320
accgtttgat attcgcccga ttggtcgggg aagtgagtgg cgaggtggga caccacctca   7380
ccgagtacca cgtcgacaac aaacgcttcc accgcctcgt gagattttat agacacgttg   7440
gcgctcgaca gaagagactc tagcgtggcg cgtttagtca tgatcgcttc tctgtttcga   7500
gctaccttgc gctcaaaaaa gctgacgtaa tctccaccca ggtcggtgat tacgtgagtt   7560
attgtaggat ggcggggggc cgcgtgaaag tgaaaattgg ccgggttcga atgctgcgct   7620
acaaactcat ctacatcgtt gcattttggg ggaatcacat aaaaaggata gagacctccg   7680
taaacttcac cagagtcgcc cactttgcaa aaaaatggaa gacgcaggct gcggccgtgc   7740
gagtaaacgc ccgtgtcgat aaacgaaaaa tccctcaaaa cggagcacat gctctctgta   7800
aacgtgcgct ccagaacaac agcctgctgt ataattcgcg ccagaccacg cagtgcttcc   7860
ggccctgcca ggaggtaagg gggtggcaca ggaaccgtta cacggaaccc catttttttct  7920
gtacactcgc atgcgtctgt gtcatcgagt cgctgcagcg gcgtttttcc accctcttta   7980
tttgggggtg tattatcaca tgcggcctgt gggcattcat tgtctaccat catcatctca   8040
tagtcgtcca tcggcccatc agtgtattcc tccatggccg catagtcatc tataaagtct   8100
gattccatgt agcactcctc caccccgtca acgtagtctg ggaaagacga gggctcgccc   8160
ctatgaagcg ctctaacgag ttgaggggga cacgaggttt tgtaaaaata acacgggtaa   8220
```

-continued

```
gagtcccact gtacggtggc atcggaaaag attagtgata atgttgttat gatgccggct   8280
ctaaaaccgc gcattgcgag gtgaagcatg cccagcggaa cccgcctctt gatgccaaag   8340
tctacatcca agatgatatt actgaccgcg agcgatgagt tgaaaatttc attgcggttg   8400
atgtacatct gggcagacgc gttagaggac gccagggctg tacggcatac gccgctggtc   8460
gtgcgcgtta gctggaggtc gcgccatgcc agcgagcaat cgtcaatctc tccaaacccg   8520
gctaaagcaa agcctccctc gtacgcttgt ttactaccac ccgggcgcgc cagattttgc   8580
gttgtggttt cccagcggtc attagctatg acagcaaaag cctggcgctt ggaaggcagt   8640
gccactcgat agactggagc ggggccggga actccttttt ggccaaatag cacttctagc   8700
ggaagggctc taccgtttac tggtggtgat gatgcaatgt gtaatagccg ccgagatatt   8760
ccacactggg acgatacacc cggggagagc tcgtcaccac gcgactgatc cagcggtggc   8820
gtggaatgga cactctgggg tttgttgggt gaaactatgg tctgtatcca gccgcggcca   8880
gccagcgagg attccaccct gtctagtagc ttcaaaattg gtgtagaggt gtcacagaca   8940
ccaagcggag cgctcccagt agacatagtc gtggacgatg ggtgtaggt tttatcctgg   9000
gcatactggc tgcctataga cgccggcaaa caaaccactc tggggttcac gttgtgggcg   9060
atgtagtctc tgatattaag ctgaattctc acctgagcaa aaaatttctc aatcgttccc   9120
cttttcaggg acgaagtaga tgttatgcga tcaatgtctc cagggtcggc tatgctgaca   9180
gcaagcaggt ggtcatatag ctgtttgcgg ttgaagctct caaagtgggc aaggtaaatg   9240
taggtaataa actctcggtc agacacgcgt agtccctgtc tgtctgccgc gatgaacccc   9300
tcgagcgcgc ttacttcggc cacgtccgcc tgaattcgaa ggtcgacgta cctaggtagc   9360
gccagtgcgc acggccctct agaataccaa ctctgacagc aaaactttga caggagcgaa   9420
aatgatgtaa ggtgggtgag atccagccca gtggggttag gtgcggccgg aacgttatac   9480
gttctaataa agtcctttac tgcctgcagg tcgtaggtgc ccccggatct ggaacagcga   9540
atggcctgga ataggtaata tctggtggcc agcacaatct ccctctctcc ggggccaaac   9600
ttggaagcga accaaaacgg cgtggtgttg ttgttgcagt atagacgcct gaacgcggtc   9660
agcactttat tctcatggtg tatatacacg gaggtcaaac cggagcggcc ggtgctgtga   9720
ccgataacgg cggccttaac tgatcctcgt tgggggtcat acttggcggc tgctgcggtt   9780
cgtccgcttc tggcggtaac attctctgta gttatcgcca gagccaggat taagtcattg   9840
tggagcagaa aggtggcctc ttccgttaac gcctggagca gtgtattaga cgatagcggg   9900
tggccgtgtg atagagtcat tgccaacgcc cgggctccgg tccacgtgga aaacacacac   9960
acaaacattg ggcgtacgcg gtcttgtggc tcgtcactag cacctcccac cataccgctt  10020
aacaaacaaa agcttactga tggtttccgc tgtaaaagcg cggtcgccaa ctgatccgcg  10080
tctgactgct cagtggagct ccagccgtca ccagcatctg tgtttggcgc gcggggctgt  10140
ctcccaaaca gatcatcgag ctctgaactc cagtcgtagc ttatagcgta cacaccctcc  10200
gagctctcct gtccggtcag aagcatcagc gaatacgtga taacgcagct gtcggtagca  10260
tagagaactc tgatagttgg ctctgggttg cgttgcgcca tgtttaagtg gctgatgtca  10320
agtctatgtg gaattagaaa ctccacatcc ccagaagttt atgagccaat tattggtggg  10380
cagaacccag ctaccatgct ccgcctacag tccgctctgg ctgccgtcaa tgcgcttctg  10440
cccgcgaccc ttactataga ggacgtgatc tcctctgccg acaacacccg gcgcctggtc  10500
aaagcgcaga ccctggctcg cacatatcag gcgtgtcagc ataacataga gtgtctatcc  10560
agacatcggg ctagttccga caacccgaac ctgaacgccg tggtgacaac tcacatgata  10620
```

```
aacgccaagc gtctctcgga cacctgcctc gcggccctca tgcacctcta tctgtctgta  10680
ggggctgtgg atgccaccac ggacaccatg gtcgaccacg ccattcgcat gaccgcagag  10740
aatagcgtgg tgatggcaga cgttgctgtg ctggagaaga ccctcggcct ggatccccag  10800
gcaaccgtcc gggcacaaga cttgctggcc ctcaacagtg gtgttttaaa ttctgtgaat  10860
gccgtagccg agatgacaga cccgacagac gacgtcgagt ttacccagag tgtacacagt  10920
cctctcctcc cccggcagct tagcaccacg gaagtagttg gcgtgccatc tccagtaaaa  10980
tcaaacctca aatctaaaca caaacccaaa cgcaaagcca gtttggttgc ggtgtaaaca  11040
aaaaacaata aactattcag agtttttat aaacgagtct gtttttattt tatatctacc  11100
taacagtcat cgtaatataa tcacgggtag tttttataa tccggttgag ccaaaccctc  11160
catccgcgcg taggctagag ggtgcctctc tatcgaagtc ggtcgtaaac ttccacagta  11220
cggggctttg gggcgccttt gtagactcag agggggagta cgtgggaaag gggttgtcgt  11280
agtttacggt cggcggtatc aacgcatcgt caatatcttc cgtcagcagt agctgcgcaa  11340
cgcgctgacc cttagtgatg gaaacaggat acttattgac gttaagtata aagaagcagc  11400
aggttctccc agctacccac ctagtcggta gcactattag accccttcga ttcatagacg  11460
atcgcccaaa gatacacggc gtgacggcgg ggttggaatt agcgaagaca atcggcaagt  11520
ccacaaagtg gctctcgtcc gggtctatag tcgcgtcttc aggcgcgctg atgtcatatc  11580
cggcatcctc gacacgcttc ggagcaaagt aatcgtaaaa caggttagct tccgatgtac  11640
gcccatccct tgtagagccg atgctagtca cgtggatgct cttcctggcc agttttacca  11700
acacgagacc caagctcatc tgtccggggg gcacggacgt gttgatccca ggtgcgaatt  11760
gtaccgcttt cacgacgccg cgatatcccg agtcgactat accgtaggcg gtgtaatatt  11820
tggcagagtt ttcaggaaac gttacgttgc taaaattccc tggctcgggt tcaacaggca  11880
acaaaccgct aatttgcgtg aggacaatgg catatccgct ggagcaggca acccgtacac  11940
ctacgtcagt gagcacacta taaaattcgc ccgcacttcc atgctcacca ctcagctcaa  12000
ctgtgtggtt gttgattaac accaacaatc tcccagcagc ttctgctcgc gctctccatc  12060
tctcaccaca ctcaaccacc acgatgctgt ccacgagatt cgtgacgctg gccattctcg  12120
cctgcctttt ggtggtgctt ggtctggcca gaggggctgg tggcgaccca ggtgtgaagc  12180
aacgaatcga cgttgctaga gaagaggaga gacgcgactt ctggcatgca gcctgctccg  12240
gacacggatt cccaattacc accccaagca cggctgctat tctattttat gtgtctctgc  12300
ttgcagtggg agtggctgtt gcctgccagg cataccgcgc cgtcttgcga atcgtgacgc  12360
tggagatgtt gcaacacctg cattgagcaa ctgtgtatgt ataactcatc ccggatattg  12420
tttcaaccgt ttgactgtat aaaaaggcta gctctctacc tacaagaatc attagtgctg  12480
aaggttcctt tcggggttta cagcgctagt attagagttt tgtaagagtt tattattagc  12540
aagtgaatat gtccgatacg tggcgtagac gtcgcagtgg ctgtaacgat gctaacgcta  12600
cggaagagct tgtatactct accgttcgta gcgaccatag gcaacgacgg ccctctcgcg  12660
ggacttttgt tatgcgagaa aacgacctct acgacaaaca gagtgtatct aaggaaaatg  12720
acttgtacga aagcgctagc ccaaacgacg acaaagttta taccaggcga ggtatgagca  12780
ctgccgcgca ctatcgtgac tctgaacaca tatacgaaac gtgtgagggt gatgaattct  12840
acgatgcatg cgaatattct ctgattggcg gtggtaaact atcgacctcc aatggccgcc  12900
aaagcccagc aaaagcgcaa ccacctccaa ggggagcagc tgctgctcca cccccacgtg  12960
```

```
ttccaacgcg accacctaca cgcgcggcgg ctacttccac gacgccccgg caacaggact  13020
gcgctcccaa acagcgcgcc tcgcctggtg taaactccat caagagcggt aagggcctcg  13080
cgtttagcgg caccccgaaa acgccaaaga gtcagtggta cggggccact cacctgttca  13140
acaaaaacgt gttttgcgcg gccgtgagtc gcgtggctgc cgcacacgcg agcgatgccg  13200
cgtccgcact gtgggacttg aacccgccaa agaccaacga ggacctggac aggtttctga  13260
aggccgcggc gattcgcata ttggtatgcg agggcgctca gctgctcgag gtggcgaact  13320
ctaccatgga aagtaccccc gatgggtatg cggcagctgg acccaacggt tacgatcgtc  13380
gacctcgtac agcctctaga cggcgatccc tgaaatgtaa accaccggcg gatgactttt  13440
tcgacgacac gaattccggt taacgcttat ttgcataaat tcataacact gtgccctcaa  13500
taaaatgtgc ctcttacata tttctttacc ttatttgtcg tgtgctctgt tacccggctg  13560
gtattttgac gcgcgcccgg cagcttcaat agttatgttt gctgccgcgg aagagaacga  13620
tgacccctat cccgggaaat ccggctataa tgacacctgc gagctcatgg atatggacgg  13680
tgctgtcgcc agcttcgatg agggtatgct cagtgccatc gagtccgttt attccattcc  13740
aactaaaaag cgtctggcgc tgccaccgcc caaggccgcc agccccggcg cgctatacca  13800
gcggctacaa ggcgagctgg gttttccgga gggccagacg cttctatccg ctatggagaa  13860
gtggaacgaa gacatgtttt ctgccctacc cggacatgta gatctataca cagaaatcgc  13920
cctgctgtcg acctcagtag acgaggtagt tagagcaggc ctcgatagcc tgcccactcc  13980
cagccactat agccccgagg tagacttgaa cgcgcatggc gacgagccct tcccagaggt  14040
tcccgccctg gaagacgacc tagaaatata cgtgatatcg gcacagcgct tttacctatc  14100
agagcttcgc acgcgcgaag agcactacgc gaggttgctt aggggctatt gcgtagcgct  14160
attgcactac ctatacggca gcgccaagcg gcagcttcgc ggaagcggct ctgacgcatc  14220
tttgatgcac aagtttaaac aggtggtgcg cgacaggtac taccgcgagg ccgctaactt  14280
ggccaggttg ctgtacctcc acttgtacgt atctgttact agggaggtat cctggcgcct  14340
tcacgccagc caggtaatca atcaaggtgt gttcgtctcg cttcactatt tttgggcgca  14400
gcgcagaaag tttgagtgcc tgttccaccc ggtgttgttc aaccacgggg tagtgatctt  14460
ggaaaacgac cccctagagt tccacgatct acagcggata aactatcgcc gacgcgagct  14520
tggcctaccg ttgattcgcg ctggtctcat cgaggaagaa aacagccccc tcgaggctga  14580
gcctctgttt tcgggaaagc tacccaggac tattggcttt ctgacgcacc agataagaac  14640
caaaatggag gcatactcgg acgcgcaccc ggcgaccccg ctctttcctc tggcggagca  14700
ctcctacagt aaacggatag ggggacgcct gtcatacggt acaacgaccg aggccatgat  14760
ggacccgccc tcccccagcg cagtgctgcc aggcgaccca gtcccgcctc ttaccgtggg  14820
ggtgcgtcaa accgccgcaa cgcttgctat tccgtctaac ctcacgctgc agagcatgga  14880
aaccgacggc cttgactact catcaatgac gggcgatgag ctcaaccaga tgtttgacat  14940
ttaatacaat aaagtatgtt tccagactta acatgttggc cgtattttcc gtcgttgtgt  15000
tacgtgaata ggacgtagtg gtgggagtgg gcgtggtatg cgggggttct ttgtttaaat  15060
tgggcccagg cggatcagtg ccagttttgt ttgcattggg ggcctgtgcg gcatgcgaca  15120
ctcctcaatt gcgtatcttc agatatcgcc catttaacag tataaaacta gagagtatgg  15180
cggttttgaa gcttgtacca agcctataaa actagcgcgc cgtgcagtga gatgggtgtt  15240
gctatctaca ccagatagca ggcgcttctt tttcaaaact tggcggttgt acgccagcga  15300
tacggaatcg ggtaacatgg accagcatca cggcgcgcgc ggcggagctc cgatacgccg  15360
```

```
acctcgcaga tccatagaat ctcgctccca cccatttcga gctaccggaa atacacagcg  15420
cacatacagc acgccgagac tcagctatag agacggtctg tccgggcgca ccgcttcgag  15480
ggacccccag gaacaagctt cgaaccagga tgagagttct aacccgagca cctctaatgc  15540
tcaacaaagc acatcattct ggggatatct tcgacgagtt ttctcagacg atgtccccgc  15600
acagccacaa gcacccagac ctcgcgcgga ctttgcaccg cccgccggcg aggaatcatc  15660
tagcgaggaa gaggaggaag agggtcccgc ccaagctccg ctggacgagg aagaccagct  15720
aatgtatgct gaccagtact ctgtagggga ctctagtgac gaaaacgacg aggaagaaga  15780
cccccgtcta ggatctgact atcccacgtc cgccgaatcc agtgaatacc atgaccatgg  15840
tgaaatggtg gccggtgcgg gagccgagag tgagtccgag acagatattg acgccgaaga  15900
agaagaagaa gacgacgaag acgatgagga tgatatggaa gtaatacgag acgaaagcta  15960
tagacttcct cgtacatggt tggacaagtc tatacgttta atggacgagg ccctcgctca  16020
atcttccgaa ttatcgaagg ctatcactaa atctacacgc agcttgtacg atagccagtt  16080
tgctcccggg ggtagaggct acacacagac ggcaacgccc tctcggcgcc tggtacagct  16140
atcgcgcgct ggaatgtacg attcggataa aatagttatg acgggggact acatggaggt  16200
tgacgacgat ccagacagcg cttaccagtc atgggtgcga gcaattcgcc acccactagc  16260
gatgaacccg tcatgggagg aaacaatttc caaccacacc aacccatcgt tttccaccga  16320
catcgactat gatatagacg agctaattga aaaaaacctg gcccgcacac cccctgtgtt  16380
tgagggatta ctagacagcg cagagttttt ttacaaacta cccatgctat acacatacgc  16440
caccattacg caggacgagg cctacgaaga gcggctagct tggtccaaca cacaggcgct  16500
acatggacac gaacaaagtt cctggcaggc actcctggtc tattactcca ggggggggaat  16560
gtacgtatcc ccgactcaag aacctcgagg gatttggcgg cgcgcgctaa aacaggcgat  16620
ggcgcttcag ctaaagatgt gtgttctcgg cctatcggac gtcgtaacaa agcagaacgc  16680
tacgcaccac catgccgcgg taacatttct cgtggacgcg cttctcagaa ccgctaggaa  16740
ttgttacttg gcgagccggc ttctggtatt tgcctgggag aggcgcaggg aaactggggc  16800
aaaacgcccc gcagagcccc tcatagcact ctccggggtt acactcttgc agccccttcc  16860
cccagaggtg tctgaactgc ttgagcagcg tacatttgac attgggttgc gcacccccaa  16920
cagtgctgtg tttagggcgt ttttcggatc gctggtgtat tgggcagaac tgcgcctggc  16980
tcttcgagac cccgcgtcca taaactgtcg ctatgtcgga ttccatctac agacctccga  17040
aatctatttg ctggcgcggg cccactccgc gagtccaggc tacaccaaag aagaactggt  17100
ggcaatggag gctattctaa ccctcgctac actcatgcta gaggtggcgc tgcagtgggt  17160
tcacgtggct tgcgcacagc tgctcagcga aaacgatacc ataaaagcct ttaggcgggt  17220
cagcgcatct atcccgcacg ctctggcgcc ccttggtagc atacgcctac acgacgccga  17280
gtttgaagtg ctcagcaacc cagatgtgat ggtggctaga gacgaaaccg ccctgagcca  17340
ggcgctgttc ctcggttact tttccgtgag gaccgcgctg accgcgtgca tgcgtgatta  17400
ctcacacgag gccgacggtg gatccaaaga aaccgttaca ggggtgtttt tgggggtggg  17460
cctaatcctt cagcgcctgg cgggccacct caactttcta ctcaactgtt tggccggggc  17520
cgcgctgtac ggcggccaaa aaatcaacat acactcgcta actctgccgc gatacagcct  17580
attggcggat gtcatggccc ccatgctcca gcggcagtcc ctggtcgact tttggcgggc  17640
ccgcgataac atgttggagg atctagaaat aacacctcgc cccggccctc ctactcaggg  17700
```

```
caagcgcgtg gtggttgaaa tgccactccc atcagacgac ctcccagaca tgaccccccgg  17760
cgcttccgtc aacaatggcg ccggcctggg acgcatggtg gacatggcca agcaactaca  17820
gcactacaga gaaacaatca taggggaaga agccacctcc tccgtgggaa aacgtggtct  17880
aatcagagct ggtgtgggcg tagccgccct gcgcggtagg cggagaaagt gagaagatta  17940
acactcggaa gcacttaatg ctgtttacgt ccggaatctc tctcacatcc cttaagcact  18000
tccccaaaac cgcctctcca gcttacacgg catccaacct gctatcggtc gtagcgccgc  18060
tccatatacc gactagctta caatggacgg agggggtct tcttcgtgga ctcacgtttc  18120
caaaaaccta atagagcggc gcgctgtcaa ggggtgcctg ctgccaaccc ccagcgatgt  18180
tatggatgcc gctgtgatgg ccctgaaaga cgtgaccgag aacattgtgg gccaacaact  18240
attttcggta gatcgtacta acgctctgtc tgttattcac accaacgagg ttccggagtc  18300
aataattgcc acggccatcg cacgcgacac atccagagac tacttgaggg aatatgaagg  18360
tgcggctaag tgtaacttgg cagcaacgga tctatcgcat gatgaaatgt gggaagtggt  18420
tatcaaaaga tactggcgct acctccgcga gtccagcggc gcagaggttg tcgatcgcgg  18480
tgcggtgggt caggcgactc aatctgtatt atccgtgttg cttctccagt ccaccttcgg  18540
caaaaaacgc ttatctaaaa atcccttcaa acacaagggc cctaatgtcg gctacaaatc  18600
caacctggag gacctgcgct cagcgtttac aaaaattgaa aagtacatgt actacatgcg  18660
ccccaatgat cccatgacga agagcgaaga cacagagctg cgcttacacg agctactggc  18720
gtacgtgacc acatgttatc gatggctgtt gtggttcatg gacctgacag acgccaaggt  18780
gctgagaaac atagacaaag ggcccgttat cacacacggc cctcgcgagt ctcgccctcc  18840
ggacgaactc gtgcggcgcc acctcaagag cggtccggca atttccgccg gaacgggtgt  18900
ggctctgact ctgtcgacgg ccaccgccga cgccttgatc gttttgctga gaatgagtgt  18960
ttcctggacg tcccactcgt ggaagagcaa tacccacggt gtcactggtg ctatcgtggc  19020
cgccgtggag ctggtcacgc tcatccacca ccacttacag tacattatta acaccgtatt  19080
tgcaggctac gtgtgttggc tcgatggtgg cgtggagaac tcatatctaa actctgccct  19140
ccgcagccag ggtaggttcg atcattttgt tggaaaacta gtgcccatca tggccaccct  19200
cagctgggcg aatatggaaa aggggacagt catgtggttc aaatacgctc tggccaagag  19260
tatagtgtgt catggatcgc ctactcagca ctacttaaca gtgctagaat ctatcgcgtc  19320
taagcgcact ggcgcctgtc ctccccaggg atcaaccttt ggacgcaacc cctccggttt  19380
tcccggacag ttttgctgtc ctccccaagg gccgctaccg gcacccccca actctaaaac  19440
tcgcggcacg tttaggcgat gccggcccgg cagcttgcgc agctccaggc agctaccaac  19500
ctcccctccg tcgaacatag tttcccccag gaccaacccg gcaatagaag ggtctacggc  19560
tgctaaaaac gtccaggggg cggagaccat ccaagtacgc tcttctggag aatttaacga  19620
ctgtatctgg tatataaacg gagcatatcc ccatcaacgc agcgacagca gctcctccga  19680
taacagcaca tgttccagca cggagactca gtatataact ctcccctcaa cgccatcgcc  19740
aaccggggac gttgtttaca ccaatccact ccttgggccc gacgaggaag tagacgcgag  19800
cccccaaccc gttgatccta tgagcgacta ctctgcgcca aaaaatcccg actatatgcg  19860
cccccgcagc actctggtcg aggaggtttg gcagctgcga gactccgatt acactcccta  19920
catgcgcccc agccgtgccg ggcgttcccg cgtgagagtg gaagaccaaa ctctggaacc  19980
atcgtccccc gccggttgta atccacccgc caattctcca gaaaacgatt cagacgatgc  20040
cgccgttgac tcacctccca ttagcccgga ggttgtgtat ggtacattta ggcccagggc  20100
```

```
caagtgcgtc tatgaccaat acggattgac cgcacttgct gccctaagcg cctcaagagc  20160
aaaggccagg cggacgcgcc ccggccccac ccaaccagat gtttgccgcg agcgtgacga  20220
ggaatctgca gagcccagac atgacggttt tatcaggcga accatgtcta cgactggacc  20280
ccctagaaaa cacccggacc agacggagcg tgttagctcg ctgtaacccc cacctactac  20340
ctaccctcta tgatgattat attaataaaa caattcaaat gataaaattg tgttactctt  20400
tatttaaagt acatatataa acaattttaa acaggttttt gcgcgacgtg tatagcgcta  20460
tttatttcag cgcatcggtt tctctattac cggggaaacg gtatgatgtg gtccagacga  20520
agcgcttggc gggccttgta gatcagctct ccaagcgggc tgagtgggcg ggctgcatag  20580
cacacaccaa acccttggt gtagcattct gcgaagctcg gtacgttgca gtaggccagc  20640
tgagtatcat cgaggttgag cttattcata acggattcgc tatctcccac gttgaggcag  20700
tccagcagac tcattattag gcctgcagtg ccattagaag ccgccatctc tgagtactct  20760
tcgcatactg cccccacccc gctgatgttg cgtgtgttgg atgatgcgtt cagcaacacc  20820
gggcgaacac actcgtcccc cagaccaaaa gtctctgcgg gacacggtgc cgtgcgtagc  20880
gcgccaatag gtactgttaa tatgaaggtg gacaccagaa tggcggttgt catcaaaacc  20940
cccagcgcaa acatgcccat cgtaaaaaaa aggcagcggc atttgcttt gcgctttgtt  21000
ctgcgtcgct ttgtataaac aagctcgttg ggttgagggg gggttgacag cgggggcgca  21060
aacaccggaa cggttttcgt tggtaagggg ggagcctgag catcgacggt ggcggtttcc  21120
agctgtagta atttataatc ttccatcgca gctgttgggt ctcctgccat gttgctttac  21180
ttagacgtta cggccgcata gagatcagcg tataccgcag agtataatgg ctttataaat  21240
atcaccgggt cgcgattgta acacaaaccc aacggttttc acctagcgcg tataaccgca  21300
tatttttagt gccatattct cgagagtgag tttgtgcgta cggttggcct atgcggacga  21360
cttgtgggag cccacctact gtttttacca gcgcttcaaa ctgtagtttt gacaaatagg  21420
ttgtttgggg gagagcggtc cagcctaaaa gtcagacttc ttgtacggcg cctgtgaggg  21480
cttggagcag taaaaacaga cggctgtgat gagaacgacc agcgccagtg ccgcggcccc  21540
gcaagtaact gcgatgatgc tcgtcaaaac cggcctgtcc tcaacaatcg gggaggcgtc  21600
atataccact gtgtccgaaa acataggcag gccgtcgggg taccccctcta ttatgcagct  21660
atactccctc tccccattct cttctgagag gggccggcgg ctttgcatgt taaccaatcc  21720
cgagtggcta gggcagactc cggttgtcat gtcttgcgac ggaacccctg gtaggtggtc  21780
gttcactgac cacgatacga acaccccggt gctcggtacg catttagccg tacagacggc  21840
gtctccgtct tctaccgaaa cggacacggt tggggcaaca aacacagagg gtgttccagc  21900
tttggctatg cgagcaaatg atacttcgtc cctgtaccag tctatgctac agcgaagact  21960
gggtgtgtat tcctcctccg gatcaaccgg gatagacacc gtagagattc gcgtgattag  22020
cccgtctacc cacacgcttg aggcgttcgt aacgtacttt gtaaagtcca cctcgcgggc  22080
atttttgtac caccgcagct tgacggagct gtgtggaaag tagcttgcga cgacgcacgt  22140
ggccctgtag ttttcccccct tcaggctcgg gtgaacggaa aggtccagca acggtgcgtt  22200
gtaggttgag acggtaacgc tggtactgtt aacgagcgtg ccatttttgg catacaagga  22260
ccacacgtaa atgccggccg tccgccaatc tacagatttg atggtcagtg gaaactttgt  22320
accaccttcc gtgtggaggg gaaggttaaa cagctggcgc tttggtagcc tgtctgggat  22380
aactcccagc tggccacccc ttcgagattt tttcctctct gccgttgaga ataacagcag  22440
```

-continued

```
agtctgatcc ttggtggcgt tatggttgat gtagttttct tcgtcgccgg ggggcgtacc  22500
cgaaaatggg gtgcgctggt tcaagtaaat ctcgaggcgg tactcgctat aatttacgcc  22560
taccgacgtt gtacagttca tatcgacaga tttgtagtag ggcacagata tgagactctt  22620
ggtgcaggtg attgtggttt catgggagtg tgtagattct gtaccgtttg cgttagttgt  22680
gttgtcagag cccgcgccgt gtgcggtagt tagattcgga gttgtgtgag ttggtgtagc  22740
gggcgtactc tggctggagc tagcactagc tccagaggca taagttaata tcgccccggc  22800
acagattaga tacgcgaccg ccacaaatct cacgagatta ggcaaccaca tctcgcgggg  22860
gccgggtgct tgctattccc cacgaaaaac gataataact ccactggtcg gagagttata  22920
aacataccat gcaccaaagg gtcagtttta aggggtttta ctttatgtga attcaccgac  22980
gttagaagca atatgctata cagtcgttgt tattactaat tggcatgttt aatgtgtgat  23040
tatagttgca taacacaaac cggcggcaac atatacacaa acaataagcc acctcgaaat  23100
gtgagttgcc gccaggcggc gcgcgcccgt tgcgcgcttg cgaaggtata gcgcccccag  23160
tatacccccg gatacagtaa atgcgagcga gaggggagcg gccacgccgt acccaaaggc  23220
ggcaagcacc atgcagacag cgtgggccgt ggagtggatg ccggaactcg cctctgccgt  23280
gtagtttact ctgatgacaa gctgctccag cagcatcgca gagacgtgtc caacagtcag  23340
acagaagaca acatacgccg gggtttgcca cacgttggaa attccgtaga ccaagcgtag  23400
gacgatccat attatggggg ttgcgtgagt tccgaccgct ggggagaaaa tcacccccgg  23460
catctccttg aaaaacttga acagcgaaac cttttcttcc gcgacttctt cgatcttggg  23520
gacggcttca acgtccgtca cccatctgta gttaataccc cggccaaggt ccgtaaaggt  23580
gcgcatgcac gcataccgtc cgattcgata gtggcatgtg tctcgaagag caagcccaaa  23640
gtcttgacag gaagctataa tagcgatagc tatccctatc cctatgggta catctttcag  23700
ctcaacgagc tttacggaaa cccctagcac acatccaccg ataatagcca ataggctcgc  23760
tctaaagtga gtccccgttc cattggctga gcatatgacg taaaataggg aaatttgagt  23820
tccggctata aacacaaaca aaatgcaaac ggtaacaact ataagtaaat gttccttttt  23880
gactgcagat cccgcgaccc agacactggc tgccactaga gtggccagcg cctgtatcga  23940
tcgacatacg gttactatag tttccatctt agatatgggt acgcggatca ggctcaacac  24000
atacatcgag atgatcatca gaatcagaca tgttgagttc cgggttagca ggtcaatgtg  24060
taagatcgat gaagtgagga cgcaagcttg tagtccgatt ccaacgaaag ctttggaggc  24120
cgcccaggta catggcatgc agcccctctg ggagccggtg cagcgttgga ccgaagatga  24180
gcttagcacc agacacgagt cttcaccggg ctctctatct ggctggtaca tcatgattga  24240
taaccttgat gtagcaagcc aacctttgga gagtttgagg tacagggacc caagaggatg  24300
gttttatgca ccaggtatta gtcataaaac aaatacttag tgggcgtgtt tctacaagtg  24360
taaatagttt taaccaaata gtgaaactaa gcaataaaca tttccgcgtc tgtcgtttac  24420
aatatgcgtt tttattttca gtatagcaag catggtatac ttatactatt acaggtcact  24480
aaaaatgcat gggctgttcc ggacagggaa ttttcgctcc ggttttgtcc attaacaaaa  24540
caaaatttga cttaaacagc ttcccgtcag gaaatagttt tttggggggc tggtcgcttt  24600
cttcctcctc cgacgcgcgt cgctttactc cagcccccat tggggtcgat gaaaaggcag  24660
caggggaaaa cccaacctgg cacggctggg tcgggtacga acacataaaa aacatcatca  24720
cgctgaacgg ctgcttggtt gagagcccga tcatgggaat agagtctgga tccaggaaaa  24780
agttaagcac cgctcccgcg ttttttagtt taagcttctg aattagctgc ttaaagttag  24840
```

```
tgtcctcatc gagtaccagc gtaaacagac ggcgaccgct gatgcccctt atgggttccg  24900
gcgccgactt tttggtcttc atcggcatct tttccaatag gctggaactc gactctacgc  24960
cgcagttgtc tgcgtgctgg tagtccaccg aaaacacgac ttgccgatct ccggatctta  25020
cctggagagt gtcgtcgaaa aggcactgaa aggtgatggg gtcgccagct tgtttacaaa  25080
cccccaaaat tttgttcagc tgagccttcg atagagacat agaaacatcc ggctgacgag  25140
tgggtaacat gagtgcatag ttgttgaact cgtgtttcac caaccgcgac gaaacggtct  25200
gagttgctcc ctctgcatca gatcccatct ccgtatcttc ttccgtttga tcgcgcgcgg  25260
agaacaccgt ctgggtgagt attctactag gagaatagtt ttctatctcg aaaactacct  25320
tactcacgtt cgtctgggtc ttcgccttga aagcgtccag taaacccctg cgcccgtcta  25380
cgttggccaa aaacacggcg gggggggcct ttttccacga gtacgactcc atgttgttag  25440
tctggatggg tatgtatacc tgctcaccgc cgacgctggt gtgaattagc aggccgtcct  25500
cgttgaagat cagaaaggcg ttcttgaggc taggggcgat gggagtgagc atctcgaaag  25560
catctctcag agattctcgc tcgaaaaccg ccatggcgcg ctgtctctcc actgggttgt  25620
cgatgaccgg aagcgtgttg aataaaaagt tgttggggtg agacccgcct ggacgcatcg  25680
cgcgaggaag agccatcgtc gatgaggaga ttataggcta ggctgctcgc gtatctcgaa  25740
gcactctata ttagagcgaa acaagcagta ctttgaccta ccccgtagcg cttcttatag  25800
agtttcgcgc tagagataaa aggattaaca tgacgtaacc aggggagtgg tttgggggaa  25860
aatggggctt ggtttaccga aaagcgaaaa aatgggggtg gtatgtaggc gtgggtgtgt  25920
acatcggtta ggccacgtca gtgggcgcag gcgcaacagg cggtgtgggt ctgctttgga  25980
aatgcctata gacgacagta tcgtgttatt gtaaaagtga aagtttaggg aggggttttg  26040
atggtgggca gagctaaact caacaccaat ggaaagcttg cctaatcgcg cacaccaatt  26100
tagattttcg actagagtag aactctgctt atattagctc gctttttggg agcaccggtc  26160
ggagttactg ctgggcaagt tttggaggtt ctacccggtg ctcatttact tccccactcc  26220
tctggtacgg gacatcgttt tggcgccagt cggccaagag aatgggactg tttggactcc  26280
taaaatacgc atactccaac cggcttgtga aacacgatgc cattacaact ccaccgggaa  26340
ttatgacacc gatcgctatc gatctttgga atgtcatgta caccctgatg gaaaagtttg  26400
accaggagcg caattttccc ctggatggcg cagcggttac cgcacggtgc ttcttttccc  26460
tactaaggct tttgttaaag aggtcctact atcccatatt cgtgtccgac agaggcatat  26520
acggcgatgg gcgcgtaaag cagggagcca aggctattgt tagtcaaaca atgagcagct  26580
acggagggtc agggcgtctg tcgagcgcat gctttacagg cgacgaacac gataccgaat  26640
tccaggaaga tcccgaagaa aacgatgtct cagttccccc gcaagacacg tgtcccccaa  26700
cagaaatatc tgccggttac gtcgaaccgg agcgcaagtg cgagcatagc tccacgcgct  26760
ggagcgcgct tgatggagcc ccgcgccttt cctaccgtct ttgtgtcaat ctgattcggc  26820
acctcggata cccatacgtc aacgcgtgta acctagaggc agatgacgtt tgcgcaaact  26880
tgtaccacac caatacggtc gcgcagatct acactaccga tacggatctg atcctcatgg  26940
gctgcgacat tattttggac atcatgccgc tgtttccgcc aaccctccgc tgctgtgacg  27000
tgttaatgga cttgggagtc acatatgacg agtttttgac cgagtttgtg cgatgccaca  27060
cggatctcca cgagccccaa accctggctt cagtgcagag cgtaattagc tcgctccact  27120
cgcccccccga cgaagatgaa ggcgccgata tgccgcagac tccctcagga cactcgtggc  27180
```

-continued

```
gctgccccaa cgagcgccga gtcatttctt ggcgcagaca ggacgaccat gactacgact  27240
cgtctacaga agatagcgac cagtcggata gcagcgaaga agaggaagaa tgtccagccg  27300
gtaaaggttt cggatacaga gaaaacccgg ccgtagaaac ttgtaaaaga cgtacgaggc  27360
ctcggcggtc tgcggaggcc tcaggtcgta ttctacacct caagtacacg tctagatatc  27420
ctccaatcat ggaatcggcc ccgcgcgctt tagtgagaat ggctcccccc aaaacccgcc  27480
acgaggttct ggagagaaag ttcgtaaagc atgtcgtttc catgctaact ccagaacgtc  27540
gaggctcgtt gtcgataatg cgacgcctac ccatcaccca ggagccgtca aacttttctc  27600
tggtccacga taccctcaaa aacctggttt cagaacacga gattgctcgg gagctagcca  27660
acatgttttg gaatcacatt cccaccccaa ctgattacaa cacggtgctg gtcaactact  27720
gggatgactg cggacaccgt agacagtggt cgtgaataaa gtttgttttg aatttcccac  27780
attacatctg tgttttttac tttccgcgcg taaagcttac acactacccg taaataagca  27840
cgctttaaat caaacaacaa caggttgtat ggctgtaaag ggtatgtttt tatttacaga  27900
tcgttaatta gagttccaga gtatgcggtg ctgcgccgct caaaaaagtt agtgtgtttc  27960
tcaactgtca tgaaggcgag aggaaagctc ggggatggtt tgggggcatt aaacaggggg  28020
gatagtccta tttcacccaa aaggcgatcc gcgctatagc gtacgtagct gatgatggcc  28080
ccgatgtcca acaggtgact atattgggga gcgtgggata gcagaaattc acactcgata  28140
ttcaccgcct cggagaacag ctcataaatc cttttgggct cgggcttctc aaatcccccc  28200
aggtagttgt tgtagatgca gcacgaggcg cgagtgtgga tcgcctcgtc gcggctgatc  28260
aaatcattgc tctggcacgt taccacaaat aggttgtggg tacggagata ggcgatagac  28320
gcaaaggacg atgcgaaaaa gagtccctcg atgaggatca tcagaatata cttctccgcc  28380
acagatccgc attcacgcac ctttgcctgt agccaggcaa ccttccgtcc gatggcagcg  28440
tctccgatga tggacgctac atacctagcg cgcgcggctg cgtcgtttcc aaacaacatg  28500
agctgtatag cgctgtatac cctggagtgt gtaacctcaa tagactcttg ctctatgtag  28560
tagtggagaa tgtccttttg agtaaacaga gctgagagat cgcccaggtt caaattcacc  28620
aagtcgtcgg cggcagataa aaaggcgaac aggaaccggt aaaactcgcg ctcggccggc  28680
gtgagcttgg ccacgtcctt gaggtcatcg gaaatgggaa ggtcggtgtc cagccagcgg  28740
tttgcaacgc tgagcgagcg caggtgctcg atatcggggc attctggagt ataaaaaaac  28800
gcacctgcta atgataattc tgcggttagg gctgcttctt tagagttttc gatagacatt  28860
cttattcacc aggtgttttg tttgaagcgg caaggcgtcc ccactacagg ctgcagctag  28920
tacagacgag gtccccgccg acaaagactc cgttgtttgt tgctttctta attttgcagt  28980
agtacatacc ggttttgagg ccgcgcttat atgcgtggac cagaaggctc ataattttgg  29040
aggcggggag ttttccgtca gcaggctcag ttataaacaa agacatggat tggctctggt  29100
ccacaaacgg agctctgtca gcacacatgt cgatcagcgt tctctgatcg tactcaaagg  29160
cagttttaaa cttgcttagg gggtggccca ccggcaaatc accaaacgcc ccgacaacag  29220
accactgcgc catctcgagg gtagacagcg cctgcaggcg cgcgcactcc cggggaaaaa  29280
tactccggat ggtgcgcatg agcaataaat tcggcctgag cacctcccca gtagccgtga  29340
ccttgctaaa taggtttgtg tagacgggcg aaaacccctc gctgctctct gtaacctgag  29400
acgatgacac ggtaggcatg tacgccacaa actgagagtt gtacagccca tgctgtttta  29460
tctcggtgcg gagtctgcgc caggcgttgc ggttggcgag ggtaaccccg gggtacgaat  29520
cgaagggtag ttccccgaga ctgtacttgc tgtcctcaaa ccccttaaag ggtttcatgc  29580
```

```
cgagtctgca tagcgtcgcg ctcgctttca tggagttcag taaaagcctc tctgctatct  29640
gcttgtttaa ttggcgagcc tccggagaag ccatgtccag gtctagcatc aggaaggcgg  29700
tatgcagccc ctggatcccc agtcccagcg acctattttc gtcgactcca cgctgagact  29760
tgactgttgg gtacgtgccg gcgcgcatca tggagttgac aaagatggtg gcagtcgccg  29820
ccgcgcgacc cagagcggca aagtcaaaat aaggcacgcc cgcggtatgc ggcgggggta  29880
tggcgaggca tttggggagg ttgatgctgg cgaggttgca caccccgttt tgggtctcgt  29940
ctgcgtgctg gataatttcc gtgcacagat tggaccccat gatagcacct tttctccgca  30000
gatcaaagtg gtagtgctta ttgcacgcgt ccttaaacat caaaaagggg cttccggtca  30060
ttacagcact cctgactatg atgaaggcca tgtcctggat gggaatggag tcgaccccaa  30120
atccacactg ctccaggcgc tcgtactcct cctcaaattc tttgccgtac atatggcata  30180
gatgtgacgc tgtgtcgtca aacagcgtcc acattacgcc gctctctccg tccaagtacc  30240
gttgatagcg gtcaaaaaac aggtctgggg tccacatgca ggcaaagatg ttgtcacacc  30300
gaacggtttc gtctctggcc agcatcccgc gcatgttcag aatcgcgcgt atgtctgcgt  30360
gccacggctc gaagtagacg cacacacctg taggccgctc gccgtcgctg ttaatggcca  30420
tggtcatgga gtctatcagc ttcagaagcg ccataacacc cctagagcac ccctctttgg  30480
ggggggtgtt aaacctctgc agagacagcc cgattccacc tctgttgcat agaatgggcc  30540
cggcctcttc cattagagcc agcatagcag agttcatgtc cgtcaccctg gggttcagca  30600
gataacagct tgccagggac ccgcagtctc tcccgccgaa caacataatg ggcgtagcgg  30660
gtatgaggac ctgtccggcc agcgccgtaa agtaggcttt gaaaatatat gtccagccta  30720
cttccccgct gaccaacacg cgcgccatag ccggttcctc catcgtatag tgcgtggctg  30780
ttgtggcaag tcttagaaaa aattgcccca tagactctat acgcccacct cgcattttgg  30840
ccaaatacat ctcctcatac tttaacgcag actgcagccc cagggcgcac agctcgcggt  30900
actccgagga ctcaaacgcg tggagggtcc gctgaataaa gtctaggtgg tcgaggatgt  30960
ctttctccac gatctcattc agagcgattt cggtagagtt tagccaatat tttaggtcct  31020
ccacgttccg cgttcgaatt cgcaggtgta ctagctcccc gcacacaacg tacagtcgct  31080
cgtctactcg acatctcggc tttagagtat ccaccaccct ggtgatgtac tccaagacct  31140
gggagcgaga cgggcgggga ggcagcgtgg ttgatagctc gttggcgtag ccataatcgc  31200
tgatagcatc cacgcgggag ataacatctt gaataattgc tagcggacag tcagattgca  31260
ggaaattcaa agccatggtc ccgtgtgatg tttgaaaaag tgcgctagaa acactaatac  31320
ccactaagcg ggagtattag gtgtgaaaac cttggggctc cgcttcgcct tatgtctggt  31380
cagatttcta cgtaacctac cacgtagact ggctttcatt ggccgctaaa atgacctccc  31440
attgtagcgc gcgtaatgta caacaaccaa caccaaagag tcaggtcgta aaatagaaca  31500
tgctttattg aaaagggttt agtaactgca ctcgacccaa tcctgtgggt cccaccgtac  31560
attttccagc caaaccacgg gcatatccac gctgccaaat ctctcgctac ggcgtgtggt  31620
tctgggggag tctgaggcta tggcccccag gcgaatatag gcggcataca tacacgaggt  31680
tctgtttggc cgaccccgca ggtctggtgc ccactggtac aacgcgttgg taaattctct  31740
gttgtttaga cgcgaaggcg ggcaccgcgg ctcacaccga ctgcttgaca gttcctggag  31800
cgggagggcg gcgtttgggt gcggctctgg cgcgtccgct ccctccgttc ctctgatggc  31860
gctctcggtg cgggctttgt gaaacagaaa gctgactgca tcctcgaagg ccacctcatc  31920
```

```
aaacttgctc accgccacgt acaccctcac tccctcccgg cgtaaccgct ggctgtacac  31980
aaatattagg taaacaaact ttgcgctcgc gtcgcccagt ttcagctcgt gatccacatc  32040
cagaaacgca cacgccggca cgtaaacgct agacctgggt accgccgagt tgttggtgcg  32100
ggcaccctct tgcacacccc cagcaacagc ggtgaggctg gcgagcttgt cctgaatcac  32160
gtgggagata aggcctccaa ataccgtcat gtgtttatga ggaaagacgt gggttcgcac  32220
catcgcctgc aaatattccc caaacctgtc taggcgctgt tccgttctac ggtcacggta  32280
gttggctagt acgtgcgccc taacggcttc cgcagcggcc ttgtcagagt actcccccga  32340
gcgggatgcc accaaaaacg tcaaagaaag caacgagggt cgcagccccg tcgtatccga  32400
gcgaccggac actgacagtt ccgacagcgc ggcccaagcc tcgtccaact cctgcggatt  32460
gcgcccgggt ggggtgcttg atggtgacga tccaatggca tcgaggtggt ggcggaggcg  32520
gattatcgga agtccgggcc gctctgctgt ggggtcgcaa aagtcggtaa gcgttacctg  32580
acgtgtaagc ttcagcgatg ggttaaagct tgaaagcatc cacgagtttt gctctgagtt  32640
gatggccgcc gttatcacac ccgcagatga aatctggatg ccgcccatgt tgctgatcgt  32700
tatactattg gggtggcct ggacaaatcc ggggagccag tccagcgtgt tggggagtcc  32760
aaacgctaca tgtccacgtc cacgtccgcg ctgttgctgg ggaaatccag ccggtgggga  32820
gatctgttcc cacctgacgg ctccatttgc gtccgtatac ataatgttgc tcatgccatt  32880
tccgatttgc acaaatctgt tgccccctag attcatcttg gtctttggcc cactcggtga  32940
gattcaagct acccttctgt gctgctatat ctcgaaggtg agtacgtaaa cagcacgtaa  33000
gaaacaggga cgtccacgga cgtgctctgc ttggggcgcg cgagagcaat tgcaacaaac  33060
gcgccccaac aggctttatc tactatccgg ctcgcgaaaa tatcatgaat tgacatttaa  33120
aaataacaca actcgggttt aagcaatcag aggcgtgtct cattttggta cgccacacgc  33180
cgtacgtctg aaagatatca agccctatta aacgagcgcg gttgctgcct gacactcaca  33240
aacccacgcg cggcggtgcg tctcgctact acgttctcgt gccgaaaaat catggcgcgt  33300
gaacatgggt ccatgcgagc cctggtcaac tctctggccg ggctgctcgg agaaaccgac  33360
actgaggtcc ccagcctcga gcctgcaatg ttgatggtcc tcaaatcctc catatcagag  33420
tttttcctgt ccaccgacac tgtgtcggtg gacgaggccg cagaactatt ccccaggcta  33480
cagtttctag cctgccgggc ctacgcagca tcgcatacac ccgatgcggc catgctagca  33540
gaaaacctgg caggcctcgt tctgtggcgc atacaccaaa actggacgga cagggaaatg  33600
gaggcggtgg accagatgtt tgtgctgctg gaaattatga acggcgaatc gggtgtgtac  33660
atgctgtcta ataacaacct gagaatatcc gccaaatacg gaccctccaa catgcacctg  33720
atcgttagca cgtggctaga tacgtttcgc aatgttatgt cggttgccgc taaatcgact  33780
ccggactcac tcttcaactc aaaacgaatg gagtctatag aagagttttc taaaccttta  33840
gtccacgcca agtttaattt gatatacgac atgccgttcg tacaagaggg cctgcgaata  33900
gtggctaaaa aaatcaactg gattctcccc ttcggcctaa tggtcaaggg ctacaaggac  33960
atgagcatgg ctcctctaac gcgggcgctg tttttgctgt ccttggtaga ctcctatttt  34020
cccaaaggaa ccgcgaccga aggtagcatg aaggcgttga cagcatactt ccgtgaactg  34080
gttagaacga tcgacaacag tgcttttgtg cctataacag aagttaacgc cacgccgcgg  34140
accgcgtacg aagttagagt ctcatcagct atagtacatc aaaacccata cgtaaccgac  34200
accaaggcgg gaatggtagc agagcgagtg cgaacggacg ctgaaatctt aacctcgggg  34260
gcgctattaa gctccggggc gctctctgcc catgcgacgg ccgtggctaa gctactctcg  34320
```

```
tccaacgaac ccgacgacgt gtcgtcccgg gccagggcgc gcgtggccga gcacgccagt  34380
aacacctggg agaccatcca ggccagcaca acacccacac aagtcgtgga agccctagtg  34440
actgcggggt ttacgtccac acactgtgga attttggagc gcgtggtggt ggactatttt  34500
acgcgcctgc gaagcaccgc caacagcggg ccggggagaa acgactccct agactacgcg  34560
caacaagtcg ttggttgcgt ggctatagta ggcggcgttg ttttcaggtt gctgttgtcc  34620
tacggctttg ggctagacta catccgggac tacacgacaa cgatatccac gctggagccc  34680
gtgtacaacg agctgctgtc tgccctgggt ctggcggaca agggagtgga acagaccctg  34740
aagcgcagca tggcaccgcg cccgtatatg aactacatct cagcggcacg cgccgcgcta  34800
gacgacgagc tgttaatagt cgaaaagcgc accactgggc ccggaaccca tagcgccgcg  34860
agggagtccc tactgacgtg gttcgacttt agggcccgag atcgatgggg tgtgcgtata  34920
ccagatagag atacgacatc gacacaggtt ttggccccaa tcacagcatc gctttattcg  34980
gacgacgacc taatagcggc ggcatctaaa ctgtcgtttg atgcactaga cgcacccccct  35040
acccaaatta tagacgaccc ctcttttgcc ccctacatgc tagccacggt ggtgctggac  35100
gcgtttaacg ccattttaac atcgcggttt tccgcagact ccgtgtctca ggcgctgcgc  35160
gtactctctt gggccaggga ctacggcgcc ggatccattg ccaacgtgga cgggtacaga  35220
actaaactaa cggcgataat agcctcggtg tccccctttt tgcaaaaaga tgcccctacc  35280
ccaaccatgg cccatgccaa caacctggag gcgcttttgg gagaactcca ctctgttgtt  35340
gtggccgcga tcgcactcat cccagaacgg gcgcgcatgc cagtgcccga acgaccctcc  35400
gttaaaacca gtacattttt ggcagggcta tttttaactg ctgtctacaa gaggctcgag  35460
acgctagttg gtcacaccgc ggagctcacc aacaacatcc taggaacggc gtcggggata  35520
gtatcatcca tagtcacgct caataggttt tttaactgtc gcatcatgcc cgttatggga  35580
cactacgccg tattgattta cccccaatcg gcccagtctg caccccttcgg taggtggcgt  35640
ctagtagacg tagtagacgc ggttggaagc atatacaacg aagtgagcga tctgcgcgcc  35700
gacctgcggg ccgacgttgt gacccttaag ggcgacataa cctcggcggc agaggcactg  35760
caagagtgcg aggccctggc tgtcaaaacg gagggtacgc gctttggtaa actattcaac  35820
tctctgctca cacgccacac gcagctggcc agggcccaga gggggttggc aataagggcc  35880
ggtaagctgc tcgggggttc tgaggctccc ggcctgaaac acgttaatac gtttctacag  35940
cgatggggag ccattagcgt catgtaccag aaagctacat cgggatctac ccccgaggta  36000
aatattacct ccctcgccaa cactttgcgt cacgtgtggg acgaggtaca acaggagcgc  36060
aaagcaactc ccccaagtcg gaaattttcc aacagagacc tcgggctcgc cgtagaacgc  36120
ctgatgggag gctatccaga agtgttagac gacgacagta atagcacagc gctgacacca  36180
aaattcaacg tcgattcatg gaatagcgta aatatggacg ctctacgcaa gcgagttacg  36240
atgcccgcta acatcgactc gattcgcggt aatgattctc tcgcgacgcg cgaatatttg  36300
aagaaagaag accttctcgc cgaaatagat gccattttta acaatacaaa gtaataaagc  36360
taattgtatg cacccagtaa tacagtgtcg cgtgtacata ttttccgcat gggggaggcg  36420
cacattcgca tgtgggtaaa aaaaggtggg cattcagggt tactaacgtt aaaagaagtt  36480
gcagagcgga gcgcggctca ctgccctgcg cgaatcacta gcgtacggtg tggattaccc  36540
caacgctctg ggatatacag actacgcttt tgcaggagct gttgccgatg gcgcaaaccc  36600
ttgttccggc gaataaggcg gggggcgctc aggccgatgt ggtagtgata ggctacagaa  36660
```

```
accaatacga ctcccaactc ggcgaggggt cccacgtatc gtgcctgaga tcttcgctgt  36720
cctttttgcg cctcattttt actcacggaa tagactttgc cctaactgcc gacagtattg  36780
atggggtgct cgtcgaaggg cgggcctgga ctgtggccgg tagcaagtcc ggggaagcac  36840
cgtgtatggt ttctatcgtg gaacttccaa acaaaattac ctacgccaac tctgcgaacg  36900
cgctatgctg cgtgttttcg agactctacg gcgacagcgg attttacatg caccctggcg  36960
atgggtttca gagcacgcaa atacccgctc gtcagttttt cgatggtgtg tggaagtcga  37020
gatctgagtc atttgctctc attacgatag gggctattgg tctggcggtg tatcgccacg  37080
gtgatgtcgc gtatgttttc gatccgcacg gccatgggag tgttaccgag gcgttcgtgg  37140
ttcgcgtact ggcccgcgat gtttatgctt atctaacggg ttacgctgcc accgatccag  37200
agtcagactg ggccggcgcg cttgtatttt ttgttacgtg cggtcccacc gagagcgagc  37260
ccggcttttt gatttctgca acgtcgctgc tatacgggat aagcgaaacc tacctatccg  37320
acgagcaata tgtggagcgg tctgtcgcga caagccaccc aggaatctct actcccccac  37380
cgctaacaga tgtggctgtg ggtgcggttt cggaggcgtg gcagtaccag gaactcgaaa  37440
atggtgcagc tacgctagat gcggacatgg agggtgtggc acccgctgcc gcacaagtca  37500
gggccagtgt catcagacag ccgacggaaa agcgagtgtc cttgcccaag cggcgtcggc  37560
ccccgtggac gcctcccacc agcagcgaaa acctaactac ctcgggcaac acgcacacgg  37620
tagcaggaag gccgagtcag aaggttagaa acgccactgc gaatgttcag aatcctacca  37680
ccggtaacgg cagtgcttgg gcggaggcct tgaacgatgg aggagtggat aacgcgagca  37740
ggcccggaca agccgtgggt gccgctggaa cactccagaa ccccgctccc ggagatgcgc  37800
ttgccatgga aaccacacag gcgtcggaag aggctcttag aactcgcaga gttttccggc  37860
tctcggggga ggatgaagcc ccgtatgacc ttggcgacgc cgtgggtgtt ctgagcgcag  37920
agataaatga actggctaca cgagccgaag agctggatgt gctaagctct acctgcgtcg  37980
actcgacggt gtgggtcacc aggccccaca acagtcccga catggacatt ctggagcagt  38040
tcatcacaat gatattcaat agacttttgt cattcctggt ggaaaatggc gcgcggaccc  38100
gcacggactc gccttcggtc attgcgggtc ttttcccagg tgtgctagcg gccattccta  38160
ctcaatccgc agtagtaaac ctgttgcagg ccaccggtat ggcgcttagt gacgtggctt  38220
cctacaagtc tatcctaaac atggtttcga acgaagactc gcccgtggga gagcttgcgg  38280
ttatcaaact agagctcgtg gcctctgagg ttatcaaatc tacgcagaag ctcgtggcca  38340
gggttgaaga attggagcgt gacgttacta gcggtagcgt caacccgttg gggttgtaca  38400
catacctgac cgaaagactg gtggccgaaa tgaccaaaca cggcggtgac ctatttgccc  38460
gagaaccgaa accgggggca gtatcactga ccgagcgcat agggtcgctc ttcaggaaag  38520
cgcgcaccag ggaggcgcgc gcgacgcgca caaacgcctc attggcacga gacctcaacg  38580
ctatagaagc tgccgttcat gcggcccacg acaagtttga cgccatagaa atcaaacccg  38640
cagaccctag cgacaccacc aacatggacg agctagcaaa gtcattggac ctatcagccg  38700
tccctacccg cgtagccaag gtgatcaaga aagtggaaag tatggtgtcc gactctattc  38760
gcgagtactt tttgaggggg gttcaataca gtgcgagggc aatagcaatg gacaaaacga  38820
gcggcgccag gtttcaagtc gcttccgctg ccgtatctaa cctagaacgc atgctagact  38880
ctttgcccaa ctttgagaag agtcttaact ccgtagtggc ctcggcgggt atccagggac  38940
ctccgccggc gcaaatatcc ggctcgcgca aggcgacgct actaggcaac ctgttgcgag  39000
ccggacagaa tctgaccacg gataatgctc tgggggcgtg ggcagcgctg ctatctgagg  39060
```

```
cgcacaccga ggggcacatc gaaaggcgtg agctcgaggc cgtcatcaaa gaaataacct  39120
ccattaacga ccatgctgcc aaaaaggcgt ccgtcgaggc cgacatggaa cgctttaggg  39180
ttttgagcgc cgcggtagac caggccacgt ccgacatgta taactctaac ccacacgcac  39240
tggacactat tatccgtggc gcggaagaaa tgattcgtca ggcaaaagtg gtcgaggcgc  39300
actttgactc gggaagaatt tctcgcgaag ccgcgtccag agttggcgtt agaaaacgcg  39360
aagtagagac gctggccaac tcggcgcgac agcgtgccgc cgaaattagc gccgcccgcg  39420
acgaaattta ctcgcgcctt cagagccttt tgcttcccct cgccgggttt gttggattgc  39480
gcgccgcacc gggggttttg gaacagctcg caaaagatgc tcagagatcg acctcagagg  39540
aattgagaaa tttaatgcac gaggcaccga agcaggtggt gtcaacagta cattctcatc  39600
tatggtccct gttcggccag tttagagaag ctctcgagca tccaaactcc accacctcat  39660
ccgccctagc gggagtgggc ccggcgtttg cgatcgtcgt cagaagtctt ctagacccaa  39720
acaaacagcg cgagagtgtg gagtttttta ttacacacgc ggacgcgcta gccgataccg  39780
tcggcgccgt cgaggcaaat ccaaactccg agctggccgt tgcgcatgcg gttaactcta  39840
tcgccgccgc aatacagaca gtcagcgtcg gtggccgcac aattacagag tttgcgtttt  39900
tggtgcctat gctggagcgt taccagtcga gactaaccat agtcagggaa acccaaagac  39960
tcgcgactgc gcagcgggca gtcgcagcgt ccgtgtctgc ggcggcagaa gtgactacaa  40020
aacttcgtgc ggtcgccgta ccgggggttc aggaggatgt gctcaaggcc gcgatagccg  40080
ccgccaaaca cgtgtcttcc gaggttactg ccgccgccac tgccgccgag cgggagctgg  40140
cgaggctgga ctctaaagca ttgagcgttg cccaggtggc ccgcgcgcat caggatctgc  40200
agaaacagac ggctgttgcc aaacagcgcg tcggcgaaat agaagaggta ttggccaacc  40260
tgaacaaaca gcagcgcgag cttcaagatc gtgctgtgca tgataggtgg aaatccgacc  40320
tactggcggc gttggacaag attgaaacaa aatcatcgtt tgacgtgtcc gaactttcta  40380
gactccggga cctcggtgct gcgcgcggct atgattctcg cgagtttgct aaacgcgcgg  40440
aacaggccct ggcggcaaac gcacgtgccg ttatcgctgt cttggataac gtgtttaaat  40500
ttaaccccta cgcgcctgtg aattcgaaaa aggaaactaa tcccaccatc tccatgctgt  40560
ataacatttc atggtgggac gactttacgc tcgcggcacc tatactcaat accctgtttg  40620
ctggtgttga cgtcgaagag ctcatgagtc tgatgcgcat ttcgactggc atgattacat  40680
ttgccagtac caacggcgga cgcccaaaat acaacgaagc cgtaaattcc ctgtctagcg  40740
acatgcttaa ggttccgcag ctagccaagt acgtagattt ctacggcaag tggtacacgg  40800
aattcaacgc cgagatggac gtgttgagca agctgcgggc agacgtgctt caagcagtgg  40860
gggttcgctc cggggaaata agcagggccc tagaagaggt cacgtacgtt cggaacgcag  40920
aagtcgctga aaaggttttg gccgacgggg taaagcttta cattccgagc gacgccctaa  40980
tagccaaagc cgtcaagtac ctggaggagt ttaatcagaa acggttcgcg ggctccgcct  41040
tcgaggaggc gatagccacg accatccggc aggacttgtc aacggcgcgc gaggctgcta  41100
ctcaagccga agccgctcgg agcgaggcca tgcacagggc tacccatatt ctgcgcgagg  41160
tggtggaagc cgcaaaggcc gcggatcgag atgccagcgc aaatcttgca aacctcaaga  41220
acctactaag actcacccca cccccacaaa gtgtggcagc cgcgctggac aaggccacct  41280
cgtcagacga cattgtgacc caagcggcgc tgttgctggg cacagtggaa tctacaccag  41340
agctggatat taaggccgtg gagtggctcc agcaggcgcg gtccattatt gattcccatc  41400
```

```
ccctaacaac taaaatagac ggcaaaggac cgatggatcc gtatgccgag cgaatagaga  41460
agctacacac actacggggg gagctagacg agctgaggcg tcagctcacg gcgacagaag  41520
ttagctggga cgaggcatgg gggaatttct cccgcgccgt tccgcgagct gatgtttcca  41580
tggatgggtt cgtggatgcc catcagaggg cacgcaccct ccaggcgtcg atgggggtca  41640
tttctgaaat gcgagcagat aacaaatatg gccgcttacc ccccaaagtt ataggagcca  41700
ttgaatcaaa gtttgcagag cgacacaaaa acttggaaac gtttaatgac acctcaaccg  41760
ttctgcagac ggccataaca cagtttgatt cgctcgtaca acagattcct ccggagatgg  41820
agtacgacgt gctacgctcc ctcttggcgt cgtttgacca attggcggct gtcctaccca  41880
agtgggttgg cgcagagtat gccgcgtaca ggagcttgct gctgatgaga ataggcctat  41940
acgacgaata ccagaaaatt gccggtatag ccgctgcggg aagccgccct cacctggaag  42000
ccgttgagta tcgcagcgcc gtggaggacg ccaatctaag acgcgccagt cgcgtgtcct  42060
ctctcatggg ggataaagat gtcatcctct cacttcgaga agcaaagtcc tctatcgaca  42120
ccgcgttccc tcaggtgttg ttggacgcca agggcgtacc cgtcgagtac agagtgtgct  42180
accgcgccgt tggggacaag cttgccgcca tgctatgtgg gaaactaggg gtcagcatgc  42240
gcccagcgat gcccagcgat cctatcgtgg agtcctcttc cgtgtctggt atcaatgtaa  42300
ctcatgacat tctccagctg cggtttgggc tggaaaaggc ctaccactcg ggattttcta  42360
cgttcgcccg atttgtgcgc cacaagaggg cagactggag ccctacagag cccgcccagg  42420
ctgcggccga gatatacgcg gcagtgctgg ctaccaccct aactcgggaa tatggcgcca  42480
cctggcaccg cataaggttc atggcgagtt cgggcctgtt tgtcgccagc ccagactcag  42540
tttgcgacac gcaaggaggc agaggaaaga aaagcaacaa catagtacac cttactttat  42600
ccgacgtggt tctgagcgcc atgttgcgga attccatgca tctagtaaac tttatgcggc  42660
tggacctgac acgccagcac gagtacatgg ccagaacaat aactccagtt ttgacaaaat  42720
cgcttctgtc tgatatttta attaacaccc tcgttcctac cgacacgtca acgcagtgga  42780
gatcgctgcc gctagctggc gacctagaag atttggctca aggcatgcta ttttccattc  42840
gcatgtccga ctggaagcaa aacagcttct ctaccaccag tctgctagat gtttggatgc  42900
gctctcccgg cgaaagcgga cgggcggcgg ccgcaaagat agcctccgcc attcccggaa  42960
accccctggc cacctttacc gtgctggcgc gtatgtgtat cccaccgaac gcattggcgt  43020
cgctgtggga agcgctgcag ccagaggcct ttagtcagca gaatctgtcc tatgatgacg  43080
tggttactag ccgcctggac atcgcctcta ccgtacagac ttccgtggcg gtggacccag  43140
aaatgaagtc tgttgacact aagtctagaa agcagctata caccactacc gggaccagca  43200
ctacgttcac gttggctggc tccgccccaa gcgccgtcaa ggaggttagc gctttggacg  43260
ttgccacgtg tgcactcatg tttggggctc ccgttgtgat tgccatggaa acgccggaaa  43320
tgttttccga agcgtctggg atgtcgttct gtctcaaaat cttcgactcc agacccgggg  43380
cgaccgacca cgaaataatt caggccgtgt cctcggacct gagctcgtgg gggacgtcgc  43440
ttttggcact agaccccaac gccatagaaa acgcctgcct gacaacgcag ctggagatac  43500
tctcaggctt ggtggcatca aagcttttag ctccagcgcc gccgtgtctt atagtgctcg  43560
accccagcat gagagtgata aaagtgttgt gggaatctga atcccccccg aatgatctag  43620
ttatcactct ggccgaagat gagattatag ctgagcttcc gtacttaaac gcggatgatg  43680
atctgctacc tccaatgaac ccggatgacc ctatctacac cagggttata agcggaacaa  43740
acattccgac ggcgaccacg gaaggcagct tatttgccga ccagcagctc gagtttttac  43800
```

```
gtccggagtc aaacccgttt ccgttcgcct cacacgacag ttcacagtct ttagatgtcc  43860
ccagttctcc gagtagcggc tccgacaaat atgaggagga cccaacgggg atagtgtatg  43920
acgcgcctgt ggacgatatg tcagacatgg caatgaacaa agcaaaggcg tggcaagagt  43980
ggttggagga tgggttcgcg gaagatgact accgagaact atccaacgcc atgccggcgc  44040
ctcccaaaac tactccggtc gttgagtcca aacagaagtc tgattctgtc gacagagcac  44100
ccacactacc gcctaaggct gctccccttc cgccatctga tgcatccgcc atcatgtccg  44160
gaaagcccgt gttcaagtat actccgggca acaagtctgc cgttccacct tccgtacctg  44220
ctcctcccac tcttccaccc gctcccctc tgccccaatc cacttcaaag gccgccagcg  44280
gccctcctcc cactcttcca cccgctcccc ctctgcccca atccacttca aaggccgcca  44340
gcggccctcc tcccactctt ccacccgctc cccctctgcc ccaatccact tcaaaggccg  44400
ccagcggccc tcctcccact cttccacccg ctcccctct gccccaatcc acttcaaagg  44460
ccgccagcgg cgccacacaa tcggacagtg gcaaaactct caccctcgat gttccaaaaa  44520
cacagtcgaa agataaggtg gtaccagttc cacccaccga taagccgtca accaccactc  44580
ccgcggcact caaacaatca gatgcaagta aacctcctac tgctgcaatt caacatcagc  44640
aaaaattagg tacacctgtc actccaaaag attctggaga taaaccaacc gataacgcaa  44700
gcgcgcctgt tggtgtatct ccagtaactc ccgatggaac acccggagcc aaaccacccc  44760
caaaagacgc accccctgtg gatgacacta aacaacctgt gaggaaatcg cttccatcac  44820
aggtgcgcgg cgggcgtccg tacatacgcc cgtctctagg accatttaag tttacgggtc  44880
cgcctggtta tacgattcca gttcatggac ttccacctag tgactcaaac gtgacccaat  44940
caaccaagga gcccccaaag cctgccgtag agacccccgc cgcggccccg gccaaatctg  45000
cggcggcccc cgccgcggcc ccggccaaat ctgcggcggc ccccgccgcg gccccggcca  45060
aatctgcggc ggcccccgcc gcggccccgg ccaaatctgc ggcggccccc gccgcggccc  45120
cggccaaatc tgcggcggcc cccgccgcgg ccccggccaa agaccaaaca aaatcagctg  45180
ctgaagtccc aaagccggcc aaggaccagg ccaaggacca ggccaaggac caggccaagg  45240
accaggccaa ggaccaggcc aaggaccagg ccaagtcaac aacaggccaa aagctggcta  45300
aggaccctaa atctgatggg ctcacagacg atgttgcttt agagattgtg cccgaaaaaa  45360
cccctctgcc ggatgactcg cccattgggg cggttcccga aaacactccc ctaccagatg  45420
actctcccat tggaagtcca gatttgtcag catctaaaaa ctcgcatacc actgacgcag  45480
tcagcagtga ccgtttttct gttgcctgca aagtaccgct cccagattcg ccggaagatg  45540
acttctactc gtatgccgtt gacgtcccat tgcccgattc tcccaccgac gacccctcaa  45600
gcggccgttc tgatgcacga gcaccaaccg tcggaggtgt tgccagcatt catcgtaaga  45660
gcgactccag aaacaaccga caatcagacg catggagacg tgcctttgct gacacgctac  45720
atgggcgtcc aagaaataga agcgctacta aaccatgtaa atcagcaccg tataaagttc  45780
ctcacgccat ttcctatacg aaaatacctt cggtacctaa cgatcaaagc ggtcttgcgg  45840
gaaaaccctg cagcgaggaa ccgaaacgtc cgactggacg agacacccct gtcggttcat  45900
ggaatgtttc gccctcgcag gcgcccgcgg acattccgac cgccattccg caaaatcaga  45960
atacttcaga gagtccacgt acgacctcgc tgaagtctcc tactcgcacg gtgcaatcta  46020
gtatgccggc agatgatatt gatgaactcg ccgagtacga tcttcagatt gcccgtgccg  46080
ttcctgttac taaacatcct cagccgccac cggcaaacca gacgccaccg cctcaagaac  46140
```

```
ccccagcacc tattgacgat agaaagaaca tacgcccacc gctaagcgag gaggagatta  46200
tagccttcct aatcaatatg gacgacgacg acgccggtaa cgcgtctggc ccggttgact  46260
tacactcggt acaagcgccc aaacttccca aacaatcaaa acctacaacc aaccagtttg  46320
taccgctgga ttggtggact gaaacggaac ccgttgtgga cgccgacagt ctggacctgt  46380
cccccaaaca gcagcgtctg ttttcctggg agtctacgcg tgacctgtta aacattaacg  46440
tgagggacag agtatacgaa gaggagtcgg acgatgagta taccgtttca tgggaccaac  46500
acttagtccc ggccgtttct cccacgtctg tatcatccta cagtagcgat accgtcactg  46560
atagctatac agacataaac gatcccagga gtgttgtgtg cccccttagac ggaaacgccc  46620
aaaacaacgt ccgcgagttt ctagacacgc atagttctag agttcgcgtg gttcctgctg  46680
acgaattgct aagtcggcgg tactttcggt ccacgagtct gagtgccatg gcgttactca  46740
ttgctgcgtg tcgcaccatc gtccgacgac ttcgggcaac tagacgagtt cttacagaca  46800
tcaaccggag cttgctctta gacttaaaac aaatacgggt cctcttgggg tagtgtatct  46860
gtttttcaat aaacaccatt ggaacatgaa ctttgtctgt aaaccgtttt tattgttggg  46920
gaattacata gccgggggtg caagggaaag gtcagtcttc cgaaatgggc tgcatgaacc  46980
gaggtgggaa ggtgcgcttg agtcctatat ttgggcgcgc ccaggtagat gcgtcgttct  47040
gcgcgaacat atcagatcgt cgaacgaggg atttcaggtg gcgttgtcgt aggctaacca  47100
tggtcctggc ggttcccata aacagctgct ttagcccttc gctaatttca tcctcagtgt  47160
atttggtgta atccagttca tcgatgttct ggtttaggat agttatcaca tcaacgggca  47220
gcatgtcttt gaagttagcc gctttgatgt taggcgggtc cgctgggttg aacgccaccg  47280
gcgcctgctg ttgctgtttg tcggcagcca tggctaaatg tttgctgcga gcgcgcaacg  47340
cacccttacg ctggccggtg tagcgacaaa tagcgcagtt tcgagtagtc gccggctttt  47400
tattagaaga ggcgcccctt tgtcgctatt gcgagtatta cagcaacaaa aacaaacgct  47460
aagatcgcgg ccgcgatcct cacagggcgg cgtttcaccc gctccgaggc gaacgcgctg  47520
gagatgctgg cgaggctggc aaaaacctct gaagcgcacc gcttgggcgt gggacgccgc  47580
ttctgccgtt ccctacactc gcgatgctcc ctgggggaga ctataccgtt actgcgatcg  47640
cacgagtcta cggtgcgctt ttggtgcaac tccatcgcac caaaactagt cgcgcgctct  47700
agcagccgct gggttctaga cgcgtcttcc ggacccatga accgaaacga cagctgcacg  47760
acgggcattc tagtgaaaca gcttatttgc atcatcgcct gcaggggcct caggtctagg  47820
cctccccctc gtttcactcg ttctatgcca gacagggcca gcccggtcgt gtgcgttgat  47880
ttgaggatca cgttgttatg ctcagacgtg attgaagcca tgggggcgtt ggggggtgcg  47940
aaaaaaaagc cctgaaatag cactgacact cccgtgtttt gaatgcgaat gtacggatcg  48000
cactgactac gagcccagtt cttcatcaac cggagcacat actctatagg aaatgttacg  48060
ctgttattat ccggcccgct aaattgaaac acgcacctgg ctggtaggtg tttgggatcg  48120
ttcagggttg catcgctctc tccgcagtgc agacttcccg agacaaccag acggatgcgc  48180
tgtaacaaac caccaccgac tgcaaaatct ctatagttgt acgagtccat ggttgtagcg  48240
aaatgtcccc aacagcggcc agtcaacccc cttaagcgac tgatgcgtgg ggcatgccgc  48300
cgctcaaact taaaccctcg ctgtatgtag ccactcccca cgacatgtct cgcactcggt  48360
gcagcagttt aggcgtcatg tagaatttgg tgtaaatcta gaaacttgtt aattattgtc  48420
gcaaatcttt ccttgcgggc gtctagggca gaggtgtgat cacaagcccc accgggcata  48480
cggttgtccg gggaatgaaa cactgaagag gccaggcgcc gcgtgaatga taaatagttt  48540
```

```
agtttggcgt ctgtcgtggg catcaacagt tccatctcag ggggcatcag gtcttcgaac  48600
cagacactaa agtcgtggtg tccgtaggca tcatctaggg cgtttaagct catcgattct  48660
acgtcgctgc tcggaatcaa gtctctgagc cttttcggag acgcctggcg cgagcgtgct  48720
tgttgcatac cgcttaaggc agcatcagag gcgttttgct ccatggcggc cagctgcaat  48780
ctagacgtca taggcgaaga cgggggatgt gcccttaccg gaggctggca gccgggtgcg  48840
ttcgagcgcc cgtacatggg atttgacgcc agacttctat caactaacag cagtctgtgc  48900
agcgagttaa tattttccgc gcacttaatg cagatttcac ctacgcccca gcctcgagag  48960
caagtcgatg tgtgcgaaga cccagacaac gatccgcccg aacctagctg cgcccagttt  49020
gtagatgcag tggccgactc cctggctctc gacaaactct gtttgatctg ccggacaatc  49080
gatttgtaca gacgccaatt tgggctttcc ccacagtgga tagcagatta tgcgatgctg  49140
tgtactaaga cgttggcggc cccgccatgt gcagtcgcca ctgtggttgc cgcattcgag  49200
ttcgtgtatc taatggataa acactacctt cggcgcggaa agactaccct agtgggcgcc  49260
ttcgcacgta gagttttaac gctcgtcgat atacagcgcc acttttttt acacgtctgc  49320
tttcgcacgg acggcggggt tccccgctgc gccgcgtccg ggacggcccc ggcggcaacg  49380
gccatggccg gcctcggtat ggcggacaaa gttcaatatt caaattactc gtttttagtg  49440
caatcgtcca cgagagccat gttactgact gtggccgacg ttccatctgg agacgacggc  49500
gcgttacagg ctgtgcccca cggcagacat ggagcgggca ggccggcgga tgggggcggt  49560
ggggtgtttg gccccaaaca acaatctacc gtggccgcgc tgatgagttg gaaggagtgt  49620
gcaaaaatga tagactgttc tgggtctgag cggagacgcc ccggcgcgac tatgacatgc  49680
tgcgagcggg ctcgggccga tgatgatgaa tacgaacgcc agctgttatc taccgagaac  49740
acatatctgg gctcggccga caatcaagca gagggggggta acgacacaca tctcaagtgg  49800
ggctacgcag acctcaccct gctgctgttg agtcagtcca gcacctggga ggccagcgaa  49860
aaaacatccc tggcgagtca gtcgcgcagg gcctgcgtgg aggagtattg ggcctcccac  49920
aggaccgtgc tggcacgaga caccgctcct aggtttgcca gattcgtgga tgcagacgcc  49980
gttccggaca cggccacggg gccggtttta gcgactaccc tcaagcacgt acgcagccgc  50040
ggaagaacct gcgccgaatg cgtgctatgt aacctgatac taacgcgcga acactggctc  50100
gcgctacgcc gctttaagcg agatgttata tcgtactcat ctaacaacgc aaacctgttt  50160
gattgtatct ccccagtact gtcggccctt tctgacgcaa atagcgagcc gctcgccggc  50220
gactgcggcg tgggtggcgg cgggacctgc ccagaagact cgggcaggtt tctagagcta  50280
atgcatgccg ccggcacaga ggccatatac aagcacctgt tttgcgaccc catgtgcgcg  50340
ttggtggagc tgcagacaaa cccgagtgtc ctttttctc ccataggccc ccctccagaa  50400
ccagacgaga tagagcttca aaaagcgcgc ctcgctagcg aaaattggtt tagtgggcgt  50460
gtatgtgctg ggttgtgggc gctggctttc acttttaaga cgtatcagat ctttacaccc  50520
aaaccgaccg cgtgcgcggc gtttattaag gacgcgggac tgctgcttag gcgccacaac  50580
ctcccgctca tatctctcga acacacgctc tgcaactatg tttgacggcc gcagcgatat  50640
ctacgactct acgagctttg ccgcagaatt agacgatcta tactcttgta ggtcaacggg  50700
ccgcgaaaat ggccgtagga gccgtgtcag cactcggggc gttcatcgcg atcgatgtgg  50760
atcggccgcc aagagacgaa gcaccaagcg acggtgcgag ttagtcgcca gggaaaggga  50820
ccgatacagc ctttacctag attacatggc cagccaccca tcggatgaaa tttcagccgt  50880
```

-continued

```
acgcgagctc gtggttcccc taattaaaac cacatcgatt acattaccgt ttgatttaaa  50940
tcaaaccgtt gctgacaact gtctctcgct atccggtatg ggctactatc ttggtatagg  51000
cggctgttgc ccaacctgca ccgtttccgg cgagcctcgc ctccatcgcg cagaccgcgc  51060
cgcgctaatt ttggcctatg tccagcagct caacaacatt tacgaatata gggggtttct  51120
ggcatccgtg ctggcggcag ccgcccaggg ggaccaggcc ggcgttgccg cctcagaggg  51180
cgttcaggcg gagcgcttgc tggaaaacgt tttggcccag ccagagctct ttttcgcgta  51240
ccacgttctc agggacgggg gcatccagaa cgtgcgagtg ctgttttacc gcgacctgag  51300
cgtatctgga tatatgatgt acgcggtatt tcctaccaaa tctgttcacc ttcactaccg  51360
tctcatcgat cgcctactgg ccgcctgccc tgggtacaaa atcatagcac acgtctggca  51420
gactgctttc gtgctggtag ttcggcgcga cgaggggcaa caaacagaca tggatatacc  51480
aacggttagt gctggagaca tttattgtaa aatgtgcgat ctcagctttg atggggagct  51540
gcttctagag tacaaaaaac tgtatgcagt attcgacgac tttcttcctc cggtgtaaag  51600
ggcgtcagct tttcaaagcc ggcgcgctca agcagtgcct gggttttcgt gggggtcttg  51660
tgggggggttt ccggaataaa ccgctttaaa agattttctg ttgttctcac atcatttccg  51720
aatagagcct taaaggtcac gcttatggta cccaacaggt gggagaaata gtagtctgtg  51780
tttagcggta cgtcattctc ggaaacatag gtcgggtctt cggcgaggtc ggaaaccagc  51840
agtttgcgtt taggttgggg gcgtgcggtc ttggttacca cggggttttg ggcggtaccg  51900
cgcattgagt ttactacacc cgcttcgcgt tccgcggcct cggtctgcgc aactatcaca  51960
tacggaattc tctcttttac gctgggcagt tcttcattcc tcatggcgag cttaaagtag  52020
acggtgaggt gcggcaggcg cttgttggta tacgattcgg gtgagcggct cagctcagca  52080
gtcataacga actcgcgcac gtccaagttg gggcagtga tacggttgta cgcctctacc  52140
agcactcgcc caaacttgtc aaagccgctc ggtagcgggc gccccaccca ttctgcggga  52200
ggcacgtctg tcacctctgc tgccgccgtg gccacatcct cgtcgtacaa caaaagatct  52260
accagatgtc gcgcgtacaa gtttatgaaa gagcagttat ttttgcggac caggtcgacc  52320
cccttcatga gcatcttccc cccgtttatg acacctatgt acttcttctt ggtgatcagc  52380
agcagtcgct gaaaggtctt ctcacactcc agtttgatgg gcgctctaaa gaggtccgct  52440
gaaatctgac gcgacatagc atcccccagc tccgataccc cctcgtacgt caggcccaca  52500
aacttgataa acacggagtc ggtgtctccg tagataaccc tgacggagta aggcttgtgg  52560
tttcggaaac ctatagcccc tggaaaattg tcctccagca gctcgcgcgt cgcccaacga  52620
gagtgaacgt aatctcgggt cttgaggagc atgtcgcgtc ctatcgtggt aacggtagcc  52680
gctatcctca gacacggcaa caggccgttt gccacccccg tgaatccgta aaccgagttg  52740
catatcacct taatcgcaga ctgctgctta tctagtaaaa ctgcctcctc gggggtgctg  52800
gtggggattc gcgccctcac cgcctttcgc atggccagcc agtcgcgcag caagatgcca  52860
agcaggcttt cgcgaatatg ggcgtggaca aaaaataact tttggtcacc cacctcgaac  52920
gtcgagtagt cgacggatgg ttgaagcccg gccagatcca cttcatcgag cgccagggtg  52980
gtgaaacaga ggttatgggc ctggataatg cttgggtata agctagcgaa gtcaaacaca  53040
accacggggt ccacatgaaa gccggatacg gggtctagaa cctttgctcc ctggtagccc  53100
acggccctcc cgacgccggg cttcccgcct ccgttttcag aagtagcgcc agatcctgcg  53160
gcgtccgggg taccgtccac accgtcgggt tcgtctgtac tgtcgaaggc gtggctttgg  53220
ctatccatag ccaactccga agtctctgac gcggcgtctg cctgactgtc aaaccggcgt  53280
```

```
ctgttgtctg gcaaaatgaa atttctctcg cgggcgagtt tcagcaagca cgtgtacacg  53340
cgaatttgct gaccgtcaaa aattacccgc gttagggtga tacgggcgag tttggccacc  53400
gccgatagtt ccagatgggg gaggtactta aaaaacagct tgcccaccag cctagagtcc  53460
tggatacaat actctcctat tacgcccctc cggtcaggcc ctcccgcgta ataggagggt  53520
atttctttat agggaaggtc tatcttatgc tcgccgagga cgtctcccac gaccgcgtcg  53580
agtttgtagc tgggtagctt tagcttttcc gtcgccacag aatacatgtc tagagatatc  53640
aggccattga ttttcacctt gctcttcttc tgaaaatggt tcgtggcgat gtcccacacc  53700
ttaaacagcc cccctttgtt gaacttgccg tacccgtcca gcttgatgtt atacaccgac  53760
gttaccttgt taactatgta cgcccagtca aaattaacga tgttgtagcc ggtggcgaac  53820
tcgggagagt actgcttgag aaaggtcagg aaggcaacca gcagctcgta ctcgctgtca  53880
aactccaaaa ccgtcggtct gggctcgccg cgctggacgc atgcaaacga gtattcctca  53940
gagatatcgc atgacccgag ggaaaacagc agggtgtgtt cgtggttctg agtagcaagc  54000
gagtacagca gacaggagat ctggatgacc aggtcctctt ggttagttgc cactgggaac  54060
gccatttcgt tacccgttcc agctttacac tctatatcaa agcacatgag cttatagtcg  54120
ggccaggcag cctcgtctgg tatcggctcc aggttatcgg gagtacagtt aatctccacg  54180
tcgcttgagg tgacgtgtcg ctcaacgggg cgaagttgaa cacgctctcc gtgggtgccg  54240
ggtcgcaggc ggtaccaccc gaaactggta aaattttcat tgtccaacaa cagccgcgtg  54300
gtcacgtcca cgctcccctc gaattttgta atctccgggt gaaagttgtc gcagatgaac  54360
cctcccaggc ggctgctgga ggcagatact ctatagtaga gagctggctt agatccaaag  54420
tagtacagcg tcgtgtggca cacggtctcc actttgaagc agtccgcaga cacgtgcttt  54480
ccgccccacc atccccgcc gctgccgccg ctctgtttgc cgccgttgcc atttcccagg  54540
gccgcgctca aagccgagct gtgcgcgcag tccaccattg cgcgcacgag ttctgcctcg  54600
gtggttattc cacaagcgct atccacctcc gcctttgcca tgtaaaaata atggcgcaca  54660
ccatagacgt gaaccgcgac tcgctttcca cactcgctca ttcccagcag tgttaccaca  54720
gacccgcttg ggcgggatag ctcagcaaac ctggatgggt catcgtgtga ggcgctctcc  54780
gaagtctcta ctatgtcgta cacgtgaaat ctctcaaatc tggggttgaa tccatcgccc  54840
cgaaaatcct ggccgttcca aacccgaatc ctgcgaggcc agcaacctcc ggaggcaaag  54900
ttcagcacgt cgtactctga gccatcgcag tacactttgg gtgggcgctc caaggtgccc  54960
acgtgtacac cgcgtcgctg gtcggcgggg gcttcttcat cgaggcatct tggagctata  55020
aacttaaagc tacccacctc tgtgcagtac gagtgttggg ggggccttgg gcgctctgtc  55080
tccgcggtct gcccgcttcc cggcctgaaa aatggcctct tgccaataaa cggattaaaa  55140
aacccgctcc tgcgaacgga gttggcctgt tcgcgcgccg ccatgtctgt gtaaatttaa  55200
agtgcgaatg gtttcctttt ttataatata tgggtcactc cacccctgg tctcgtgatg  55260
tgtggtttac tgggcgtgtt tagatttagc tttaaagtct gcccgccaac cttgcttaaa  55320
cgcttcgagt aaatctcgtt aggaagctcc tagctatctt tttaacaagg acccctacag  55380
cagcgctctc aaccatctac atctaaccat cttggtctta cctgagctcc cgggccgagt  55440
ttcgtaaaca ccatggagtc tgcgcccaag acagtgagcc taccggtgtc gcccctgggg  55500
tatgtctacg cccgccagaa agcgtctctg cagacgggca cggttagtct cacggccgcc  55560
cggagcgtcg attcggacct cgcggtactg cctgtgatcc gcggacttac cgtcgaacag  55620
```

-continued

```
accttcacaa ctaacgtcgc cgtggttgcc gggtcgaaaa ctaccggact gggtggtact  55680
gggattactc taaaactcac acccagtcac tttaacccca acgcctttgt gttttatgga  55740
ggctcggtca tcggagccag ctctaatgcc cccaacctca cccgcgcttg cgaggctgcg  55800
agacggaggt ttggcttttc tgcattctcc tcgccacccg ttgagaacgc cgtggaaacc  55860
tccggggaag aaatatgcgc ttctctcaac ctgtctccgg agaccaccgc gctgtacctg  55920
gtggtaaccg aaagtttcaa agagatggtg tacgtgtgca acaccttcct ccactacggc  55980
ggaaccagca cagttaccat cgatggacaa gatgccatga agattccaat ctatccggta  56040
cagctgtata tgccggatgt caacagactg gcgtcagagc cgtttaacgc taaacatcgg  56100
tccatcggcg acgagttcgt gtactctagg ccgtttttca actcggacct ctgtaggctg  56160
cttcatggct acgtactggg tccggcggct gtggcacttc gcgtcagaaa ccttgacggc  56220
gttgccagag gagcggccca cctggccttg gatgaaaacc acgagggctc tgtgttgcca  56280
caggatgtaa cctttacgct gtttgactcc acccagggaa acgccggcaa gggttcggga  56340
cgcgctcagc gccaagggga tggcagcgga tcgaaaaaca gcgcctctag cggtatagag  56400
cgacggctag cctcggtcat ggctgccgac acagccctct ctgttgactc cataatggga  56460
gcggggatat acgacacgga gctaccgtct gtagaagatt ggccagtgtt gtcttccgga  56520
gacgatacag agagtctcga ggccctcggc gcgtacgcgg ctagactgtc tggactggta  56580
ggagccatgg tgtttagcgc caactctgtg ttgtacatga cagaggttga cgacgggggc  56640
ccggcagacg gcaaggatgg atcaaatcct tcctaccacc gcttctacct aatagccgcc  56700
ccctacgtcg cggggaaccc acagacggac aaagatggac gcgttttacc gcacacggca  56760
gaccaacagg ctgcgcccat caatggctcc aaccaagagt ttccctgga ctatctagcc  56820
ctggcctgcg ggttttgccc ccagatactg gcgaggcttt tgttttacct ggagcgatgt  56880
gacgctggca cctttggggg tcgcaacgag acggacgcgc tgcgctacct ggctaacacg  56940
ctagaatctg atgttccttg cgggttgtgt aaccaggcca ctcggcctgc atgcgcccac  57000
accacgcttc atcgtttgcg tcagcgcctg ccacgttttg ggcaccggt tcgagctccg  57060
ataggaatat ttggtacgat gaacagcgcg tatagtgact gtgacgtgct gggtaactac  57120
gcttcctacg gagccctgaa gcggcccaat gacaacgagg caccaaagag catcatgcag  57180
gatacctatc gggccacgat ggagcgcctg gtcaacgaat tggaacaagc caaactcatt  57240
gacaaggaaa cgctcgcgca agccagcccc tgctcagccc ccaccagcgt agtgcatgat  57300
caagctagct tcataggact cctgtcaaac atcaaagaca ccatcgaggg tgcagcagaa  57360
cagtttatgc gcactctggt tgaggcgcgt gatttcaaaa tccgcgaggg cctggccgac  57420
gcgaaccaca ccatgtctat ctccctggac ccgtactcta gcagcttttg tccggtcaca  57480
tcatttcttg cccgccgcac agtttttgct gtcttacagg acctcgtgtt gagccagtgc  57540
cactgtctgt tctacggcca atctgtggag gggcgcaact ttcgcaacca gtttcagcca  57600
gtgctcagac gcagattttt ggatatgctc aacgggggct ttatcacagc caagaccgtc  57660
accgtgacgg tttctgactc tggagttttg gcaccagacc tcacacgtcc cgcctctgag  57720
ccgcccacca aggactacga cggggacatg gccagagtca gcatggaggt gctgcgagac  57780
cttcgagtta aaaacagggt gctgttttct aacggagggg ccaacatgtc tgaagcggcc  57840
agagccaggg tggccggcat ggccagcgcc tatcgcaggc cagataaggg ttctaacatc  57900
ttgaatggcg ccgtcgggtt tctcgtcaag cagtatcacg gagtcctctt tccccgggga  57960
caccccccg gcatcgacac tccaaacccc cagtggttct ggaccctgct ccagcgcaac  58020
```

```
cagatgccgg cgcgtctgtt gagcaaggag gacatagaaa cgatcactgc catcaagcgg  58080
ttttctgacg agtattccgc cataaacttt attaacctga caccaaacaa catcggggag  58140
ctggcccagt tctactttgc caacctggtg ctcaaatact gcgaccattc ccagtacttt  58200
atcaacggcc tcacggccat agtcgttggc tctagacggc ctcgcgaccc tgctgcggtg  58260
ctggcctgga tcgaccgtac aatcaacggc gcggcagatg tagagccggc tgcccaggag  58320
gtgctgcagc ggctcgggtc taacccggcc gcgtggacgg gcacgtttac gtccaccaac  58380
atggtccgct atgtcatgga ccagcgcccc atggtcgtta ttgggttgag catcagtaag  58440
tataacggga gcgcaggaaa caatcgcgtg tttcaggcag gcaactggaa cggtctcaac  58500
ggtggcaaaa acgtctgccc gcttatggcg tttgacagaa cccgccgttt tgtgttggcg  58560
tgcccgaggg tagggtttac ctgcgaggcc gggggatttg gcacgggggt tagagagaac  58620
acgctaagcg agcaggtcag aggaatagtc tccgaaggag gaccgatggt tcagaccgcg  58680
gtgtttgcgg cagtcctgca cgctttggga gcccgcacgc agcacctggc cgtagatgat  58740
tggatcggtc tggtagacga cgagtttttg gcggcgagtc tggatgccct gaatgccacc  58800
gtcgttgatc aatttggaga gtggagcgtg gaggctgccc aggagctggt gaaaaacatg  58860
gaggcgcaaa caaccgccgg agcggtagct gccggcgagg gagcgtttga cttcggggca  58920
tgcgtgggtg atactccaca acaatccact tcagcattta acggtggcct ggccatggca  58980
gctgcccctg ctggacaaaa acggtcccta ccggatgata tcctgtttga catgggtgcc  59040
cccccggaga aaaagtcggg gctcaccttt gacatgctct aaggctacag atgattacta  59100
ctacccccct cccccgttgt gtttgtatct taactcatct ctattggtcc aatttggagt  59160
tcaataaacg ttttacattt tatattcggt tgactcgtgt tatatttcac tatttctgac  59220
acccaccacg cctctatcag ctatggagca agacgatgca cccgctgcca tgggtagcgc  59280
acaggcccgt cagcgtttac tcgcaatctt tggtcaggtg caggcctaca tatttcaggt  59340
ggaaatgtta aagcgatgcg acccatcggc gctgctacct ctggtagggt cgctaaaact  59400
aaacgcctta acgatacgca tgcttagacg caagctgggg ggagctctca tcgaacaggc  59460
gcagcatcag caaacaccac tcgcatgcgc cctgaccatg gccctagaat acgccgaggt  59520
tgaaggcgaa cgtgttctgc gtgcggtgga tgacgtgaat ctggctgggc cagaggggtt  59580
tttcagagcc acgatgcggc tagacgaacc gtgcgaatac cacgtgcggg tgcacctgga  59640
tacctacgga ggccccatag acgcggaagt tcagttttta cacgacgcgg aaaacttcct  59700
aaagcagtta aactattgcc acctgatcac ggggttcgag gccggcctcg atgcattgga  59760
aagcgtggct cgctttctta cccgcactgt gggcagcggc atagtggtac ccccggagct  59820
gtgtgacccc acccatccct gctccgtctg ttttgaggag ctttgcgtaa ccgctaacca  59880
gggggaagca gttcatcgca gactgctcga gtgtacgtgc gatcacatca ctcggcaaat  59940
ggctgtcagg gtcgcaaata ttgacattgc gcggcaccta ccgcacgcgc tcagtgtagc  60000
ctccgagcgg cgcgcggcgg cggaagcggc tctcagggcc ctcgaggcca ggcgcgtgca  60060
aggacacaac ggcaagagcg ccggcacgga ggacccgacg caacaagttg cgtcgcggct  60120
gctggagtcc caccacgtct tcaagcctgc ctcgcggtgc ctgtacgccg tgagcgagtt  60180
aaagttttgg ctcgcgtcta ccaaacacgg tgatatggga cagccaaggg ctatagacac  60240
gtttacagaa aacctggaga ctctggacaa gcaggaaaag ttttttcacc tgcaagccgc  60300
aaccgttgaa ttggcactat tcggacgcac cctagaccac tttgacagac tgtttgcaga  60360
```

```
ccagctgctc ggtctggacg tgatcgatgg aatgttggtg gggagctgtg cggtgtcacc  60420
ggacgatcac atagaagccc tgataaaagc gtgttatact catcacatgt ctgcgccgct  60480
cctgcagagg ctcacggacc cagacaccag caacagagag gccctcaagc agctgctggg  60540
tcgcataggg gtggataccg acgacggggc cggcgagttg ggggacgcct tagacgtgga  60600
tttggataat ctaggtgggg cccctcctgt caacagcacc ccctgtggtg aggacgccct  60660
ctgtcgaacc gtttccgagg aacgcccgtg ggacaaactt ttagagcggg cgactgcgga  60720
tgcttcgcag cgcaggcgca tgtacgcgga gcgtctgtca aagcgttcca tcgccagttt  60780
ggggcgctgc gtgcgcgaac agcgaagaga actagaaaaa accctgagag ttaacgtgta  60840
tggcgaagtg ctgctacata cgtacgtatc gtcctacaac gggttttgcg ccaggcgcgg  60900
gttttgcgcg gcggtgagtc gagcgggtac catcatagat aaccgctcta gcacgtccgc  60960
gttcgactcg catcagttca tgaaggcggc gctgcttcgc caccccattg accagtcgct  61020
catgccgtcc ataacacaca agtttttcga gctgatcaac gggcccgtgt ttgacaacgc  61080
tggccacaac tttgcgcagc cgccaaacac ggcattatat tacagcgttg aaaacgttgg  61140
gttgttaccg catctcaagg aggaactagc tcggtttatg attactgcgg ctaaaggtga  61200
ttggtcaatt agcgagtttc aaaggtttta ttgctttgag ggagtgacag gtgtgacggc  61260
cacgcagcgg ctggcgtgga aatatatcgg ggagctcatc ctagccgccg cagtattctc  61320
ctcggttttc cactgtggag aggtgcgcct cctgcgcgca gatcgtacct acccggactc  61380
cagcggcgca cagcgctgcg tgagcggcat ttacataacc tacgaggcgt catgtcctct  61440
ggttgccgtt ctgtcggcgg ctccacatgg ggcaattggc gcggagacgg tggtgattta  61500
cgacagcgac gtgttctctc tcctgtatgc agtgctccag cagctggctc ctggatcggg  61560
agccaactag gcaatgttgg aaacttactc gccacccccc acccgctggg aaagccggca  61620
tcatcgaggg tgggcacaat agttctagcc tgtttgttgc tttttggaag ctgtgttgtt  61680
agagccgtac ccaccacgcc aagcccccca actagtactc ccacttccat gtcaacgcac  61740
tcccatggga cagtagaccc tacgctgctc cccacagaaa cgcccgaccc actcagactg  61800
gctgtgcgcg agtccggtat actcgctgag gatggagact tttacacctg cccaccgcct  61860
accggatcca ccgtcgtacg catcgaacca cctagaactt gccccaagtt tgaccttggg  61920
agaaacttca cggaggggat tgctgttatt tttaaggaaa acatcgctcc ctacaaattc  61980
agggcaaacg tatactacaa ggacatcgtt gtaacacgtg tgtggaaagg atacagccat  62040
acgtccctgt ccgacagata caatgacagg gttccggttt cggtggagga gatcttcggt  62100
ctcatcgaca gtaagggaaa atgttcgtca aaggccgagt acctcagaga taacatcatg  62160
caccacgcgt accacgacga cgaggacgag gtggagcttg atttggtgcc gtccaagttt  62220
gcaactccgg gggccagagc ctggcagacc accaacgata ctacgtctta cgtggggtgg  62280
atgccatgga ggcactacac gtcaacgtct gtcaactgca tcgtcgagga ggtggaggcg  62340
cggtccgtct accccctacga ctccttcgcc ctgtccaccg gtgatattgt gtacgcgtct  62400
ccgttttacg gcctgagggc tgccgctcgc atagagcaca atagctacgc gcaggagcgt  62460
ttcaggcaag ttgaagggta caggccccgc gacttagaca gtaaactaca agccgaagag  62520
ccggttacca aaaattttat cactaccccg catgtcaccg tcagctggaa ctggaccgag  62580
aagaaagtcg aggcgtgtac gctgaccaaa tggaaagagg tcgacgaact cgtcagggac  62640
gagttccgcg ggtcctacag atttactatt cgatccatct cgtctacgtt tatcagtaac  62700
actactcaat ttaagttgga aagtgccccc cttactgaat gtgtatccaa agaagcaaag  62760
```

```
gaagccatag actcgatata caaaaagcag tacgagtcta cgcacgtctt tagcggtgat  62820
gtggaatatt acctggcacg cggggggttc ttaattgcat tcagacctat gctctccaac  62880
gaactcgcca ggctgtacct gaacgagctt gtgagatcta accgcaccta cgacctaaaa  62940
aatctattga accccaatgc aaacaataac aataacacca cgcgaagacg caggtctctc  63000
ctgtcagtac cagaacctca gccaacccaa gatggtgtgc atagagaaca aattctacat  63060
cgcttgcaca aacgagcagt ggaggcaacg gcaggtaccg attcttccaa cgtcaccgcc  63120
aaacagctgg agctcatcaa aaccacgtcg tctatcgagt ttgccatgct acagtttgca  63180
tacgatcaca tccaatccca cgtcaatgaa atgctaagta gaatagcaac tgcgtggtgt  63240
accctccaaa acaaagagcg gaccctatgg aacgaaatgg tgaagattaa cccgagcgcc  63300
atagtctccg caaccccttga cgagcgagtt gcagcgaggg tcctggggga cgtgatagct  63360
ataacgcact gcgccaaaat agagggcaac gtgtacttgc aaaactccat gcgctcgatg  63420
gacagtaaca cgtgctactc ccgccccccc gtaacattta caattactaa gaatgcaaac  63480
aacagagggt cgatagaagg ccagctggga gaggagaacg agattttcac ggagcgcaag  63540
ctgatcgagc cgtgcgccct caatcagaag cgctacttta agtttggcaa agagtacgtt  63600
tactacgaga actacacgtt cgtccgcaaa gtgccccccca cggaaatcga ggttatcagc  63660
acgtacgttg aactaaactt gacccttttg gaagaccgcg agtttctgcc cctggaggtg  63720
tacacgcggg ctgagctgga ggacaccggc ctgctagact acagcgaaat acagcgccgc  63780
aaccagctcc acgctctcag gttttacgac atcgacagcg tggtcaacgt ggacaatacc  63840
gcagtgatta tgcaggggat cgccagcttt ttcaagggcc tgggtaaagt gggggaggcc  63900
gtgggaacgc tcgttctcgg cgccgccggc gctgttgttt caaccgtatc tggaatagct  63960
tcgtttttaa acaacccatt tgggggcta gccatcggcc tgctggtaat cgccggcctg  64020
gtagctgcgt tttttgctta cagatatgta atgcagatcc gcagtaaccc catgaaagct  64080
ctatacccca taacaacaaa ggccttgaaa aacaaagcca aaacttccta cggccagaac  64140
gaggaggacg atgggagcga ctttgatgag gccaagcttg aagaggctcg cgaaatgatc  64200
aaatacatgt ctatggtttc ggccctggaa aagcaggaaa agaaagctat aaagaaaaac  64260
agtggggttg gcctgatcgc cagtaacgtc tcaaagctgg ccctgcgaag gcgcggtccc  64320
aaatataccc gactccaaca gaacgatacc atggaaaatg aaaaaatggt ttaaacatgt  64380
ttaataaata ttatgacacg tactcaaagt gtgacctcat atttgcataa ccactttcta  64440
gttccggccc caaggatatt taagcctagt atctccgccg aggtttcatc ctcattcacc  64500
aactcacact tagagttgac gcttcctctt gcgcctttgc tctcgccgct cctgtgttag  64560
cgtatactgc ccaagaaatg gattctccac gcggtatctc cacagctacc ggtgatgccc  64620
acgccgaggc cgcggtttcc ccagccgcgg aaatccagat aaaaacggaa gcccccgatg  64680
tagacggacc agaagccact actgagtgtt tagaccacac ctacacccaa cagacaagcg  64740
ggggtgatgg cctagatgct atcgatacgg acgatctgct ggagatggtg ctgacttccg  64800
aaaacacaga gagcgaaccc ggtattccgt ttgccctgcg gggaaacttc atctgctgtc  64860
gagacgacaa ctgtcgcgcc tgccgggagc tgccattccg tccatctgtg atcgggtttt  64920
cgagggaccc ccacgtttct atggcgcttg acatgaccag cggcaactgg gcttacgtcc  64980
cacgtgtttt tcccgacacg cccaccgccc cgtggatggc caactactgc atccctgacc  65040
tcgacgaaca cgcggattga taaaaaagca aaaaataaac aatttttagt ttatatacgt  65100
```

-continued

```
gtatgtattt attgttagtt tacaaagtag ggggaggggg cctttatcca gtttaccgag  65160
cgctcatcat ctgagacacg aatatgtccg cgtcatcgcg cccaaactcc aggccggtgg  65220
acgcactggc gtcgaccgtc tgactgctag cctggggttg agtgacgggc aggaccgccg  65280
ctgacgtaac cgcctcaaac tgctggggtg cagctctagc ctgctcggcc tgctgcgggg  65340
cggtagaagc ggctacgacc ttggcactgc ccggggcttc cccggctggc acctgtggcg  65400
ccaacactgc ttgggttggc tgagagggga ttcccggtag ctgcggagcg acgatggcgg  65460
aaaccgcgtg ctgcggttgg atatactgat attggctgta ttgaggagga acggctggta  65520
tgggtttgta tagccccgcc ggtgcggctt ggggctgcgc ggtcacggtt tgtatagctc  65580
tgagctgcga cacctcttgc tgcagagagg aaaccgcccc cattagatcc gcgatggtgg  65640
tggacgggcg cccggctctg cgctcgcctg ggcgcggtga gcgctctccg ggtaataga  65700
taccctctag gtcatcgcgt gtggttgcgt cccagtcatg gcggcgcttg cgtgcatatc  65760
gccgctcttg ctgcggagac agaggcggtg agcactgtga gccttgaata acatgggggt  65820
cgctaccctt ggtagctttt cggtccgcgg ccagggctcc gactagcgct gtgatctgcg  65880
cctctaggtt agcactgtgt ggcacgctcc agtatggagg tgcctggtac atcgatggtg  65940
gcatcaggga attgtaagcc ggcggtatat actgagaagg caccgcgtga gtgacgggag  66000
ccgggccagc gtttattgga ggatgagaag tgtgttggcc aacaacgagc tggttatact  66060
gcgccgcggg gactaaaatg tagtcccctg aaaccagagg ggcgccagcc gccgacagtg  66120
tctgggggtt tgacgaggcc atcgcactta tatgtttttg tgtgcgttcg cctatcccac  66180
ccttgtcgtt gtctgatgag ggtaacgcgt tggggcttga ggaagtgaaa gcctttgcgc  66240
cgagcgttac gcgtgaataa ggtgcgccgt gaaccttttc tccgctttta taaccgcatg  66300
tgtctaccag ctccgccccg caaaagtcgg ctttgttgca gccgttggtg atcccgaagc  66360
tcgcgctggc ctgcaggtac gtgtgcccct ctatgccagc ctctctccgt cgtcgcgcca  66420
ccaggttcca gcggtttcgt aggagcatgt tgttaacggc ggttgacagt aagacccggg  66480
tcagggtgtc ctctgatagg tgccacgtgg ccgcgtcccc caagcgcgat tgtgcctcgc  66540
gtgccgttat taacaattcc tcgcgtgagg acggcgacag cctcttgaat ggcgccaccg  66600
cattttccgg ggtggcgtcg taagtgacga ttgttcccac tctacggccg attacgcaca  66660
gggagacgtg cgcaaatagg gtttcgtcag gctcctcgtc cggcccaagg cgccgggaag  66720
acagcgacgc tgacggcaaa tagttgctca cgaggtacag cagccgctcc tgctcagaca  66780
gcccttcgga tagctccccg aaaaagtcgg ggcccgcagc cgtggctaaa accgcaccca  66840
gctgggggca gttaataatt cccagaaaaa acgggcctcg tgcgtcatcc actatggata  66900
acacctcccc aaccacacac ccgttgcggt ggtcgatgtt aatgggtaat ctagatgccg  66960
ggggaagcgc tgccgcgacg gtttccctgg taagcgttag ctccccccca tcacccatat  67020
catagagagc tatataccca gccacgtaga taggaaggct tactgcgtta ccgtccacgg  67080
tgtacgcgtc catagtaaga tatgcgtggg tttattccga gtaaaacaca ccagttcccc  67140
gcgcgcgcgg ctaataaaca atcttgttca cagtctaaga ctttattgta gtgactatgg  67200
gtaaggcgtt attacattgc ggatgtcaac gaaggaatgt atccaagaca aacaaagtat  67260
aacaggtcat aatcgctggc cacgttaaac tgacccaggc gtctggtctc ctcgagcgag  67320
gccctcaatc tgggcttttg catcagcagc cccaggccgc gctcgtactg gagggctacg  67380
gcgtcgtgcg cggcaagcac ctcgtttatt gggaccgggg ctgtccggcg tctattctcc  67440
agctctatgc ctattaacct ggtcaagttg gtctgattgc gcccggtaga cacgttaaca  67500
```

gcgcggtgct gcggctgatc gcgagctacc gtctgagcgt ctaagcatag ggctgccagg 67560
ccgggaaata gctgggtcaa ttccacctcc ctgttggcta tgtatatggg ggagacgtaa 67620
cgctcgcata aaaaggtgaa gttgttgtta ccgctacgac taaccatagc ggcagcatct 67680
cccccgctcg ccccccctggc gtcacgctgc gatactgcga ggttgggtac gattgccccg 67740
agctgaaaat tattgcgtaa tctgtccgta tagacgttgc cgttccacag cagacgacgc 67800
agcagcagca gcgcggtgat ggtgttgatc gtcgagcgta gtagggtttg gtcttccgtg 67860
agaaacaggt tttgggcgcg caccaaaaag gccgcagcgg ctttgtttac gtcgtctatg 67920
tacgcagtct ggtccgcgtc gagttcgggt ccgacggcgg tgctcgtggt tcccagacta 67980
cccggaatgg cgggcaaaac ctttaggcgt atcagcgtct ctagaacgcc atggccgttt 68040
agcgcgcccc gttcgtatct tccccctcct ccgggaacgt gaaactggtt ctttgggaga 68100
cgcgcgccgt tgaactcgta cccgaccttt ccgagcgttc cgtctccgag tgccgtggag 68160
aaagcctcga tgtacacggg cagctgttcg attagcccag aaaagctagt gggatacgtg 68220
tagttgctgt ttacggcgcg atgggctaaa tggaggcata gcacggctgc ctcgaatgcg 68280
gaatagggtc tgtttcctat gtaaagccta ccgcatgact gcagagatac gacagccgtt 68340
gtcataaacg ttttagacat gcgaccgtct ctatagtcga tgctgcgcgt ggccaccggc 68400
cgctccgtga ctagacggtc ctgaagcgct ctgtaccagg tgccgaatac caccccgttt 68460
gagccgcccg cggcgcggct cacaaacacc gtggctaata agtctacggc caggttcgtg 68520
tcgaactcca tgggaacgtc gttcttagcg atttgaattt cactgagcga ttgtccgatg 68580
ttgtcggggc gctgatccgc ttcactcgcg tttacctggg gcgtggcggc gtcggcgctc 68640
tccgctgcac gcgcggcatc ttcgagggcc gccagggcat cagctacttt ggcaacctgt 68700
cgctctaggg gtctaatcaa cgcatctacg tttgcaactc cgtactgact ctgcgcctcc 68760
aacgtgtcta tggccgctgc ggcggctcta tggcgggccg caaccagctt caggggatcc 68820
gccctggtgt tggagctgac ggtgaatgta ggtccgctcc aaaagttaag cggaaatggc 68880
ggggctataa agtttcgcac gtctgtcggt atagtggacg tggccgtatc gcttacgtaa 68940
agcgatccta acacataatt cacatactcc gccatctcca ccgcgactat aaggtcttta 69000
gcttcgatct tagtgtttat acttgcgtgt aggcgcgccg acaaaaaaag gggcactcgt 69060
ctttaattgc accggctttt attttgggga aaaaagggac gccgcccagg cgagggggtt 69120
tacgtgcgat acagccaccg gctgatggac cgcggctgcg ttagtggtgt ttgccgggac 69180
cgcagctgga aataaactca cgacggcggc tgccgctgac ggctgggctg gcgttataga 69240
tggcactggc tccgctgccg cctttgtact aaaggctttg gccttggttc ctttggcgac 69300
gcaccgcctc cttgtcgatt tagctgaaac tggtggagcg tattccgcca aacgtgatat 69360
ggtgcaggat agcacggcag cgttgctata tacaacctgt ggcgataaac gcgttacccg 69420
caacacccgc attcctcgtt gagctacaaa cactagtacc ggagctagta cgatctcacc 69480
gcttcccggg ggtagcgttc tcgccagcaa cctgcacgag tcatgtagct gtcgcatgcc 69540
ccccttccgc tgtagatttt tactcgcggt gttcatattt ttggaaaagc gacacgtttt 69600
tagctctatt aggatgcaca ctcccttggc gtcagaaccc tttccaaatt gcacggtaca 69660
gacacaatcc gggcgccgct gtccgaggtt aacctcaaag gccagagaca cgcccagtgc 69720
cgttttaaga gtttccgctg gcaccagttc actaaaaagg ggagcaagcc tctctccgta 69780
cacgccgttt cgcttggcgc ttgccaggtc ttgaaccatc gcgttataga agcggttgtg 69840

```
gcaccgtata ccagctctga gtctgcttct agctgtcaga cgctgtctac gtttcatttt  69900
cagaaatcaa tggcggctcg cgtaccttcc ggggaagctc gacggagcgc cagcggggcg  69960
ccggtcaggc ggcaagtaac aatagttaga atttacctcg atggggtcta cggcatcggc  70020
aagagcacga ctggacgagt tatggcatcg gctgcgagtg gaggaagtcc aactctatac  70080
tttcctgagc ctatggcgta ctggcggact ctctttgaag cggacgtaat tagtggtatt  70140
tacgacaccc agaaccggaa acagcaggga gatttggcgg ctgatgacgc ggcgtcaata  70200
acggcgcact accagagccg ctttaccacg ccctacctta tcctacacga tcacacattt  70260
gggttgtttg ggggcgacag cctacagcgt gggacaagac cagacctaac cgtcgttttt  70320
gaccgccacc cagtcgcctc tgccgtgtgc tttcccgccg ctcgctacct catcggagac  70380
atgtccatgt gcgcgctgat tgccatggtt gccaccctac ccagggaacc gcaaggcgga  70440
aacatcgtgg ttaccaccct caatgtggac gagcacgtgc gaagactgcg cacccgcgcc  70500
agaatcgggg aacagattga catgaagcta atcgccacac tgcgaaacgt gtactctatg  70560
ctcgctaata ctagcaactt tttgcgctcc gggagagtat ggcgcgacgg ctggggggag  70620
ttgccccttt cgtgcgagac ctataaacat cgcgcaacgc agatggacgc cttccaggag  70680
cgcgaatctc ctgagctgag cgacacgttg tttgccatgt ttaagactcc cgagctgcta  70740
gacgatcgtg gagtgatatt ggaagttcac gcctgggcgc ttgacgcgct gatgctaaag  70800
ctgcgcaacc tgagtgtttt ttgcgctgat ctgagcggga ctccgcgcca gtgtgctgca  70860
accgtggagt ctctaatacc cctcatgagc agcaccctct ccgattcgga gtcggcctcc  70920
tccctggagc gggccgcgcg caccttcaac gccgagatgg gcgtctgaaa ctatatgtaa  70980
tgtttgttgt gccagtgtaa taattatgaa ataaagattc ctttgcctat atccctcata  71040
ccgcctcgtg tgtccagtgt gtaaacttcc aggttctagt tttggggata tataagtggc  71100
tgtgacctgg attcatttag tacagtgcgg ccgagccact caagatatac cgtggctgta  71160
cattaacttg ggaatcatta cttccgcgat catgttacaa ccgtatcgaa aaatgctgat  71220
ctttgcagtt gttactgttg cctttgcgat ggctgtctgg tcaacgcccg tcccagccac  71280
tccgtctggc gtgggtaacg ctacttgggc aaacaatagc ttcaacataa ccaggtatga  71340
caagataacc atgggacagg tttatagtaa cacttcaaac tctcccatct tcttcgttgt  71400
tatatcggag cggaattttc gcatcgttaa cactccgctg ggcgcgtcgg tattttggat  71460
accaaagggc gctatgaatc ctccgcaaca ccaaccctgt gtcgccaacg ggccggaacc  71520
tggggaccca cgcgggccgt gtgtcaactc gaccgtcagt ttattgttta atgaaaacgt  71580
ggagccgttc ttaatgtcaa aaaatctttt agagtttgaa gtgttgcccg acacctacat  71640
aaccggttgg acgtttgagc ggtctaaaac agcgaccaca aaaagcaacc cggttggtgt  71700
ggttttatcg ccacccaggg gcagtccgtc agctaacaca acaatcaggg acgatggcgg  71760
acccaaaaag cccctgagca ttatagacga atacaccacg ctcgtggcgg acttgcaaaa  71820
tttcactatg acattgactt acataagccc ctttgccgcg gtgtggccta ttgaagcctt  71880
tcaaacgggc atcacggtca tggggtgcga cactacacag gttgttgcgt atctcggcca  71940
tgggtttatg ggcctgcaga taagctcggt taacaacccc ccgctggaaa tgatcgtcgt  72000
acccaatgac gtcagtgctc gtatacttaa ccgacgcccc tccagacttc gattggagcc  72060
cccgggacct cacgcgggac ctatctacaa ggtttacgta ctcagcgatg gaaattttta  72120
cctgggccac ggaatgagca ggatctccag ggaggtggcc gcctacccgg aagagagttt  72180
agactaccgc taccacctat ctctagccaa cctcgacact ctggcgatgt tggccgaact  72240
```

```
ctcctctggt aagagcacgg atgtaagcta ttacatgtac cgcattgttg cgcgtctggc  72300
cgtagccacg ttctctctgg ctgaagttat acgcctaagt gactatatgc tcctgcaaga  72360
agccattgat gtggatatga acctccgcct cattgtcccc ctcgtgatga agtacgccgc  72420
aggaggggcc gcggatagct cgtacacatc ttctgacgtg gccatggacc agtttgacgt  72480
tgcacaatcc cagattgaga aaatagtgtc agatatcaac gtggaggccg aattgcgcaa  72540
accgatgtac gagcaccgct cactgttgag aagcgtttac gcttattcca gaaagccgct  72600
gccaaacgcg gtggccttag cggaccggct aatattggct atgtataaag aagccattaa  72660
ggacagaatc acgtggaact ccacaatgcg cgaggtgcta ttttttgctg ttggcgcggc  72720
cgccggttcg catgttatcc tcactgacga acccgagcca ggcgcgcccg cccacaaaga  72780
cgcctcgcta tttctatccc tcaaccgcaa catcctcttg ctgtgcacgg ctatgtgcac  72840
ggcatcgcac gccgtatctg caggtctgaa actagaggaa gtcatggccg gcctcgttgc  72900
cggcggggtg caatttagcc tcctggaagt attcagcccg tgtatggcgt ctacccggtt  72960
tgacctggcg gaagaggagc acgtgttgga tttactttcc gtgatcccac cccgtctgta  73020
caccgacttg aacaccggct tcgaggacga cggaactacc atccattctt acgggcgatc  73080
tgctaacggg attctaaact ctcgcatcgc gtacaacttc gatgctgtta gcgtgtttac  73140
cccagagttg gcctcgtgta gcactaaact gcccaaggta ctggtggtgt tgcccatatt  73200
taccaacaga agctacgtca tcactcgtac cgcccccaagc atcggcctga cctactcact  73260
cgatggggtg aatatagcaa agcctatcgt tatcagttat atcacgtatg gaaactgtga  73320
agtctccaga gctaccatca agtctggtta tttggataac cctggccaca cgcagacgtg  73380
cgtatactgc gggagcgtgt ttatgcggta catggtgtct ggagcaatca tggatttaat  73440
atacatagac gacaaagaag tggagctgca gctcgttgct ggagaaaact caactatccc  73500
cgcctttaat cccaaactgt atacgcctag catgaacgct cttttaatgt ttcccaacgg  73560
aacggtgacg ctaatgtccg ccttcgcgtc ctattcgtcc ttcaaagttc caagcactta  73620
tctctgggct tctatcggtg gtctgctgct cgctatttta attttatata taatcatcaa  73680
aatgttatgc ggtggtgtaa ccaacgatgg ttataaattg ttattgagtt atgagtaaac  73740
aaatatcccg tgtgttgtta ccccccatgt tagacaatat ttgtgcgact gtggtatgta  73800
tgtgctaaac cagaaataaa cactattaaa atattacgcg taaaattgtt gaatttattt  73860
tcgctatatg cgggagcgag ggctgctgcg gcggcggcgc ggcgggagcg agggctgctg  73920
cggcggcggc gcggcgggag cgagggctgc tgcggcggcg gcgcggcggg agcgagggct  73980
gctgcggcgg cggcgcggcg ggagcgaggg ctgctgcggc ggcggcgcgg cgggagcgag  74040
ggctgctgcg gcggcggcgc ggcgggagcg agggctgctg cggcggcggc gcggcgggag  74100
cgagggctgc tgcggcggcg gcgcggcggg agcgagggct gctgcggcgg cggcgcggcg  74160
ggagcgaggg ctgctgcttg aatgaaaacg gctctggagc tcccagtgct taaataggaa  74220
attggggcgg cccaccggct agatgtgacg acataacgtt cgcactgagt tacaataatt  74280
attatatatt attagcaatt ggtgcgaacg gagctctggg ccaatcaacc agtctaaaac  74340
gaaccacgtg acatagaatc caatcaaaac atgcgtatcg attaggtatc gatacattat  74400
cgatacctaa tcgatactca atttcgccta atgcgggttg taagagcccc aaggtgttgg  74460
ccggtgagca aatagcctcc ccaagaaatg cgcatcccgg tattaccata gacgcggcgt  74520
atagtaccag cgtatctcac ctggtagcgg cgcgtagtgg attttgccca ccttaacatc  74580
```

```
atcagtctta gtaaaaggtg cggtgaaacg gtgttaaggt acagagtgtt tttattttct  74640
gcttacatgc acagttacac ccccgcgctt cagcctctcg ctgagtaagt aatataagta  74700
gtatgccccc tttctgctta agtccaggcc atcgaatgct gttattgaag acacattgag  74760
cactattgcc actggtaggc cgctccccaa gatgcgacag gctacctgcg ccgctcctcc  74820
gattccgtct ttggcgtata gcttgttgag gacgctcgcg attctagctt ccatgttacg  74880
tacctcgtcg tacgaactga gcccaagctc aacccgggtg gcgtttgcag caaactccgc  74940
cagtagtcta gcctccagtt cgactacttc cgaaccgctg ccgttgacgg gatcggtggg  75000
ttgggtatag cgcacgatta tctcgcacag ctcacccaaa ataccacttt cgcgtattat  75060
ctcattgaca gcgtcggcca ccaggtgtgg gtctgggagg ggatcgcgag cctctggaac  75120
agctccgatg tagctctcgg ctagttgttc aagggccgcg tagcagttga taaggttcca  75180
cttgcccaag ataaactggc agagcacgaa ccgctgtagg gttgtgacac cctgctgagt  75240
cagctttccc ccgaaaaagc gcagtttccc ctcgttgccg tatactgcca aaatggcatc  75300
aacgattgtg cttcgcgcct ggttgaggtg ttcatccaac ccgggccacg gttcttctat  75360
cagaatgatt tcatcagcaa ttttaaatag tagttgtagt gattgtagcg atgcgccgct  75420
ggccacgcga ctcgccgaat cccagatgct gcagggcttt ggaatcaggc gcacctggac  75480
aaagtcgctt accacagttt ttctaagggg tcgtttggag caccgggttg tgccccctat  75540
tgccattgtt tttacagctc tgggggaggt aacgataata tcggtgcggc tatgtcctcc  75600
tgactcgtct cgtagggggg gtcttgctac tggaatacga tcaaatagtc cacttatcag  75660
tgtctctagt tctgggggca actcggttag gtacgcctga accaaagtga aacacgctat  75720
gtttggggtg tagataaacc ccgaggatgc gtttgtgata gtgggaacag tatagaggtg  75780
tagcattccg tcttgtggta tatctctccc cgtagatacg atgagtccag acgttacttt  75840
tagagatacc atacactcgg cgaggtaggg gtcgtatact tccagatcga agctcccgca  75900
gatgtctctg ccaaaggcct gggcgccctg ggccaatact tctaaacgat caacgaacac  75960
gtcctcttca gagctgggcg cactctcatg gcgtcccgtt cggttcaatt cgctgcgcac  76020
ataattggcc actactcggt cgttgtgtgt tagccccccgt aaggtcagcc caaactttgc  76080
gatttcaccg ctctcggccg tggcatgggg tctaggcaca gagagcagac acccaccgta  76140
tagaaaatac acgcgatggc caccgtcggt tatgtagaac acaacgccgt tgtggatgac  76200
tgtgtcgctg tacttgaagt ccatgattcc taccgcggcg ggtgtaagac acacagcgat  76260
aaaatcgtac ttggtggggt ctagcgaccc gtttggcttt taaacttatt ggctggggtt  76320
tgcgagagac gctgcctctt tgcggtcgca gctgcaaatc cacaattgtt taaaagcaaa  76380
ttggttttat atcgaggagc cactttaaat atgagatacc tagaacggac ggtgagtggt  76440
ctacgcctgc ctaggaacgt ttatcacgtg ggtcaacgca tttatataaa ctttgcggtt  76500
tttagtttta gggggaaatc actcgggaca aattaggggg tgtccctaac ggtttatggc  76560
tacttttgcg atccctattt ggcgttttta ttcccggaaa tgccgcatta cgtgatagat  76620
atataaacgt taaactgtat gtcacgatat tgacttttaa ttatacacgc ttcaacgtgg  76680
gctatagcct cgcatataag gtttccatcc tggcgctggt tagactagtc catacccctgc  76740
accgctcgca ggctgccaga aatatttctc tccgaatttt tgagggttgg agatgccaca  76800
ggtattaatg gggaataccc gtttacacgc acccctcgaa gatggcattc ccctgatcga  76860
aaacgatgaa aattcatccc aaaatgaagt tgatctctat gactatgtgt ctatgtcgtc  76920
ttacgggggc gacaatgact ttttaataag ctcggccggg ggcaacataa cccccgaaaa  76980
```

```
tcgcccatca ttttctgccc acgtcgtcct gtttgccatt tctgccctag tgataaaacc  77040
cgtatgctgt tttatatttc tcaaccacta cgttataacc ggaagttatg actttgccgt  77100
ggctggagga gtttgtaccg tactatacta catgcggctc gcgctcaccg cctggttcat  77160
gtttcgcaac atccaatcgg acatgctacc gctgaacgtc tggcaacaat tcgtcatcgg  77220
gtgtatggcg ctcggtagaa ctgtcgcgtt tatggttgta tcctacacta ccttatttat  77280
acgctcggaa ctgtttttca gcatgctggc ccccaacgcg gggcgcgagt atataactcc  77340
aataattgcc cacaaactga tgccacttat tagcgtccgc tctgccgtct gcttggtcat  77400
aatatctacc gctgtttacg ccgcagacgc gatctgcgac acaattggct ttacgctacc  77460
gcgcatgtgg atgtgtattt taatgagatc cagctccgtt aagcgtagct agtaggggtg  77520
cctccgtggg aggcaccact ggggtagcgg ccgactgaca gtataaaacg tgagaagaga  77580
gcagccccac gcgccattag cgctaggcca gttagcgcgg aggacctgag cgctacaccc  77640
agacggtgca atcggcgggg tacaggtttg tcaccaacga caggcatttt accactacga  77700
taatggaccg gcgctcagag gcgttcaaaa ttccggtacc agaagtaatc cccgccggac  77760
agattctatc aactatagaa gtgtcgtccc accgcactct atttgacttt ttcaagcaga  77820
ttcgctcgga cgataatggc ctttatgcag cgcagtttga cgtgctactc ggaacgtatt  77880
gtaacacgct aacgctggtg cgcttcttgg aactaggatt atccgtatcg tgcgtgtgca  77940
ccaagtttcc agagcttaac tacgttaatg atggcaccat ccaatttgaa gtgcagcagc  78000
cgatgatagc tcgggacgga ccccaccctg tggatcagcc cacccacacc tacatgatga  78060
agcacatcga gcagcgatct ctgagcgcgg cctttgctat cgcggcagag gccctgggcc  78120
ttatcggggg cacaacccta gacggtacgc agatctcatc ctccctgcgg gtgagggcta  78180
tacagcagct ggccagaaac gtgcagacgg tgctagactc gtttgagcgc ggaaccgccg  78240
atcaactttt gcgtgttttg ctggagaagg cccccccgct gaccctttttg gctcccctgc  78300
agatttaccg cgatgaggga cgccttgcgt ctcgagtcaa tcgcgccgtg ctggtctcag  78360
agctcaagcg gcgagtgata gaagacacct tctttctcac caagcacgag cgtaacagaa  78420
aggagctggt ggtagcccgc ctggctgagc tggttaactg tacggccccc tccgtcgccg  78480
ttactagaat gactcattcg gacacaaagg gaagacccgt ggacggtgta gtcgttacaa  78540
ctgctggcgt gcgccagcgc ctcttacagg ggattctaac tctggaggat atggccgccg  78600
atgttccggt tacgtacggc gagatgatga ttaccggcac aaacctagtt actgctcttg  78660
taatgggcaa ggccgtgaga aacctggacg acgtagccca ccacttgttg gggatgcagc  78720
gtgatcaggt cagggcgaac gaaaaactta ttaaagacta cgaggatgtg cccagcacgg  78780
cgcgagtacg tgccgaccta gttctcgtgg gggaccgcct agtctttctg gaggccctgg  78840
aaaagcgcgt gtaccaggcg accaacgttc cgtacccgct tgttggaaat ttagatttga  78900
cgtttatcat tcccctgggc atcttcaagc cggccaccga ccggtattcg cgccacgcag  78960
gaagctttac gccaaccccc ggacagccag accctcgcac ctacccaccc caaaccgttt  79020
actttttcaa caaggacggt aatctcgtac agctatcctt tgacagcgcc gcggggaccg  79080
tgtgccacag ctcgtttttg gatgtggatt ctgtgctggt ggccatccga cgagaacccc  79140
acgagcttca ctgcgcgttt ggggcatacg tgaccctacc cccagccggc actctgcttg  79200
accagatgag aaggtttttt gagcgctggc atatgctcat gccagcgcga ccccgctgga  79260
ccgcggaggc gctaatgacc atcgaccaac ttctttcgcc aggcaacgca aacctgcgcc  79320
```

```
tggaacttca ccccgcattt gattttttcg ttgccccggc ggatgtcgtc attccaggtc  79380
cgtttgacat gccgaacgtc atgcccactg tgatggccat gccacgcctc atcaacggta  79440
acatcccccct cccccctatgt cctgtggaat ttcgcgacag tcggggcttc gaactgagcg  79500
tggatagaca caggctcaac ccggcgacgg ttttggcagt gcgtggtgcg ttcagagacg  79560
ccaactaccc catggtgttt tacatcctcg aggcggtgat tcacggtagc gaacgcacgt  79620
tctgcgcgct agccagactt ataattcagt gtatcgtcag ttactggaga aacacccacc  79680
aggtggcgtt tgtcaacaac ttttacatga tcatgtacat aaacgcctac ctaggaaacg  79740
gcgagctgcc agaggagtgc acggctatct accgcgacct tctggagcac gtccaggctc  79800
tcaggcggct agtagccgag tacaccgttc ccggagaagc cgtgggcggc cagggacacg  79860
acgcgctgaa caatgtgctg ctcgatccgg ccctgctacc gcctctcatc tgggactgcg  79920
acccgatttt gcacagggcc gacatgggca gggccagggc tcaggagcta tgggtggatg  79980
ggtggacta cgccgccatt ccttgggtgg agatggccga agttaacttt ggaaacaccg  80040
gcggccattt ggtgcacaac aggcccattc gaggagagaa caagagaaac ccgattgtac  80100
ctcaccacga cccagagtgg tcggtgctat ccaagatata ctactatgcg gtggtgcctg  80160
cattctcgcg cggtaactgc tgtaccatgg gagtacggta cgaccgcgta tacccgctcg  80220
ttcagacagt tgttatccca gacttggggg cggaggaaat tgccccaacc agccccagcg  80280
acccgcgcca tccgctgaac ccacgccacc tagtgccaaa cactctaaac atcttgtttc  80340
acaacgccag agtggccgtc gacaccgacg ccctgctgct actccaggag gtagtcacca  80400
acatggcgga gcgcactact cccgtgctgg caaccgccgc gccggacgcg ggaaccgcca  80460
ccgccgtaac tcaggaaatg cgcactttcg acggaaccct ccaccacggc attttgatga  80520
tggcctacca gcgtaacgac gaaactcttt tggagggcac cttcttttac cccgcccctg  80580
tcaacgctct ctttgcctgc cccgagcact tgggggctct tcccgggctt aacgcagaag  80640
tcttggaggc cgctagggat gtgcccccag ttccccactt tttcggtgga aattactacg  80700
ctacagtcag acaacccgtg gcgcagcacg ccgtacagag ccgcgcggat gagaacacgc  80760
taacgtacgc gctgatggcg gggtacttca aactcgggcc aatagccctg tcccatcagt  80820
ttgccactgg gttccaccca gggttcgcct ttaccgttgt gcgccaggac aggtttctca  80880
cggagaacat cctctttgcc gagaaggcgt ctgaatcgta ctttatgggc cagctacagg  80940
tgaaccgcca cgaggcggtt ggggggggtta actttgttct cacccagcca cgtgctaacg  81000
tggacttggg ggtgggcttc accgccgcct acgcagccgc cgcactacgc acgcccgtta  81060
cagacatggg aaatctgcca caaaacctgt atctgacacg cggtactata cccatgctgg  81120
acggagacgc ggatgcgtac ctgcggcgcg tggtcaacac cgggaatcgc cttgggcccc  81180
agggcccaag gccaatcttt gggcagctga tgccggccac gccggcgggc gttgcccacg  81240
gccaggccgc cgtgtgtgaa tttatcgtca cgccggtgtc tgcggactta aattatttta  81300
ggcggccatg caaccccaga ggaaggagcg ccgggcccgt gtacgcgtgc gatggagagg  81360
ccgacgcagt ggacgttatg tacgaccaca ctcagggaga tccggcctac ccgagccgcg  81420
ccaccgttaa cccgtgggca tcccagcgca actcttacgg cgatagattg tataacggca  81480
agtataacct gaacggggca tccccggtgt acagtccatg ctttaagttt ttcacaccca  81540
ccgaagtgga agccaagggg cgtaatatga cacagctcat agccgatgtc ggtgccagcg  81600
tcgcccccag cacgtctaac accgaaatcc agtttaaacg cccccacggc tcgacggacc  81660
tggtggaaga cccgtgttcg ctgtttcaag aagcgtatcc tctactcagc tctacggaca  81720
```

```
cggccctgct ccgcacgcct cacatcggtg aaatcggcgc tgatgaggga catttcgctc  81780
agtacctaat tcgcgacgaa tccccgctaa aaggctgttt tccgcgaatt taggttgggc  81840
ccgcctccaa gtttcacatg ctgccaaaac taaataaaac gcacagttta tatactcact  81900
tgtcagtttg ctctgcttga gcgctagcgc tccgtctcga cctcccagag tggttattgg  81960
tacggttggt gggtggtttt gactgccttt aatccctagc agactttaat cgatagaagg  82020
ggcataataa ggaagtcttt ttgggggggc gtcgctcggg tttggggtgc ctccacgtag  82080
agatggcgag tgccgccttt gagattgaca tcctactgcc cagtgaccta tctcccgctg  82140
acctgtcagc tcttcaaaaa tgcgagggta agcttgtgtt tttgaccgct ctgcgtcgtc  82200
gcgtgatgct ctccagcgtc accctctcgt catactatgt caacggcgca cccccggaca  82260
cgctatccct gatggcggcg tttcgtaggc gttttcccgc tataatacag cgcgtgctgc  82320
ccaacaaaat gatagccgcc gccctgggag tcgcaccgct tcctcccggg gcgttcatac  82380
agaacacagg cccgtttgac ctgtgcaacg ggactctgt gtgcgcgctg cctcccattt  82440
tggacgtgga ggacaagctg cgcctaggat ctgtgggcga ggaaatacta tttccgctga  82500
ccgttccact cgcgcaagcg cgcgaactca tcgcgcggct ggtagcgcgc gcggtgcagg  82560
ctctcacccc aaacgcccag gcccagcgcg gagcggaggt gatgttttac aacggacgaa  82620
agtacaacgt gaccccggat ctcagacacc gagacgccgt taacggcgtg gcgcggtctc  82680
tggtgctaaa catgattttt gccatgaacg agggatcgct tgtgctgctc tcgctgatac  82740
caaacctgct caccctggga acccaggacg gatttgtgaa cgccataatc cagatgggaa  82800
gcgccacccg tgaggttggc cagctcgtcc accagcagcc cgtgccccaa ccgcaggacg  82860
gcgctcgccg cttttgtgtg tacgacgctc tgatgtcatg gatcagcgtt gcctcgcgtc  82920
ttggtgacgt ggtcggtggg aaacccttgg tgcggatctg tacgttcgag ggccaggcta  82980
cgatttcccg cggcgagaag gcccctgtca ttcaaacgct tttgtaacct caccctcccc  83040
ccaacgccca ttttaacccc cttatgcaaa taaacttgac accatgttat atattacatg  83100
tagtatgagt ttttaatgat gtcggcaaac aaaactaaca cgtatcctca ctgcgcgggg  83160
agactggaaa acgcatcgct ggttggcggg aggctggaca aataaacggc catcaccagg  83220
gccaccaaca tatcgtccga cgcgccgttg cgtttaccgg taaacactct agtttcggag  83280
gttccggtaa ccacctcggt taagtttttc atttgcgtca gcaggtactc caccgggtct  83340
gtttgcaggc gcaccgtatt tgatactagc tcctgcgaag ctagcaccga gccggagttg  83400
aacgctttga taaagtggtc gaaggccccc gttttctgtt tctggagtag aaaaaacggg  83460
taggccactg agcttccatg ggcgtgcaa tgataaaaca gcaccgcccc gggcatgggc  83520
accacgtcgg cacggcgtag cgtgttgagc tccagctgaa tgtttgttgc gatggcgact  83580
gcagcgtctt ggctactgtt accctctacc gcaactcgaa ctgagtcaaa ggggcgtttg  83640
tgaatggcga aaacctgcgc caggcactgg gcaacacacc tagctatcag ctccgcggaa  83700
ctccccgtaa gggcgctcag gaaaaagtgc tccatgccga acacgaccca gtttgagcga  83760
tagcggccga ctacagccac accggttcct gaagccatag catttgtagt aaacgcagga  83820
tccacgtata cgtaaaggtc gctggacata atatcttgat tagcgacagt agaaggtctg  83880
tacaacaaga aacggtcttg agcagttttt gtaaaaacgg gctcatctcg atgtgctcca  83940
gacacgtttc ctccaccaat tatctcctgc ataaacgagt ccggtaaaaa tagctccgct  84000
gtgttacgca tggccccgtc cattgttatg aaaacgggct tgtttaaaat gtagcacgag  84060
```

```
cacgccgtgg cgtttgtgtg cgcctttacg cgctccatgt gctcgtcgca tatgtaagtg  84120
actacgttca gcaggtcgtc tgccgccccc tttaggttat ataaaaagct ggtactggcc  84180
ttgcccgtgt tggtggagga cacgaagatg atcttgcagt tggtctggtt cagaaagcct  84240
ataatcgttt gcaccgcttc ggggcgtata aagtttgcct cgtccacaaa tagcaggtta  84300
aagtcctggc cgcgaatccc ctgaaacata gagagaataa aaaaagggat cgacgggtta  84360
ggcgtttcac ttaagctcgg ctctcgacgc gggccgcagc aatttcttgt taaaccggct  84420
accctgttcc atacctcccg gcgcaccaac ggcgcagcaa taatccgtct gacactacta  84480
tggacgcgca catcgctaac gaaaccaagc atctactggt acacggaaac agtaaaactc  84540
gcgcgctggt gcacataatc gttcctgacg cgtgcttaaa gaaggctggc gtcgatccgg  84600
ttaagcttag cgaccgccat agagctagcc catccgcggc tcccgtattt cgggtgtttg  84660
cccagactcg atatcacgcc actggggaat gttcgttatg gcgcactgtt tttgctggat  84720
atgtgcccag cggggctatt gtgagcgcgc ttgtgccgac agttccagcg gaccacccac  84780
ggctatttca atcgactccc gactccggtg ggctattcgt atcactagaa attgagtgcg  84840
atgccgatgg ccgctttgac gcgtttactc tggttgcgct gagagtcgac attgccgacg  84900
acccacgtac cactgaagtt ttgtttacct atgatgagct gttgccccca ggcactcgct  84960
acggggccga ttccaagcgc gtagcactcc tctgtcgaca attcgtggcg tatgtcaaca  85020
gccaccccac agtttcccag agcgccgtta ctgcggcatc gcacatagaa gccgcggtcg  85080
ccgaggatgt aaagtcggct agcggtcccc aggtatccta cggggctcgc atcgacccgg  85140
ccgagtactt attttcgggc gggggtttcg acaaccacca agccctggcg cggctcgaag  85200
atgacgataa agagataatg tctctgatcc gcagggcgtc tgaggtgatt gcaaaacgca  85260
acccggttag ggtgctcagc aatccagagg ttaacggcga cgcccatagg cggcaatgcg  85320
tggcgtccgg cctccgacag ggtgcccgcg gggcacacgc gtccgactct catgcgcgtg  85380
ttgggtttaa ttccagtatc cacgatgcga cggccttgct gttgggcctg gagcccccag  85440
attctggcag atttgttaac agcggccccc agcggcatct gccccctcag ggacccagga  85500
gccccgcgag tcgggactgc cagtccggga tgctcgatga cgtgctgttg ctcactccgg  85560
aaaactccaa cccgctcacc cccctcgact ggctggacgt gggccacgcc gccgtggccg  85620
gaggagacac ccccagagac gtgtggcggc gcaggccgat ctccctagtg gcacgaaagc  85680
actacgggac ctgcgaaacc tttgtagtgg tgtcgtatga aaactccacc gcgtgggggg  85740
gtcggagggc gcgcgacgaa cacttggccg ggtccatcaa ccccccccgtg atgcaggcgt  85800
gtgtggcggc cggtgtggac catcccagaa atttgccgcc tgagactcgc ggtgaactca  85860
tcgctaagtt tccgatgttg actgtgcccc tgggcgacac gccgccgccc gtggccgcgt  85920
ttgacgccgc tgccgagttg gctctgatag atcactttcg aggggcctgt gtttccgccc  85980
ttctaaaagc tatatcggaa cgcctgcgcg cggaacctag gatgtcgcag ctaatcgagt  86040
atgacattcc aaacaacaac cgcgactgca tcatcagcgt ggcgcagcgc gcccccgagc  86100
tgctagaagc cgtggcactc gccattcaaa acgttactgt aacggagttt tgcaatagcg  86160
ccctgatgct atcggctctt tcgcatctaa acatcctctc cggaaacaaa cgtgggcgcc  86220
taccctacca cagatcttgg cttcccagcc tggcgggggg ggcggacgcc tttcttttcg  86280
actactacag ctccggtggc gaagttgtta aagtttcccc cgtcccactg gctatattag  86340
ttaccgcaac cagaacgggc caacattcgt gcaggtttgc ccgaggagcg ccggactcct  86400
cctctaagac gtatgagcgc tacctgccgg gggagtgcta cgcgtacata tgcgtcggcc  86460
```

```
taaacagatc gtttgaggct ttggtagttt taccaggagg ctttgcctgc cgagctagcg  86520
cggctcggaa actcgcgtgg cccgctcatc tcgtggagcc catcctagag cgctactgtt  86580
ggacaattcc ttctcactga gatcatctct acgtgccgca tgatggccgc cgcctcagac  86640
agctgtttga gtttatggga ggggtccgcg tcgtccccca accgccaact aaccccggaa  86700
gcggtgaact gtttaacgga ggcgctcacg gaagacgtcg ccgtgctacg cctcatacgc  86760
agcgatcccc gcgttaagat ttttatggcg gttagcgttt tgacccccag gctggctagg  86820
tttgcgcctc ccccgcccaa gctcacccac accgccaagt gcgccgtgat catgatctac  86880
ctgactcgcc ccaaggccct ggcgctacaa cccaaacagt ttcacatgct ggtaaccttc  86940
aacaaggcca gcgtatactc tctggtggtg cgggtgaaga caaagccctt tcccgtaggc  87000
acccagagat tccgcgccgt gtttcaagac cccgagttta ttgggctacc gtccgacatc  87060
cctgacccgg cagcagagaa catcccaacc gagattaacg accgcctgga cgtgagcaat  87120
tttgcaaccc cggcacaacc ccccaaagac aagtacgact gttgcgtcct ggctcctggc  87180
gtctggtggt ctaacgcaaa caaggctata tactttctac agatggacgt agctctgctg  87240
gctctttgcc cggctggatg gaaagccagg ggtctgggga tcattcttgg gcgtctgctt  87300
aaccaccaag agggttgtgc tacgtgccgc ttcaccgaac attcagatcc gctgaatgca  87360
acggcagact cggtggctac cccgaatcg tgtctatgct gggcgccgtg tctgtggcga  87420
aaggcacacc agcgagagtt aaccgtggag ggggatcgat atctgtttcg agttctcttt  87480
atggatgcgg tggagcgagt gcgtttgact ggcctgaggc gcagcccaaa gataacagcc  87540
aatctcgccg acttggttgt ggggattggg ccgcacggac agcagattcc cgtcaacaac  87600
gccggatgga aactggtggc gctagacgct gatatcagca gactaatcgt ttgcggatgc  87660
tacgccctgc gatacatctg tccgcccaca aacagcaaac accaaccgtc ttccccagac  87720
gagtacgcat aaaccccgtt cctagcctag tatatacgcc catcacccac tcgatactga  87780
cagccttgcc ccttttaaac cgccaataaa cagttaaaac ccaacaccgt ttaccctctc  87840
tctgttttta acccacaaaa cgcgtcgctt gggggtggta cttacgttgg tgttgtgact  87900
agatgcgaac acgattgtgc ttttcgatcc gtcgggaaag gagaatgata tattttcccc  87960
tttgacgtga tctactggag agttcccgaa ccactggcgg agcctcgcgc ctatctcatc  88020
aaaaaccggt tcggtggcct tgcgtatgtg ggccgtatat ccgatcttaa tccccttgaa  88080
ggtcgctagc gccagagcta tcaggggcac caaaaaccag gtttttccat gacgtcgcgg  88140
aaccaagaat acagtcgcgc gttgccgaaa atggcggatt gttgcgtcag aaaactccgg  88200
ggtgttaaac accatcttta gaaacgcccc tatacggtca gcatggtccc ccaggatgac  88260
tgcagctata aagtatgtag cgtgcatgag aatcatcttt tgaaatagct ccagagtccc  88320
gcgctgcttc ccgtaggtgg gaacgtccac cctggcccgc ttgcttgcct gttggccgtc  88380
cccgtctagg tcggctccgt taaaagaggt gtccaccagg cgactgaagc gcgccacaaa  88440
gctggctact tggtgaaagg cgtctgagga gcggagagcg tcgaaggtgt tcatgatact  88500
gtagtacgcg tttctacacg agcgcgcctc atcgtcgctg tactcgacaa aggagatagt  88560
cttaagagcc tgtcgcacct tggggtccac ataagcctcc acggaggccg ggtctaaccg  88620
ttctctcgcc tctccgctct gccattttga caggcttcta aacagcagcc tcctagccac  88680
agaagcaaat atttgcgcgg tctcgcagca gtcgtgtaac gtccctaccc caggaacgac  88740
ggtctggtgg cgctggggag taggaatcgc aaagttgaga aaggccgttt tcgcatcatc  88800
```

```
ctctccacca ttttgagctt ccgcggctct gtttttggcc cctcgacgcg cttggacctc  88860
tcgccgcagc gcttcaaaat actggacggt ctccctgccc agcaccctac caaacattgc  88920
agcccgaacc cccggtggtt aacggtatga gcttctcggc acggtctagg cgccagaggc  88980
tgcaattgga agaagcctac cagcgtgaaa tgatttttaa gatgcacacc ctggacttgg  89040
tacgcgaggg cgttaacaaa cgcagtcctg cctttgtccg tgcatttacg tcagcaaaag  89100
aagcaagttt ggacctggat agatacatgc aagcacattc cagggtgggg cgagtagaac  89160
aaaacgccag agcgctcgcg cagcgagtgg aggcccaagc tgcagtcggc gagatactag  89220
acaggcaccg caggtttctg cacccagatt ttattgataa ctttgattcg cgcgaggact  89280
ctatagtaga aagggaggag cgcctgggtg atgtgctatc agatataaac tgcgacggag  89340
gaggcggtga ggtcggagac ccacaggaat ggctaggtca cgaagacgaa gctctgttga  89400
tgagatggat gttggaggaa gcgccacgag tgagtacgag aattgcggcg gaccctcatt  89460
ctccccgctc aacctgtccc gccccaagaa aagcaccaga ggacgctcgc tgcggagcgc  89520
gcaagcctgg ggaggtaaac aattacaccc cgagcgctca accccgctcg caagaaacga  89580
ctgtggacca tctagcaagc ccagacgaag gcacgaggtt gggcgatcga acaagggact  89640
tggagcatca ctcgaccgca ccgatgagga cacatcccaa tgtcctcgca tcagagcgtc  89700
ggcgattagg tgtggtgcat caacgcgaaa aatcgtcaga atcacaggag agtgcgacgc  89760
gcagcaaggc gatagtcggc caggaagatc agaaatggct gggtggcatt ccccccctaa  89820
gcgacgaaga actccaagtc gacatgggaa ttccgacaat gaacggtccc atttacccag  89880
attatcatcg cacggcgtag ttagggttgg gggtcgcccg ctcacacaga ctcccctcca  89940
gaaaacgata attttacaac caaagctcgt acgcaaagtg tttatgccta cctttacagt  90000
gaacccagag atgcactaca ggcgcgtggc tctgggtgag ataccaaaat ttggaggcgc  90060
cggtagctat ggagaggttc agattttcaa acagaccggc ctggctatca aaacggcctc  90120
gagtcgctcc tgttttgaac acgagcttgc cgtgagtctt ctgacggggg aatgctcgtt  90180
gcgcgcgcaa gctagcctcg gcatcggggg aatcatctgc ctcatggcct tttctctgcc  90240
gtccaagcag atggttttcc cggcctatga cgcggatcta aacgcgtacg gatacagact  90300
ttctcgcagc ggccctccct ccgtcctggt tacagagtca atcgaacgag cgttcatcgg  90360
acttggtcgc gccctggtat acctcaacac cagctgcggc ctgactcact tggacgtcaa  90420
gggcggcaac atattcgtca accactctca ttttgtgata agcgactgtg taatcggaga  90480
cctgagcctg atgacattga atacaaattc tatggccatg cgggcggagt ttgaaattga  90540
taccggcgag gaggagatta aaacactccg cctacccaga agtgcgtcac agatgacatt  90600
cagctttgta attggccatg gacttaacca gcccataagc gtaattgctg actttattaa  90660
caatagcgga ctggcaaaga gtactggtcc gataaagcac gacgtcgggc tgacaattga  90720
cctgtacgcc cttgggcagg cactactaga gctactactt gtcggctgca tctctccttg  90780
cctgtcggtg ccaatccttc ggacggcaac ctactactac tactccaaca aactctccgt  90840
ggactacgcg ctagacctcc tggcgtatcg gtgttctctg taccctgccc tatttcccac  90900
cacccccttg acgactatct acggcatccc ctgggaccag gtagaaggcg tctttgagag  90960
tatcgccggg gctcaccacc gcgaggcgtt tagagctcac ctggagagat accgcttgac  91020
gcacaggcgg ttgtttgcgt ctatacgaat accgtccgcc tttaccggag tgcttgagct  91080
cgtctctcta ttgtgccacg ccaacgaaaa agcccgcctg tcgattcctc tgttatggac  91140
tcctcgcccg tgacttacag cggcgaaccc ccgtataagc tgcgtcgcct cagcccctcg  91200
```

```
tatccatacg tttcaaagtt acgcgagcgc tgtgcgtcaa agatcgaaac tctttccgag  91260
ggcagcgcac gagatagcct cgaagagagg acgtgtctga ggccatggca accggtgcgt  91320
ttctagctac ccgtctgtac ttaccatccg ttttacctca aagaataaca acgctgacgt  91380
ttttggacca ctttaagaag agccgtcctc tccccaatag cgataagcga ttgaatccca  91440
tcttttatcg cctggcctac atacgcgacc tggtaggaga gatggagcta gaggggatcg  91500
tggaacgcgg aactgcctcg cgtttactcg gcgccagctc cccggctggc tttgtggccg  91560
gaacgtacac ccacgcgcgg gatctgtcca aaacaatgtc cctggccagc gtcagggacg  91620
ccgtgctagc gatagaggcg cagactcgcg accagagcga gagccagctg tgggctttgc  91680
ttcggcgtgg attggctacc gcgtctacca tgaaatgggg ggcactcggg ccgcagtacc  91740
acccgcagtg gtgcgaggtt agcaccaacg ccaagggaat cccaaacaac cccgctctcc  91800
agtttggaca aacaaacgaa cggacggcca ggtctctcat ctcggctctc tatgtcgccc  91860
gctctgaggc tgccacccca gacttactgg tggatcctgg atgcggtcaa tgctttgtgt  91920
ttgacgagtc cgcaagcgtc ccgggagacg cttatgcctg tggcctactg atggacgcca  91980
gaaccggcgt cgtgggcgcg tccttggata tgctggtgtg tgaccgggac cccagcgggg  92040
tgctgtctcc ccactcgact cagactacat tggatttttt cgaaattaaa tgcagggcaa  92100
agtatctatt cgaccccgat ctatttagcc ccgtggctac ggcgtacgcc aacttgctga  92160
aacaccgcac cgcggtatgc ctgcgaaaat ttctcaggtc tattaaaaac cccgcagtag  92220
agtatttcgc accgactagc gtgcccgggg caaccgaagc gctgattacg tgcaactctt  92280
cgtggaaacc acgtgaggta aatgagacca acaggcgttg cggtgacttt gatagggacc  92340
acattgcttt aaacctggac gcgtcatcag acgtttggct atttagtgag ccggaccttg  92400
agtcggagac tattactcca gcccgctggg acacaggaga gttggcgctg tcggttccgg  92460
tgttcgcaaa ccccagacac ccgaacttta agcaaatact ggtgcaggcg tacgtgctat  92520
ccggccattt tcccgaccat caactcaggc cgtttttggt aacgtttatt ggccgtcatc  92580
gcaagaggtg tgaggaggga aaaacgttta ccatctgtga tcgccctgag gggagcccgt  92640
acaatctgaa cgaggttgtc cactctagct gcgctatccc cattctgcta tttgtgaccc  92700
cggtgattgt ggaccgcgag ggttgctggg aagacattga gatcgagagt ctcaccgcgt  92760
tcaacaaaac cgccgacgcg atatgggaca gcgactctcc tgcggatgtt tcagaaccga  92820
ccagctcgta actcactctg gcgaagtggt atccctgaac gcggacacct ttgaggaatt  92880
tagcatggaa gagtttgata ttccccccacc cccacctctc ccgaaacccg tcttcaagca  92940
accaggccct tacaaaatcc cagccagatc tcaacgctgt ccttctaaac gacgagaccc  93000
ctattaaata aaatgactgt aaacgcatat aaacgtatca ggtgttttat tttttctata  93060
gtagtgcgtg gtagcgtaag cagattcatg gcctttgtat accactggca cgttgatgct  93120
atcggtactc ccggcgatgg cttctttccg ggacgcgctg tgggtcgtca taatattcgg  93180
tttcaaattc ctcgctcacc acgtcgtaaa ttggctcttc tgcgtccgtt tccgagtctt  93240
cggctaagag catgcccctt gactctgcca cgttcaaggg ttgtgggttt ctgcgcgggc  93300
ccctcacctt gttggcgtat ctacgcgcct tggaagacac ggtttttacg cgcccgtaaa  93360
attcggtatt ccgcttcttg tggaacatga tagctctgac cagtctcacg actagcatga  93420
tgatggagat gaccgccatg attccaacta tggctttgga tgcggtggcc agattcgggg  93480
cctggacgga aaccatggca tggaagtgaa cgaagtagct gtgggttgct acggccagcg  93540
```

```
tggagctcgc caccaaaact gcgagggccg gtcccactag aacgtgtacg tagtgggaca  93600
cgatgagttc gacgattatc aaaaacatta gtccgagggc cacaaacacg cccacggcaa  93660
cagtcaccgt ttgccacagg gtgatgtgaa agctgttggc gagtataatc cctagcatca  93720
gcgacagtat cggcagggaa attcctagca tccccatgcc gaggttggtc ataaccgcgc  93780
gtccgggtcc ggccatttta tgtagcgccg gtaggttggt ctttagtatc cgaagattac  93840
tagagtattg agcgctcgcg gttcccaggc cgctgaagct catgcaaaaa aatactagcg  93900
atacaaagtg aaccacgtaa actgccgccc ccaggactgc ctgcttgtgc gagagtagca  93960
gtattacaac ttgcagaagc cacgtagcca gcgtcccgag tactagggtc acgtgggacg  94020
caataagcgt ggtcgttggc cgggtgcacc cggccaccgc ggtgcactct ttcccccggg  94080
catatctccg aactagaacg gccgagatta tgaggtagaa ggatatcgcc accaggacga  94140
gtgtagtgta gtaaagaaac gcaaccaacg acgttgtctc caaaaataga gtcggggcta  94200
ctccaccagc tatctgccgc atccacactc catcgaccac gctgtggttt ttctgcgtgt  94260
agtcaaccaa tgacccataa aaacacggat atccggtctg aggaagagac gccgtcacta  94320
gagtgataaa aagcacggag gttgtaagtg cgaaacagaa cacttgcacc agccacgttc  94380
tccagttgat gccttcgatc ggacctatcc caacaatccc cgacgagggt agcagaggct  94440
cttctgcgac agctgctccc cgtcgtgcca tggcgagtta tcgagatact acgctgggcg  94500
gcagagcgga aggtgtagct ttctcggccg tggaagacag ctatacttcc agcgtttctt  94560
tggccaggat gttatatggg ggcgacctgg aagagtgggt gcgtcacacg cggcccggtg  94620
tgagtttgga aatccaatcg agggctccgg tacgctttcc tccgcccaac aacccgtcca  94680
gcaggcgcgt aaccgtcgta agagctccta tgggttcggg caagacaacg gcgctgctaa  94740
aatggctcgg agaagcgctg gacgcgcctg atattagcgc tctcgtcgtt tcgtgccgga  94800
gaagcttcac tcgcacctta gctaaacgat ttaatgacgc tgaattgcct ggttttgcta  94860
cgtattttac gtccacggac tacaccatgg ctggggagcc ttttcgtcgc ctgttggttc  94920
agattgagag cctgcaccgc gttgacgata acctcctcaa caattacgac attttagtac  94980
tagacgaggt gatgtcaaca atagggcagc tatactctcc tacgatggtt cacctcaaca  95040
aagttgacgc ccttttgact aggttgctaa agacatgccc ccgggttata gccatggacg  95100
caaccgcaaa cgcgcagctg gtggatttct tggcttcggc gcgcggcgag cgcagcgttc  95160
acgtgattat aaactcattt gccgcgcctg gattctcgca gcgcgacggg acactactgc  95220
gaactcttgg aactgacgta ttgcgggcag ccctaggatt tgttcttgtg gacgatgaaa  95280
acggaaccaa ggttatggag acggattcca gacccatttc agctagactg cgcgaggtca  95340
actccgcggg gtttttcggc cgcctgatgg acagactcgt ggcggggcgc aacgtttgtg  95400
tgttctcttc tacggtttca ttttcggaga tcgtggctag gttctgctcg cagtttacag  95460
actctatttt ggtgttgaac tctctacgac ccagcgagga tgtagccttt tggggggggag  95520
taagggtgct gatatacacc actgtggtaa cggtgggcct tagttttgat acggctcatt  95580
tccacagcat gtttgcctac gtcaagccca tgagccacgg accggatatg gtttctgtat  95640
accagtctct ggggcgcgtc agagagctta ttcacaacga gctgttggtt tacgtggata  95700
gctcgggagc ccgtgcggag cccatcttta cccccatgtt actcaaccac gtggtgagcc  95760
gccagggtgg gtggccggct gagttctcgc aggttacgga cgccctctgc tgtcagttta  95820
aggctcgctg tggaccggct tatagaacgg cgtccacgcg cgggctcgct ttgtttgtta  95880
ggtttaaata taaacacttt tttgagaggt gcactctggc gagcgttggc gacagtataa  95940
```

```
atattttata cactctcctc gagtctaacc aaatgcgcgt cgctatcgag gggtgccaat  96000
tccctctaac ggccgcaggt ttttgtgact ttctgcaaga tctgagactc gacgcatacg  96060
ccgctaggaa agagataaag cagctgcgcg gacccggggg tattgccgcc accccgacgg  96120
aggtttttga aaacgacgat gtggcggtgt ttattcaaaa gtacctgcgc cccggtgttg  96180
cgcacgatga gatattggca ctactggtag agctaaacag tcccatcgtt cgagagcagt  96240
tcgtcaatgt ggcggtcctg ggcgcctgcc tgcgcctccc agcggccctg gagagtcccg  96300
aagtatttgc cggagtttac aagcattacg cttccggggt cgtgccggtg attagtgacg  96360
ccggagcgct tgagagtgta tcaataacac cggacgttaa cgttctagcg cgctgggatc  96420
tgtataaaag ctgcacgcgc catgcccgcg atctagcctg ggacccgtcc cgcggggggt  96480
ccgggctgga catgtcggaa gattttatta caaacactct gagcgccgac tataacagat  96540
tccagagtct gctggtggag atagcaaagt gtaacgtaac acctttagag atgctagctg  96600
cgggtgccgt tcgaggcgtc actaccgcgc tctcgggtcg ccccaaaagc agggtcccgc  96660
tatcaaaagg agagcacgca gtctccctct ttaaggtgct gtgggaggac gtgttcgggg  96720
caaagcttgc caagagcacg caaacttttc cggggggtgt gcgggttaaa aacttgcgga  96780
aggacgaaat agtcgccctt ttagagtctg taaatgtaaa ccactcagag tgcaaaactc  96840
acagagagct gtacgccctg ttaatgtgca acaggaagct gtttgcggga cccagatata  96900
agctgagggc gccaaagtgg agcagaaacc tctgttttct agaattggac aatactggca  96960
cctgcaagac tccgcttgat gccgcgctgg cagacctagc ccctagcgcg tggccacagg  97020
tttacggagc ggttgacttc gacgcactgt aacatcaacc aacccacatg gagggcagcg  97080
tcgaatggtt taacggacat gtttgtgcta ccagtattta ctctctatgg acagatccgc  97140
accacccagg gcatcttcag gcgctcgtct acatgctgtg tcggcgcggt agcgactaca  97200
ccgcagagtt ttgtcacgtt cccgtctcgg gcgaactctt gaaacgcgga gctcgcgacg  97260
catctctggt aacaccggcg cgcgttgcca gcgccgcgca gaccgcggct gtgcctgggt  97320
gctggcccct ggctcccctg ggaaacgcca tgttgtggaa atccgtctac ggtggcataa  97380
cggcggcgct taagcgcgcc gtgggaagct ttgctttcta tcaacccctg gtgttaggaa  97440
ttaacacgca aactggactt ttagttaccc tccgacccgc cgcgtctgcg ggtgaaggcg  97500
gtggcgacca cgtctctccg cgggcggcga tcgtaaatgt gtcggtggag gtagacttgg  97560
acccagcggg cattgaagcg agcgcggcta gctccacagg atcgtctctc gccagggcca  97620
gactctgcac gcttcgagat ggatattttc tctcaaagcg ggacattgcc ctagaagttg  97680
agatcgctac aaaggaggtt tcattttaca gaaagtatga ctctgtgcaa cagcctgcca  97740
acaagcgtcg cggcgacatg gcagatttgt tcgtcgtgca cgaacgaacc cttttgctag  97800
ggggatgtaa acgaatggga gttaaggttc tattgccgcg aacgtttgac tgtttagttg  97860
ccagctccca gtcagtgtcg ggtttagctg ccatggcgct gtacaaacag tggcacgcta  97920
ctctattctc tgtagagcta ccagatactg ttgtgcaaat ttttgcttac ctagggccag  97980
aattaaaccc gtgtggagag gaagtcgact attgttgctt tgttggattt cccggactcc  98040
cgaccctcaa ggctagttcg agcaccacgg aggctgtgcg cgatgcaatg gccgcctata  98100
gactgtccga cgggctgtgg ccggctctag gtatgagcgc gtttcacttt ttggctccat  98160
gggacccgga agacaggtgg cccggtgaat cggaggcaaa acgggtagag gggcggtac  98220
acaggcttca gcttggtacc gaggatgatt ggggggctgg gcgggtatca tgcattttag  98280
```

```
agtcggacgc tgtaatgcag gggccgtggt tcgcaaagtt tgacttttcg gcgtttttcc  98340
ccacgctgta cctgttgctg tttcccgcca atgagcgctt ggctgaggtg gttagattga  98400
gggcacgtgg ccaacacccc acccttaagc tcgccttggt atcctttttt ggggggctgc  98460
agcacatcaa ccccgtagcc tataggtcca tcatagccct atccaacgga atcagtaagc  98520
ggctggagca cgaagtcaat cagaggggtt ttgccatctg tacatatgtc aaagatggct  98580
tttggggggc agccggaaat ctgccatcag actctgtatc ctacgccgac gcgctggttt  98640
acgcagagga gctaagaagc gccgctcaga aggcggccct cggacacgtg tccgagatgg  98700
ggttttcgct gccggagggt gtccacttga atttgcggct ggagggtttg tttacagacg  98760
ccatctcgtg gtccacccac tgttactggt tgtacaaccg cttcaccaag atggaagact  98820
ttgtaggctt ccccgccaag agcggggccg gcagagccgc gaaggcgagc ttgtctgcct  98880
tgctaccgct ggtagccgcg gtatgcgact ctagcgatat gagcaccctc catcagtctg  98940
tgcggggggc ctgcgaacag ctggtagccg gcgcttttgc cgagcgcaac aacccgcagt  99000
tttggagtac caggacgggg atcgagtcgt ctacgctact ccccccggca gtttacagga  99060
acggcagctt gctcgacaga gactgtgggc agagggaaat tgtgttgact cgcaaacacg  99120
actgtgaatc cccatcgccc gtaccctgga cgctcttccc accacccttg gttttggggc  99180
gcattgactg tatggtctat cttacgtcca ttttcaaaac ttatctaagc atgttaaaca  99240
gagcaatatc tgcctcgtgc gacgcggatg aatctatgaa tgtggacttt ccaatctctg  99300
attatgcatt tttatttacc taaaaataaa gaccataaac gttatttttt ttttcagttt  99360
atttttgttg tttggggtac acacggtatg ggcatcataa aacccctcca tctcaccagc  99420
tagtcgtata aaacatatat tgattccggc acaggctttt cgtccgtagc ggtccaccag  99480
ctatagagag tatcagccac tactttagta catagcggcg cattgaggtg ggctttatta  99540
caacgcaaga cgccagaggg gcagggggtg atgggtcttt tggataaagt ctgtctgtac  99600
cctgcgctgt aaatagcatc aagtatggca ggggtgtttg atttttggcc cagtagcatc  99660
ttggccatca tgtagttggg cagcacccgt gcctggtcaa aggggttgtg gttggtaacg  99720
cacatcagcg tgtttagcgt ccacgtggcg cctatataca tcaaccttcg catctttaga  99780
agggggtga ttgtcttgga tatgttacgc agtatacact caatttgcac aaaaagcgat  99840
gatgtggcgc gctttgtgga gcagttctcc aggtacatct ggatgataca cagggtaaag  99900
tctataaggt cggtcgggcg atacagcacc agcctgtgcg acagtataac cggagccact  99960
ccgagcacgt ttacccggtc ttccagggga gtcaccacaa aaagagagaa ccccttaaag 100020
gcgggcagat ccaagcacga gcgcatgtag gtctcgcagg atatctccga gccctcctgt 100080
ccgtcgaggg tcaacatcag tttctccgac gacgcgtcta ctctcatgtc agtgaccgac 100140
gtggtcgtga aggagggggg taggcctgga acctctctga cttctgtcac gaatcgagga 100200
gtcgcgtgcc agaccagatc gtcgacgata gttgttactg aatcgtcgcc ttttgtgata 100260
gcctctacca tttcgtccac ggtcgcgctg tgggctagcg gatcgatctc ggccctcata 100320
gtagcgctca tcactaggtt tgcccagctg ctcctcgtca gactgggcct cgttgtcgtt 100380
aactggcagg tcccgctttg tggaattgag agccgcgatg gagtttctaa ctctcgccac 100440
aaagagagta gatagctctg taagataagc ctcgagccgg gttttttttga acaccgccac 100500
acacagctcc tcctccgagc ggtacgcctc ctggtgtgta atcaaaaatc caagatgacg 100560
tgccctgagg atggagaaaa agtatggcgc tagcagtagg gagattgagc tgttggagta 100620
ggaaacggac atctcctgac cttggttgtt ggttattctg ttcattttga aacagcgtag 100680
```

caactcctga tcccacagac gagataggcg ctccatatcg gccgtgtacg ccggtatgta 100740
cctagactga aagctattgg ccacgtatcc gtcgtctccc attaggtttc tgatgtcgat 100800
aacctcgtgc ccgagtcctc ccgcgccgga cttggcgcca ctcccgggaa gggccgctga 100860
gctcgcaccg ggctgggtac tcccgtctgc cgccgcctgg gagacgcgca gcagttgttc 100920
gcggaggtgg gtgatctcgc tctctcggtc ccggagctga tccaaaagcc cgctattccc 100980
ggttctcagg tcctctatgg tcttaaacaa gttgtttacg tatccctcca acatcccgtt 101040
aatgccgttg atcacagacg tgcgaaaggc ttcttgcacg ggcatgttgc cgccctgttt 101100
ggttttcccg ctctgcccaa atccgggcag ggaggtgtct acctgcgcgc cgctgagcaa 101160
attggtactc gtctcgttta gatacgatct aacggtctct gttatgtccc ctatgtgccg 101220
catgcttttc atgttgacga tgagtttaac cagccgcgac gcggcggagc tggaatgcag 101280
ctcctctccc tcgcccatga gcttgtccac ggccttggag gcccacccag ggccctgggc 101340
ctcgtccttt ttcctgccca ccaaaatctt gacgggtacc gtgttgagaa gctggcacag 101400
ttttgcgtgt tcccgcaggg cgtggcagtt acacacctcg ccgcagattc gctgtagcgg 101460
tgagtcgaac agcacgctgc cgtccttcca tattggctgc cacaacacca gacactctcc 101520
ccgcttgccc gtggtcgagt ctatcgccac cacctctctg cgggtgtagt ggtagaatat 101580
attcaccctg tcgtagtcca tgatggccac gctggcggtg cacctggcca gctccaccac 101640
ggcctccaac ccctctcgca ggaggctgtt ggccacatac agtttaccgg ccaggtcacg 101700
ctcgtccacg cagctctcca gcgagggaac gtccgtgggc agcttccgcc acagcttagg 101760
gtggacggtc gcgccggggg cgcgcttgag ccgctggagc ggaatcagac ccagacaggc 101820
tatccagtct atgtacttgg caaagctggc ggtgccgtcg ggttcgctgg cggagaaaca 101880
cgcggttata ctgcgaacaa agtccaagag cgacatctgt aacgtgcgat gccacgtggc 101940
aaaaatctgt tcggcgactc gcaccgcttc cccctcgctg tacattccat acgtggcggc 102000
tatttcctcc gcgctcacac cacggctgtc taggtgggtt tgccaatcct tggcgaggtc 102060
ctcgtagcgc gtagcgttga gcgtgttggt cagaatagtc gtctgtatct gtctaatagc 102120
cgcctcagtt gaccgaatgg cgttgtatac tccctgacct tctgtgtacc ctagctcccc 102180
catgaggatc tccttgaaga gcattgtttt gggggttggg tgaataagca cccaaccccc 102240
atcagcggat atttgctcct cctcacccgg actctggagg ccagttgtag cctcaaagcg 102300
cggggtgttt ttccgctcta cctttcgccc tttgtttgca tcagcatagc gaaggcgttt 102360
ttgcttgggt tcgatggagt ccgccgacat tttaccgggg agtagaggga ccgtggatag 102420
acgctgcgag ggctccgagg agaaaataac gccgcctcgc cccgtcgaag attttaatcc 102480
gcagcttttc ccaaacgagg tatatttgaa ctttacgtct atgcacggaa ttcagcccgt 102540
tgtagctcgt atacgagagc tgtcaagaaa aacggtttct gccgctatgg tgccgccgtt 102600
agaatggttt gaaaggctgc caagactgga aactcctcta gatatagagc cgttacatct 102660 accctttcc gtatacctca ttagcgggaa cgccggctcc gggaaaagta cgtgtattca 102720
gacgctaaac gaaaccatgg actgcgtcat tacaggcgcc acccgcgtgg ccgcacaaaa 102780
cgtttacacg aaactttcct cggcattcgc aacccgccac atcaacacta tttttcagga 102840
gtttggattt cggggaaacc acgtccaggc gcagctcgga aagtaccaat actcgtgttc 102900
ctcgagcccg cctcctatcg aggagctgca aaagcgggat atcgtttact attgggaggt 102960
gctcgtagac atcacgcgcc gccttttcga atctacggcg tcccgcggtg agtttgaaaa 103020

-continued catcagggct ctggagcgcc tgctggggcg tgcaccggga tccttgacta ggctcgcctt 103080
ctgcaccaac ggctcgctac cggcgtttac cagaaccaat atcgtcatca tagacgaagc 103140
tggactactt ggacgccatc ttctcaccgt ggttgtttac tgctggtgga tgttgaacgc 103200
ggcttacaaa tcgccgcaat acgccgaggg aaaggttccc gtgatcgtgt gtgtggggtc 103260
gccgacccag acagattcgc tggagtctcg ctttgagcat aaaaacttaa agtgtcacgt 103320
caggtcgagc gagaacgttc taactcatat tataaccaac agaacgattc gtgagtacgt 103380
ttctctatcc accaattggg caatttttat aaacaacaag cggtgccagg agtacgagtt 103440
tggcgagcta atgaaggtgc tagagtacgg gcttccgata acggaggagc acatgcgcct 103500
agtagacacc tttgtggtcc cagaggccta catcaacaac cccgcaaacc ttcccggctg 103560
gacgcgcctg tactcgtccc acaaggaggt gagcgcctac atggcaaaac tgcacgccca 103620
cctgaaagtg tcaggagaaa ggcaattcgt ggtgtttact ctaccagcgt acacgtttgt 103680
gaagacggcg gcattcgatg agtataaaaa gataacccag cagccatctt tgtcgctgga 103740
taagtggctc gcggccaacg cgagcagggt gagtaactac tcccagagca gggaccagga 103800
cgcgggaaag acgcagtgcg agtactactc ggaacacgga gtagtggtgg ccagaacgga 103860
cgtaacctat gtcctcaaca gtcaggtgtc ggttactacg cgcatgcgca agtttgtgtt 103920
tgggttcagc ggcacgtttg aaacgtttga tgccgtgctc aaggacgacg cgtttatcaa 103980
gactcagggg gagacgtccg tggagtacgc ctaccgcttt ttgtcgaccc tgctcttcag 104040
cggcatgata aacttttaca actttttaaa gcgaccaggg ctggacgagg ggagggtccg 104100
ggaggcgtac aggcgcatgg ccgctctcac cgccaagctg attccaggcg cgtctgtgtt 104160
agagagcgcg tgcgataatc ccagcggggc gccgctaaac tttaggggtt tgaccgaccc 104220
accaggcttt acgggcggaa ctacaaacga ctgggatgac gacaacgacg tggtgttcgc 104280
ggccctgaac gaaggagcta tagacatgtt atactgcaac tacgagtttg tgagaccaga 104340
gaccacgcag gaggtttact cgcagtttct gatgctcaag actatgtttg tgggtagata 104400
ctccatattc atggacctgt ttggtgggga ctttgaatct tccccctttg acacgtttgt 104460
agataatata agctataagg ggtgtgagat ttttgtgggc agtatgcgcg ggggcgtctc 104520
ttcgatcgcc ctccagacag acagctacac gcttatgggg tacacgagcg ccccggtcta 104580
cccgtttgtg gaggagctgg cgcgcagaaa gctacacgaa ggaatcgcgg aactctttgg 104640
ggccatgaac atgcctcgca tggttctgcg cgaccagcac gggttcatgt cggtgctgaa 104700
cgtaaacctg agcgagtttg tggagtcggt ggacgacgtg gagctggaca tggccaccgc 104760
ggtagactat gggctgagct ccaagctcgc catgactatt gccagatcgc aagggctgag 104820
cttagacaag gtggccatat gctttccccg caacaacctg agaattaaca gcgtgtatgt 104880
ggccatgtca cgcaccgtgt cgtcaaggtt tctacggatg aacctaaacc cgctgaggga 104940
acgtcacgag cgcgacactg tcataagcga gcatatatta gcagccctga gggacagaga 105000
cgtccagatc gtgtattgag gtcaggcacg caagagtcga caaccgaccg cgtgcgtggt 105060
ttgcgccaat ggaaacgtgt agtcctcccg ttacgtttat tacctatgct ctgtatggaa 105120
taaaaacttc tcctgcttgg accctcccaa actttgaaca ggttatttgt agctgcgatt 105180
gggggtacag actgatcgcc gtgggggcag agtctaaatg cgatgtaaca ccgcagggca 105240
gcttcgtgat tcagcacggc gcctcaataa cggcgttagt gttggactgt ggcgtagagt 105300
tttgctcgta cgcgtttact cacgctgaga acactagggt ccccctgacc accgaggacg 105360
ggtcggtact ggtggttccc ttctgcggct gggtctgcgt aggccgggac aggtgcttgc 105420

```
gtagcatgtc cggcggggtc cttactataa gctgggatac gagccagaca gcttacatta 105480
gcgttgccgt ctatcgcccg cctaccttac agtgtcacgc cctagactgt acccgtgcag 105540
aaactaccgt atgttccacc gctgccataa ccgacgcctc cgagtcagat cccttatacg 105600
ccgaccagga gggggaccag acgcaagatc aagatggagg tcacgatttt ttggaaacta 105660
ttctgatgga gtctgatctc tacggtacca acggagcctc ggcgttgctg gagccgtgtt 105720
ttccctgcct ttccaacaac gactgacgac ggaccactcg acaagaaaac aattcctcta 105780
accccaccct accccattta aaaaatgaca ataaaaaaga gtttatgtaa acagataacg 105840
tttatttggt ttttattgat tgcttggcgg gttttttaca tgtgcctgag cgtgtttctt 105900
ctcggcctcg gtcgtccctg gtgcggctgt gtctgcctgg ctgctgtgga ttgggttaca 105960
gattgccgcc tctgagcgtg gttggcctcg ccgcggctgc cgccgcgctg ggtctgtcct 106020
tcgccgcggg gattgcgaac gtcaccacgc ggtcgttgag acgaccgcaa cgcacttccc 106080
atggccgcgt tcactggcgt gtctggccga ccgattgatt ttcttcgctg tgctgccatg 106140
gccagggccc cgagcgttcc agaaggcctc tccgagaggg ccagctgtcc gtcgccaccc 106200
gccccggcgt gtgggtcgta atgaggcaca gagttgcgcc tagacgacag agatctgtgc 106260
ctgggtcgcg ccgacacctc cggttgctgt ctggaggaag ccgtgtgcgt tggcgttgta 106320
gcggcggcaa gcttggcggc ggcccggctg ttcctttcta ggaacctgcg atagtcgtct 106380
gcggtcgcag cgcgtcctcg cccaaacacg tccatcctac gcaaggacgg tggttggttt 106440
gtatcggata gagagaagcg cgccgcctag acacactcac ttggcttgcg cgtcggcttc 106500
tataacgtta tccctgtgga ggtacacttt atccaccgca gaaaattcgt aaatgtacac 106560
gggaaccacc ggatgtgtac gtccgtccga cgatcgcgtg taatactttc ttggttttcg 106620
cgcttgaatt acagactgga gctggtctct aatctgcttg gcgtgagctc tgcgacacag 106680
gacgaacatc tgcaggcttt tattgcttcg catgacccgc tccgaggagg ggcagtgacg 106740
cttcctgcgg cgcgtcgagc ttgcgctgga gaacgaggag gttttggtgc acgcaatggt 106800
gaatttagcc agcgtcacgc gcaggtcttt tctaatggtg tccgtcagct gacggcggcc 106860
gagttcgtca atggaggata ccataaacat ggtgtcaaag ccgacatagt tggcgttctc 106920
tccatccggg gcgagaccct tgatggattc cacggaaagg tcgggtacgc aaagcggggt 106980
tggggtggaa gtggtagtgc aagttgtgcc cgtgggggct ggtggccgca tttctgtaag 107040
gtggtcagct actggcccgg tgaccacctc tactggccac ccccacccac taagcacggt 107100
caatgcggac tccatttact gtcgcggtta ggaaccggta ccaacctgtg caggtctagc 107160
ttatgtagcc accgggtatg ggtaggcgtt gttttcaccg taacttactc aatctgccag 107220
tctacgggct ttctacctgt cttcgtgagg tacgcattgg cctccaaaaa gtgcgggcag 107280
tctctgaaat tcacacgaga caggggcgaa gggtgtccgt aggtgagcac caggtggtgt 107340
tgtctgttcg gggagcagga cttctgggcg tgggcgcccc acagcatgaa gacgagccct 107400
tgggacgtgg tacacagcct gtcgataacc gccctgacca gcctgtgcca ccccagagtg 107460
gcgtgtgatc caggttttcc gcgtgcgacc gtcagcgtgg tgttgatgag aagcactccc 107520
tgttccgccc acctttccaa aaacccgtgc atgggatgcc gaaacgacgg gtacgatttc 107580
tgaacggccg agtagatgtt gcgtaagctg ggaggcacgg gtaccccctt ccggacgcta 107640
aaggctaacc cgtgcgcctg gcccggcgcg tggtacggat cctggcccac gataactaca 107700
cgcaccttct cggggggcga aaagcgcgtc caggcaaaaa tgtcttcttt tggggggaag 107760
```

```
acttcttcgc tagcgcaccg cagtttgtat tcgttgagaa gaagtctcac gtacggctgt 107820
tgcatttccc tttctagaat gggacgccat gagggggcta tattaaattc ccgctcgacg 107880
tcttcccacg agctctggca gctggtcgta aagagtgggt gtgtggatac gctggtgttg 107940
atgagagcca ccccctgcgg tagcccacag ggtctccttc gtttcggtgg gggagctcct 108000
gtctcacctg gcgccgggga gacgacacac gccgggccaa tttcgcttgt gggggtagaa 108060
ctatttgatc cgttttcctc tggtgttgtc tcgggtatgt ttacatgaga tgcctcggtc 108120
tcgtgatcac aggcgctact catctttagg tcttttgaag attggcgtag taggaagccg 108180
gtatacaact gtcctttaat ccttcggcta tgtccttaga ctttggcggc gacaaaaaga 108240
aaggcccagt aaagcagccc aggggaggcg gaccgagaat ctcgtctgga gatgactgag 108300
attgagaaag ggaatcatct aaagcgaaaa gcagcttctc tttaaagtct tgaggcatgt 108360
ttccatttgt gacgtcttca gccaatccct gaacgactgc aaacggatta acccaaaccg 108420
gttttggagg tgtgtcaacc cacagaatag cttcaggggg gttgcagtgt gcctttacca 108480
taattccggt cgttcggttg agcaagtttt tgatgttggg agatgtaaac agttgacctt 108540
tcattatcgg accgctaccg cagctggcct ctaaaatacg cttgggctct cccggtcccc 108600
atgtgaaatc tagccttgtt gctttgacga gcttggtagt tactatccat gctagcatat 108660
agaccagttc gagcctagcc cagcagcgca taaaccgcct cattctttcg ggagtcacga 108720
aactaagtgg cggttggaat tctgtacatt ggtttatgta cgggcttttt tgccagacac 108780
acccaattag gatttgatac atcgggttgt ttgcgttaat ataaacacat acaagtttac 108840
gatcaggttt agtaccgact ctatatgtaa agcgtgtata aaactatgtt atgagggtca 108900
gaggttagat ccaagcaacc ctttgtttca caattcaata gaatcataaa tttaactttg 108960
gcgctagcgc taacgctagg gctagcgcta acgctagggc tagcgctaac gctagggcta 109020
gcaatgaggc tggccaccag caccggaagc ttgtcatatt tgtgagcctg gagcagccat 109080
tttccaaaat ctgtactgtc atgtttcttg acctttggat gtcatatctg tggactggag 109140
gcagccattt tccaacttgt gcatatgcaa cgcccaggaa gctgtaatat tcccaccagg 109200
aagcggtcat atgcccagga cgagcaaggc tgcggggggc ttcgatctag aggaggaggt 109260
cttttggcag cggaccgcgg ataggtaaaa ggtaagacct ttcaatggta gatacaccat 109320
tagaccgcgc ggggggcagt cgtccaaggg gggcttgcag tatatttaag tgggctcata 109380
aaaaatgtat gcgatcgttc cgcaaagtca ctttgttttt ttgtttggta gaaagccatt 109440
gcattagtgc ggcgtgaaag tgtacccaat taacaagatt ggagaacaac aaactgtcga 109500
cgggacagga tatgccaaac atcaatagaa gcttggatcg gtgccaactg tgacgctagc 109560
caaaattcag ctaagttgca tttacagttg actttgggag ggggcgtagc atgaatgggg 109620
caacatttca tatttcttag tgcatgcata ttatataccc ccaattagcc cccaattggc 109680
acatggtaat ataccgccat ggcgccgtgc ttggtattgg tggtgatgtt cacataaaca 109740
gccagctggg ggtgttttgt ttaggtgggc ttttgtggta tataggtatg cacgcgctgg 109800
acattagggg gcgccttatt aatacgatgt ggaaagccca gctgcaatag catcagtaaa 109860
cagttttcca ttctaaaaat atctatggga ttatgctatg cactgtgggt ttaagattgg 109920
caaaagatct cccccatgca aatgttttag ggtaggctgt acatggaata ggtaaacgct 109980
tgggggtctt ctaactcggt tgcattaaag gggtcaaggc tttggtttgg ttttaaggcg 110040
attattacag catcgtgttt caaggcgctg tttgggaaaa ggagatttct gcaggtgcag 110100
tggttccccc gggccttata tcttgcagct ttagaaatct gctttctcaa acggaactgt 110160
```

```
gtaatcgtca taatgctgca gagcaattaa acccaaagat atctattttt aaagctcccc 110220
ctttcgcggt tgcccccacc cacacccctg cataggtttt tgtaataggt tccatatacc 110280
cagggcggcg actattaaca ctctctcaga ctgatagtaa actttttaaa aaaacagctt 110340
tatttaaaaa tgggggtaca aaactttaca ggtgtggtaa aaaagttatt ggtttctccg 110400
gtatctttgg cagttgtggg gacatcgcat ctcctctggt tcagcgggct gtgtctgaaa 110460
cgcccgttgc aggtcacgga cacgctgacc cccttgtcta atcaatgggc tggtggacgc 110520
tatgtctggg tagggcaccg ggggcacact ctgccgtctc ggtctcagaa gcacattgcc 110580
gcgccgccta gcggattcat cctcagttcg tctgcgcacg tgttgtgcga aacgcccacc 110640
aaatagccct gctccctcag agcttcggtc gactaaaaca accgcaacag agaagggctc 110700
tgttgcgcgg gggccagcac ccaggcgact ggggcccgcg gcttcgctcg tggagctgtc 110760
tcgcggtgcc agtgccataa acctgcgcgc aaactcccgc aggctgcatc taggccgcat 110820
gggccgctca cccgcagaac tgccagatgg tgcaacgggt tggtcccggg ggggttcttc 110880
agactcaggc gtgagttcag acaccaggca gattattgca gagtttgagc ttgtatgtgg 110940
ggatgcgggc gccgcctctt cctcgtcggg gataagcact ggctgatcgg tggtattcag 111000
gctgccgcta acatcggcag gttcggtgtc cccatcgctg tccagagtta agtctataat 111060
ttccccgttg tcccccccgt tggtgcggga gttggttctg ggctggcgtc ttctcagcct 111120
ggcgctgcgc cgactagctg gtcctggggc agccggcctt ctcccccgtc tgcgccctct 111180
ggtgggtggc cccggtcgtg cacgtgctgg tctggagtct tcttggcggg gtgcctgagc 111240
agaactattg tctgtgctgg tttcatcgct cgtatcttct gggtcggtta ggttgttggg 111300
gtcaacctct atgtcgctgt ctgtttcttc ctcagacgaa gagctcgatg aagaggagtc 111360
aatgtattct accccctcttc cgcgggctat tggcaagatc ggtctcgacg ctacgcacag 111420
ttctgcttgg acgatgagat ccgtgacaaa gggcacagtg tcttcgtgaa acatcggcca 111480
aaactggcga gtgagctctt cctcgttaca gccatgctcg cacagtgtat ccataacaat 111540
gttccgcatc accaacgcta gctctggggt ctcgaatagc tggtcgagcc tttcgaccag 111600
ccagtccacc agtggctgca gtcggggagc cccggcagtc ccattagcgt tgaggggcac 111660
aaatgccatg ggtccgttcc acgcagagat attggcggga gcatcgccag aatccacggc 111720
caaaaattgc ccctcaaaac tgtcttcgtc ttcttcgctg tcatagtcaa agtccacgct 111780
cacctttgtt tctttaaact cgctgtcgct ctcgatggtg tgcaccacag attcgaccgg 111840
cactttgcaa agtggacagg tcgggttttg tcgtatccag cgcgtaatac acacgtagca 111900
gaacgcatgt aggcatggaa gcgccataga gtagttgctg gggtcctcca ggcagatcgg 111960
gcatcgctct gcaacagttg ccatggtggc agcgatttgg aagagtttcc aaatgaaaag 112020
gctgtatcag ctgttaaaac caggcttggt gccattcata tatctggctg caaaactcac 112080
gtggctgtgc acgcccattc aacaccaccc atatgcttaa aattagcatc ttgaacgcat 112140
gccaaatttg cacgggatac ggttccaatt tatcgaacat ctgtatctca ggggtatagc 112200
atggggaccc gtttgaatgc gattggtggg cgggaaaccc ccgggtgagc acacggtggc 112260
gctctattct ctgcgtgtgt actacgctgc tttttggggt tgcatagtta agggtttggc 112320
catcggtgcc atttaacaca aaacggtttg ccctagcccc ctgccctagc cccctgccct 112380
agccccctgc cctagccccc tgccctagcc ccctgcccta gccccctgcc ctagccccct 112440
gccctagccc cctgccctag ccccctgccc tagccctatt aaactccagt ttatctgctc 112500
```

taggggggat gccgctattt accaccacac cccccccccca attggcctat tagcacacct 112560
aacctcctga gtgtgagcgc ggtatagaca agctgagcat atagtgggga gaaactaatg 112620
gcagtagtgt tactaggggt cacagactat atatcacaca aatggacaca ttgagtcctt 112680
tctactctcc tcctcggacc agcttagaaa tgctataacc gtggaatagt accagtagta 112740
actagtttac tatatttccc ccattttccc cctccccaac catctccggc cacggtgttg 112800
agccacttcc caccacccgc gtcccactcc cttgtcttta cagacccact ctggctcttc 112860
tgaacccagt ctctctctac ccgggccata tctggtcaag ggtcacgggc ccgcgcccga 112920
gagagagcct ggcccccccca gcccgcgtct caccccccgca tttgaatagg ggggcgtggt 112980
ctaagggggg gggtcaaagt gacgtcactt cctgtgacgt caccggaagg ggcgtggccg 113040
gaagcggaag gggaggagtc cggtagtgac gtaggcggta gtgacgtagc ggaaggggag 113100
gagcaggaag gggaggagca ggaaggggag gagcaggaag gggaggagca ggaaggggag 113160
gagcaggaag gggaggagca ggaaggggag gagcaggaag gggaggagca ggaaggggag 113220
gagcaggaag gggaggagca ggaaggggag gagcaggaag gggaggagca ggaaggggag 113280
gagcaggaag gggaggagca ggaaggggag gagcaggaag gggaggagca ggaaggggag 113340
gagcaggaac catcaacccg cccatcaacc cgcccatcaa cccgcccatc aacccgccca 113400
tcaacccgcc catcaacccg cccatcaacc cgcccatcaa cccgcccatc aacccgccca 113460
tcaacccgcc catcaacccg cccatcaacc cgcccatcaa cccgcccatc aacccgccca 113520
tcaacccgcc catcaacccg cccatcaacc cgcccatcaa cccgcccatc aacccgccca 113580
tcaacccgcc catcaacccg cccatcaacc cgcccatcaa cccgcccatc aacccgccca 113640
tcaacccgcc catcaacccg cccatcaacc cgcccatcaa cccgcccatc aacccgccca 113700
tcaacccgcc catcaacccg cccatcaacc cgcccatcaa cccgcccatc aacccgccca 113760
tcaacccgcc catcaacccg cccatcaacc cgcccagtaa acaaagacca cgcggtcaat 113820
caaaatttaa aaaaaacttt attaaaaaca accactcagc gataggggaa agcctggaag 113880
tgcccaccga ttgggcagac atgtgagcaa taaggaacgt gggctgctag atacaacgcc 113940
cccttcgttc ctcacatgtc gtccggggag ggccttgtct tcgcgtcagc agagggcggg 114000
gcggggttca gcgtcagcgg atggaggcgg gagtctaggc ggagtctgcg ttgtgctggg 114060
cggacacata gttgtggatg tactgatttt tcttgttttc ggccgcaggg aggcgctcca 114120
tcgtgttcag gagaggtacg gattgcacca gtctcctccg tcctcgtcgt ccgacaccac 114180
ctcgatcttg atgggagcgc ggcggagggc ctgggccacg ccggggctcg ggccggggtg 114240
ctcaaccacc agctccacat cgccggcccc gtcgatctcg agctcgtcgt cgggctccgg 114300
caggcacagc tccgtggccc ccatgtgcag gaccgaggtg gagcgagagc cgaacccggg 114360
ctcccagtcg acccgcgggg ctcggcggcg gggagcctcg gtgatgggca gcaccagggg 114420
ctcggcctcg gcgtcgggct ccagcagcgc cacccggcag aactcgctca gcagctcggg 114480
gatcagaagc tccgagggct ccacggcccc agcgccgcgc cggccgcagg cgaggtacac 114540
ggggcgcagc caggccccga gtccccatcg gttggccgcg cggtggctct gcgcggcgcc 114600
ctcctcaaag tccgggtcgt ggaacccgag gccctcggcc tgggcccgca tgtccttgca 114660
gccgtcgtag tcgggcagga cgcgctggcg gtactccctc ggagccaggg gaacgcgggt 114720
gcgctcgccg gcgcgagtgt ccaccgtgta ggccacgttg gaggagcggc acagcctcag 114780
gggcgcagag tccgggtaca ggcgcgcgaa cgcggcctcg gccctcgcga acagtccggg 114840
cccgaagagg gtgctggagg tgaggaccgc gcggctgagg tggcgctccc ggggccagcg 114900

```
cacggcgcag gcgacccgcg gagtcagggc ggcccgcatg tagatgtggt actggctgat 114960
cgcgggaccg tcctggggcc aatcctcggt ggagaccgcg tccagcacca ggagcttgcg 115020
cctggcggag cccaggcgca ggcagaggta ctcgacgcag ccggtgaagg ccaggtcccc 115080
ggtcgacagc agcaggaccc cctgggcgtt gagggccgag acgtccgggg ccccggtcca 115140
gttgccggcc caggcgtggg accgcttggt gaggatgcgg ttccccaggg ccgccagcag 115200
cgccgagagt ccccccttga ggtcggacca gaggggctcg cgccgagagc cgccggggcg 115260
ggaggccggg agtccgccca gcaggtcctc gtcctggagc ggggagtaga ggaccaccac 115320
cttcacgtcc tcggggtcgg ggatctggtg catccaggcg gccctccgtc tcagcgggcc 115380
gctggccgcc agctccccga agcgcgcgcc gtcccgggcc ggggggccgc tgcagcgggc 115440
cgcgatggtg gccagggcct ggggatcgaa ggtgagcgcc gggcgccagg cctcggggaa 115500
cagctggttg tcgatgagct ccgccaccag ctcgggggga cagtaggccg cgcaagccgc 115560
gtcgctgggc cgcggagtgt ggcagtctcc gcggggaacg cgcctgaatc cgccccgacg 115620
gtcggggccc tcggctggca tgggtcccag ggcccgggga gcctggtggc ccggggtggc 115680
caccctgcgc ttgggggccg gagggctgtc gaccggcccc gagggatcgt acccccgggc 115740
ggacgaggag aaggaggccg aggctccggc ctgggccgcc ggctccaggg gctcggagcg 115800
ccgcttgccg ctcttgcccc tggggcgccc gtggatggca cggtcgtccg aggaggagcc 115860
gggcatcgcc tcctggctga ggtgggccgg ggaggcggcc gcctgagggg agcgggcctt 115920
ctgcggctgg tgctgctgcc cccgggagcg ggcgtttgtc tgggtggccc ggcagcaggt 115980
ggcggtcgta gccccggcgc ctccgccgct ctgggagtgc tggggggact gggagtggga 116040
cgaggggacc gtcgcggact gcttcccggg gacggtgggc cacaggggcg gcagggtctg 116100
aaggctcccc tccgcggccg cggagccgga gaagggctcg ccgccgggcg aggacgatga 116160
gggctgctgg gaccgagtcg gtggggccag cagggacacg gcctccccca acatcccccc 116220
gaccaggctg ggtatgctga acacggcctg ggtgacggtc caggccgagg cccgggcccg 116280
ggccccctcg gcgttgtagc gcaccagcgg cgccacggtc cgggccacca ccagaacggc 116340
gcgcaccgcg aggcgcagct cgtcggagcc caggcggtgg gtagggtcag agtccccgag 116400
gagcctggcc cgctcgacca ggtccctgag ttcgtagagg gagagggccg ccgtctccag 116460
cccggccggg ttggagcaca gcgcctcggg agggcaggcg ggagagggga tctcgctggg 116520
gtccagtccg gggacggcgg acgccccgcc gcggaggcgc aggagggcct cgaagacggc 116580
ctggcaggcc agcacgcagg cgtccccgag ctccctgagt ctgaaggcgg acggcctggg 116640
cgccctggtc cccggagcgg ccgcggccgc ggcagccttg cgtcggggcc cgagggccgc 116700
gcagacccgg gtgtacgctt cgcggacgcg gaccgagggc gccggggcct cgggctgttg 116760
ctggctggcc gcggcagcgg cggcctgggc cgggtagccg gccacggcgg cgagtgagtc 116820
cggcctcccc gcctcgtctc tcgggtaggc catgtccgcg taggcgcgcc ggaggctctg 116880
gaggatgaag ctcttctgag tgcgatcgta gcggcggctc atggccaccg aggcggccgc 116940
gtgtggcagg gcccagagcg cgttcccggc cgccatggcg tccccgatgt ggggcagggg 117000
gttggccacg ctcccggtga tgaaggaccc gtgtccgcgc ggagcgtgga tgaacttctg 117060
gcagaactgc gccaggttct ggtcttgccc gctgagctta gagttctgca gccaggacat 117120
ggcttcgcgg ctctcgaaca ccatgcggac cagagcgttg tactgcttgg tggagtcccc 117180
catctccggc acgaagaccg gtactggggc ctgcgcctcg gcgtagcgcg aggcggccag 117240
```

```
gactatctcg gggtcgtccc acagcccgtc ccgcgagtcc ccggtccccc cgtatcgcac 117300
cctccccatc ggtggtggat ccgacccggg ccaggggtcc ccggacgggg tgagaagcgg 117360
ctcgcgctgg tagacgcccg gggcgcacga agccgccgcc ggggccgatg ctgctgctgc 117420
cgccgccccg gtagcctggg atgagttcat gtccagcaag tcccacacgg ccgtctgcgg 117480
ggcctcctcg gccggtgcct gggtctgggt ctggggtatg ggtctggggt tggcccgctt 117540
gcgcttcgac gctcccgcca gagccgattt cggacgctgg tccttgggga gccggtgagg 117600
gctccggccc ggcggagaag ccatccccgc gggcggttcg ggcctctcca gcgtcttggc 117660
cagattggcc tcgcggacgc cctccaggta ctctaaaatg cgagcccccg gagggaggag 117720
gcctcctccc gggcggctgg gagcgggcgc cgaagctgga gccggagcgg gtgcgccggg 117780
ggaagcggcg ccggagcggc agctcttcgg ggtggcggcc ccagcggccg ggcgatcccc 117840
tccggaggac ggcccgggag agccggcggc cgacggggtt ttcgcggcgt tctgcgagtg 117900
ccgcgggcga ggggtctcct cctcgccgcc ttcgtcgctg tcgctgtcgt cggaggacga 117960
cgaagaggag ctactcgccc cggcaccatc cgcctggtcg tcctcgtcca tcgaggacga 118020
ggacgaggac gacgatgaga tggagatgct ccggacccgg ggtgccgggg accctccgcc 118080
cggggaggcc gaggatggaa actcgggctg cggggacccc gggcaggtct cggtatcgct 118140
gtcgagggcg accgggtcgg ccgcgtcccc accgccgggt gatgaggagc ccgtggcccg 118200
gcgaccgttc cccggggcca cggaggagtg gaccatcttc agcatcgcgg cgagccccgg 118260
agccgggctg ggtgccgggg acgccggctg ggcggcagcc gccggggtag gaggaccgcc 118320
gctgccggcg gccgagggcg accgcttcgc cttccctccg cggggctcgg gagtcggaga 118380
cggcggaggg atgaccaccg ccggggtgga gagcggagcg tcgtccaccc cgaacatgtt 118440
ctggctgccg tacagcaggt cgggcgcggc gggctgggtg aacccctctt cggccgcgct 118500
ggctgcgcgg atgagggggt cctcgccgaa gtcgttgctc tcgatgaagt cgtagaggtc 118560
cggggcgaag tcgctgcgct ggctggccat ggcgtgctag ctccggcttc ggggtcgaga 118620
accaaccgca cgagaaggct cgctcggaag accgagaagg gaaggttggc gggtggccgg 118680
tggcggggtt ccgcggcggg cgctcggacg acgggcgccg cttctctacc ctggaaaagc 118740
agaggcggaa aagatgttga gttggagcgg agccgaatgg taaaagggaa cgcgggcggc 118800
ctgggcctct cccccgcttg ggtggtaacc acgccccgtc agatatccag gcttccgcgc 118860
cgagctccgc cgaggcagaa gccgcccggg tctgcccggg gaaggtatag ccttcgccgg 118920
cttcgaggta agtatcccca ccgcgcttcg accgctaggt cgaagcgggc ctcggagcca 118980
ccccctcggg acatcgttgt tggaggggtt ccatggcctt tttggcactc gccccgttct 119040
ctaacgctct ccccgggaga agaagcagat cgaagccggt cgtgtccccg gggagctctt 119100
acctccgcaa gccgaagaag gagtgccaag agcgggtaag ctttccaaga tgcgatcgat 119160
agtcctcgaa ggctggctgg tccagtgagc tgaaaggctc tctagtccgc gatgctacga 119220
tgggtaagca acaggtgctt tatactacta cgatggagtt ttgccttccc cctagtggga 119280
gtggccagcc cacactatcg attgtgattg gccgttgatg atgggcggtg ggcgtgtagc 119340
ggctctagcc tatggggccc ggtcccgcgc tttgcatttg catgcgcttt tcgcctcccc 119400
cccgctccaa ccaattagaa cccgtgtgtc gtttctaatt tgcgtatgtc tcctcccagg 119460
gaagcgcgtc gcgccaacgg gatgccgaat agcgcctctc atatgcataa aggtgaacgc 119520
ccctggacgc catgacacct cgatgcacat ctcatctgca tgcgtctcct ccccgggaag 119580
cgcgtcgcgc caacggggtt cgtgatcgcg ccgctcatat gcataaagac gaacgcccct 119640
```

ggacgccatg acacttcctg gtaaatctca tctgcatact gacgagcttg ggaggagccg 119700
agggagtggg cttcaaaagt aatttcaata aaaatggcga gtgcgatatt tccgaccgaa 119760
acggaaatga tgtaaaaaaa gtgggagggg gagggggaaa ggtgggcgtg aacgcgtctc 119820
tgtatttccc ggttgaatct cattaaagtt ataccaatta aaacatgtat cgctatcgcg 119880
tgtattttgg gcgggatgat atctacgtgt gctgatttac atattatctc acaaggagcc 119940
aggcggtggc gctgtttcaa aacacggttt tacatgcgcc ttcatacacg tccgcacgag 120000
ggcgccctcg tgtgttaacc ctcacagatg cggttactac atctaaccgc ttcgtggcgc 120060
catgtagtcc attaacatgt gacgccacga tgtgacgcta tacacacacg cgccggcccc 120120
accccatcga cgtaacacgg cgcccctccc aatattcaaa tgacatgagg gggcgtggct 120180
tgagacagct gtgtgggggg agatgcccgg tacccacctt ccacccacgt ccacaccccc 120240
ccccatgccc cgcccacggt tttttttgag agccgaccgc acacacgcac aatcgttgta 120300
ccgtgtaaac ggtttcgatc cgttacattt tcccacgggt accgggtcat acataaaata 120360
cctaaagcgc ccccatccat acactccggg agatacacat cgatgtttca ctttttatcg 120420
ttacacacta ccccccgtta tcgatttttt ttgccacgcg tgtacagagg tgcccctccc 120480
cccagtatgg ataagggggg ggtgtcaata aaatttttgc gcgatgaaac ctaggggagg 120540
gtgcacggtt attgagggtg gggggggggc aaaaattttt gagcgcaaca gatagcatgg 120600
ctgggttacg gtgtgcggct atgggggggg gcgctaaaat acggttaccc ggcacatact 120660
ctcgtcgagg tatgggccgg gtcacggtac ccactagttg gcacggtgcc atgcgcgctc 120720
ccgagacggg gggtgggggc gtggaacgga taagaagtcc gaacacgtag tgttcgcact 120780
ttgttgcaat aattattatt ataacttatt ggtgattggt gcgaacgggc ctctgggcca 120840
atcagggtgc aggatttgtg ccacgggacg cgtttccaat tttcgtccga taatcgataa 120900
tctgtcgatt gcaaaggcgt ggtgatgtac cggtatccgc ctccctaagg gcggagaata 120960
tggaactcgt gtatatatta ccctgcggat caccaggtgt gggtacacac gcagcttgaa 121020
gcttagagcc ttttaacgtg catccacacc acggaaaaca gggcaaggta agtggtatcg 121080
cgagtgggtc tgcccatgag atcggtggtg gtcggtggtc ggtggtcggt ggtcggtggt 121140
cggtggtcgg tggtcggtgg tcggtggtcg gtggtcggtg gtcggtggtc ggtggtcggt 121200
ggtcggtggt cggtggtcgg cccatggggg agggcccact aattgatggg tgtggttata 121260
atgtttttcc attcgttatc tccagcaacc ccagctccgg cgaccccggc ccagcccagc 121320
tccggcgacc ccggcccagc ccagctccgg cgaccccggc ccagccatgc cccacggaca 121380
gccgtgcggg gcgtgcgacg gatcctgccg catggcccag cgggggacgc cgtccaccag 121440
ccccctcatc ccgtccctga ccccctcgcc cccggcgggg gacccgtccc cacgctccag 121500
ccagcgcatc gacgccgtgc gcgtgcccgc gaggctcccc ggcggctcgg accatccgga 121560
atacggaatg ccgctatccc cgcgggccct gcgcccgtac ctggcccggg ggccaggggc 121620
gttctgcgcc ccgccgtggc gccccgatgt gaaccgcctc gcgggggacg tcaaccgctt 121680
gttcaggggg atatccacct cctcgatcca cgtgaccgag gactcgcgca ccctgcgcag 121740
ggcgctgctg gatttttacg ccatggggta cacgcacacg cgccccacac tcgagtgctg 121800
gcagtccctc ctgcagctgc tgcccgagca gagcttcccg ctgcgcgcca cgctgcgggc 121860
actgaactcc gaggaccggt acgagcagcg gttcctggag ccgccgagcg accccccgaa 121920
taccctcttt ggggaggagt gtgacgtgag cggcgacgag tcgccctccg aggaggagga 121980

```
agaagacgag gccagcgggg agagcagcgt ttcggagttt agccccgagg aggagactgc 122040
cagcagcgag tacgatagct tttcggacgt gggggaggac gactcgagct gcactggaaa 122100
gtggtctagc agcgaaagcg aaagcgatag cgagtccgat gcccccacca acaaccacca 122160
ccctacaacc cgcgctagcg ctgccaaaaa gcgccgcaag cgccaacccc ccaagggtga 122220
gcgtcccacc aaaagcgctc gccggtgagt cggataggtg tacgcatgca cgctttccaa 122280
aacacaccaa cgctacgttc taaccagtaa aaccaccact cgttgtcacc ccgatgaacc 122340
gcaaccccaa tacacacctt ttgacctctc cctccacacc tccaaaaccc actcgccaac 122400
ccacccatac cacccaaaac gagtaaccaa taaaaacatc gttgacggca ctctctgtag 122460
tttggcttcg tttatatggt tgtttttttcc cctcttgctt ggctgggatg aatagttggg 122520
tgctccgagc cccggctggg ggagcggtag cgaaaaaacg gttgttgttt agcgttgctc 122580
atccacgcga ctcggggcga ggtcgggggga aagcgtgaat gacagcgcca tcacacccaa 122640
tccccgacgg ctattggaga gataacaaca cccacgcaga gggagggaga gctatgggaa 122700
gggtggggtg ggggggagga ggaacatcta tagctaccta aaccacgcca gcaggcgtgt 122760
gtgtgttccc gcgattccac gccccgccga ggaaatacag ctcgcggagg gccgcgcgca 122820
atcagtgcgc ccgatctccc ggccactgaa ccacaacggc atggacggcg cgtacggcca 122880
cgtccacaac ggctccccga tggccgtcga cggcgaggag tccggagcgg ggacggggac 122940
gggggcgggc gcggacgggc tatacccgac cagcacggac accgcggcgc acgcggtctc 123000
gctgccgcgc tccgtggggg actttgccgc ggtcgtgcgc gccgtgtcgg cggaggcagc 123060
ggacgcgctc cggagcggcg ccgggccgcc cgcggaggcc tggccgcgcg tgtaccgcat 123120
gttctgcgac atgtttggtc gctacgcggc cagccccatg cccgtcttcc actcggcgga 123180
cccgctgcgc cgcgccgtgg ggcggtacct cgtggatctc ggcgcggcgc cggtggagac 123240
ccacgccgag ctcagcggcc gcatgctctt ctgcgcgtac tggtgctgcc tgggacacgc 123300
gttcgcctgc tcgcgcccgc agatgtacga gcgcgcgtgt gcgcggtttt tcgagacccg 123360
gctcgggatc ggggagacgc cgccggcgga cgcagagcgc tactgggccg cgctactcaa 123420
catggcgggc gccgagcccg agctgttccc ccgccacgca gccgccgcgg cgtacctgcg 123480
cgcccgcggc cgcaagctcc ctctccagct gccctcggcc catcggaccg ccaaaacggt 123540
ggccgtgacc ggccaatcga taaacttttg aaaaatatac tcactatata ctaaacccca 123600
attccgcgag tctgcccctg tttgtgtttc cgtctctcta tccatttccc ccaccaatac 123660
ctcaactatc gagcgggcgt ggggacccgg ggagagacca ccaggcctcg ccggttttct 123720
ctctctccgt tggggggggg atggtaggga ttggtgggtg aggtggttgt ggtagtcatt 123780
gtgagtaaac caacgcagac tgctactggg caaaaaaaca aaggggaagg ccgagcgggg 123840
gagagcggta ggggaggccg agcgggggag agcggtaggg gaggccgagc gggggagagc 123900
ggtaggggag gccgagcggg ggagagcggt aggggaggcc gagcgggggga gagcggtagg 123960
ggaggccgag cgggggagag cggtagggga ggccgagcgg gggagagcgg taggggaggc 124020
cgagcggggg agagcggtag gggaggccga gcgggggaga gcggtagggg aggccgagcg 124080
ggggagagcg gtaggggagg ccgagcgggg gagagcggta ggggaggccg agcgggggag 124140
agcggtaggg gaggccgagc gggggagagc ggtaggggaa acgccgcctg ggatgagtgg 124200
gaccgagtag tgtgtgatag gcactagagg gcgccagcgt acaggggagt gtacccacca 124260
aaactccaac accacggaaa atatggttta cgttttttta ttaaaaaagc tgaaacgctc 124320
aataccacag acttttcaga gatacagatt atttacaccg ttccaacttc ggcctcaaac 124380
```

```
ggccacgggg gtgtcttcgg ggttttctgc agacacgtgc gcgcggctgc ggggctgcct 124440
ggcccctctg gggtgggggt caggggagct ctggagatcc agccgcatga agctggtatt 124500
tacttcctgg aaggcgtctt cagtgacgtg caactggtac tcgaatccca gcttcatcac 124560
gtagcgctcc gatgggatag gaatcctctt cggcccctgc caatttgtga tcccctcggc 124620
gatggcgggg ggaaccttgg cgaatgcttc ttccgggaga gtgctggggt ccgcgctgct 124680
ggcatcggcg gcgtcggccc ttatgtaata gcgctcgtcc gcgggttcct cctcgccctc 124740
gtagtacacc tccgggtaga ggaacggcag gcggacgaag gttccgtcgt tcagctgctt 124800
gtagaacctc ttctcgatct tgggcagcgg cagggcggag tagctgagca cctctccggc 124860
caccaccccc tcgaccggca cgcggcacgg cacctcgctg ggtgcgacgg ggaagtagcc 124920
cgtggggacc ttggcgaagt acccctcgtt catctcttcg cgacaccgcc tgaagtagga 124980
gcgcccgagc atgcacccga acgggttgaa caggtgctta cgctcgcctc tcggcgcctc 125040
ctcgccgctg gagttggcgg ccccccggc cgcggctgcg gcgaaggtgg gggccaagac 125100
gaggtggggc gggttggcat tgcggcggcg agcgagcgcg cagcggaaga cctcggtgcc 125160
ggcggtggcg gctgtcatca tgtcggagtt catcacgtct gttatcttca aaggtgtctt 125220
ctctcttttc tcccttcaaa atggagggga tgttgtgcag ggctaggcgg tggtgggtgt 125280
aaaggcgagg cttttgcaag gcaagaaacc actgctcaac ccacaaagcg aggtgaggta 125340
ctggcgagag tcccctacct tttaacgtgt ggatgtccgg ccgaacactc cccagagtag 125400
gcgttccatc cacgtcacgt ctcccgcccg gcgggcggcg ggcgcccgcg ggtccccggg 125460
gcggggcggc gtcgcggcgg cggccgtgga ccgagcgggc gcgggagcgc gcgagcgccg 125520
cctcggggcg cgcatccccc ccctccgacg gccgccgccg cggcagcggc cgccccgggg 125580
cgggaatttc ccgaaggcgc gcggggtcga ccaccgcgta aatcacccgc ttaactgtgg 125640
gtggacgaac taatgaattc gagctatgtt tggaaaaccc acactcaccc actacggtgt 125700
cttctccacc cgccgctctt aatttgagcg gatgattatg ctcaacggtg gtccatggta 125760
ttgtctcaaa cagttttcca cacacgaagg gaggctgcca agatttatga aactcatctg 125820
ctatctctgc gtataccatt cgtttaggac cgggtatcag gtcaaacacc ggcttgcaca 125880
agtctgctgc cccagcacc cagaggtgat agggctgatt aatgataagg ctggagttga 125940
gatggttata gccagagagt acagagagcc actctatgct cacacccatt ctatcttcgt 126000
ggtaaaccac cccgtttcta tctagagcta tagctgtagc ccccctggtt ctgactattg 126060
gcctacacgc ctttggtagg gtcaataaac tcgatgaaaa tctgtagaga tcggcggagc 126120
gtaccactat gggtattcca agcggttcag atgccaatac gaaacattgt cggctcaaaa 126180
actcccacag atgtccatcg acgtcgatgg aactgtttgg caatgctttg tgtctgtcga 126240
caactgtaac aactgtaatt aagaccacac ccatgttatt aacaaatggg tgggttgaac 126300
caactccata aatttcagca gagctgctct agatacacac tctgttgtga aaaagactcg 126360
ccgtgcgcca agccctatag ctttataggc acacgcccac ggcatcggaa tggaaaataa 126420
acaatgcgac cacctaaccg actggttttc cactacgagc gacgcgtcag aatcgatgga 126480
caccacgcct ccgctaccac ctcccacacc ctcggtggat cccagctaca gcggtgcggc 126540
cgcggacgag gacctgtact ctgacataag cgagggcgat ctagaataca gcgactgcga 126600
tagcgcctct gaaagcgatg aggatgacga cgattgtctt ataccatcca aagagaaagc 126660
tagggaagtg gctgcttcgt ttgggtacac ggtcatcaaa acgcttacgc ctggttcgga 126720
```

gggacgtgtg atggtggcaa ccaaagatgg ccagccggaa ccggtcgtgt tgaagattgg 126780
tcaaaaggga actactctca tcgaagccat gatgctgagg aatgtgaacc atccctccgt 126840
gatacaaatg aaggacacct tggtatcggg ggcgataacg tgcatggtcc tgcctcatta 126900
cagctcggat ctgtacacct ttctgactaa ggaatcaagg cgcattccca ttgatcaggc 126960
tttgattata gaaaaacaga ttctcgaggg gctgcggtac ctgcacgcac agaggatcat 127020
ccacagagac gtcaagactg aaaatatttt cataaacagc gttgatcaag tatgtatagc 127080
tgactttggg gccgcccaat ttcccgttgt ggaacccgcg gacctgggcc tggctggtac 127140
cgtcgagacc aacgccccgg aagttttggc cagagcaaaa tacaactcca aggcagacat 127200
atggagcgcc ggcatcgtct tgtttgagat gctcgcctat ccatcaactc tattcgaaga 127260
ccctccgagt accccagagg agtatgtgaa aagctgccac tcgcaactac tgaagataat 127320
ttcaacgctc aagataaatc cggaggagtt tcctcgagac cccgggtcga ggctcgtgcg 127380
cggatacatc gagtattcta gactcgagcg caagccctac acgcgctacc cctgctttca 127440
acgcgtcaac ctgcacattg acggggagtt tctggttcac aagatgctag cgttcaatgc 127500
cgcgatgcgc ccatcggccg aggagctgct gtcataccca atgtttgcac aactttagga 127560
tgactaacct gtttctggga ggagacagcg tgggcgacgg tgtataaagt tggtctgctt 127620
tcaagccctg ccactgcgct acagtgccac caactgtaaa gcggtagtaa gctgcagtga 127680
tgttgactgt cttagcagcc ctgagtctgc tcagcttgct tacgagcgca accggacggc 127740
tcgccccaga tgaactctgt tatgccgaac cccgcagaac tggcagccca ccaaacaccc 127800
agcccgaacg cccacccgta atatttgagc cccaacaat tgcgattaaa gctgaatcca 127860
agggttgtga gctaatttta ttagatccac ccatagatgt aagctatcgc agagaagata 127920
aggtgaatgc gtccattgct tggttttttg actttggcgc ttgccggatg cccatcgcat 127980
acagagagta ttacggttgt attggcaatg ctgttccctc cccagagact tgtgatgcgt 128040
actcatttac ccttattagg accgagggta tcgtggagtt taccatcgta aacatgagcc 128100
tcctgtttca gcctggaata tacgatagtg gcaattttat ctacagcgtt ctcctggact 128160
accacatatt tacaggacgt gtaacgttgg aagtggaaaa ggacacaaac tatccctgtg 128220
gcatgattca tggactcact gcttacggaa acatcaacgt agatgaaacc atggacaacg 128280
ccagcccaca cccgcgtgcc gtggggtgct ttcccgagcc catcgacaac gaagcgtggg 128340
caaacgttac atttactgaa ttggggatac cagacccaaa ctcatttctc gatgacgagg 128400
gtgattaccc gaatatatca gactgtcact cgtgggagtc atacacctac ccaaatacgc 128460
tgaggcaggc cacaggaccc cagaccctgt tggtgggtgc ggttggactc agaatcttgg 128520
cgcaggcatg gaagtttgtc ggtgacgaaa catacgacac catccgcgca gaagcaaaga 128580
atttagagac ccacgtaccc tcaagtgctg cagagtcgtc tctagaaaac caatcgacac 128640
aggaggagtc taacagcccc gaagttgccc acctgcgaag cgtcaacagc gatgacagta 128700
cacacacggg gggtgcgtcg aacggcatcc aggactgtga cagtcagctc aaaactgtgt 128760
atgcctgctt ggctctaatt ggactcggca catgtgccat gatagggttg atagtttaca 128820
tttgtgtatt aaggtcaaaa ctgtcctctc ggaatttttc gcgcgcgcaa aatgtaaaac 128880
atagaaatta ccagcgactt gagtacgttg cttaacacct gtcaaataaa agtttcaaat 128940
caaaaacatt gttgtctgta ataactgagt gtggttttaa aaatactaaa tcgcggcaat 129000
tccggaaata gccccataca aaagggaggg ttgttggtgt ttagaaaata gtttccccgt 129060
tgatgagttt cgcgtagagg tctaactcat ccgcgatggg gttcatctat gcgcgcaaac 129120

```
tgttgctgtg catggctgtt agtatatacg ccatagggtc cactacaaca actgagacta 129180
ccacctctag ctcgtccacg tctgggagtg gccagtctac atccagtggg accactaata 129240
gtagcagttc tcccaccacg agtccaccta ccacatcttc atctcccccc acatcaaccc 129300
acacatcctc cccatcttca acctctaccc aatcgtcgtc aacggcggcg acaagctcgt 129360
ctgcaccctc tacagcgtcc agcacaacct ctattccaac atccacatca acagaaacca 129420
ccacaacaac cccaaccgca tctacaacga ccccaacaac aacgaccgcg gctcccacaa 129480
cggccgctac aaccacagct gttactacag ccgcgtctac atcagcggaa accaccacag 129540
ctactgcgac tgctacctca accccaacca caactacgcc tacgtccaca acaactacta 129600
cagctaccac cactgttcca acaaccgctt ctacaacaac tgatacgacc acagcagcaa 129660
cgaccacagc agcaacgacc acagcagcaa cgaccacagc agcaacgacc acagcagcaa 129720
cgaccacagc agcaacgacc acagcagcaa cgaccaccgc ggctactact tcctctgcaa 129780
ccaccgcggc taccaccacc gcggctacca ccaccgcggc taccaccacc gcggctacca 129840
ccaccgcggc taccaccacc gcggctacca caacggggtc tccaacctct ggttcaacat 129900
ctactacagg ggcttccacg tccacccct cagcttccac tgccacatct gccactccca 129960
catcgacgtc aacatcagct gcggctacta catctacccc taccccaact tcagctgcaa 130020
catcagcaga gtctaccaca gaggctccaa catccacacc cactactgat acgaccaccc 130080
cttcggaggc aaccacagct actacatcac cggagtctac cacagtttca gcctcgacta 130140
cctctgctac gaccacggca ttcacaaccg agtcccacac atcgccggat tcgtctactg 130200
ggtctacatc cacagccgaa cccagctcaa cgtttacttt aacaccttct actgcgaccc 130260
cctccacgga tcagttcaca gggtcatctg cctcaacaga gtctgactcg accgactctt 130320
ccaccgtgcc cacgactggg actgaatcta taacagaaag ctcatcgacc accgaggcgt 130380
caactaactt gggatcgtca acctacgaga gtaccgaagc cttggaaact ccagacggga 130440
atacaacttc cggaaatacc accccatcac cttccccgcg taccccaagc tttgctgata 130500
cccaacagac cccagacaat ggtgtatcaa cccaacatac caccatcaat gaccacacca 130560
ccgccaacgc tcaaaaacac gcagggcacc acagaggtcg cgcagggggt cgtcggggta 130620
gccctcaggg ggggtcacac acaacaccac acccagaccg tttgactcct tctccagacg 130680
acacctatga cgatgataca aatcacccta acggtaggaa caattcaata gagatcgtgc 130740
ctcagctccc gccagaccga cccatcatag agctgggggt ggcgactctc agaaaaaact 130800
ttatggaggc gtcctgtact gtggagacta actcaggctt ggcgattttt tggaaaatcg 130860
gcaacgcaag cgtagacgcg tttaatcggg gaactactca cactcggctg atgcgcaatg 130920
gggtaccggt ttacgccctc gtatctacgc ttagagttcc gtggttaaat gttattccac 130980
taacaaaaat tacttgcgct gcttgcccca cgaatctagt cgccggcgat ggggtggacc 131040
tcaactcatg taccaccaaa tcaaccacaa taccgtgtcc gggccaacag cgcacccata 131100
tttttttctc tgcgaaaggg gacagggctg tgtgtatcac atcagaactg gtgtcccagc 131160
ccacaataac ttggtcagtt ggatcagata ggttgcgtaa cgatggattt tctcagacgt 131220
ggtatggaat acagcccggg gtgtgtggta tactgcgcag cgaggttcgc attcaccgca 131280
ccacctggcg ctttggatca acatcaaagg actatctctg tgaggtcagc gcatcggact 131340
caaagacgag cgattacaaa gtgctaccca acgcccactc aacttccaac ttcgctttag 131400
tggctgcgac cacgctaaca gtgacaattt tatgcctgct gtgctgcttg tactgtatgt 131460
```

```
taacccgccc ccgagcgtct gtatattaac tcaaaaatta tcccttggcc tttacaacca 131520
gtggtggcgt gtatgcagaa gcgtgccacc gccctggtac gtgtttttca ataaacgaag 131580
catgtctacc ttcaagctta tgatggatgg acgtttggtt tttgccatgg caatcgcgat 131640
cttgagcgtt gtgctctctt gtggaacatg cgagaaagcc aagcgtgcgg ttcgaggacg 131700
ccaggatagg ccaaaggagt ttccaccacc ccgctataac tatacaattt taacaagata 131760
caacgcgact gcgctagcat caccgtttat taacgaccaa gtaaaaaatg ttgacttgcg 131820
gattgttact gctacgcgcc catgtgaaat gatagcgctg atcgctaaga caaacataga 131880
ctcaatcctg aaggagctgg ccgctgccca aaaaacttat tccgccagac tcacctggtt 131940
taaaattatg ccaacgtgtg caacgcctat acacgatgtt agttatatga aatgcaaccc 132000
gaagctatca tttgcaatgt gtgatgagag atcagacata ctatggcaag ctagtttaat 132060
tactatggct gctgaaactg acgatgaact tggacttgta ctggcagccc ctgcacattc 132120
tgcctcggga ctgtatcgcc gtgttataga aatcgacgga aggcgaattt acacggactt 132180
ttctgtaact attcccagtg aacggtgtcc gattgccttt gagcaaaact ttggcaatcc 132240
ggatcggtgt aaaactccag agcagtactc gcggggagaa gtttttacac gtcggtttct 132300
tggtgaattc aacttcccac aaggagagca tatgacatgg ttgaagttct ggttcgtcta 132360
cgatggtgga aacctaccag tgcagtttta tgaagcccag gcattcgcaa gacccgtgcc 132420
tccggataac caccctggat ttgattctgt tgagtcggag attacacaaa ataaaacaga 132480
cccgaaacca ggccaggcgg accccaaacc caatcagcct tttaagtggc ccagcatcaa 132540
acacttggcc ccaagactcg atgaggtgga tgaggtcata gagcccgtaa caaagccccc 132600
aaaaacgtct aagagcaact ctacgtttgt gggcatcagc gtcggtttgg gtatcgccgg 132660
cctagtattg gtgggcgtca ttctatacgt ctgcttgcgt cggaagaagg aactgaaaaa 132720
gtctgcacag aacggcttga ctcgcctacg ctcgaccttt aaggatgtta aatataccca 132780
gcttccgtaa acagtgttgc gtaacctgct gggaggtgtc cacggcctta aagcttcgcg 132840
gtttggagat ataacgcaca acctacaaca aacgcgacac agcaagtagt agtcgctatg 132900
gccaaactca ctgggatgtt cagcgctgcg atattactgt ctatggctat atgctcaacc 132960
gcaatcatat atcgcggaga acatatgagc atgtacctaa acgccagctc tgagtttgcc 133020
gtgtacccca ctgatcagtc ccttgttttg gttggccact tgctctttct cgacggacaa 133080
cgcttaccca ccaccaacta tagtgggctg atcgaattga ttcattacaa ctactccagc 133140
gtttgctaca ctgttatcca aacgatatcg tatgaatcat gcccgcgtgt agccaacaat 133200
gctttcagat cgtgcctcca caaaacttct aagcactacc acgactattt ccgagtcaat 133260
gcctctgttg aaaccaacgt tctcttaaac atcacaaagc cacagcctac agattccggg 133320
gcgtatatcc ttcgcgtaaa acttgaccac gcgccaaccg cagatgtttt tggagtttcc 133380
gcctttgttt acgatctaaa atctaaaacg gtccccgatc caatgcccac cacacaaacg 133440
gtagaaccta caacgagcta tgtgtcgact cccacatacg actataccga tgacgtaacc 133500
accgaaactg aatccacatc aacatctacc caacaggcga tgacctccac tcaaacccct 133560
agcgctacat ggggaaccca gctaaccaca gagctgccga caaacgaaac tgtggttatt 133620
ggtcaggagg ccctgttatg ccattggttc cagccatcga caagggtgcc gaccctgtat 133680
ctgcatctgt tgggacgcac tggcaatctc ccggaagatg ttctactggt cgaagactct 133740
gagtttcttc gtaccacatc gcctgcacat aggccttctg catcacccgc tgacggtgat 133800
gattttaaac agacaaactc aacttccctt aaggcgcgca acaagatcgt cgcaatggtg 133860
```

```
gttatcccga ccgcgtgtgt actaatgctc ctgttggtgg ttgtcggtgc catcataaac 133920
ggtgccgtgc gcaaacattt attgagttgc gcaagccgca ggatctaccg ctccggacag 133980
gggggcgcat cggcggccga acggagacgg ctgacttgcg gtcctacttt agccgcgtca 134040
tcggagtcgc tggccgacga tacaacgtca tcacctccaa cccccaaacc ttcgaagaaa 134100
accaagttgg agaccgatcc gcttatggaa cagctgaacc ggaaactgga ggccatcaaa 134160
gaagaatcat agttgtgggg gtagatgggg ttggtattaa agtttgtgta ttatcgattt 134220
tatatttatt aaaatttgtg aaacataaac atcttgtgca atgtttacat tatttgtgat 134280
tgggacggtc cactgggagg tggtacaact cgggtttaaa gctctggatg tttggtagga 134340
aactcacagt tctccacttt ggcgtcaaag caatcagacg tctaattcga agtagaacgt 134400
cacaatggag ctgttggccg caagtcgcgc ttgtatattt tttgggctag taacagtact 134460
cgatgcgtgg ggagtccaac aagttgaact ttccgagggg gcttgggcta tgatcgacgg 134520
aagggacgtt ttaacccccta ctaacacaac tactcgggtc acaaaggcct ggacgttttt 134580
ggaaacccct cccggttgcg ctggcgacat atcagttaag aaggtgtgcg tgagccatag 134640
tctgtgcgaa gataacatta taataggaaa gcactgtaac ctcttaactg gggaacatgg 134700
cattgcgttg gccgagttta acgtagtaaa cggatcgctg cgcagaacag acgatgtgta 134760
ctttgtgaat ggtacagtct ttccaatcct tgccgaaacc cgcagcgtcc tacaaatcca 134820
tagggcaacc ccctctatcg caggggttta caccctccac gtttccatcg acggaatgat 134880
gaaacactcc gtcgtgctgc tcaccgtcaa gaagccgccc aaacaaccgc aaccacgctt 134940
gcgcgttaag accccgccac ccgtaaccgt tcctcaggtt cccgtaaaga cccacacgga 135000
ttttgtggtg cacggatacc actcgcgcgt gtacgctgat ggcgaatctt tcgagctgtc 135060
ggtgaacctg gagtcacata tcgtagagcc cagcttcagc gcggagattc agtggtacta 135120
tatgaataca tcatcgtcat catgcgatct atttcgagtt ttcgaaacct gcatctttca 135180
cccgacagcc atggcctgcc tgcacccgga acaacacacc tgcagcttca catcccccat 135240
cagagcgacc aagatcctac accgggtgta tggaaactgc agcgatcatg gaaattcgtg 135300
gccttctagg tgccatagca ctctgctggg caatcgtcta tactttattc aaccagcaca 135360
gaacagagtg gacctgttgt tcaaagacac tcccgcgtcg gctaccgggc tgtatgtgtt 135420
tgtattattg tacaacggac atccggaggc gtggacgtat acgctgctgt caaccgcaaa 135480
tcactttatg aatgtgctta ctgacgtgac ccgcccacgg ctaggagagc acttttatac 135540
ggacctcggg cacaaaatca tcactcctca tccatctgta gctaccactg aagagttggg 135600
agcttggact cgacactacc tcgccttttt gctggttatt atctgcacgt gcgcggcgct 135660
gctagttgca ttggtggtgt ggggctgtat tctctacatc cgaagcaacc gtaagccgta 135720
tgaagtgctg aacccctttg aaacggttta cacgagcgtt ccaagcaacg acccctcgga 135780
cgaggtcttg gtgtttgagc gcctagcttc ggactctgac gactccttcg actctgattc 135840
agacgaagag ttggaatacc caccacctcc caaaccagct ccacagctcc caccatacca 135900
gtttgtagac gggggagacg cccctagcgg caggtccgga ttcaaggttt ggttccgcga 135960
tacacccgag gcgtccccgg ttcctcttca taaaccaacg ctacagggtc cagactacag 136020
ccgggtagcg tcgaagctaa agtcgatact aaaatgagca gcaacagcga taacacagag 136080
tgcttcgggg gagtcaacta tgccgaggga atgcgcaagc gtaaacgcaa ccctgtcaga 136140
aacagcacct ttcaagagta tctcgacgcg cgtaacgcgc gttatcccag atccggctca 136200
```

acctccgatt ccgacgagga ctacacaacc agatcaaagt acgagtcaga tgtcagcgag 136260
tttaaaaaaa tgatggatct ggaaactcta cctcccccaa aggctgagcc gcaagctcag 136320
aaggccgagc ctgatgctgc gaaggaggag ccagtcagca ccactagcta catcttaaac 136380
gaatgggtgg ctcctatgat tgggcatttt ctggcaatgt gtatgtatga gttgcttttc 136440
aaataaaaac aaacattaac ccctgtaaac atccgtttgt ctactgtgta tgatagagtt 136500
aaacccaacc ctagagagtt atgtatttaa tcccctggga ccccgcggaa gtcatatatc 136560
cctcggcccc ctcatttggg cgcacattgc ctgcccggcg gcagtcttac tcccttagct 136620
cgccctcttg cataagataa actattcccc tcccagctag tttcacccac cagattaagc 136680
gaggttttcc ctctcagcga tcacttttca ccaccgaaga acaggccctc atcggtttcc 136740
ctccgtgttt tcccatccat ctatccaacc actacatttt catggagaag gcggaggctg 136800
ccgcagttgt tataccccctg tcagtttcca accccagcta ccgtggaagc ggtatgtccg 136860
accaagaagt aagcgaagaa caatctgctg gagatgcctg ggtgtctgca gcaatggcag 136920
ccgcagaggc ggtggctgct gccgctacct ccaccggaat tgataacact aacgactaca 136980
cgtacaccgc tgcttctgag aatggggatc ctggtttcac actaggcgat aacacctacg 137040
gaccgaacgg tgctgcctca gggtgcccgt ctcccccatc accggaggta gtgggtctag 137100
agatggtggt tgtgtcgtcg ctcgctcctg agatcgcggc agccgtacca gcagacacga 137160
tttttgctag cgcagcagcc ccggcaaccc gcgtagacga cggtaacgct ccgctgctcg 137220
gaccggggca agcgcaggac tacgactcag agtcaggatg ttattacagc gagagcgaca 137280
atgaaacggc cagcatgttc atacggcgag tcggacgtcg acaggcccgc aggcacaggc 137340
ggcggcgcgt ggcgcttact gtcgcaggcg tgatcctggt tgttgtccta tgcgcgattt 137400
ccggcatcgt tggggcgttc ttggcacgcg tgtttccgta acaccacctt ttaccccaca 137460
acagcccctc gcccccctgg tcgaccagct accggacgtc tcccaagcct cgtccaccca 137520
cagttaagcg ggtgatttac gcggtggtcg accccgcgcg ccttcgggaa attcccgccc 137580
cggggcggcc gctgccgcgg cggcggccgt cggagggggg ggatgcgcgc cccgaggcgg 137640
cgctcgcgcg ctcccgcgcc cgctcggtcc acggccgccg ccgcgacgcc gccccgcccc 137700
ggggacccgc gggcgcccgc cgcccgccgg gcgggagacg tgacgtggat ggaacgccta 137760
ctctggggag tgttcggccg gacatccaca cgttaaaagg taggggactc tcgccagtac 137820
ctcacctcgc tttgtgggtt gagcagtggt ttcttgcctt gcaaaagcct cgcctttaca 137880
cccaccaccg cctagccctg cacaacatcc cctccatttt gaagggagaa aagagagaag 137940
acacctttga agataacaga cgtgatgaac tccgacatga tgacagccgc caccgccggc 138000
accgaggtct tccgctgcgc gctcgctcgc cgccgcaatg ccaacccgcc ccacctcgtc 138060
ttggcccccca ccttcgccgc agccgcggcc ggggggggccg ccaactccag cggcgaggag 138120
gcgccgagag gcgagcgtaa gcacctgttc aacccgttcg ggtgcatgct cgggcgctcc 138180
tacttcaggc ggtgtcgcga agagatgaac gaggggtact tcgccaaggt ccccacgggc 138240
tacttccccg tcgcacccag cgaggtgccg tgccgcgtgc cggtcgaggg ggtggtggcc 138300
ggagaggtgc tcagctactc cgccctgccg ctgcccaaga tcgagaagag gttctacaag 138360
cagctgaacg acggaacctt cgtccgcctg ccgttcctct acccggaggt gtactacgag 138420
ggcgaggagg aacccgcgga cgagcgctat tacataaggg ccgacgccgc cgatgccagc 138480
agcgcggacc ccagcactct cccggaagaa gcattcgcca aggttccccc cgccatcgcc 138540
gaggggatca caaattggca ggggccgaag aggattccta tcccatcgga gcgctacgtg 138600

```
atgaagctgg gattcgagta ccagttgcac gtcactgaag acgccttcca ggaagtaaat 138660
accagcttca tgcggctgga tctccagagc tcccctgacc cccaccccag aggggccagg 138720
cagccccgca gccgcgcgca cgtgtctgca gaaaaccccg aagacacccc cgtggccgtt 138780
tgaggccgaa gttggaacgg tgtaaataat ctgtatctct gaaaagtctg tggtattgag 138840
cgtttcagct tttttaataa aaaaacgtaa accatatttt ccgtggtgtt ggagttttgg 138900
tgggtacact cccctgtacg ctggcgccct ctagtgccta tcacacacta ctcggtccca 138960
ctcatcccag gcggcgtttc ccctaccgct ctccccgct cggcctcccc taccgctctc 139020
ccccgctcgg cctcccctac cgctctcccc cgctcggcct cccctaccgc tctcccccgc 139080
tcggcctccc ctaccgctct cccccgctcg gcctccccta ccgctctccc ccgctcggcc 139140
tcccctaccg ctctcccccg ctcggcctcc cctaccgctc tcccccgctc ggcctcccct 139200
accgctctcc cccgctcggc ctcccctacc gctctccccc gctcggcctc ccctaccgct 139260
ctcccccgct cggcctcccc taccgctctc ccccgctcgg cctcccctac cgctctcccc 139320
cgctcggcct tccccttgt tttttgccc agtagcagtc tgcgttggtt tactcacaat 139380
gactaccaca accacctcac ccaccaatcc ctaccatccc ccccccaacg gagagagaga 139440
aaaccggcga ggcctggtgg tctctccccg ggtccccacg cccgctcgat agttgaggta 139500
ttggtggggg aaatggatag agagacggaa acacaaacag gggcagactc gcggaattgg 139560
ggtttagtat atagtgagta tatttttcaa aagtttatcg attggccggt cacggccacc 139620
gttttggcgg tccgatgggc cgagggcagc tggagaggga gcttgcggcc gcgggcgcgc 139680
aggtacgccg cggcggctgc gtggcggggg aacagctcgg gctcggcgcc cgccatgttg 139740
agtagcgcgg cccagtagcg ctctgcgtcc gccggcggcg tctccccgat cccgagccgg 139800
gtctcgaaaa accgcgcaca cgcgcgctcg tacatctgcg ggcgcgagca ggcgaacgcg 139860
tgtcccaggc agcaccagta cgcgcagaag agcatgcggc cgctgagctc ggcgtgggtc 139920
tccaccggcg ccgcgccgag atccacgagg taccgcccca cggcgcggcg cagcgggtcc 139980
gccgagtgga agacgggcat ggggctggcc gcgtagcgac caaacatgtc gcagaacatg 140040
cggtacacgc gcggccaggc ctccgcgggc ggcccggcgc cgctccggag cgcgtccgct 140100
gcctccgccg acacggcgcg cacgaccgcg gcaaagtccc ccacggagcg cggcagcgag 140160
accgcgtgcg ccgcggtgtc cgtgctggtc gggtatagcc cgtccgcgcc cgccccccgtc 140220
cccgtccccg ctccggactc ctcgccgtcg acggccatcg gggagccgtt gtggacgtgg 140280
ccgtacgcgc cgtccatgcc gttgtggttc agtggccggg agatcgggcg cactgattgc 140340
gcgcggccct ccgcgagctg tatttcctcg gcggggcgtg gaatcgcggg aacacacaca 140400
cgcctgctgg cgtggtttag gtagctatag atgttcctcc tccccccac cccacccttc 140460
ccatagctct ccctccctct gcgtgggtgt tgttatctct ccaatagccg tcggggattg 140520
ggtgtgatgg cgctgtcatt cacgctttcc cccgacctcg ccccgagtcg cgtggatgag 140580
caacgctaaa caacaaccgt tttttcgcta ccgctccccc agccggggct cggagcaccc 140640
aactattcat cccagccaag caagaggggga aaaaacaacc atataaacga agccaaacta 140700
cagagagtgc cgtcaacgat gtttttattg gttactcgtt ttgggtggta tgggtgggtt 140760
ggcgagtggg ttttggaggt gtggagggag aggtcaaaag gtgtgtattg gggttgcggt 140820
tcatcggggt gacaacgagt ggtggtttta ctggttagaa cgtagcgttg gtgtgttttg 140880
gaaagcgtgc atgcgtacac ctatccgact caccggcgag cgcttttggt gggacgctca 140940
```

```
ccccttggggg gttggcgctt gcggcgcttt ttggcagcgc tagcgcgggt tgtagggtgg 141000
tggttgttgg tgggggcatc ggactcgcta tcgctttcgc tttcgctgct agaccacttt 141060
ccagtgcagc tcgagtcgtc ctccccccacg tccgaaaagc tatcgtactc gctgctggca 141120
gtctcctcct cggggctaaa ctccgaaacg ctgctctccc cgctggcctc gtcttcttcc 141180
tcctcctcgg agggcgactc gtcgccgctc acgtcacact cctccccaaa gagggtattc 141240
ggggggtcgc tcggcggctc caggaaccgc tgctcgtacc ggtcctcgga gttcagtgcc 141300
cgcagcgtgg cgcgcagcgg gaagctctgc tcgggcagca gctgcaggag ggactgccag 141360
cactcgagtg tggggcgcgt gtgcgtgtac cccatggcgt aaaaatccag cagcgccctg 141420
cgcagggtgc gcgagtcctc ggtcacgtgg atcgaggagg tggatatccc cctgaacaag 141480
cggttgacgt cccccgcgag gcggttcaca tcggggcgcc acggcggggc gcagaacgcc 141540
cctggccccc gggccaggta cgggcgcagg gcccgcgggg atagcggcat tccgtattcc 141600
ggatggtccg agccgccggg gagcctcgcg ggcacgcgca cggcgtcgat gcgctggctg 141660
gagcgtgggg acgggtcccc cgccgggggc gagggggtca gggacgggat gagggggctg 141720
gtggacggcg tcccccgctg ggccatgcgg caggatccgt cgcacgcccc gcacggctgt 141780
ccgtggggca tggctgggcc ggggtcgccg gagctgggct gggccggggt cgccggagct 141840
gggctgggcc ggggtcgccg gagctggggt tgctggagat aacgaatgga aaaacattat 141900
aaccacaccc atcaattagt gggccctccc ccatgggccg accaccgacc accgaccacc 141960
gaccaccgac caccgaccac cgaccaccga ccaccgacca ccgaccaccg accaccgacc 142020
accgaccacc gaccaccgac caccgaccac caccgatctc atgggcagac ccactcgcga 142080
taccacttac cttgccctgt tttccgtggt gtggatgcac gttaaaaggc tctaagcttc 142140
aagctgcgtg tgtacccaca cctggtgatc cgcagggtaa tatatacacg agttccatat 142200
tctccgccct tagggaggcg gataccggta catcaccacg cctttgcaat cgacagatta 142260
tcgattatcg gacgaaaatt ggaaacgcgt cccgtggcac aaatcctgca ccctgattgg 142320
cccagaggcc cgttcgcacc aatcaccaat aagttataat aataattatt gcaacaaagt 142380
gcgaacacta cgtgttcgga cttcttatcc gttccacgcc cccacccccc gtctcgggag 142440
cgcgcatggc accgtgccaa ctagtgggta ccgtgacccg gcccatacct cgacgagagt 142500
atgtgccggg taaccgtatt ttagcgcccc cccccatagc cgcacaccgt aacccagcca 142560
tgctatctgt tgcgctcaaa aatttttgcc ccccccccac cctcaataac cgtgcaccct 142620
cccctaggtt tcatcgcgca aaaattttat tgacaccccc cccttatcca tactgggggg 142680
aggggcacct ctgtacacgc gtggcaaaaa aaatcgataa cggggggtag tgtgtaacga 142740
taaaaagtga aacatcgatg tgtatctccc ggagtgtatg gatgggggcg ctttaggtat 142800
tttatgtatg acccggtacc cgtgggaaaa tgtaacggat cgaaaccgtt tacacggtac 142860
aacgattgtg cgtgtgtgcg gtcggctctc aaaaaaaacc gtgggcgggg catggggggg 142920
ggtgtggacg tgggtggaag gtgggtaccg ggcatctccc cccacacagc tgtctcaagc 142980
cacgccccct catgtcattt gaatattggg aggggcgccg tgttacgtcg atggggtggg 143040
gccggcgcgt gtgtgtatag cgtcacatcg tggcgtcaca tgttaatgga ctacatggcg 143100
ccacgaagcg gttagatgta gtaaccgcat ctgtgagggt taacacacga gggcgccctc 143160
gtgcggacgt gtatgaaggc gcatgtaaaa ccgtgttttg aaacagcgcc accgcctggc 143220
tccttgtgag ataatatgta aatcagcaca cgtagatatc atcccgccca aaatacacgc 143280
gatagcgata catgttttaa ttggtataac tttaatgaga ttcaaccggg aaatacagag 143340
```

```
acgcgttcac gcccaccttt cccccteccc ctcccacttt ttttacatca tttccgtttc 143400
ggtcggaaat atcgcactcg ccatttttat tgaaattact tttgaagccc actccctcgg 143460
ctcctcccaa gctcgtcagt atgcagatga gatttaccag gaagtgtcat ggcgtccagg 143520
ggcgttcgtc tttatgcata tgagcggcgc gatcacgaac cccgttggcg cgacgcgctt 143580
cccggggagg agacgcatgc agatgagatg tgcatcgagg tgtcatggcg tccaggggcg 143640
ttcaccttta tgcatatgag aggcgctatt cggcatcccg ttggcgcgac gcgcttccct 143700
gggaggagac atacgcaaat tagaaacgac acacgggttc taattggttg gagcgggggg 143760
gaggcgaaaa gcgcatgcaa atgcaaagcg cgggaccggg ccccataggc tagagccgct 143820
acacgcccac cgcccatcat caacggccaa tcacaatcga tagtgtgggc tggccactcc 143880
cactaggggg aaggcaaaac tccatcgtag tagtataaag cacctgttgc ttacccatcg 143940
tagcatcgcg gactagagag cctttcagct cactggacca gccagccttc gaggactatc 144000
gatcgcatct tggaaagctt acccgctctt ggcactcctt cttcggcttg cggaggtaag 144060
agctccccgg ggacacgacc ggcttcgatc tgcttcttct cccggggaga gcgttagaga 144120
acggggcgag tgccaaaaag gccatggaac ccctccaaca acgatgtccc gagggggtgg 144180
ctccgaggcc cgcttcgacc tagcggtcga agcgcggtgg ggatacttac ctcgaagccg 144240
gcgaaggcta taccttcccc gggcagaccc gggcggcttc tgcctcggcg gagctcggcg 144300
cggaagcctg gatatctgac ggggcgtggt taccacccaa gcgggggaga ggcccaggcc 144360
gcccgcgttc ccttttacca ttcggctccg ctccaactca acatcttttc cgcctctgct 144420
tttccagggt agagaagcgg cgcccgtcgt ccgagcgccc gccgcggaac cccgccaccg 144480
gccacccgcc aaccttccct tctcggtctt ccgagcgagc cttctcgtgc ggttggttct 144540
cgaccccgaa gccggagcta gcacgccatg gccagccagc gcagcgactt cgccccggac 144600
ctctacgact tcatcgagag caacgacttc ggcgaggacc ccctcatccg cgcagccagc 144660
gcggccgaag aggggttcac ccagcccgcc gcgcccgacc tgctgtacgg cagccagaac 144720
atgttcgggg tggacgacgc tccgctctcc accccggcgg tggtcatccc tccgccgtct 144780
ccgactcccg agccccgcgg agggaaggcg aagcggtcgc cctcggccgc cggcagcggc 144840
ggtcctccta ccccggcggc tgccgcccag ccggcgtccc cggcacccag cccggctccg 144900
gggctcgccg cgatgctgaa gatggtccac tcctccgtgg ccccggggaa cggtcgccgg 144960
gccacgggct cctcatcacc cggcggtggg gacgcggccg acccggtcgc cctcgacagc 145020
gataccgaga cctgcccggg gtccccgcag cccgagtttc catcctcggc ctccccgggc 145080
ggagggtccc cggcaccccg ggtccggagc atctccatct catcgtcgtc ctcgtcctcg 145140
tcctcgatgg acgaggacga ccaggcggat ggtgccgggg cgagtagctc ctcttcgtcg 145200
tcctccgacg acagcgacag cgacgaaggc ggcgaggagg agacccctcg cccgcggcac 145260
tcgcagaacg ccgcgaaaac cccgtcggcc gccggctctc ccgggccgtc ctccggaggg 145320
gatcgcccgg ccgctggggc cgccaccccg aagagctgcc gctccggcgc cgcttccccc 145380
ggcgcacccg ctccggctcc agcttcggcg cccgctccca gccgcccggg aggaggcctc 145440
ctccctccgg gggctcgcat tttagagtac ctggagggcg tccgcgaggc caatctggcc 145500
aagacgctgg agaggcccga accgcccgcg gggatggctt ctccgccggg ccggagccct 145560
caccggctcc ccaaggacca gcgtccgaaa tcggctctgg cgggagcgtc gaagcgcaag 145620
cgggccaacc ccagacccat accccagacc cagacccagg caccggccga ggaggccccg 145680
```

-continued

```
cagacggccg tgtgggactt gctggacatg aactcatccc aggctaccgg ggcggcggca 145740
gcagcagcat cggccccggc ggcggcttcg tgcgccccgg gcgtctacca gcgcgagccg 145800
cttctcaccc cgtccgggga cccctggccc gggtcggatc caccaccgat ggggagggtg 145860
cgatacgggg ggaccgggga ctcgcgggac gggctgtggg acgaccccga gatagtcctg 145920
gccgcctcgc gctacgccga ggcgcaggcc ccagtaccgg tcttcgtgcc ggagatgggg 145980
gactccacca agcagtacaa cgctctggtc cgcatggtgt tcgagagccg cgaagccatg 146040
tcctggctgc agaactctaa gctcagcggg caagaccaga acctggcgca gttctgccag 146100
aagttcatcc acgctccgcg cggacacggg tccttcatca ccgggagcgt ggccaacccc 146160
ctgccccaca tcggggacgc catggcggcc gggaacgcgc tctgggccct gccacacgcg 146220
gccgcctcgg tggccatgag ccgccgctac gatcgcactc agaagagctt catcctccag 146280
agcctccggc gcgcctacgc ggacatggcc tacccgagag acgaggcggg gaggccggac 146340
tcactcgccg ccgtggccgg ctacccggcc caggccgccg ctgccgcggc cagccagcaa 146400
cagcccgagg ccccggcgcc ctcggtccgc gtccgcgaag cgtacacccg ggtctgcgcg 146460
gccctcgggc cccgacgcaa ggctgccgcg gccgcggccg ctccggggac cagggcgccc 146520
aggccgtccg ccttcagact cagggagctc ggggacgcct gcgtgctggc ctgccaggcc 146580
gtcttcgagg ccctcctgcg cctccgcggc ggggcgtccg ccgtccccgg actggacccc 146640
agcgagatcc cctctcccgc ctgccctccc gaggcgctgt gctccaaccc ggccgggctg 146700
gagacggcgg ccctctccct ctacgaactc agggacctgg tcgagcgggc caggctcctc 146760
ggggactctg accctaccca ccgcctgggc tccgacgagc tgcgcctcgc ggtgcgcgcc 146820
gttctggtgg tggcccggac cgtggcgccg ctggtgcgct acaacgccga gggggcccgg 146880
gcccgggcct cggcctggac cgtcacccag gccgtgttca gcatacccag cctggtcggg 146940
gggatgttgg gggaggccgt gtccctgctg gccccaccga ctcggtccca gcagccctca 147000
tcgtcctcgc ccggcggcga gcccttctcc ggctccgcgg ccgcggaggg gagccttcag 147060
accctgccgc ccctgtggcc caccgtcccc gggaagcagt ccgcgacggt cccctcgtcc 147120
cactcccagt ccccccagca ctcccagagc ggcggaggcg ccggggctac gaccgccacc 147180
tgctgccggg ccacccagac aaacgcccgc tcccgggggc agcagcacca gccgcagaag 147240
gcccgctccc ctcaggcggc cgcctccccg gcccacctca gccaggaggc gatgcccggc 147300
tcctcctcgg acgaccgtgc catccacggg cgccccaggg gcaagagcgg caagcggcgc 147360
tccgagcccc tggagccggc ggcccaggcc ggagcctcgg cctccttctc ctcgtccgcc 147420
cgggggtacg atccctcggg gccggtcgac agccctccgg cccccaagcg cagggtggcc 147480
accccgggcc accaggctcc ccgggccctg ggacccatgc cagccgaggg ccccgaccgt 147540
cggggcggat tcaggcgcgt tccccgcgga gactgccaca ctccgcggcc cagcgacgcg 147600
gcttgcgcgg cctactgtcc ccccgagctg gtggcggagc tcatcgacaa ccagctgttc 147660
cccgaggcct ggcgcccggc gctcaccttc gatccccagg ccctggccac catcgcggcc 147720
cgctgcagcg gcccccccggc ccgggacggc gcgcgcttcg gggagctggc ggccagcggc 147780
ccgctgagac ggagggccgc ctggatgcac cagatccccg accccgagga cgtgaaggtg 147840
gtggtcctct actccccgct ccaggacgag gacctgctgg gcggactccc ggcctcccgc 147900
cccggcggct ctcggcgcga gcccctctgg tccgacctca aggggggact ctcggcgctg 147960
ctggcggccc tggggaaccg catcctcacc aagcggtccc acgcctgggc cggcaactgg 148020
accggggccc cggacgtctc ggccctcaac gcccaggggg tcctgctgct gtcgaccggg 148080
```

```
gacctggcct tcaccggctg cgtcgagtac ctctgcctgc gcctgggctc cgccaggcgc 148140
aagctcctgg tgctggacgc ggtctccacc gaggattggc cccaggacgg tcccgcgatc 148200
agccagtacc acatctacat gcgggccgcc ctgactccgc gggtcgcctg cgccgtgcgc 148260
tggccccggg agcgccacct cagccgcgcg gtcctcacct ccagcaccct cttcgggccc 148320
ggactgttcg cgagggccga ggccgcgttc gcgcgcctgt acccggactc tgcgcccctg 148380
aggctgtgcc gctcctccaa cgtggcctac acggtggaca ctcgcgccgg cgagcgcacc 148440
cgcgttcccc tggctccgag ggagtaccgc cagcgcgtcc tgcccgacta cgacggctgc 148500
aaggacatgc gggcccaggc cgagggcctc gggttccacg acccggactt tgaggagggc 148560
gccgcgcaga gccaccgcgc ggccaaccga tggggactcg gggcctggct gcgcccccgtg 148620
tacctcgcct gcggccggcg cggcgctggg gccgtggagc cctcggagct tctgatcccc 148680
gagctgctga gcgagttctg ccgggtggcg ctgctggagc ccgacgccga ggccgagccc 148740
ctggtgctgc ccatcaccga ggctccccgc cgccgagccc cgcgggtcga ctgggagccc 148800
gggttcggct ctcgctccac ctcggtcctg cacatggggg ccacggagct gtgcctgccg 148860
gagcccgacg acgagctcga gatcgacggg gccggcgatg tggagctggt ggttgagcac 148920
cccggcccga gccccggcgt ggcccaggcc ctccgccgcg ctcccatcaa gatcgaggtg 148980
gtgtcggacg acgaggacgg aggagactgg tgcaatccgt acctctcctg aacacgatgg 149040
agcgcctccc tgcggccgaa aacaagaaaa atcagtacat ccacaactat gtgtccgccc 149100
agcacaacgc agactccgcc tagactcccg cctccatccg ctgacgctga accccgcccc 149160
gccctctgct gacgcgaaga caaggccctc cccggacgac atgtgaggaa cgaagggggc 149220
gttgtatcta gcagcccacg ttccttattg ctcacatgtc tgcccaatcg gtgggcactt 149280
ccaggctttc ccctatcgct gagtggttgt ttttaataaa gtttttttta aattttgatt 149340
gaccgcgtgg tctttgttta ctgggcgggt tgatgggcgg gttgatgggc gggttgatgg 149400
gcgggttgat gggcgggttg atgggcgggt tgatgggcgg gttgatgggc gggttgatgg 149460
gcgggttgat gggcgggttg atgggcgggt tgatgggcgg gttgatgggc gggttgatgg 149520
gcgggttgat gggcgggttg atgggcgggt tgatgggcgg gttgatgggc gggttgatgg 149580
gcgggttgat gggcgggttg atgggcgggt tgatgggcgg gttgatgggc gggttgatgg 149640
gcgggttgat gggcgggttg atgggcgggt tgatgggcgg gttgatgggc gggttgatgg 149700
gcgggttgat gggcgggttg atgggcgggt tgatgggcgg gttgatgggc gggttgatgg 149760
gcgggttgat gggcgggttg atgggcgggt tgatgggcgg gttgatggtt cctgctcctc 149820
cccttcctgc tcctcccctt cctgctcctc cccttcctgc tcctcccctt cctgctcctc 149880
cccttcctgc tcctcccctt cctgctcctc cccttcctgc tcctcccctt cctgctcctc 149940
cccttcctgc tcctcccctt cctgctcctc cccttcctgc tcctcccctt cctgctcctc 150000
cccttcctgc tcctcccctt cctgctcctc cccttcctgc tcctcccctt cctgctcctc 150060
cccttccgct acgtcactac cgcctacgtc actaccggac tcctcccctt ccgcttccgg 150120
ccacgcccct tccggtgacg tcacaggaag tgacgtcact ttgaccccccc cccttagacc 150180
acgcccccct attcaaatgc gggggtgaga cgcgggctgg ggg                   150223
```

<210> SEQ ID NO 2
<211> LENGTH: 145597
<212> TYPE: DNA
<213> ORGANISM: Equine herpesvirus 4
<300> PUBLICATION INFORMATION:

<301> AUTHORS: Telford,E.A.; Watson, M.S.; Perry, J.; Cullinane, A.A.; Davison, A.J.
<302> TITLE: The DNA sequence of equine herpesvirus-4
<303> JOURNAL: Journal of General Virology
<304> VOLUME: 79
<305> ISSUE: 5
<306> PAGES: 1197-1203
<307> DATE: 1998-05
<308> DATABASE ACCESSION NUMBER: NC_001844
<309> DATABASE ENTRY DATE: 2000-08-01

<400> SEQUENCE: 2

```
ggccggcctc tctctcgggc gcgggcagtt gaaaaaaaaa atttgcctaa tcgccatcgt     60

gataagcaca cgttatgggc ggtgggggat gggatttcaa tggaggccac acccacatgg    120

aggccacacc cacatggagg ccacacccac atggaggcca cacccacatg gaggccacac    180

ccacatggag gccacaccca catggaggcc acacccacat ggaggccaca cccacatgga    240

ggccacaccc acatggaggc cacacccaca tggaggccac acccacatgg aggccacacc    300

cacatggagg ccacacccac atggaggcca cacccacatg gaggccacac ccacatggag    360

gccacaccca catggaggcc acacccacat ggaggccaca cccacatgga ggccacaccc    420

acatggaggc cacacccaca tggaggccac acccacatgg aggccacacc cacatggagg    480

ccacacccac atggaggcca cacccacatg gaggccacac ccacatggag gccacgcgat    540

cgaggcacgc ttgtagctgc catgccacat agtgcgggtt acacagtgcg tgttacacac    600

cgggtataca caattgttcc tgctcgttaa cttctattag ctcgcgccag ggtgtcaccg    660

tcgtgcttct ggtaaccacg acggctgcag ttatcccatt gttagtgtta tttctatccc    720

cgcaagtaac gttttcatat tgctattgct agtcccaccg cccataacgt gtgcttatca    780

cgatggcgat taggcaaatt tttttttca actgcccgcg cccgagagag aggccggccc    840

cctaaacatt tcctaagctt ttcctttgga gctcctccct aaatgccttg gctatttagc    900

cttccgctcc tgtctgctta cactttacac ttttctgctc gtcatgaggc ccacggaagt    960

ttcacgtggt cgcgcctcct cggtatccat ctctgtgtgc ccacctcaac caagcgggaa   1020

acgacgtgca tcgctggggt gtgcacctcc acaacacagc cacgcggcat gctgtgcacc   1080

tccgcgtttg gattccagtt actcccagga acgctcgctg tcggcgctgc gcccgtcccg   1140

tgattcgcgt gtggattcca tacactcttt agggtcagtt acctacctat ccgagcaaca   1200

gcttccatca aggcctccat catacacggc tattaacccc gagggtttat tagagcgtgg   1260

agttgagaga cctcgagcgt ggaccgcgag cgtgattagc gccccaccaa gttactcgga   1320

agccatgttt caagctccgc ctgcatacga actggttcca gaactttctt gtcatcccac   1380

gcaagacccg cgcgtaattt actcacagcg ctcacgcccc caaccttctc gtagaagaga   1440

gaacccagta tgcatttttg tgattgttgt gataactatg cttttaatac tagcgttgct   1500

gctaactatt actcttagct cgctcacaaa atccaaaaat taaaacaagt ggttcaacac   1560

agttgtatta tgtttatttt cacaaacacc cctttccaaa tccacggtac actattccgg   1620

tcaacactag aatgttcaac atcagcaaga taatgtttat agcggcaaac tgtctgcaaa   1680

actttttgct gtaaagacgc ctctttactg gtcccatgtt ttcaaagctg ttactgcggc   1740

tgcgggtggt tacaaagcca tcgaggtaca cttcttctga atccagtgcg tctgtttcgc   1800

gtaaatctct tgggattcgc tctagatgta aaacagctgg actctcggag tatgtattgg   1860

aacaattgtt agcggtagcg ttctgggtgg gggttagaga ctcggtgaga acgttgttta   1920

ggctggcaga acttatgcaa gtgtattctt cgttctcgga gtcgctttca tacccatagg   1980
```

-continued

```
ggctaacgcg ggctggaccc tgccacgctg acggtggaaa tgcgactttg tcataccaca   2040
cggtagaggg tttcttttgg cgctttttct taaatagctg agccattcgt ttgaagaata   2100
actgggacaa taactgtcgt ctgagcgact cgcgcctggg acgtacttcg gcgttaattg   2160
tggtaggtct taaagcgtgt atgcgccttc tccgcttttg gtccatgctt aaacactcca   2220
tgcctagtgg gcggagtggg ggagggcgta tgcttgtaat ttaagatcca cgttacaccc   2280
aaggagaaat tacaatctgg acagacgtcg cccttttata tgtagaacgt cacacttacg   2340
tgacgcatgt accgctgcag tactcaagaa cgccgttctt gattgaccca gcggcaaata   2400
tcgcctttgt tcctggcgtg ttgggtgtta agggcacacc cctgcagtta acatcgatgg   2460
gggtgtgctg ttctgtaaga cgcaagcact caccatcgct gacagccttg gctgaagaaa   2520
cagaaattgt actgcgttgc ttagcgggac gggttgtaga cctcccaggt ggggatgaag   2580
tgagaattgc accagatgtt ggacggtcgg gacaaaattt tggatatttt aaattttctg   2640
gaccgtctcg atttgcctat gtgaagttta taggcagagc atacgcactc ggcagcgggc   2700
gcaagtttct actgtatcta tccagaaact atcaggtgtt tggatacgaa gacggcaccg   2760
gcttgcatat gctcgccaag acactccacg attttttaaa gtttaaagga ctatccaaca   2820
gagatctggt ggtagttgac tccgttgcgc taacctcaca acttcggcct ctgacgcttc   2880
ctatacggtc tacctcggac gttgaaactt tattagcaga ggaagctacc accaaccacg   2940
cttccaccga aaacctttta ggtgagtcac aaaacactca ccagcagcca ttaagtttct   3000
cgcttccaag cattagatct aaagcggcat cacaagtaca accaagtaac caacggttaa   3060
aaggccgcgt tgagcgagct acgtcccaca agtctactct ggaggaaact gtttcgcgta   3120
aatcaaatct atgtggagag ggtaacccac ccagcgagcc aaactgcctt acaccagaga   3180
tggcggactt tgacagcgac gcatctgtag cttctgtttt cttttaaata aaaaaaacat   3240
aacaccaaat actgtttaaa tttattgttt attgcatcgt tggcgctctt ttgcagaggt   3300
aattcccctt gcaacgctta aaattttagc ttgagcagca ttggctgctt gccaacattc   3360
tagagagaat ggagttttgc agtggcagtg aaaacacagt ccgtttatcg tagtctcctc   3420
cccgtcctgg tcacagtcgt attgtgttgc cgcactaaac ggtgcgccac acacgctgtg   3480
ttccatagcc agttcctgca ttattctggt attattgagg atgctccgaa agttgatcag   3540
gtctggaagc gagatttgtt tttcggggtc cctcttttca aacacaccta taaaaaaggc   3600
atggaggcgc gcctgtatat cgcagcacgc tctaatggta taggtccgcg tgttaaggta   3660
ggacctgctt ttggcgggtt gggaggtggt ttcccacgaa ctccacgtta ggtccagagg   3720
cagcggcgac accacgttgc tgatgtccac cagtagcccc agcttgcagt cgctgctgta   3780
gcacccgcca tggtctctac agtgggtacc attatctcgt tgcttagatc cggatgcgtg   3840
ttccgcgcgg gctacgggta gcatttctaa tcggatggcc tgccgaccaa ctggggatct   3900
gcttagctct gggtaggaaa actcagtatt tccaacttta ctaaagacac caccttttaa   3960
attcaacccc caagcacctc cccgtttata ttttaaaact caacaaagct tttataaaat   4020
aatcaaaaca gtatttatta actggttaca caaacagaat ttgggttacg taacacaatt   4080
ttaaaagatt tggttacagt aaaagtattt gccgtgaagg taaacaggga ctagggtgta   4140
acttgaaacc aggctacatg tagattcttt gcaccgccgc ttgtgcaagt ctatagcctc   4200
tagggttcca gccaaacatg tccccggaac gtagttggct agagcatgcc cagcgggtcc   4260
aagtgcgtcc ggagacaccg cctcggcgcc actcccaacg gcccgagcta tgcgcgccaa   4320
ggtcacaaac atgaaggtcg gaacgcacgc aacgtccgat aggcgctggt ggtcgcatag   4380
```

```
ctctgcgaga gttgggctgc ctgatgacga gaggtagcac cgcatgaatg gttctagttt   4440

taggcgcagg ttttccaaca aggctattga agagtggatg attggatctc tggtgcgcat   4500

cggaaggttt ttggtgataa tcatcttaca ccaagatatg gtttcgtcag cggaagccag   4560

tgcttcgagt aggttctccc ctcgcataac caagtcccgt agggaccgcg ccgcttctgc   4620

cgcgtgagat ctcacctcaa acagcttgta caagttttct ccatgggtaa ccagcgtgtc   4680

ccatgtaatt cttcgccctt ccggattaaa ttgttccaag ccaaagttga gcaccggaga   4740

ccacggcgat gagtgttcgg ctctaaatcc gccattttta acgggagacg taagcgtttc   4800

gcgtgcccca tggaacatgt cactgatgcg agagctcgtt acacgcttag agacgtcagc   4860

aatggcgttg gcggctgcgg cgttgagtct atcgcccgat gagcgactag acgcattacc   4920

gcttttgttg gtgttgcctc gttgcctgtt gtgatagact ctggatgcgc tgtgggttct   4980

ggtcttaaag cgccacccgc cagacggtcc ggcggtgcaa tgtccggcat cggcagattg   5040

gaaatcgcca ctcctatgac ctaggcgcat gtgtaccggc atgctcgatc tctttggcca   5100

gtttcgcgac ccctggttag cgggtgctgc ttcttggctc tgtttttccc aggcgcgctg   5160

tttccagttg tttcgccgaa agggtcgccg gcgatttttg cgaccgtggg gaaatgctga   5220

tctctcgctg gtggtgtttt gcggtttggg gtttttaggc gacgctgcaa aactcaccac   5280

taggctcttc ggcacttcag agaccacatt tcgaatcgta gacattgtgc cggtagattc   5340

ggacatttca aaggcgcgct tgttaaccac ggcgctctga gcagcttcca cacacgaccc   5400

accgagagta tcatcggtgt cagatcccat tatgctcatt tcgtcatcca taggctcaca   5460

actgcttacg cttgaaagag ccatagtttt gatacagcag agtatgtctt ccagggttgt   5520

aagttttaat cagtaggtgt acccaaaaag gccaagagtg cggatctcct gggtgtcagg   5580

atttttatag agacttacaa gccgcgccca ctagttatta ttgtgacaag gactcgccca   5640

ataagccaat ttgaatacgc tgttcgtagt gaagcaaaat cgacacagcg ccaactacaa   5700

gcaacaggta cactattttt ccgcataggt tcgcaagcac agtggaacaa caactggtac   5760

acagtccttt cactccgtgc accatggggg ctgggggct tacattagag ccgggtttgg   5820

ggggtttttc gtatataatc gcaactatct ccacgattgt tacagcgatt acaaaccccc   5880

acgaagcaat tttaacataa atggggtata gctgggagca gggagtatgg actaaggtta   5940

cagttccaac aaccagaatt cttgcaaaaa gatgcgcacc cacctcgagg ccgataagcg   6000

ccagggcagc tgtgtgctca cagagaaatc ctatagggtc tcgcttaaag gttttgctga   6060

gagctaccct gcgcagagac gcttcacata gcagcagggc aaattttgta tagtgggttt   6120

ttaaaacggt agtagctaga gtgtaagcag catagttaaa ggtatagctt gtaggcgata   6180

gaaactcgtt ttggtttctg aagggtccca gcaagcggcg ctcctgccgc aaacacaaga   6240

acgcaatgta tatgatccac gctacaatga tcatctggag ctgtacgctc cataggtagg   6300

ctttacagtt tcgagttccc actactattc gcaccttatc atgtaattct ttcatgttct   6360

ttaaaacgtc cagcttggtt tcgttgaccc agttttctct gcagatatag tcaaatcctg   6420

ataggccatc accaaatcgc tttgctccat tttttgggta cgcatacact atagtggagt   6480

tgtagacttc ccacctggta gcgattccat cttttgagtc tatagaaact gtagcgtaga   6540

cgcatgggtt atgaagctta gctgtgaggg tataccaaac ggtgaacgcg gcataggcag   6600

tgatcaatcc cagtacagat aggtatgccg ttctcccccc gaataacatt gtgtatatta   6660

ttttgctctg ttcacctcta gcgtaaaaat ggtgcacatt ttattgttgc cgcattttgt   6720
```

```
agcaaagcac tgttgactta tggatgcgca aagtctaccg tgagcgtcag cacttattga   6780
caaaaacgtg cgggccaatc cacgtgctga gcgaaggtgt ttagctcgca agcagctgaa   6840
cccctgtgat ctgtaggcgc ttccagatcg attaatttgc agtaaaatcc agtcaggctt   6900
ggtcactact gtgtgtactc caaccgtgtg atattcaccg gcgtggttag ggaaatgcgc   6960
actgaggtgt aacaccacct cacagagtac cacgtcgaca acaaacgcct cgacagcttc   7020
gttagatttt atagacacgt tgtagctcga cagaagaaac tctagcgtgg cgcgtttagt   7080
catgatcgcc tctctatttc gagctacctt gcgctcaaaa aagctgacgt agtcaccacc   7140
gaggtttgtg attacatgag ttactgtaga actacggggg gatgcatgaa agtgaaaatt   7200
ggcagggttt gaatgctctg ctataaactc atttacattg ttgcagtttt ttggaacgac   7260
gtaaaaggga tatagaccgc cataaacctc cccagagtcg cccactttac aaaaaaatgg   7320
aaggcgaagg ctgcgaccat gcgagtaaac tccagtgtct aaaaatgaaa aatcccgtaa   7380
aacagagcac atactctccg taaacgtgcg ctctaaaaca acagcctgtt gtatgatgcg   7440
tgccacacct cgcaaagcct ccggtcccgc caagatgtac ggtggtggta ccggaacagt   7500
gatacgaaac cccatttttt ctgtacactg gcaagcgttg gtttcaagga gcagttgtag   7560
cggcgttttg tcggttgttt tattttgggg tttaaaatca cataccgctt gagcacattc   7620
attatcatca acaatcattt catagtcgtc tgtcagatca taagtgtatt cttccatggc   7680
ggcataatca tctagaaagt tagattccat gtaatattct tctacgcagt caacgtaatt   7740
tgagagcgac gagtgctcgt ttttggtacg cgctttaaaa agttgagggg gacactgagt   7800
tttgtaaaag taacacgggt aagagtccca ctgtactaca gcctcggtaa agatgagtga   7860
taatgttgtt atgatgccat ttctaaagcc tcgcattgct aggtgaagca tacccaacgg   7920
aatgggcttt tttatgtcaa aatctacatc caaaatgatg ttacttacgg caagggacga   7980
gttaaaaatc tcgtttcgat taatatacat ttgcagcgat gcgtttgaag aggccatagc   8040
ggcgcggcag acgccagtgt cgtcgcgcat aagctgcaaa tcgcgatgtg ccatcgcata   8100
atcgtccatt tgtgacaacc catcaaatga caaatcatgc tcagaagcca gccgataggt   8160
ctggtggtac atattttgtg ttacagtctc ccagcggtca tttgctataa ccgcaaatgc   8220
ctgccgtttt gagggtaaag ccactctata tacaggtgtt gggcccgaaa ttcctctttg   8280
gccaaacagc acttctagcg gcaaaactct accatcaatt ggttgtgatg atgcgatgtt   8340
taataaccgc ctagatattc cacattggga tggaacaccc ggagatagtt cttcaccacg   8400
tggctgatca agtggcggtg ttgtagtaat acactgaggt ttggtagatg gaattaaggt   8460
ttgtatccag ccatgtccag ccaaagatgt ttccacccta tcaagcagct ttaacatttg   8520
cgtagaagtg tcacagatac tcagcgggtt gttacctgca aacatcatcg tggatgatgg   8580
ggtataagtt ttgtcactaa catactgttt gctgatagac acgggcaaac gaaccacctc   8640
agggcttaca ttatgggcaa tgtaatctat tatattgagc tgaattcgaa cctgagcaaa   8700
aaatttctca atagtgcccc gtttcagtga cgaggtagaa gttatgcgct caatgtccgc   8760
tgggtcagat atgctaaccg caagcaggtg attatagagc tgtctgcggt taaagctttc   8820
aaagtgtgcc aagtaaatgt aggtaataaa ctctctatcg gaaacacgca gtccctgtct   8880
gtctgcggca ataaactcct ccagcgcgct gacttcagac acgtctgcct gaattctaag   8940
atctacgtac ctgggaagtg ctagtgctga cggccctctg gcataccaac tttgacagca   9000
aaactgcgag aggcgggcaa acgatgtcaa gtgggtaaga tccaagttag ttgggtttgg   9060
caaacaggga acgttatacg ttttgataaa gtccttggtg gcttgtaggt cgtaggtacc   9120
```

```
accgcatcca gaatggcgaa ttgcttgaaa gaggtagtat ctggtggcca gtacaagttc   9180
cctttctcca ggaccaaatt ttgaagtaaa ccagaacggt gtggtgttgt tattgctgta   9240
tagacgtctg aacgcagtta gcaccttatt ctcatggtgt atatacacag aagttagccc   9300
gggacgacca gtactgtgac cgagaatagc agcctttacg gaacctcgct gggggtcgta   9360
ctttgcggcg gctgccgttc gtcctgttct cgctgtagcg ttgtccagag ttatagccag   9420
agccagtatc aagtcattgt ggagctggaa ggtatctccg tctacaagcg cctgaagcag   9480
tatcttagac gatattgggt gaccgtgtaa caaagtcttg gttaacgctc ttgctcctgt   9540
taaagttaaa aacgcacaca caaacattgg gcgtatgcgt tcttgcggct cgtcactagc   9600
acctcccaca ataccgctta acaaacaaaa gcttactgat ggttttcgct ctaaaagagc   9660
agccgccaac agctcctcgt ctgactgatc agttgtgtcc cagctgtcac caacatcagc   9720
gtccaatacg cgaggctggg agccaaaaag atcatcgagc tcagaactcc agtcgtagct   9780
tataacataa gcatcctcag agctctcctg gccagttaga agcatcagcg aataagtgat   9840
aacgcagcta tccgtagcat aaagaaccct aatagtggga tttgggttgt ttaacgccat   9900
gtttaagtgg ctaatgtcca gtctatgtgg aactaaaaac cccgcatccc tagaagaagt   9960
ttatgagcca attatgggtg ggaagaaccc agccaccatg ctccgcctac agtccgccct  10020
ggctgcagtt aatgcacttt tgccagcaac cctcactata gaggatgtga tttcatcggc  10080
agacaacaca cggcgcttgg ttaaagccca gaccctggct cgtacctatc aagcgtgcca  10140
gcataacata gagtgtttat ccagacatag ggccagttcc gacaacccaa atttgaatgc  10200
cgtggtggct acgcacatgg ccaatgctaa gcgcctttcg gatacctgcc tcgctgctct  10260
aatgcacctc tacctgtcgg ttggggcagt ggatgccact acggacacta tggtagatca  10320
cgccattcgc atgactgctg aaaatagcgt ggtaatggcc gatgttgctg ttttggagaa  10380
gactcttgga ctggagcccc agccatcagt aatggcacat gacttactgg ccctcgaaag  10440
cagtgtgtat aattctggca attccgtgcc agtaaatgac tatccagcgg aagatgttga  10500
gtctacccag agtgtacaca gccctttgct gtccaagcgg cctagcaaca ccgaggttgt  10560
ttgtagctcc atcccagtga aatcaaacct caaatccaag cccagacgca aacccagttt  10620
ggtagcggcg taaaatttaa aaaccaataa acgatttaaa gcttttaaag gactatgttt  10680
attttatatc ttcataacac gtatagtgaa accaggggca gttatagtcc tgttgaacca  10740
aagcccccct cagagcgggc actcgagggt gcgtcgtgat caaatgcttc tgtaaacttc  10800
caaaggatgg gcgtcgggtt atgtttgaca gctccggtgg gcgaataggt aggaaagggg  10860
gtgttatagt ttacgttggt gggtatcagc gcctcgtcaa tatcttccgt taacactagc  10920
tgagcaacac gctgaccctt ggtgatatat acgggatact tattgatatt aaggataaaa  10980
aagcaacacg ttctcccggt tacccaccta gttggtagca ctattaaacc ccttcgattc  11040
atagacgagc gtccaaatat acacggagta accgctgggt tagaggaata aaacacaatt  11100
ggcagttcca caaagtagct ctcatcaggt tctatagtgg cgtttgtttg tgcgctgatg  11160
tcatatcctg cgtcttcgtc gcgttttgga gcaaagtaat cgtaaaatat gttaactctt  11220
ggtgaccgcc cattttcagt taagttaatg ttagtcacgt ttatggtctc cgtgctgagt  11280
tttactagca cgagccccaa actcatacat ccagggggca ctaccgtatt tactccgttg  11340
gcaaattgta ccgctttcac gacgccgcga tatcccgagt ctactatacc gtaggcggtg  11400
tagtagttgg ctagattccc agtaaacgtt atgttgctaa aattccctgg ctcacgtcca  11460
```

```
acatgcggca aaccgctaat ttgcgcgaga acaatggcat atccgctgga gcaggcaacc  11520
cgtacaccta cgtcagtgag cacactataa aattcgcccg cacttccaag cccggcactc  11580
agctcgactg tgtggttgtt gattaacacc aacaatcttc catcagcttc tgctcgcgct  11640
tcccatccat tactacattc aaccaccacg atgttgtcag cgagattagt gacgctggcc  11700
attttaacct gccttttggt ggtgtttggt ttgaccagag gggctagcgg cgaccttgaa  11760
gcaaagcaac gactcgacgt tgcaagagaa gaagagaggc gcgacttttg gcatgcagcc  11820
tgctccggac acggatttcc aattaccacc ccgagcactg cagctattct attttatgtg  11880
tctttgcttg cagtaggcgt ggccgttgct tgccaggcat accgcgcctt cctacgaatt  11940
gtgacgctgg agatgttgcg acacctacac tgagcaacat tgtatgtata atcccggata  12000
tgttgcaacc gtttgactgt ataaaaggac tagcgctaaa cctactagaa tcattcgtgc  12060
tgaaagttcc tttctagtct acagcacttc cattagagtt tgtagaggtt tttactagtg  12120
agtaaatatg tccgatacgt ggcgtagacg tcgtagtggc ggtggtgatg ttaacgccac  12180
agaggagttc gtatactcta caattcgtaa cgaaaatagg caaagacgac cttctcgcgg  12240
aagctttgtt gtgcgagaaa acgaacttta cgataaacag cgtgtatcta gggaaaatga  12300
tttgtatgac agtgcatgcc gtaacgatga cgaagtttac accagacaaa gcagaggcgc  12360
tgccgctcac tacaaccccc aagaacacat atacgagacg tgtccaggag atgaatttta  12420
cgatgcctgt gaatattctc tcgttggagg tggtaaatta tctacctccc atggccgttt  12480
gagccccaca aaaaccacac cccacccaaa gagcgcgggt gtaaccccac cccaacgtgt  12540
accagcgcga ccagctactc gtgcggcggc accgtctgca acaccaaccc agccggattg  12600
tgttgcaaaa caacgcactt cgccaggtgt aaactccata aagagcggta aaagccttgc  12660
gtttagctgc acccccaaaa cgccaaagac gccatggtac ggtgcaactc acctgttcaa  12720
caaaaacgtg ttttgtgccg cagtgagtcg cgtagccgcc gcacatgcaa gcgacgcagc  12780
atcagcacta tgggacctag accctccaaa aacgaacgag gacttggaca ggtttttgaa  12840
ggctgcagca attcgcattt tggtttgcga gggatctaaa ctcctcgaaa tggcaaacgc  12900
aacaatggaa agatccccag atggggctgc agcggtcgcc cccatcggtt acgatcgccg  12960
tcctcggtta gcttctagga ggcgatcaat aaaatgtaaa cctccagcgg atgatttttt  13020
cgacgacaca gattccagat aacgcatttg cataaattta tagcattaca atctcaataa  13080
aatgtaccac ttgcttattc ctttacctta tttgtcgtgt gctctgttac tctgctggta  13140
ttcaacgcgc taccatggcg gctaacatag ccatgtttgc cgacatagaa gattacgatg  13200
acacccgctc ttgtgaatat ggctatggta cctgtgagct tatggatgtt gatggtgtgg  13260
ttgctagctt cgacgaggga atgttaagtg ccagcgagtc catttattct agcccagccc  13320
aaaagcgttt ggcgctacca ccacccaaag caactagccc caccgcatta taccagcggc  13380
tacaagccga gctgggcttt ccagagggcc aggcaatgct gtttgctatg gaaaagtgga  13440
acgaggacat gttctcggca ataccggtac atgtagattt gtacacagaa atcgccctgc  13500
tatcaacctc ggtaaacgag gtagttaaag cggggctcga tagcctgccc atacccacca  13560
actatattcc agaggtagac ttaaacgcac acggaagcga gccctttccg gaggtgcccg  13620
ctctggagga cgaactagaa acctacgtaa tatcggctca gcgattttac ctatcagagt  13680
tacgcgcacg cgaagagcac tattcgcggc tgcttagagg ctactgtgta gcgctattgc  13740
attacctgta cggcagcgct aagcggcaac tgcgcggagc cggatccgat tccgcattaa  13800
tgcataagtt taaacaggtg gtgcgtgata ggtactaccg cgagacagca aaccttgctc  13860
```

```
ggttgcttta cctacacctg tatatttctg ttaccaggga agtatcttgg cgcctccacg  13920
cgagccaggt agtgaatcag ggcatatttg tctctctcca ctatacgtgg ccgcagcgta  13980
gaaagttcga gtgcctgttt cacccagtgt tgtttaacca cggggtggta atcttggaaa  14040
acgatcccct cgagtttaat gatttacagc gtataaacta ccgccggcgt gagcttggac  14100
tgccgctgat tcgggccggg ctaattgaag aagaaaacct acccctggaa tcggagccga  14160
cattttctgg aaaactacca agaacgatcg gctttttgac gcaccagata cgaactaaga  14220
tggaagctta ctcaaacgcg catccctcga ccccgctatt tccgctagct gagcactcgt  14280
acagtaaacg tatagatggg cgcttgtcat acggcacaac agcagaagcc atgatggacc  14340
caccatcccc cagcgccgtt ttaccagggg atccagttcc accgcttacc gtagggattc  14400
gtcagactgc tgaaacgctt gctcttccgt ctaacctcac cctacagagc atggaaactg  14460
acgttcttga ctactcatct atttcaggcg acgagctcaa ccagatgttt gacatttaat  14520
acaataaagc acgtttccaa acttaacata atggccgtat tttccgtcga tacgctgcgt  14580
gaatagaacg taatgggggg aggtgggcgt ggtctgcggg tggtgtatgt ttaaattggg  14640
cccggaggtc tataggcaag ttttgtttgc attcgtgatc tgctgcaaca aacgacaatt  14700
aactaccaat cttcaaatat cgcccattta acagtacaaa actagggggt atggcggttt  14760
tgaagctcgt agcttgccta taaaactcgc gcgccttgcc gcgagatggg tgttgctatc  14820
tagcgtagat agcgggcgtt tgccgtcaaa acctgacggt tgtactacag cgatacggaa  14880
gtagttagca tggaccaaca tcacggcgtt cgcggtgggg cgcctatacg caggcctcgc  14940
agatcaatag aaacgcgctc ccatccattt agagccgcag gaaatacaca gcgcacatac  15000
agcacgccaa gacttagtta tagagatgga ttgtctggca gagcctcttc acttgaaccc  15060
gggggccaag ctcacgatca aaatgagagc tctacacaaa gtacttcaaa taatcaacca  15120
agcacctcat tttggggata tctacgaaga gttttttcag atgatgcccc cgcgcagcca  15180
caagcaccaa ggtctcgcgc tgattttgct cctccccccg aggaggactc atccagcgag  15240
gaagaagacg aggaaggtcc ctcacaagct ccgttggatg aggaggacca gctcatgtat  15300
gctgaccaat actcagtagg taactctagt gatgataacg aagaagacta cctacagcca  15360
gaagttgaat atccaacttc cgcagaatct ggcgaatatc ataacagtgg gatgtttgca  15420
gaagaggagc cggaaagcga gtctgagtca gacatggaaa actacgaaac gtacgaggaa  15480
aatgatacgg aagtcatatc agatgatagc catagactta ctcgtacgtg gttggatagg  15540
tctatacgct taatggacga cgcacttgca cagtcttctg aaatttctaa ggctatcact  15600
aaatctacgc gcaggttata cgatagccag tttactccag gggtcgaggg ctacaaacaa  15660
acggaaaccc cctcccagcg tttggttcat ctatcacgcg ctggtatgta cgattctgac  15720
gaaatcgtta tgacagggga ttacatggag gttgacgacg acccaaacag cgcttaccag  15780
tcatgggtgc gcgctattca ccacccggtt gccatgaacc catcatggga ggaaacaatt  15840
tccaatcaca ccaatacatc gttttctgcc gacatagact atgatataga cgagctaatc  15900
gaaatgaact tggcgcgaac acccccagtg tttgagggat tgctagacag cgcagacttt  15960
ttttacagac tacccatgct ctatacatat gctactatca ctcaagacga ggcctacgaa  16020
gagcggcagg catggtctaa tacacaggcg ctgcatggac acgaacaaag ttcttggcca  16080
gcgcttgtga gtgattactc taaggggggg atgtacgtgt cccctactca ggaaccccgc  16140
gggatatggc gacgcgcgct aaaacaagca atggctcttc agctaaagct atgtgtgctt  16200
```

```
ggtttaacag aatttgtaac taagcgtgag ctcacacaac accattcagc tgtaactttt  16260
ttggtcgact cgctccttag aacagcaaaa aattgttact tggccagccg acttttagta  16320
tttgcctggg aaagacgcag ggaaactggt gtacgacgcc cagcagagcc cctcatagca  16380
ctctccgggg ttacgcttct ccaaccgctt cccccagaag tctcagaatt acttgagcag  16440
cgtacatttg atatagggtt gcgcaccccc caaagtggag tgtttagagc gttcttcgga  16500
ccgcttgtgt attgggcaga actacgcaga gccttgcgag acccagctgc cataaactgt  16560
cgctatgttg gatttcatct ccaaacatca gaaatttatt tattggcacg cgcccactct  16620
gccagcccag gctacaccaa agaagaactg gtggcaatgg aggcaacgct cacacttggg  16680
accctcatgt tagaggtagc gctacagtgg atacacgtgg ccagtgcaca gttacttagc  16740
gaaaacgatg cactgaaagc ttttaggcgt gtgagtgcgt ctattcccca cgccctggcg  16800
ccacttggta gcatacgcct acacgacgca gagtttgaag tgctaagcaa cccagatgtg  16860
atggtggcac gtgatgaaac cgccctgagc caggcgttgt ttcttggata tttttctgtt  16920
aggaccgcac taactgcgtg catgcgtgac tatgctaatg aggtggatgg gggatctaaa  16980
gagaccgtta ctggtgtgtt tttgggcgtg gggctaatta ttcagcgcct cgctggccat  17040
atgaactttt tactaaactg tatggccggc gcggcacttt atggcggtag caaaatcgcc  17100
atacactcat taactctgcc cagatacagc ctattggcgg atgttatggc ccctatgctt  17160
cagcagcagt ctttggtcga cttttggcgc gccagagacg acatgttgga ggaactagaa  17220
ataacaccac gccctggacc cccaacgcaa ggcaagcgcg tggtgctgga gatgcctttg  17280
ccctcggacg atcttccagc tatgactccc agtggccaag taaacaatgg cgccggtttg  17340
gggcgcatgg tggacatggc caaacactta cagcactata gagaaacaat tatcggagac  17400
gatgcctctt cctctgtagg taaacgtggc ttaatgaaat ctggtgtggg cgtagccgcc  17460
atgcgctgga ggcggagaaa gtaataagat actcacccaa aagcacttaa tgctgtttac  17520
gtccccggta tgctctcaca ttccgcaagc actttcatga aacctcttct acttacctag  17580
cacccaactt gtttgtacgt cttcgtaaca atctatacat taactgaata caatggaagc  17640
tagtgggtct gcctcatggg cccgcgtttc caaaaaccta atcgagcgcc gtgcagtcaa  17700
agggtgcctc ttgccgaccc caagcgatgt tatggacgct gctgttatgg ccttaaaaga  17760
cgcaaccgag aacgttgtga gcaaacacct attttctgta gatcgtacca acgcactgtc  17820
tgtgatccac accaatgctg ttccagaatc tataattaca accgccattt tacgcgatac  17880
aaacggagaa tatcgtagag aatacgaaga ttctgcaaag tgtaacttag ccgctacgga  17940
tttatcacag gatggaatgt gggaagttgt tatcaaaagc tattggcgct accttaggga  18000
atccagcggc gctgaggttg ttgatcgcgg aggcgtggga aacacaaccc agtctgtgtt  18060
atctgtactg attctccagt ctacctttgg caaaaaacgt ctatcaaaaa atccatttaa  18120
acacaaaggc ccaaatgtaa gctacaagtc taacttagaa aacctgcgcg ccgcctttac  18180
taaaatagaa aagtatatgt actatatgcg acccaatgat ccaatgacta aaagcgagga  18240
cacagaacta cggttgcacg agttactggc atacgtggca acatgttaca ggtggctatt  18300
gtggtttatg gacctgacag acgcaaaggt gttaaaaaac atagacaagg ggcccgtaat  18360
tacacacgga ccgcgcgaaa cgcgccctcc ggatgaactt gttcggcgcc acctcaaaag  18420
cggccccgca atttccgccg gaacgggtga tgctttaacg ttatcaacag caacggccga  18480
cgctctgatc gttttactga ggatgagcgt ttcttggact tctcactcgt ggaagagcaa  18540
tacccacggg gttacgggtg ctatcgtggc cgcagttgag cttgtaacgc tcattcatca  18600
```

```
ccacttgcag tacataatta atactatatt tgctggatac gtatgttggt tggacggcgg  18660
cgtggaaaat tcatatttaa attctgcgct tcgcaaccag ggaaggtttg accattttgc  18720
gggaaaactt gttccaatca tggctacact cagctgggca aacatggaaa agggaacggt  18780
tatgtggttt aaatacgcgc tagctaaaag tatagtgtgc cacggatcac ctactcagca  18840
ctacctaacc gtgcttgact caatcgcatc aaagcgcacc ggcgctggtt tacctcctgg  18900
ggcaaccttt ggtcgcacag ctaattttca aggacaattt ggctgcccgc cccagggacc  18960
tcttcctgcg ccaccaaact ctaaaactaa aagcatgttt aagcgacctg gacgtggcag  19020
cgttcgcagc ttaaaacagt tacccgcatc cacaccaaac atggtttctt cagcgactac  19080
ctacaatgca gggggtaata cggccgctac aagcggtcaa ggtgaggaag ccatacaaat  19140
acacgcttcc ggtgaactta atgactgcat ttggtattta aatggtacct actcacatca  19200
gcgcagcgac agtagctcgt ctgataatag ctcgtgctct agcacagaaa ctgagtacat  19260
cactatatcc tccacgcctt cgccaaccag agaagttgtg tataccgatc cgcttttggg  19320
ttcggacgaa gaaaaagacg caagtccaca accagctaat acagtgagcg aatactcatc  19380
tcccgcaaat tccggctata tgcgcccccg gagcacgctt gcggaggaaa tttggcaatt  19440
gcgggactct gattacactc cctacatgcg ccctagtcgc gcgggtcgcc cacgtttaag  19500
attggaagac cagactttac aaacattacc gggttgcaag ccacccgcaa attctccaga  19560
agacaatttt gaggacacct tattttcgtc gtcccagatt tactccgata acgcacacag  19620
tacctttaga ccaagagcca ggtgtgttga cgacgaatat gggttaactg cacttgcagc  19680
tctcagcgcc tcccaagcaa aagccaggcg ggtgcgtttg ggtactacca ctcccacttc  19740
tgctaacgaa gcaactgaga aatacaccac acccagcagt ggcggctgta tcaggcgaac  19800
cctttcaaca agcgagtctc ccgaaagcag cccggagcaa caagagcgtg taagctcgct  19860
gtaaccaccc catgtaccat ttaaaattat attaataaaa acatttaacg aataaaatct  19920
taaaatatta atactttatt taagcactca caaacacctt taaacagggt caaatgttgc  19980
gcctataact ctgtatattc cagcgtggag ttatctatta ctgcaaaaat ggaagaatgt  20040
ggtcaagccg aagcgcctgg cgggccttgt aaatcaactc tccaagtggg ctgagtgggc  20100
gggcggcgta gcacacacta acgcgttttc tggagcatac cgagttttgt gaaaagttac  20160
agtttgcaag tggtgtgtcc gtcagattta gtttttctcc agccgattcg ttgatgccaa  20220
tgtttaggca gtccagaagg ttcattatca ggacagtagt gttgtccggg gccggcatct  20280
cagaatatgc tccacataca gcccctattt cgctagagtt gctgctgttg taagcgtcta  20340
gcgacacggg gcgtacacac tcgtcaccca gaccaaaggt ttgcgctgga catggtgctg  20400
tgcgtagcgc gaccatgggt actgttagga caaaggtaga caccaaaagt gtggtggtca  20460
ttagaacccc catcgcaaac atacccatcg taaaacagag gcagcggcat ctagatctgc  20520
gttttggtcg gcgccgtttt gtataaacga gttcggttgg ttggggtaga gtcggcagcg  20580
gtggtgtaaa ccccaaaaca gtctttgtag gtagttgggg agcttgatca ttaccggcag  20640
ctgtatcaag ctccagtaat tgataatctt ttagcgaagc tgttgggtct ccagacatat  20700
tttcgcttta cttagacgtt atggctgcat agagatgagc gtataatgca gagtaaaatg  20760
gctttataaa tccagccggg gcgcgattgt aacacaaaac taacggtttc cacctagagc  20820
atgaaaacgc atatgtttaa taccgtattt ataagagtgc gtttgtgaag acagccagcc  20880
agactgcggt ttgaactgta tttaaaaaaa ccagctgctg ttcaaactga cgacgagctt  20940
```

```
agaagtctgc tttcttgtac ggcacctgcg agggttttga gcagtaaaaa caaacggctg  21000
taatgagaac aaccagcgct agcgctgcgg ccccgcaagt aacggcgatg atgctagtta  21060
aaacgggcat gtcctcaaca ataggggatg catcatatac aacgctgtca gaaaacattg  21120
gaaggccgtc cgggtaaccc tctatgatgc agttatactc tcgctctccg ttttcttccg  21180
acaggggcct gctactccgc atgttgacta atcctgggtg gcttgagcaa actcccgttg  21240
ttacgtcttg tgatgggacc cccggtaaat ggtcgttaac gacccacgat acaaacactc  21300
cgttgctagg tacacattct gccgtacaaa ctgctgcacc atcttcaacg tttacggaca  21360
cggttggggc cacgaacaca gagggcgtgc ctgctttggc catgcgagaa aaggatacct  21420
cgtctctgta ccattctatg ctacagcgga ggctgggggg atattcttcg tcggggtcag  21480
ctgggattga tacagtcgag atgcgagtga tgagaccatc cacccacaca ctagaagcat  21540
tggtaacata ctttgtaaaa tcaacctctt tggcgttttt ataccacctc agcttaacag  21600
agttgtgggg aaagtagcta gcaactacgc acacggctct gtggttttca cccttcaaac  21660
ttgggtgaac ggagaggtcc attaggggtg cgttgtacgt taacacggta acgctggtac  21720
tgttaatgag tgagccgttt ttggcaaaca agtaccacac ataaactccc gcggtacgcc  21780
agtctataga ttttatgttt agtggaaaat ttgtaccacc gttcgtgtgg gccgggaggt  21840
tgaacagttg acgcttaggt agcctgtctg gaataacgcc cagctggcca acccttcgag  21900
atttcgcgct agaatgtgcg gttgaaaata acagcagggt ttggtctttg gtagcgttgt  21960
ggttaacata gttttcttgg tcaccaggag gcgtgtctga aaatggggtg cgctggttta  22020
ggtgaatttc tagtctgtat tcactgtgat ttacacttac tgttgtagaa cagttaatgg  22080
taacagatgt gtagtaggga accgatatga gactatttgt gcatgtaatt gtattttcat  22140
gtgaatgtgg gtgactcggc gttggtgtag cttcggtgcc gtttacatcg gttgagttgt  22200
tcgtggctgt tgaattatta gagtccgtac tggttgtgta agttggtgtg actggagaac  22260
tggtgccttc gccagtattt gtggttggtg tggctggact ggcgctagca ctggtcccag  22320
acgtgcgtgt taatataaac cccccacaga ttatatacgc aaatgttatg aatcgcatta  22380
tatttaccaa acccattgct gtgggttata tgtttgcgat tttccacaaa gaacaataat  22440
aactcttctg gtcggagagt tataagcata ccgtgcccca aagtgtgtca tttaaaggcg  22500
gccttcttta tgtgaattcg accgatgttt aaatcaatac accttgtggt tgttgttaat  22560
actaattgac atgtttaatg tgtgattata gttgcgtaac ataaacccgc tgcaacatac  22620
acactaacaa tcagccacct tgaaatgtgg gttgcggcca aacggctggc cccgttgcg   22680
cgcttacgaa ggtacaaagc cccaagtacg cccccggacg tagtaaatgc aagcgaaatg  22740
ggagcggcca cccaataccc aaatgctgct aataccacgc aaactgcgtg ggccgtggcg  22800
tgaattccgg agctagcctc ggcggtgtag tttattctga cgataagctg ctccaaaaac  22860
atcgcagaaa cgtgtccaac ggttaaacaa aaaacaacat atgctggcgt ttgccacacg  22920
tttgaaagtc cgtaacccaa gcgcagtacg atccaaataa tcggggttgc gtgtgtcccc  22980
acggccggag aaaatatcac ccccggaagt tctttgaaaa acttgaacag ggaaaccttt  23040
tcttctgcaa cttcttcaat ttttggttcg gctccagcat ttgttatcca cgtgtagtta  23100
actccgcggc caaggtcagt aaaggtgcgc atacacgcat accgtccgat gcgatagtga  23160
caagtgtctc tgagattgag tccaaagttt gcgcaagaag tgattatagc tatggctatt  23220
cccagaccaa ctggtacatc tttgttgtta atttctacga gcttggcgga agcccctagc  23280
aaacacccac taataatagc aagcaggctg gctctgaagt gagttcctgt tccgtttgcg  23340
```

```
gcgcatatga cataaaataa agagatttga gcaccagata taaacacaaa caagatacaa  23400
actgtaacaa caataagcaa ctgttccttt ttgatgatgt gtccagcaac ccaaacaccg  23460
gcagctatta gtgttgagat cgcctgaaca aatcgacaca cagtcactag ggtttccatc  23520
ctagatatat gaacgcgaat taggcttaat acatacagcg atattagcat catgatcaga  23580
catgttgagt tcttggtgag taagtcaacg tgtattatcg atgaagttaa aacgcaggct  23640
tgaagtccaa ttccaatgaa agcttttgaa gctgcccatg tacatggcat gcagcccttc  23700
tgggatccgg tgcagcgctg cacagaaaac gagcttaaca caacacatga gtcttcccca  23760
agttctctcc ctggacggta aatcatgctt gccaaccttg atgtagcaag ccaccctctc  23820
ggagagtttg aggtacagga ctccaaaagg acggttttat gcccaaggta ttagtcataa  23880
aacaattagt gggcgttttc tacaattcta aataggttta ataaaaacaa aacacttgat  23940
tatacgttat ttaaaatatg cgtttttatt tttcataaca caggtatggt aatagctcaa  24000
attaagaaaa gttaatggga gcttcgggac agggaatttt ggctccgttt ttgtccatca  24060
acaaaacaaa atttgtttta aacagctttt tgtctggaga tagtttcttt gggggactgt  24120
tgctgtcgtc ttcgtctgat gcgcgccgct ttaagccaac gccgagtgag tttggtgaaa  24180
aagcagaatg ggaaaacccc accttgcacg gctgctgagg ataggagcac ataaaaaaca  24240
tcatgacgct aaacggttgc ttggtcgaga gtccaatcat gggaatagat tctggctcca  24300
aaaaaaagtt gagcacggcc ccagcgtttt tgagcttaag cttttgaatt agctgcttga  24360
agttagtgtc ctcctctagt aacagcgtaa acagcttgcg accgctaatg ccccttattg  24420
gttctggcgc tgtctttttt gtttttagcg gcattttttc caataaactg gaacttgact  24480
ccatgccaca ctttgtcgca ttctggtagt ccacagaaaa caccacctgc ctatctccag  24540
atcgtacctg gagagtgtcg tcaaaaaggc actggaatgt aatgggctcg ttggcttgtt  24600
tgcagacccc caaaatctta tttagctgct gtttagatag cgacattgaa acgtccggct  24660
tgcgcgtggg tagcatcaga gagtagttgt tgaactcatg tttaaccagt ttcgttgaaa  24720
ttgcttgggt tgtgttttct ggatccgatc ccatatccat atcgtcttcc atttgatcgc  24780
ttgtggaaaa cacagtttgc gtgagtatcc tggtaggtga agcgttttct atttcgaaaa  24840
ctactttact cacggttggc tgggccttgg tccggaatgc gtccaataaa cccctgcgtc  24900
cgtccacgtt ggctaaaaac accgcaggtg gggcttcttg ccaagagtac gaggccatgt  24960
tgttcgtttg gatggggatg tagacttgct cgcccccgac gctggtgtga attagcaatc  25020
cgtcctcgtt gaagatcaaa aaggcatttt tgagactagg agcaatagga gtgagcatct  25080
cgagggcatc tctcagagat tcgcgctcaa aaacagccat ggctctttgt ctctccacgg  25140
ggttgtcgat agctggtaat gcgttcaata ggaagttgtt ggggtgagat ccacctgagc  25200
gcatcgttcg aggaagagcc atcgctgtag ctgcaaagat tgggccaagc agctcgaagc  25260
actctatatt agagcgtaac aagcagtact ttaacccacc ccggagcact tcttatagag  25320
tttcacgcta gagataaaaa gggttaatat gacgtaacca tgggagtggt taatgaggga  25380
tgggacccaa ttcaccgtca gttaagatat cgaggcattg taggcgtgta gttttaagct  25440
gcgccagtta gagcaagcgc aatattgtgt tgtagtgccg actcgaaatg ccgttaagga  25500
taaataatcg tattattgta atagggaaat ttaggggagg ggtttcaatg gtgggcagag  25560
ctaaacttaa caccaatgga aagcttgcct aatcgctcac attaatttag attttcgact  25620
tgtgtccaac tctgcttata ttagcccgcc ttttggtagg gccagttgga gttactgcgg  25680
```

```
ggcaattttg gaggttttac ctggtgccca ttcaatttac tacttcagta ccatatatcg  25740
atttgttgcc cagtttttat caagatggga ctgtttggac tcttaaaata cgcgtactca  25800
aaccggcttg tgaaacacga tgccattact actccaccag gaattatgac accgatagct  25860
atagatcttt ggaatgttat gtacactctc atggaaaagt ttgagtatga ccgcagcttt  25920
cccatggacg gcgctgcagt tactgctaag tgttttttt ccctgcttag gcttttgttg  25980
aagaggtcat actatcccat cttcgtgtcg gacagaggta tatacggtga tgggagagta  26040
aagcaggggg ccaaggctat tgttagtcaa acaatgagca gctacggtgg atctgggcgc  26100
atctcgagct cgtgttttac cggcgatgaa catgatgttg aattgctgga agagtatggc  26160
gaaaccaacg gttccaccac ccagccagac atctgccaac ccaatgaaac ggccacggtt  26220
tgtgtagagc cagcgcgtaa atgcgaacac agctctacgc gctggagcgc acttgatggc  26280
gctccacgcc tttcgtaccg gctctgtgtt aacttgattc gacacttggg atacccctac  26340
gttaacgcat gtaatcttga ggctgatgac gtttgcgcca acttatacca caccaatacc  26400
gtcgcgcaaa tctacactac cgatacagat ctcattctaa tgggctgcga tattattttg  26460
gacattatgc cattgtttcc ccctaccctt cgctgctgcg acgttttgat ggatttgggt  26520
gttacctatg atgagttttt gacggagttt gttcggtgcc acaccgatct ccacgagact  26580
caaaccctag cttctgtaca gagtgtcatt cgctctttat actcaccccc agatgaagac  26640
gaaagcaccg agacgcagca tgctatatca ggacatgcat ggcgttgccc taaagagaaa  26700
cgaggaatct catggcgcag acaaaacgat gattattctg gctcatcaaa tgatgatagc  26760
gacaactcag atagcagcga tgaggatgta gcatgtttat ctgatagagg ttgtaggtac  26820
cgcgaacgcc cagcagcaga taccgtgaac aaacgtcagg ggcgtaggtc aatagaagcc  26880
tccagccgta ttgtacacct aaaatatacg tctagatatc cgcccattat ggaatcggct  26940
cctcgtgctt tagtgcgaat ggccccacca aaaactcgtc atgaagtttt ggagagaaag  27000
tttgtaaaac acgttgtttc tatgctaacg ccggaacgca gaggggcatt gtctataata  27060
cgtcgcctac ccattactca agagccttca aacttttctc tggtccacga taccctaaaa  27120
aacttagtat ccgaacacga aattgtcaga gagcttgcta atatgttttg gaaccacatt  27180
cccacccccca ctgattacaa cactgtgttg gttaactact gggatgactg tggacaccga  27240
agacaatggt cttaaataaa gttaaatcgg gagtatcttt tctcagtatt tttttaaatc  27300
gcgtacatcc aacacgcaaa caagacaaat aagtgaatca aaattagttt ttatttttac  27360
attacagatc gtttataaga gttcccgagt atgcggtgct tcgcctttca aaaaagttgg  27420
tatgtttttc cacagtcatg aaagctaggg ggaagcttgg tgggggtttg ggagcattaa  27480
acagcggaga tagtccaatt tcccccaaaa gcctgtccgc gctatagcgt acgtagcata  27540
tgatggcttc aatgtccaac aggtgggtgc ttttgggggc atgggaaagc aaaaattcac  27600
actcgatgtt tacggcctca gaaaacagcg cataaatcct cgttggagct ggcttttcaa  27660
aacccccaag gtagttgttg tagatacagc acgaggcgtt ggtgtgaatt gcttcgtcgc  27720
ggctaattaa atcattactt tgacaggtta ccacaaagag attgtgggtg cgaagatatg  27780
cgatggacgc aaaggacgac gcgaagaaaa cgccctctat taatatcatc aaaatatact  27840
tttccgccac agatttgcat tctcgcacct ttgcttgcaa ccaagatacc tttaggtcta  27900
tggccacgtc tttgacaaca gatgcgacat acctagcgcg cgctgttgcg tcgtttccaa  27960
acaacataag ctgtatagcg ctatatactc tggagtgcgt tacttcaata gactcttgct  28020
caatgtagta gtgaagaatg tccttttgag taaatagtgc ggataaatct cccaggttta  28080
```

```
aatttaccaa gtcgtcagca gcagataaaa aggcaaacaa aaaccggtaa aactctcgct  28140
cggctggcgc gagtttagca acgtccttga ggtcatcaga aattggaagg tccgtatcca  28200
gccagcggtt ggcaacgctc aacaagcgta ggtgttcaat atcgggacat tccggcgtat  28260
agaaatacgc atttatcaat aactcgtcag caaaatctgt ttttttagag ttttcgaggg  28320
ccataattat tttcccgccc tgggcaaaat ggcgaggctg ccctacaagc tgcagctggt  28380
gcagactagg tctccgccaa caaagactcc gttgtttgtt gccttcttga ttttgcagta  28440
gtacatgcct gttttaagtc cgcgtttata tgcgtggacc aaaagattca taattctgga  28500
ggcggggagt tttccgtcag caggctcagt tataaacaaa gacatggatt ggctctggtc  28560
cacaaacgca gccctgtcag cacacatgtt aattagcata gtctggtcgt actcaaatgc  28620
tgttttaaac ttactgaggg ggtgaccaac tggcaaatca ccaaacgctc ccacaactga  28680
ccatttcgca gcttctagcg tagatagcgc ttgtaagcgc gcgcattcct gtggaaaaat  28740
acttctgatg gtgcgcatta gcagtacatt gggcctgagt acttccccgg tagcagtaac  28800
tttgctaaac aggtttgtgt aaacaggaga aaacccctcg ctgctctcgg taacctgtga  28860
cgaagatact gttggcatat aggctacaaa ctgagaattg tacaagccgt attgttttat  28920
gtcagtgcga agtctacgcc aggcgttgcg gtttgttagt gttacatttg ggtaggcatc  28980
aaagggtagt tccccccgac tgtacttgct gtcttcaaac cctttaaagg gttgcatacc  29040
cagcttgcag agcgttgcgc tggccttcat agagttcaat aacagccttt ctgctatttg  29100
cttgtttagt tggtgcgcct ctggagatgc catatccagg tccagcatca aaaacgtggt  29160
atgtagcccc tgaattccaa gtcccagcga ccggttttct tcaacgcctt tctgggattt  29220
aacagttgga tatgtgctgg cacacatcat cgcattgaca aaaattgtgg cagttgcggc  29280
agcgcggccc agagcggcga agtcaaaata tggcacacct gcaatatttg gaggtggaag  29340
ggctagacat tttgggaggt tgatgctggc tagattacac accccgtttt gggtttcgtc  29400
ggcatgctgg ataatttctg tgcatagatt agaccccatt atcgcacctc tcttgcgcat  29460
gtcaaagtgg tagtgcctgt tgcacgcgtc tttaaacatc aaaaatgggc ttcctgtcat  29520
tacagcactt ctaactatga taaaggccat gtcctgtatg ggaatagcgt ctatcccaaa  29580
tccacaccgc tccaggcgct catattcccg tgtgaaatca tttccgtaca tatggcagag  29640
gtgcgatgca gtatcatcaa acagagtcca cattatgccg ctttctccat ccacgtaccg  29700
ttgatagcgg tcaaaaaaca ggtctggggt ccacatacaa gcaaagatgt tgtcgcagcg  29760
cacagtttcg tctctggcca gcattccgcg catatttaaa atggcgcgga tgtctgcgtg  29820
ccagggttcg aaataaacac acactcctgt tggtctttca ccgtcgctgt taatggccat  29880
ggtcatagag tctagtagct ttaggagagc catgacaccc cgtgaacaac cttctgtggg  29940
tggagtgtta aacctctgta aagacagtcc aattcctcct cggttgcaca aaatgggtcc  30000
aacctcttcc ataagagccg gaattgcaga gttcatatct gttaccctgg ggtttagcaa  30060
ataacagctg gccatagacc cacagtctct cccaccaaac agcataattg gcgtggccgg  30120
aatgacaacc tgtccggcta gcgcagtaaa aaaggctctg aaaatatatg tccagccaac  30180
ctcaccgcta accaacacgc gagccattgc tggttgttcc atagtatagt gcgtagcagt  30240
agttgcaagt ctaagaaaaa attgccccat ggactctaga cgtccgcctc gcattttggc  30300
taaatacatt tcttcatact ttagcgcaga ttgcaggcct aatgaacaca aatctcggta  30360
ttccgatgtt tcaaacgagt tgagggtttt ctgaacaaag tcaatgtgtt ccaatatggc  30420
```

```
ctgttccacg acatcgctaa gatcaatctc agacgatttt agccaatatt tcaggtctgt  30480
gttgcgtgct ttaattcgta ggtgtacaag ctccccgcac gcaatgtaaa ggcgttcgtc  30540
gactctgcac agcggcttga gtttatccac gactctggtg atatactcta acacctgttc  30600
tcgagacggg cgaggtgcca gcgttgttga taattcgctg gaatatccat actctttgat  30660
ggtattcacg ttggatataa tatcggaaac aatccccagt ggacagtcgg tgctcaaaaa  30720
atccaaagcc ataatttcgt ttagggtaaa agtgttccaa gacactatta ccaaaaacta  30780
gagcataaag tgtaaagaac agtggttttg caccgactta tgtatggtaa gctctatacg  30840
tagcttatta cgtatattag cttttattgg tcgctaagtt tatccctaat tgtcacgcgt  30900
ggtaaaaaca acaacatagt caagatcgtt aatttgcaaa gttatactgg ctttatttaa  30960
actggtttag tagctacact cgacccaatc ttgtgggtcc catcgtacat tttccaacca  31020
aaccactggc atatccacgc tgccaaatct ctcgctgcgg cgaatggttc tgggggagtc  31080
cgaggcaatc gccccaagtc gcatgtacgc tgcgtacata cacgaggttt tgtttggcct  31140
accccgcagg tcaggtgccc actgatataa cgcgttggta aattctctgt tatttagacg  31200
tgagggtggg catctaggct cgcacggccg gttggcaagt tcctgaagcg gtagagcagc  31260
gttagggtgt ggatctggtg cgtcggctcc ctcggttccc ctaattgcgg tttcggtgcg  31320
ggctttgtga aataggaaac taacagcatc ctcgaaggct acttcgtcaa acttactcac  31380
cgcaacatac accctcacac cttctctgcg taaacgctgg ttataaacaa aaattaggta  31440
aacaaacttt gcgctggcat cacctagttt tagctcgtgg tcaacatcca aaaacgcaca  31500
cgctgggacg taaacactag acctgggcat cgcagagttg ttggttcggg cgccctcttg  31560
aacaccacac gccacggcgg taatactggc aagcttgtcc tgaattacgt cggacagaag  31620
gccgccaaac acgctcatgt gtttatgtgg aaaaacgtgg gttctgacca ttgcctgtaa  31680
atattcccca aacctatcca ggcgctgttc cgtccttcgg tcacggtagt tagcaagcac  31740
gtgagcccta acggcatcgg ccgcagcctt gtctgagtac tcgatggatc tagaggctat  31800
caaaaacgta agagatagca acgatggtct gagtccagtt gtgtctgatc gacctgacac  31860
agatagttca gacagcgctg cccaggcttc gtctaaatcc tggggatttc gccctggtgg  31920
ggtgctagat ggcgacgacc cgatggcatc aaggtggttt cgtaggcgaa ttattggaag  31980
tccgggtttc tcagcggttg ggtcacaaaa gtctgtcagc gttacctggc gggtaagttt  32040
tagcgaaggt tgggagtttg acagcaccca cgagttatgg tctgagttga tggccgcagt  32100
tactacaccc gcagatgaga tttgaatgcc gcccatgttg ctgatcgtta tactatttgg  32160
agtagcatga acaaaacctg gcagccagtc cagcgtgttg ggtaacccaa aggctgcatt  32220
gctgcgtccg cgctgatgtg gaaatccagc gaaggggga acctgttccc atctgacacc  32280
cccattggcg tctgtataca taatgttgct cattccattt ccaatttgaa caaatctatt  32340
tcccccgaga ttcattttgg ttttttcacc agcggcgtat aagatagctg ctatactact  32400
ttcttgaagg tggtaactta accaacttta ataacgaaaa cacacgctga cgtgctctgc  32460
tcggggcacg cgggagaaat tgcaacaaac gcgtgccaga gggctttatc taccactcag  32520
cgcgcgaaaa tatcattatt gggtatttaa aaataacaca acccttgtct gatcaatcag  32580
aggagtgtta gtacgcaatg cgtaatacgt ttaaaaatac cgggccatat taaacgcgta  32640
agcgctaacc tcaacactca cacaccgtcg agtggtggcg cgttcggcca caaagtcatt  32700
ctgcaaaaat catggcgcgc gaagactggt ccatgcgagc cctggttaac acactggctg  32760
ggctgctagg agaaaccgat acagatgtta ccagcatgga gcccgcgatg ttgatggttc  32820
```

```
tcaaatcttc aatatcagag tttttttgt ccaccgacac ggtatctgtg gaagaggcag  32880
cggaattatt tccccgttta cagtttctag catgcagggc ttatgcagca tctcatacac  32940
ccgaagctgc catgttagca gaaaacctgt cgggtttggt cctatggcga atacaccaaa  33000
attggaccga ccgggaaacg gaagccgtgg accagatgtt tgtgctgttg gaaattatga  33060
acggagaatc tggagtctat atgctctcca ataacaacct gaggatatcg gccaaatatg  33120
gcccatccaa catgcaccta atggtcagca cttggcttgg tacctttcgc aatgttatgt  33180
tgtcaattgc gaacacaacc ccagatgcaa tgtttaatgc aagacgaatt gaggccatag  33240
aggagttttc caagcctctc gttcataaaa ggtttgactt gatatacgat atgcctttttg  33300
tacaagaagg tttgagaatt gttgctgcaa aaattaactg gctactacca tttggactta  33360
tagccaagag gtccaaggac acgagcatgg ctccactcac acgggcacta tttttgttgt  33420
cgctagtaga ttcatacttt cccaaaggaa ccgctactaa tagtagcatg aaagcattga  33480
cgatatattt tcgcgagata gtaagaaata ttgacaacag tgcgtttgtg ccagtaactg  33540
aagttaacgc taccccgcgt accgcctatg aagttagagt gtcatcagct atagtacatc  33600
aaaacccata cgttactgac acaaaggcgg gaatggtagc ggagcgcgtg cgcaccgacg  33660
ccgaaatttt atcgtccggt gcgctgttga gttcgggagc gctttctgca catgtaactg  33720
cagttgctaa actactggcg tttaacgacc aaaacgacac gtcgtctgtg gctagagcgc  33780
gtgtagcaga acatgcgagt aacacctggg aagctattca agccagtaca acaccggccc  33840
aagtcgtgga agccctagtt actgcagggt ttacttcgac acactgtgga attttggaac  33900
gtgtagtagt ggactatttc acacgcctac gtagcacagc tgaaagtagg ccgggtcaag  33960
acaactccct ggattacgca caacaagtgg ttggatgtgt gtccatagtc ggaggagtcg  34020
ttttcagatt actgatgtct tatggatttg gccttgacta catacgtgac tacacaacaa  34080
cgatatctac actggagccg gtgtataacg agcttttact agcactcggt ttggcagaca  34140
agggcgtgga acaaacttta cggcgtagca tggcaccgcg cccgtacatg aactacatat  34200
cagcagcacg cgcagcacta gacaatgagc tactaatagt tgaaaagcgc actactggtc  34260
caggaaccca tagcgccgca cgagagtcac tcctaacatg gtttgacttt agggctagag  34320
atcgctgggg tgttaggata ccagatagag atacaacacc agcgcaagtt ttagcgccaa  34380
ttactgcatc aatttattca gacgacgact taatagcagc ggcagccaaa ctttccttcg  34440
atgcattgga tgccccacct gctcaaatta tagacgaccc ctcgtttgcg ccatacattc  34500
tatctacggt ggtattagac gcgttttacg ctattttaac agctcggttt tccgcagact  34560
ctatatccca agcgctgcgc gtactttcat gggcgagaga ctatggcgcg gggtcaattg  34620
ctaacgttga cgggtacaga actaaactaa cggctataat agcatcattg tccccatttt  34680
tacaaaagga cgcgcaaaca ccaacgatgg cacatgccaa caacgtagac gcgcttttag  34740
gtgaacttca cactgtagtg gctgctgcta tcgctttaat accagaacgt gcgcgcatgc  34800
ctttaccgga acggccaacc gttagaacca gtactttttt ggcaggcata tttttaacgg  34860
ctgttttcaa gaggctagaa actctagctg gacatactgc agagctcacc aatagcatct  34920
taggaaccgc gtctggaata gtttcatccg ttgttactct taatcgtttt tttaactgtc  34980
gcttgatgcc tgttatgggc caccacgctg tattaattta cccacaatcg tctcaggctg  35040
cgccatttgg tagatggcgt ttagttgatg ttgttgacgc cgttggaagc atatacaacg  35100
aagttagcga cttgcgcgcc gacctgcgcg ccgatgttgt tacccttaaa ggagacatgg  35160
```

-continued

```
cactggccac agaggcccta caagagtgtg aagccctggc ctccaaaaca gagggaactc  35220
gtttcggtaa actattcaac gctctgctta cgcgccacac acagctagcc agagcgcaga  35280
gtggtctcgc cataaaggct ggtaagctgc tggggggctc cgaggcaccc ggcttaaaac  35340
acgtgaatac gtttttacag agatggggag ccattagcat catttaccaa aaagctactt  35400
ccggatctac cccagaggca aatattacgt ctctcgcaaa cactttacgt cgcgtatggg  35460
acgaggtaca gcaagagcgc aaattaactc cccccaaccg caaattttcc aacaaagatc  35520
ttggccttgc tgtagaacgt ctaatgggag gctatccaga agtgttagat gacgacagta  35580
acagcacggc gctgacacat agatttaacg tcgattcgtg gcaaagtgtt aacatggacg  35640
ctttgcgtaa gcgagttgaa cttccggcta acatcgactc tattcgcggg aacgatgggc  35700
tattaacgcg cgaatattta aagaaagaag accttctcgc agaaatagat gccatttttta  35760
acaccacaaa gcaataaagt taatttttca gacccggtac ttgagtgttg tgtgtaccta  35820
ttttccactg agggaggcgc gtattcgcat gtgggaaaaa aaggtgggca tacaatttaa  35880
ataacgttaa aagaagttgc agcgcgcaac gctgctcact gctccgcgcg aatcactagc  35940
gtacggggtg gattacccaa acgctctggg ttatacaaac tacgctagtg ttggattttg  36000
taccgatggc acagacgctc ccacctgttc caacggccgg tggggcccag gctgatgtgg  36060
tggttatagg ctacagaaac caatacgact caaaacttgg ggtggggtcg catgtatcat  36120
gtttaagatc atcgctgtct tttttgcgcc taatttttac gcatggcata gactttgcat  36180
taactgcaga tagcgtggat ggagcgcttg ttgagggacg agcatggaca gttgctggaa  36240
gcaagtcccg ggaagcgtgt atggtttcta ttgtggagct tccaaacaaa attacctacg  36300
caaactctac taactcgcta tgctgcgtat tttctcgact atatggtgac agtggatttt  36360
acatgcaccc cggtgaaggg tttcagagta cacaaatacc agctcgccag ttcttcgatg  36420
gagtgtggaa gtcacgatca gagtcttttg cactagttac tatagggggct accggcttgg  36480
ctgtgtatcg ccacggggat gttgcgtatg tttttgatcc gcatggccac ggtaatgtta  36540
ccgaggcatt tgtagttcgc gtaccatctc gcgacgttta cgcgtatctg actggatacg  36600
cgtccacaga tcctgagtct gactgggctg gcgcgcttgt atttttcgtg acatgcggtc  36660
caacggaaag tgaacccaac tttttaattt ctgcaacgtc actgctatat ggtataagcg  36720
aaacctacct atcggacgag aactatgtgg agcgtcaggt tgagactagt caccctgaaa  36780
tcactacacc cccaccaata acagatgtgg gcatgggatc ggtatccgaa gcgtggcagt  36840
accaggaact agacaatggt gcggctgcac aagatactga catggacgct tcaactccaa  36900
cggctacacc agttagagcc agtgttatta gacaaccaac agaaaagaga gtgtccttgc  36960
ccaagcggcg tcggcccccg tggactcccc ccaccagtag cgaaaaccta actacggccg  37020
ataacacaca cacagctgcc ggcaggccta gtcaaaaaat taggacatcg acggcgaagg  37080
tttcagatgt aaccgcaagt aataacggcg acgtctgggc cgaggtattg gatgatgggg  37140
gagtaactaa cgcaggtatt tctgaccaaa cattgagtaa caatgtaccc gacaccccag  37200
cgcatggtga cgcgctagcc atggaaacca cacgagcggc cgacgacgta ctcaaaaccc  37260
ggaggatttt caggatttct ggcgaagacg aagcaccgta cgaccttggt gatgctgtgg  37320
gggtcctagg cgtggagata gaggacctaa ttacgcgagc cgatgagctg gatgtgctca  37380
gctctgcgtg tgttgactca acggtgtgga ttaccttacc aaataacaat ccagatatgg  37440
accttataga gcagtttatc accatgatat ttaatagact tttggcgttt ttggtggaaa  37500
atggcgcacg aacacgctca gactctccat ccgtcgtagc tactctcttt tcggatgtgc  37560
```

```
tagcggcagt accagaccaa tccgccgtgg taaacctgtt gagggttacg ggaatggctc  37620
ttagcgacgt tgcatcttac aagtctattc tgaatatggt cgctaacaac gattcgcatg  37680
tgggagagct agcagttatc aaactggagc tcgtggcctt ggaagttaca aaactaacac  37740
ggtcgctcgt ggcaaaggtt aaagaattgg agcgcgacgt tacaagctgt acagttaacc  37800
cgctggggtt gtacacatac ctaactgaaa aactggttga tgagatgact aaacacggcg  37860
gtgacctatt tgcacgcgaa ccaaaacctg gcgaagcaac gcttacagag caaatcggat  37920
cgctgttcag aaaagcgcgc accagagagg cgcgagccac gcgcactaac gcatttttgg  37980
caagggacct caacgccata gaagctgccg ttcatgcggc acacgacaag tttgacgcaa  38040
ttgagattaa acccgcggac cccagcgaca cctcaaacat ggacgagttg gcaaggtcgt  38100
tagaccttgc ctcagtccct aaccgcatag ctaaagtggc gaagaaggta gaaagccttg  38160
tagctgactc tattcgcgag tactttctca ggggtgttca atacagcgtg cgggcaatat  38220
ctatggacaa aacaagtggt gccaggtttc aagttgcatc tgcggctgta tcgaatctag  38280
aacgcatgtt ggactctttg cctaactttt ataaaagttt gagttccata gttacatcag  38340
cgggcataca gggtccccca ccgacgcaga tatctagctc gcgtaaggct gcacttcttg  38400
gcaacttatt gcgagctggg caaaatttaa ccactgataa tgcgcttggg gcttgggtgg  38460
cgctgttatc cgaagcgcac acagaaggac acatagagcg gcgtgagctc gaggcagtta  38520
ttaaagaaat aacctcaatt aacgactacg cggccaaaaa ggcgtcagta gaggcagaca  38580
tggaacgctt cagagttttg agtgcagcgg ttgaccaagc tacgtccgac atgtataact  38640
ccaacccgca tgcacttgac actatcatac acggtgccga tgaaatgatt cgccaggcaa  38700
aagtaatgga gtcacacttt gacgctggaa gaatttcaag agaggccgtg tctagagtga  38760
gcgttagaaa acgcgaagtt gaaacgttag ccaactcggc gcgacagcgt gctgcagaaa  38820
ttagcgccgc cagagatgaa atttactcgc gcctccaaac cctgttactt ccactcgctg  38880
ggtttgttgg attacgcgcg gctcctggag cgttggaaca gctggcgaag gatgctcaaa  38940
gctctacttc agaagaattg agaaatctta tgcatgatgc ccccaaagcaa gtggtgtcaa  39000
ccgtacattc ccatttatgg tctttattta gccagtttag agaggcgctg gagcatccaa  39060
actctacaac tgcgtcttct ctggctggcg taggaccggc gtttgctata gttgtgcgaa  39120
gtcttttgga ccctaataag cagcgcgaga gtttggagtt ttttattaaa catgcagaca  39180
cacttgccga ggctattggg gccgtagagg caaattcaaa ctccgagctt gccgtgggac  39240
acgcagttaa cgcaatatca gcctcgatac aaacagttac cgttgggggc agtacaatta  39300
cagagtttgc gtttttggtg cccatgttgg agcgttatag gtctagacta actatagtca  39360
gagaaaccca aagactggct acggctcagc gagccgtagc cgcgtctgtg tctgcagcgg  39420
cagaggtaac tgctaagctt cgcacagttg cagtttcggt catttcccag gatgtaatta  39480
cagcggcaat agcatctgcc aaacatgtat cttctgaggt taccgctgca gttactacag  39540
cggagcgaga gctggctggg ttagacgcca aggcattgag cgtggcccag gtagcccgcg  39600
cacatcaaga tctacaaaag cagacagctg cggcaaagca gagagttgta gaaattgaag  39660
aagttttggc caacctaaac aaacaacagc gcgagctgca agaccgtgcc atgtatgaca  39720
gatggaaggc tgacctgttg gccgctttgg acaaaatcga aactaaatca ttgtttgacg  39780
tgtctgagct ttccagactt cgcgacatgg gggccgcccg cagctataac tcacgcgagt  39840
ttgctaaacg cgcagaacaa gccctggctg caaacgcacg cgcagttatt aatgtattgg  39900
```

```
ataatgtgtt taaatttaac ccctacgctc cagaaaattc caaaaaggaa actaatccca  39960
ccatttccat gctttataac atttcatggt gggacgactt tacgcttgcg gcacctatac  40020
ttaacactct atttgctgga gttgatgttg aggagctaat gagtttgatg cgcatttcta  40080
cgggaatgat tatgtttgcc agtaccaatg gggggcgccc aaaataccac gaggcggtaa  40140
actctctgtc tggtgatatg ctcaaaatac agcagttgaa taagtacgtt gacttttacg  40200
gcaagtggta ctcagagttt aatgccgaaa tggaagtgct aagcaagctg agggcggatg  40260
tgcttcaggc tgttggtgtt cgctctgggg aaataagtag ggctttggag gaggtaacgt  40320
acgttcgcaa tgcggaaata gctgaaaagg ttttagccga aggggtaaaa ctgtttattc  40380
caagcgacgc cctgatcacc aaagccgtta agtatttgga ggagtttaac cagaagcggt  40440
tcgccggatc tgcctttgag gaggctatag cagcaacaat acggcaagac ttgttagtcg  40500
cacgtgatgc agccacgcaa gctgcggcgg ctagaagcga gccctcaaca gaggcaaccc  40560
atattctacg cgaagtagtt gaagccgcaa agtcagccga tagagatgca agcgcaaatt  40620
tagcaaacct taaaaaccta ctaagactaa ctccaccccc acaaagcgtg gccgccgccc  40680
ttgacaaggc aacctcttcg gaggacattg taacccaggc ggctttgctg ttgggcacag  40740
tggaggcaac accagagctg gacgttaagg ccgtggagtg gttacagcag gcgcggtcca  40800
ttatcgactc ccacccacta acaactaaaa tagatggcaa aggacccatg gagccgtacg  40860
cacagcgcat agagcagcta cacaccctcc ggggggagct ggacgagcta aagcgccatc  40920
ttgctgctac tgaggttagc tgggatgagg catggggaaa tttttcccgc gctattccac  40980
gggctgatgt caccatggat gggtttgtaa cggcctacca tagagcgcgc acccttcaag  41040
cgtcaatggg ggttatttcc gagatgcgtt ccgatagcaa atatggtcgt ttgcccccaa  41100
aagttatcgg ctcgattgaa tcaaagtttg cagagagaaa caaaaccctt gaaacgttta  41160
atgacaccgc aacagtttta caagcatcta ttgctcagtt tgattccctt gttaagaaaa  41220
ttccaccgga aatggagtat gacgtgttgc gctctctttt ggtatcattt gaccagctag  41280
cggccgtgct tccaaagtgg gtaggcgctg gattttctgc tttcagaaac ttgttgctaa  41340
tgagaatagg cctttacgac gaatatcaaa aaattgccgg aatagccgct gccggtagcc  41400
gcccccacct ggaagccgtt gaatatcgca gcgcaacaga agaagataac ttacgacgcg  41460
ccagtcgcgt ggctgctctc atgggtgata gggacgtcat actctcgctg cgggaggcaa  41520
agtcaactat agacgttgcg ttcccgaaag tgttgttgga tgcaaagggt gtgcctgttg  41580
agtaccgcgt gtgttaccgc gctgtgggag ataaactcgc agcaatgata tgtggaaaac  41640
ttggggctac catgcgcccc gctatgaccc gcgagcctat agtggagtct tcgtcggttg  41700
cgggtattaa tgttactcat gacatactcc agttgcggtt tggccttgag aaggctcacc  41760
aatctggatt ttctacgttt gccagatttg tgcgccacaa gagggcagac tggagcccta  41820
ctgagcccgc atatgcagca gctgagatat actctgccgt gttggcaacc accctcacac  41880
gagaatatgg cgctacgtgg caccgaatac ggtttatgtc tagcgtaggc caatttacta  41940
ctgacagcca ctctggtagc gaatcacatg tagggaaggc aaagaaaaac cgcaacatag  42000
tgcatttaac cctatccgat gtggttatca gcgctatgct acgcaattca atgcatcttg  42060
taaactttat gcggcttgat ttgacacgcc aacatgagta tatggccaga actatgactc  42120
cagttttaac aaaggcgctt ttatcagaca ttttaattaa cacactagtc caaacagacg  42180
cgtctgtgaa ttggagacct ttaccactaa ctggtacccc agaagatttg gcacacggca  42240
tgctgttttc aattcgcatg tccgactgga agcaaaccag tttttctaca acaagcctgt  42300
```

```
tagatctatg gatgcggtcc cctggtgaga acgggcgggc cgccgcagct aaggtagcct  42360
ctgctattcc aggcaacgcc cttactacct ttaccgtttt ggcgcgaatg tgtattccac  42420
cagacgcatt ggcgtcgctg tgggaagcgc tacaaccaga gtcactaagt cagcaaaatc  42480
tttcctatga tgacgtggtt actagcagac ttgacattgc gtctaccgtg caaacctctg  42540
tagctgtgga cccagaaatg ccgtctgttg acaatacagc accaaagcag ctatacattc  42600
caacgggggc cagcacaacg ttcacgcttg ccggctctgc ccagagcgcg gttaaagaag  42660
tgagcgcgct agacgtggcc acgtgtgcgc ttattttggg ggcgcccgtt gtaattgcca  42720
tggaaacgcc agagatattc tccgaagcct ctgagatgtt gttttgtctt aaaatcttcg  42780
actctagaag gggtgctaca gaccatgaaa taattcaggc cgtttcctcc gacctgagct  42840
cctgggggc gtcgcttttg gcactggatc ccaatgctat agaaaacgca tgcctaacta  42900
cacagctgga acggctgtct gggttggtgg cgtcaaaact tttatctgca tcaccgccat  42960
gtcttatatt actggatacc agcatgagag tgatgaaggt gttgtgggaa ccagaatccc  43020
aaccccaaga gctaatcatc actctagccg aggatgagat tatcgccgag cttccgtact  43080
taaatacgga tgatgacatg ttacccccac taaatactag tgaccctatt tacactaggg  43140
taataagcgg aacaaatatt ccaacagcaa tggtagaagg cagtttgtat gccggccagc  43200
agttagagtt cttacgtccg gattcaaatc cttttccatt tgcattactg aaccaacagc  43260
ctctagatgt accgagttct ccaagtagct gctctgataa atatgatgac gatcatactg  43320
gaattttgta tgatacaaat ggtgacgata tgtcaaacac agcaatgaac aaagcaaagg  43380
cgtggcaaga gtggctagag gatggatttg ccgaagatga ttaccaagaa ctatccaacg  43440
cagtaccaat tcccacaaaa actgctccag agtcaaaacg gagtttgggt ctacccgaca  43500
aaattcctcc tctattgcca cccaaaaagg cgccgcttcc accatcaaca gcctctgata  43560
ttttggctgg aaagccagtt tttagacagc cgcacaataa caaatcggtt gttaaacccc  43620
tagtaacgtc ttcatccaca gtttcaccaa cacctcccct cccagctgct acagaaaagc  43680
tttctagtat taacacacag tctccgagcg ataaaaacat accgcctagc aacacaaaga  43740
cacaaccacc cgataacagg ttaccagtcc catcggaaaa caatctccct cactttgttc  43800
cccaaacccc tgcacccccc acagatacta gtaaaccctg taccgtaatc caatctcagc  43860
aaaatttagg caccccagct ccccaaaaag agccggaaaa aaaaccaaca aacaacgcaa  43920
gcacggcggt tgggtctacc aataaaacca cagatgaacc ccaagtggtt caaccaccat  43980
ctaaaaacgc cagtgaagca aacaacataa aacagcttaa tgaaaaatcg ctttccaaac  44040
cttggcgtcc atcgatacgt ccatctttgg gaccatttaa atttacggcg ccacctgggt  44100
actctattcc catggatgga ctaccacctc ctgatccaaa cgaggcgcta ttgaccgctc  44160
cgtccaaacc cgcagcggcc ccggctccgt ccaaacccgc agcggccccg gctccgtcca  44220
aacccgcagc ggccccggct ccgtccaaac ccgcagcggc cccggctccg tccaaacccg  44280
cagcggcccc ggctccgtcc aaacccgcag cggccccggc tccgtccaaa cccgcagcgg  44340
ccccggctcc gtccaaaccc gcagcggccc cggctccgtc caaacccgca gcggccccgg  44400
ctccgtccaa acccgcagcg gccccggctc cgtccaaacc cgcagcggcc ccggctccgt  44460
ccaaacccgc agcggccccg gctccgtcca aacccgcagc ggccccggct ccgtccaaac  44520
ccgcagcggc cccggctccg tccaaacccg cagcggcccc ggctccgtcc aaacccgcag  44580
cggccccggc tccgtccaaa cccgcagcgg ccccggctcc gtccaaaccc gcagcggccc  44640
```

```
cggctccgtc caaacccgca gcggccccgg ctccgtccaa acccgcagcg gccccggctc  44700
cgtccaaacc cgcagcggcc ccggctccgt ccaaacccca aaacacactt gtggcaattg  44760
ttgccaagga tcaggccaag gatcaggcca aggatcaggc caaggatcag gccaaggatc  44820
aggccaagga tcaggccaag gatcaggcca aggatcaggc caaggatcag gccaaggatc  44880
aggccaagga tcaggccaag gatcaggcca aggatcagga tctcacaaaa caaaaaagca  44940
atcctgcgtt taaaactggt tttgaaacta cacccttacc aaatacctct ccctctgggg  45000
ctgtaccaga aaacactccc ctcctggacg attttcccat cgatgcagtt ccagaaaaca  45060
ctcccctacc agatgatgac tcgcctatag gagctgttcc agaaaacact cccctaccag  45120
atgatgactc gcctatagga gctgttccag aaaacactcc cctaccagat gatgactcgc  45180
cacttggaag ccctccacat cagccagtat ctaaaactct gcataacacc aacttagtca  45240
gcagtgaccg ttctgctgct gccgccaacg tacctctccc ggactcacca agcgatggct  45300
tctactcgta tgcagttaac ataccattgc ccgattcacc caccgatgat gaacctttca  45360
gcaaccagtc ccgtgcgcaa gcatcagccg ccggaagcgt ttccggcagt agttacaaga  45420
ttaacacagg aaccgggaga ataccaacag cctggcagcg tgcctttgct cacacgtcgc  45480
atgggcgttc aagaaataga agcactagta aaccatctca atcagcgccc tacaaagttc  45540
ctcccgctct ttcctatacg aaaatacctg cggtgcctaa tgctcaaagc catcatgcgg  45600
gaaaacccag caacgaaaaa cctaaatgtg atactggacc aacggtgctg ttcggttcac  45660
ggaatatttc gccctcgcaa acgtctacga ccgcgaacat ttcgtccacc cttccacaaa  45720
atcagagtac tgctaagagt tcgcataagg tagctaaaaa aacccctctt cgggtcgtgc  45780
cgtctagcat gccggctgat gatatagatg aacttgaata tgatctacag ataaaccgcg  45840
cggtttcgaa caccaaaccg ctaccaaagt ctccactgca acaaccccaa cctgaatact  45900
cctccgtaac tacagactat aaacaaaatg tccgacctcc gatgagcgaa gatgagatta  45960
tagcgttgtt gataaatatg aatgacaaca ctgaaaatga tgccgaacct attgacataa  46020
aatcgatacg agcacaaaac ctaccaaaac aaatcaaaca agctgcaaat aaatttgtgc  46080
ctctagattg gtggacggaa accgaatcgg ctgctgacgc cgacggcttg gaactgtctc  46140
ccaaacaacc aaagctgttc tcgtgggagt ctaagcgaga cttatcgaac attaacctta  46200
aggacaaaat ttacgaggct gaatcagacg atgaatatac catttcatgg gaccaacact  46260
tagtacctgc agtttccccc agatctgtat cgtcatctag tagcgatacg gctactgata  46320
gcgatacgga cacaaataat tcttcgagtg ttttaaactc gttagccgat aacacccaaa  46380
acgacgctag cgagcttgtt gacacacaca gctcaagggc ccgtgtagtt cctgcggaca  46440
atttgctaag cagacggtac ttcagaaaca cgagtttaag cgcaatggcg ttacttatct  46500
ctgcgtgtcg aacgattata cggcgacttc gggcaacaag acgggttctt acggacatta  46560
accgtagctt gatcatggac ctaaagcaaa tacgggtttt gttggggtag agtattttta  46620
ttttttaata aaaacattaa catatgctgc gtttaactga tgtttattaa taatgaaccg  46680
caaagtcgcg aatgggggga ggtggtagtt aatcttcaga aatgggctgc ataaaccgcg  46740
gcgggaaggt gcgttttagt cctatatttg gccgggccca ggtagatgcg tcgttgtgcg  46800
caaacatggc agatcgtcga acaagggctt ttagatggcg ctgacgcaac acaaccatag  46860
ttttggcagt tcccataaac agctgcttta acccttcatt aatttcatcg tcgctgtatt  46920
tggtgtaatc gagctcatcg atgttttggt ttaaaatagt catcacgtca acaggtagca  46980
tgtccttaaa gtttgcagct ttgatattag tcgggtccca tggatcaaac gcaactggag  47040
```

```
cttgttgttg tttttggtca gcagccatga taaatttctg cgagagcaca ccgcaccctt 47100
acgctggctc ggatagctac gaatagcgca tggaattgtt gctggcagct ttttattaga 47160
aaaggcaacc ctttgttgct atcgcgagta ttacagcaac aaaagcacat gcaaaaatta 47220
cagccgcaat gcgaccggga cggcgcttaa ccctctctga agcaaacgcg ttagatatgc 47280
tagtaaggct ggcaaaaacc tctgatgcgc accgcttggg agtagggcgc cgcttttgcc 47340
tctctctaca ctctcgctgt tctctcgatg cagccaaact gttgtgatcg cataggtcta 47400
cggtacgttt tcgctgcatt tcaatcgcac caaaactggt ggcacgctcc agtaaacgct 47460
gggtcctgga cgcgtcttct ggtcccataa accggaacga tagctgcacg actggcattc 47520
tagtaaaaca gcttatttgc atcatcgcct gtagtggcct taagtctaac cccccccctc 47580
gtttaacgcg ttctatgcca gagagcgaga gaccagtcgt gtgcgttgac ttaagaatca 47640
cgttgttatg ctccgatgtt atagaggcca ttggggcgtt tggtggtgca aaaaaaaagc 47700
cttgaaatag caccgacact cccgtatttt gaattcgaat gtagggatca cactggcttc 47760
gagcccagtt tttcatcagc cgtaacacat actctatagg aaatgtaacg ctgttattgt 47820
ccggcccact gaattgaaac acgcacctcg cgggtaggtg ttttggatcg tttagtgttg 47880
catcgctttc tccacaatgc aagcttcccg atacaaccag acgaatacgc tgcagtaaac 47940
taccgccaac cgcaaaatct ctatagtcgt acgccttcat gggtgtaatg acaggtcctt 48000
aacagcggcc agtcaacacc caaaacaact gatgagaaga ggcatgccac agacagaact 48060
taaaccctct ttatatgtag ccactcccca ctacgagtac tacactttgc agatcaatgc 48120
aacttacgcg tcgtggagaa tttgatgtaa atctagaaac ttgttaatta tagtagcaaa 48180
tctttccttg cgggaattta gcgctgaggt gtggtcacat gcacccccctg gcgtacgatt 48240
atcgggggcg tgaaaaaccg aagatgccaa gcgccgcgta aatgataaat agtttagttt 48300
ggcgtctgtt gttggcatca acagttccat ctcgggggc ataaggtctt caaaccaaat 48360
accaaagtcg tggtgtccat aggcatcgtc aagggcgtct aagctcatcg attccaggtc 48420
gttaggcgga attaagtgtc tcagcttttt ttgtaaagct tggcgcggct gagtggacat 48480
attgccagtg gccacactag agacattttg tgaaatggcg tttaattgcg atttagacgt 48540
catgggtgca aacgttgagt gtggtataac aggaggctgg cagccagaag cgtttgagcg 48600
cccgtacact ggatttgacg ccacgctttt agccaccaac tgtggtctgt gcagcgagtt 48660
aatattttct gcgcatttaa tgcaaatttt acccacgccc aaacctcaac accctggcga 48720
agtgtgcgat gagatggaca tggaccagcc cgagcctagc tgcgccccgt ttgtagaagc 48780
ggtggccgac tcgctagcta tagacaaacc ctgtttgatt tgcagaacaa tagatctgta 48840
taggcgcaaa tttgggcttt cgccccagtg gatagccgat tatgctatgc tgtgtactaa 48900
aacgttggca gcttcaccgt gtgcagtagc cacggtggtt accgcatttg agtttgtgta 48960
cctaatggat aaacactacc ttaggcgtgg aaaaactacc ctagtgggcg cctttgcgcg 49020
ccgagtttta actctggttg atattcagcg ccactttttt ttacacgttt gctttagaac 49080
agacggtggc gttccacgcg gagttggatc tgggacggca cccaaatcta cggcgttaac 49140
ggggcctggt atgatggata aagtgcagta ttcaaattac tcgtttttag tgcaatcgtc 49200
tactagagcc ttgctgttaa cggtatctga tacagcaccc gtagacaacg aggcgggaca 49260
acagccaact acatccatta gaccaggagc gccaaaatca ggcgatgggt ctggactgct 49320
atgccctaag caagaatcta ccacagcagc gctaatgagt tggaaggagt gtgccaaaat 49380
```

```
gatagactgt tccggatcag agagaagacg tcccggtact accataacat gttgcgagag  49440
agctcgtgca gatgacgatg aatacgagca ccagctgttg gccacggagc aaacatacgt  49500
tgacacaaat atcacagaaa tatgcgacgg tgcacctatt aagtgggggt atgccgacct  49560
ggcgctgttg ctactaagcg agtcaagcac atgggaaaat agtgaaaaaa catttctggc  49620
gagtcagtct cgcaaggcct gcgttgagga gtattgggct acacacaagg cggcgctgtc  49680
tagagataca gctcccaggt ttgctagatt tgtagaagct gacgctacac ccgacacagc  49740
tactggccct gtcttagcaa ctactctcaa acacctacgc ggtcgaggta gaacgtgcgc  49800
cgaatgtgtg ctctgtaact tgctattaac acgcgaacac tggctagcgc ttcgccgatt  49860
taagcgggat gtaatatctt actcatcaaa caacacaaac ttgtttgatt gtatctcccc  49920
ggtgctggcg gcactttctg acgcgaatag tgaaccgcta gttagcgatt gtgatgaggg  49980
taaaacacgt gttggagacg cgggtaggtt tatggagctc atgcatgccg ctggtacgga  50040
ggccatatat aagcacctgt tttgcgaccc aatgtgcgcg ctctcggagc ttcaaacaaa  50100
ccccggtgtt ttatttttgc cactggggcc tccccaggaa ccagacgaga tagagttgca  50160
aaaggcgcgc ctggccagcg aaaattggtt tagtgggcgt gtatgtgctg gactgtgggc  50220
attggcgttc acttttaaga cgtatcagat ttttacaccc aaaccaactg cgtgcgcagc  50280
gtttattaag gacgcgggac tgctactgag gcgtcacaac ctaccgctca tatctctaga  50340
acacacgctc tgtaactatg tttaacaacc acggcgatgt ctacaacccc atgagtctct  50400
cggccgaact aaacgatctg tattacgcta aaccatcagg ccgtgaaaat ggcaggcgga  50460
gtcgcaccag cacgcggggt gttcatcgtg atcgatgtgg atctgcagct aaaagacgta  50520
gcaccaaacg ccggtgtgag ctggccagca gggaaaggga tcgatacagc ctctaccttg  50580
attatatggc cagccaccct tcagatgaaa tttcggctgt gcgtgagcta gtagttcccc  50640
tcattaaaac aacatcgatt acactaccgt ttgatttgaa tcagacagtg gctgacaact  50700
gtctttcgct atctgggatg ggatactacc ttggcatagg cggttgttgt ccaacttgca  50760
ccgtgtccgg tgaaccgcga cttcatcgcg cagatagagc tgctctcatt ttggcctatg  50820
tccaacaact aaacaacatt tacgagtata ggggtttttt ggcatctgtg ctggcggctg  50880
ctgcccaagg ggagaccgcc ggtggaattg aatctgatgg ggcccaggcc gagcgcttgc  50940
tagaaaatgt tctagcgcaa ccagagcttt tctttgcgta ccacgttttg agggacggtg  51000
gaattcaaaa cgttcgagtg ttattttatc gcgatttgag cgtgtctgga tacatgatgt  51060
atgcggtatt tcccacaaaa tctgttcacc tgcactaccg tctcatagat cgcctcctgg  51120
cagcttgccc gggctacaaa atcatagctc atgtctggca aacagcgttt gtgctagtag  51180
ttcggcgcga cgagggacaa caaacagaca tggatatacc aactgttagc gctggagaca  51240
tttattgcaa aatgtgtgat ctcagctttg atggggaact gcttctagag tacaaaaaac  51300
tgtatgcagt attcgacgac tttcttccgc cgatgtaaag ggagttagcc tttcaaatcc  51360
agcgcgctcc aacatctcct gggtttttgt ggaggtcttg tggggtcttt ctggaataaa  51420
tcgctttaaa aggttttctg tggtctttgc atcatttcca aataatgcct taaaggttac  51480
gcttatcgta cccaacaggt gggaaaaata gtagtctgtg ttaagtggaa cgtcattttc  51540
tgaaacatag gttggatcct cagccaggtc cgaaacgagc agtttgcgtt tggattgggg  51600
gcgttgtgtt ttgatggccg gggtttgtgt agtaccacgc atggagttta ctatacaagc  51660
ttcgcgttca gcggcttctg tttgcgcaac aatcacatac ggaattctct ccttcacact  51720
gggcagttct tcattccgca tagcgagctt aaagtaaaca gtgaggtgcg gtagccgctt  51780
```

```
gtttgtatat gattccggcg gtcggctaag ctcagacgtc atcacaaact cgcgcacatc  51840
caagttgggt gcggttatac ggttgtaagc ttctatcaac actcttccaa acttgtcaaa  51900
gccgctcgga agggggcgcc caacccactc tgagggaggc acgttagtta cctccgccgc  51960
cgcggtagct actgcctcgt cgtacaacag aagatctact agatgtcgcg cgtagaagtt  52020
tatgaaggca cagttatttt tacggactag gtctaccccc ttcatgagca ttataccccc  52080
gttgataaca cctatgtact ttttctttgt aattagtagc agccgctgga aggtttttc  52140
acactctagt ttgataggtg ctttaaaaag gtcagctgaa atctgtcgcg acattgaatc  52200
tccaagctct gaaaccccct cgtatgttag cccaacaaac ttgatgaata cagagtcggt  52260
gtctccgtaa ataactctga cagaataagg cttgttgttg cgaaaattta aagcccctgg  52320
gaagtttgtt tccaacagct cacgcgtcgc ccaacgatag tgaacgtaat ctctcgtttt  52380
gagaagcatg ttgcggccta ttgtagtaac ggtggctgct attctcagac atggcaacag  52440
tccgtttgcc acaccggtga atccgtaaac tgagttgcat attactttaa ttgcagactg  52500
ttgcttatct agcaaaactg cctcctccgg ggtacttgtt ggaattcgtg ccctaacagc  52560
ctttcgcata gccagccagt cgcgcagcaa aataccaagc aagctttcgc gaatgtgcgc  52620
gtgcacaaaa aacaactttt ggtcgcccac ctcaaacgtt gagtagtcaa cacacggctg  52680
aagcccagcc aaatccactt cattaagggc taaggtggtg aaacaaaggt tgtgggcctg  52740
gatgatgctg ggatacaggc tcgcaaagtc aaacacaacg actgggtcaa catgaaagcc  52800
ggatatagga tctagcacct ttgctccttg gtatcccaca atcctacctg tgccgggttt  52860
tccgcccccct gtttccaaac tggcagacga gctaatacca tcttggctcc cattaatact  52920
atctgagttg ttattgttgt caaaggcgtg gtcttcacta tttatggatg tctcggaact  52980
ttccaacaca gcgtccccat ggtagtcgaa tttgcgtcgg ttgtctggta aaataaaatt  53040
ccgctctctg gcgagtttta gcaagcatgt gtaaacgcga atttgctgac catcaaaaat  53100
tacccgcgtt agagttatgc gggctagctt tgcaacagca gagagttcca gatgtgggag  53160
gtacttaaaa aatagctttc caactaatct tgagtcctga atacaatact ctcctattac  53220
accccgctgg tttggtccac ttgcatagta agaaggtatg tctttgtatg gaaggtctat  53280
cttgtgctca cctagaacgt cttcaacaac tgcgtcaagt ttatagctag gtagttttag  53340
cttttctgtt gccaccgaat acatgtccag agatatcact ccattaattt ttaccttgct  53400
ttttttttgg aagtggtttg tagcaatgtc ccagacctta aacagccctc ctttgttaaa  53460
cttgccgtac ccatcaagtt ttatgttata aacggacgtc aacttgttaa ctatgtacgc  53520
ccagtcaaag tttacaatgt tgtagccagt ggcaaactct ggagagtatt gcttgagaaa  53580
tgttaaaaat gctatcaaca gctcatattc gctatcaaac tccaagactg ttgggctagg  53640
ttccccgcgt tgtacacagc cagaagcgta ttcttcagaa atatcacacg accctagaga  53700
aaacagcagg gtgtgttcat gcttttgggt tgctaaagag taaagcaaac aggaaatttg  53760
aattaccaag tcttcttggt tagttgcaac tggaaacgcc agttcgtttc cggtaccggc  53820
tttacactct atatcaaaac acagtagctt atagtctggc caggacgcct cttccggaag  53880
aggctctaag ttatccgaag tacagttaat ttcaacgtca cttgaggtca ggtgtcgctc  53940
tacctggcgc agttgaacac gctctccgtt ggttccgggc cggaggcggt accacccaaa  54000
actggtaaaa ttttcattgt ccaacaagag ccgcgttgtt acatccacac tcccctcaaa  54060
ttttgtgatt tccgggtgga agttatcgca gataaacccg cccaggcgac tgctagagga  54120
```

```
tgaaacccta tagtagaggg ttggctttga tccaaagtag tacagcgtcg tgtggcatac  54180
tgtttcaact ttaaagcaat caggagatac gtgctttcct ccccaccagc cgccgctgtt  54240
tccaccgctt tgttttcctc cgttgctatt tcccagggcg gcgcttaaag ctgagttatg  54300
cgcgcaggca accatggcgc gaactaggtc ggattcgctg gttattccac acgctctgtc  54360
tacttctgac ttttcaatat aaaaataatg gcgcacaccg tacacgtgaa ccgctacgcg  54420
ctttccacat tcgctcattc ccagcaatgt taccactgat ccgcttgggc gagatagctc  54480
agcaaaccgc gacgggtcgt cgttcgaagc gctttccaca aactctacta tgtcgtacac  54540
gtgaaacctc tcaaatcttg ggttaaactc atcaccgcga aaatctttgc cgttccaaac  54600
ccgaatcctg cgaggccagc aaccgtcagc ttcaaagtct aggacgtcgt actctgcgcc  54660
atcacagtac acttttgggg tgcgctcaag tgttcccaca tgcacagcgc gtcgctgatc  54720
ggttggagca tcttcatcaa gacacttggg tgctatgaac ttgaagttgc ccacctcggt  54780
gtagtatgag tggtgtgtaa cttttgggcg gtggtcatct gctttctgtg cgtttttctgg  54840
atgacggacg aagggctttt ttccaagaaa tggattaaaa aacccacacc tgcgaacaaa  54900
tctgtcctgt tcgtgcgccg ccatgtctgt gtaaatttaa gaagtgcgat ttgtttcctt  54960
tttatgtttg ttgctccgcc ccatagatct cgtgatatgt ggtttgttgg gcgtgtttag  55020
atttaccttt aaatcctgcc caccaaggtt ggtcaaatgc tttgagtaac tctcgttaga  55080
aagcacttag ctattctacc ggagttccca acgctttgtt ggtgcgccat cagcctttgc  55140
gggtgtgatt tgaaatcttt ggagttttgg caacaacatg gagtctgcac cgaaaacggt  55200
gagccttccc gtgtcacccc tcgggtacgt ttatgccatc cagaatacat ttatggaaac  55260
agaagcgttg actctaatgg ctgccagaag cattgattct gacctcgctg ttctgcctgt  55320
gattcgcgga ctcacagtag aacaaacttt tacaaccaac gttgcggtgg ttgcaggctc  55380
gaaaactact ggccttggcg gcgctgggat tactctgaag ctaacgccta gccattttac  55440
acctaacgcc ttcgtgtttt atggaggctc tgtttttggg gcaagctcta aggcccccaa  55500
ccttacacgc gcttgtgagt tggcaagacg gaggtttgga ttttctccat tttcctcccc  55560
accggtggat aatgccgtgg aaacctccgg ggaagaaatt tgcgcttcgc taaacctgtc  55620
tccagagacc actacgttgt acctggtggt aacagaaact tttaaggaga tggtgtacat  55680
gtgcaatacc tttctacatt acggtggaac cagcacggtt accatacacg gacaagaagc  55740
cgtaaagatt cccatttatc ctgtacagct ttacatgcca gatgtcaaca gacttgctgc  55800
tgaacccttt aactccaaac atcggtctat tggagacgag tttgtgtact caaagccttt  55860
ctttaactcg gatttatgca ggctgttaca cggctacgtt ttggggcccg cggcggtcgc  55920
gcttcgcgtg agaaacctag atggcgttgc cagaggagcc gcacacctgg ctttggatga  55980
aaaccacgaa ggatcagtgt tgccccagga tgttaccttt acgctttttg actcagccca  56040
gggaacttct ggtaaaggtt ctgggcgcac tcagcgccag gggacggta gcgggctaaa  56100
aaatggatcc tccagtggca tcgagcggcg gttagcttca attatggcag ctgacacagc  56160
cctctccgtt gactccataa tgggagctgg cgtatatgac acggagttac cgtccgtaga  56220
agacctgcca attttgtctg tcggggacga ccgtgaaaga ctagaggccc ttggggcgta  56280
cgcgagtaga ctgtctggcc tggttggcgc catggtattt agcgcaaact ctgttttgta  56340
catgacagag gttgacgacg gggacccgc agatggcaag gacgcatcca atccttctta  56400
ccaccgcttt tacctaatag ctgctcctta cgttgccgga aacccacaaa cagacaagga  56460
tggccgagtc ttgcaacaca ccgcagacca gccagctgct cccataaatg gatcaaatca  56520
```

```
agagttttcc ctggactatt tagcactggc ttgtggtttt tgtccccagc tattggcgcg  56580
gatcctattt tacctcgaaa gatgtgacgc tggaacattt gggggtcgca acgagacaga  56640
tgcactgcgt tacttggcaa acacgctaga gtctgaggta ccatgtgggt tgtgtacccc  56700
agctacgcgg ccggcatgcg ctcataccac gctccatcgt ctccggcagc gtctgccacg  56760
ctttggaacg ccagttcgtg ctccaatagg aatatttggc acaatgaaca gcacgtatag  56820
cgactgtgat gtactgggta actatgcttc ctacggggcg ctaaagcgac ccaatgacaa  56880
cgaagccccc aaaagcatca tgcaggatac gtatcgtgct actatggagc gactggtaaa  56940
tgacctggaa caggctaagc ttattgacaa ggaagcgctg gctcatgccg gcacctgctc  57000
ggcctccaca ggcgtagtaa aggaccaggc cagctttata aatcttttgt ctacaatcaa  57060
agacataact gagggggcag cagagcagtt tatgcgcact ttggttgagg ttcgcgattt  57120
taaaatccgc gaaggcctgg cagatgcaaa ccataccatg tcaatttccc tggatccata  57180
ttccagcagt ttttgtccag ttacatcatt tctctcgcgc cgcaccattt ttgctgtttt  57240
gcaggaccta gtattgagcc agtgtcactg tcttttctac ggtcagtcgg tggaggggcg  57300
caactttcgc aaccagtttc agccagtttt aagacgtaga tttttagata tgctcaacgg  57360
gggctttatc actgctaaaa ccgtaacagt aactgtttca gactctgggg ttacggctcc  57420
caaccttacg cttccatcat cagagccccc aaccaaagac tacgacgggg acatggctag  57480
ggttagcatg gaggtgctgc gagatcttcg tatcaaaaac agagtgcttt tttctaatgg  57540
gggagctaac atgtcggaag cggctagagc tcgagtggcc ggcatggcca gtgcctatcg  57600
aaggcccgaa aaaggctcaa acattttaaa cggtgcggtt ggctttttgg ttaagcaatt  57660
tcataaagtg ctctttccca ggggacaccc ccccggcatc gacacccccca accccccaatg  57720
gttttggact ctgctccagc gcaaccaaat gcctgcgcgt cttttaagca aagaagatat  57780
agaaactatc accgccatca aaaggttttc ccacgagtat tccgccataa actttattaa  57840
cctaactcct aacaacattg gtgagttggc ccagttttac tttgccaacc tggtgcttaa  57900
gtactgcgac cactctcagt actttattaa cggccttaca gcaatagttg tcggctccag  57960
acgacctcgt gatccggccg cggtattggc ctggataaac cgtactatca acggggcgtc  58020
agatgttgaa ccggcggccc aggaagtgtt gcagcaacta gggtccaatc ctgcagcgtg  58080
gacaggcacc tttgcgtcca caaacatggt tcgctatgta atggaccaac gcccaatggt  58140
agttatcgga ttgagcatta gtaagtataa cgggagcgcc ggcaacaacc gcgtgtttca  58200
ggcaggcaac tggaatggcc tcaacggcgg caaaaacgtc tgcccgctta tggcctttga  58260
tagaacacgc aggttcgtgt tggcttgtcc gagagttggg tttacctgtg aggctggcgg  58320
atttggtatg gggggcaagag aaaacacact aagtgagcaa ataagaagta tagtctctga  58380
tggaggcccg atggttcaaa cagcagtgtt ttcagtggtt cttaccgctt taggcgcacg  58440
cacgcagcac ctggctgttg acgactggat tggcctcgtc gacgacgagt ttttggcagc  58500
tagcctggat gctttaaacg cagccgttgt tgatcaattt ggggagtgga gcgtggaggc  58560
cgcccaggat atgatcagga ccatggacgc tcaaacaaac atgggtgttg tgtctactgg  58620
cgacggggcg tttgactttg gggcgtgtgt gggggatgct aatcaatcct ccaccacatt  58680
taacatgggg ccggcctcga gttctgcgcc cgccggacaa aaacggtttc acccagatga  58740
tattttgttt gacatgggag cacccccaga aaaaaagtct ggtctcacct ttgacatgct  58800
ctaggctgga tattatgtat cccctcccac ttcttttttt ctgtattttg tcaaatagtc  58860
```

```
attggtctga ttaaaaaggt ttaataaatg ttttacattt atatttggcc gactctgttc  58920
atattttact gtcgctgata tacggaaact ttctgcatta gctatggagc aggacgatag  58980
ctccactgct atgggaaatg cgcaggcgcg tcagcgttta ctagcaattt ttggtcaagt  59040
tcaggcatac atatttcagg tggaaattct aaagcgatgc gacccatcgg cgcttcaacc  59100
tctgattggg gcgctaaaac tcaacgcttt aacaattaga aagcttaaac gaaagcttgg  59160
cggtgctctc atggaacaag cgagacatca gcaaacacca ctcgcgtgtg ccttggctat  59220
ggctctagag tatgcacacg tagaaggtga gcgtgttttg cgagcagcgg acaacgtaac  59280
tatagtaggc gcagagggtt tttttagagc tactatgaag ctagacgatc cgtgcgagta  59340
ccatgtgcga gtgcaccttg agacctacgg tggccctata gacgctgagg tgcagttttt  59400
gcacgacgct gaaaactttt taaaacagct aaactactgc cacctaataa ctgggtttgg  59460
ggctggcctc gcagcattgg aaaacgtggc cagctttcta acacgcaccg tgggaagcgg  59520
aatcgtagtg ccacctgagc tgtgtgaccc cacccatcca tgctcggtgt gtttcgagga  59580
gctttgtgta accgccaacc aggggggaagc tgttcatcgt cggctactcg aatgtacgtg  59640
tgatcacatc acgcggcaaa tgtcagttag ggttgcaaat atagacatcg ccaggcacct  59700
accgcacgct cttagtgtat cggttgagcg acgggctgcc gcagaagctg ccctgaaagc  59760
actcgaagct aggcgcgttt ccgggcataa taaaaacgat aacacagaag accccacaca  59820
ccttgttgca tctaggctgc ttgaagccca caacgttttt aagcctgctt cgcgatgcct  59880
gtacgctgtg agcgagttaa agttttggct cgcgtcagct aaacattgtg atgagggccc  59940
ccctagagcc atagacacat tcacagaaaa tttggaaacg ctaaataaac aggaaaagtt  60000
ttttcacctt caagctgcta ccgtggagct ggcgctattc ggccgcacct tcgaccactt  60060
tgagaggata tttgcggata gtttgattgg tttggacgtt attgatggaa tgttagttgg  60120
aagttgtgcc gtttcccccg acgattacat agaagctctg ataaaggcgt gttacactca  60180
tcacatgtct acgccgttac tacagagact cactgacccc gacactagta accgtgaagc  60240
cctaaaacag ctattgggga gaattggagt tgaaaccaac agcggctccg ctgaacttgg  60300
gggtaactta gaaatagatc tggatactat gggctgtaac cctcaggtaa acacccccag  60360
tgacgagggc gctctaggga agcccgtttc agaagagcgc ccgtgggaca aactttttga  60420
gagagcttca gcggatgctt cgcaacgaag gcgtatgtac gccgagcgtt tatctaaacg  60480
ttctctcgcc agcttggggc gctgcgtgcg cgaacagcgc aaagaactag aaaaaacatt  60540
gagggttaac gtgtatggcg atgtgttgct acatacgtat gtgttatcct ataacgggtt  60600
ttgcgctaga cgcgggtttt gcgaggcggt gagtggcgcc ggtacaatca tagataaccg  60660
ctctagcaca tcatcctttg actcacatca atttatgaag gcggcgctgc ttcgccaccc  60720
catagaccag tcgctaatgc cgtctataac ccacaaattt ttcgagctca tcaacgggcc  60780
agtgtttgac aatgcgggtc acaactttgc gcaggcgccc aatactgcat tatattacag  60840
cgttgaaaac gttgggttgt taccgcacct caaggaggaa ctagctcggt ttatggttac  60900
tgcggctaaa ggtgattggt caattagcga gtttcaaagg ttttattgct ttgagggtgt  60960
gacaggtgtg acggccacgc aacggctggc gtggaaatat atcggggagc tcattctagc  61020
tgccgcagta ttctcttcgg ttttccactg cggagaggtg cgccttctgc gcgcagatcg  61080
tacatatcca aacaccaacg gcgcacagcg ctgcgctagc ggcatttaca taacatacga  61140
gacgtcatgt ccacttgttg ccgtgctatt tgtggccccc aacggtgtta ttggcgaaga  61200
gactgtggta atttacgaca gcgacgtgtt ctcgcttcta tacaccgtac tccagcagct  61260
```

```
ggctcctggc tctggagcca attaggaaat gtaaacttgc cagctacctc ccccatgtct  61320

aaagactcga catctctggg ggtgagaaca atagtcattg cgtgtttggt tctcttggga  61380

tgttgtattg tggaagctgt accaaccacg ccaagttctc agcccagtac tcccgcgtca  61440

acccagtccg ctaaaaccgt tgaccaaacg cttctaccaa ctgaaacacc agacccgctc  61500

agactggctg tacgcgagtc cggtatactc gcagaggatg gagactttta cacctgcccg  61560

ccgcctactg gatccacagt tgtacgcatt gaacccccac ggtcatgtcc caagtttgat  61620

ctggggagga acttcacgga gggcattgct gttattttca aggaaaacat agccccgtac  61680

aaatttagag caaacgtcta ctacaaagac attgtagtga caaaggtttg gaaaggatac  61740

agccacacct ctttatccga tagatacaat gacagagtgc cagtttcagt ggaggagata  61800

ttcactctca tcgatagcaa aggaaaatgt tcttctaagg cagagtacct ccgagataac  61860

attatgcatc acgcttacca cgacgacgaa gacgaggtgg agctcgacct ggttccgtct  61920

aagtttgcta ctcctggggc cagagcatgg caaaccacta acgacaccac gtcttatgtc  61980

ggatggatgc catggaggca ctacacatca acctctgtca actgcattgt cgaagaggta  62040

gaagcgcggt ctgtttaccc atacgactcc tttgccctat cgaccggtga tattgtgtac  62100

acctcaccgt tttacggcct tcggtcagct gctcagttag aacacaatag ctacgcacag  62160

gagcgcttta gacaagttga aggataccaa ccaagagact tggacagtaa attacaggcc  62220

ggagagccag ttaccaaaaa ctttattact acacctcatg ttacagtcag ctggaactgg  62280

actgaaaaaa agatagaggc gtgtacacta actaaatgga aggaggttga cgaacttgtc  62340

agagatgagt ttcgggggtc ctacaggttt actattcgat ccatttcgtc cacgtttatt  62400

agcaacacta ctcaatttaa gctagaagat gccccactca ccgactgtgt gtcaaaagaa  62460

gccaaagatg ccatagactc tatataccga aaacagtatg agtctacaca cgtttttagt  62520

ggggatgtgg aattttactt ggcacgtgga gggttcttaa tcgcatttag accgatgatt  62580

tctaacgaac ttgccaggct gtacctaaac gagcttgtga gatctaaccg cacctatgac  62640

ctaaaaaatc tgttaaaccc caacgcaaac cataatacca atcgaacacg caggtcgcta  62700

ctatcaatac cagaacctac tccaacccaa gagagcctcc acagagaaca aatactacat  62760

cgcctacaca aacgagcagt ggaggctgcg aatagtacaa actcttccaa cgtcaccgcc  62820

aaacaactag agctaatcaa aacagcgtcc tctattgagt ttgctatgct acagtttgca  62880

tacgatcaca tccaatccca cgttaatgag atgctaagta ggatagcaac tgcgtggtgt  62940

acactacaaa acaaagagcg gaccctctgg aatgagatgg taaaggttaa cccaagcgct  63000

attgtttccg ccactcttga cgagcgagtt gcggcaaggg ttttgggaga cgttatagcc  63060

ataacacatt gtgtaaaaat agagggcaat gtgtacttac aaaactctat gcgctcctcg  63120

gacagcaaca cgtgctactc ccgcccacct gtaacgttta ccattactaa aaatgcaaac  63180

agcagaggga cgatagaggg ccagttggga gaagaaaacg aggtttatac ggagcgcaag  63240

cttatcgagc cgtgcgctat caatcaaaaa cgatacttta agtttggcaa agagtatgtt  63300

tactatgaga actacacgta cgttcgcaaa gtgcccccga ctgaaatcga agtgatcagc  63360

acctacgttg aactaaactt aactcttttg gaagaccgcg agtttctacc cctggaggtt  63420

tacacgcgag ctgagcttga agacacgggg ctattggatt acagcgagat acagcgccgt  63480

aaccagcttc acgccctccg attctacgat atagacagcg ttgtcaacgt ggacaacact  63540

gctgtcatta tgcagggaat tgccaccttt tttaaaggcc ttggtaaggt gggagaggca  63600
```

-continued

```
gttgggacgc ttgtacttgg agcggctggc gcggttgttt ctacagtatc gggtatagcc  63660
tcatttataa acaacccatt tggggggctc gcaataggcc tgttggtaat tgcgggctta  63720
gtggctgcgt tttttgccta ccggtatgta atgcaactgc gcagcaaccc catgaaagct  63780
ctatacccaa taacaaccag gagccttaaa aacaaagcca aagcctcata cggccaaaac  63840
gacgatgatg acactagcga cttcgatgaa gccaagctgg aggaggcacg cgaaatgatc  63900
aaatatatgt ctatggtttc tgccctggaa aaacaggaaa aaaaggcaat gaagaaaaac  63960
aagggggttg gacttattgc cagcaacgtt tcaaaactcg cactgcgcag gcgcggtccg  64020
aaatataccc gtcttcgaga agacgatccc atggaaagcg aaaaaatggt ttaaaaatgt  64080
taaataaata ttttgacacg tacttgtggg ttgactcata tttgcataac atctttctag  64140
ttccggctat aagcctattt aagcctagta tttttgccaa aagtttatca tcctctacaa  64200
gcgcacatcc tctcaaaaga gttgaatttt gctgtttatt acgctatcct aaagctaaac  64260
gcctgtaatg gaatctcaat gcaaaacttc tacatcagcc gctgatgaaa ctctgttggc  64320
tgcatcggct accgcggcgg aaatccaaat aaaaacagaa gcacccgatt cagacacgcc  64380
cgctgccacg gggtgtcaag accacaccta cgctcgccgg ctcaccgaga atggtgcaat  64440
cgaagagata aacacggctg atctactgga aatggtgctg gcttctgaaa acgctcaaag  64500
cgaacccgga attccgtttg ccctgcgagg aaacttcatc tgctgcagag acaataactg  64560
tcgcgcttgc caagaactgc catttcgccc gtcagaaatt gggttttcca gggaccccca  64620
tgtgtccatg gcgttagaca tgaccagcgg aacttgggct tacatcccac gagttttccc  64680
agacacaccc accgcccctt ggatggccaa cttttgcatt ccagacctcg acgagcacgc  64740
agattgttaa aaaacaaata aactagtttc agcttatacg tgtatgtgtt tattgttaat  64800
ttttaaagta aagaccaaga aacggtttat ctagcactca tcatctgaga cacaaatatg  64860
tccgcgtcat cacgcccaaa atctaggccc gtagacgcgc tagcgtctac cgtttggctg  64920
ctagcttgag gctggttaac gggcaaaaca gctgctgaag taacagcctc aaactgaggc  64980
tgtacagcct tagagtgctc caccgcttga tgggtagctg ttggggctgc gcaaaccttt  65040
gcaccacctg gtgtttctac ggcgggcacc ggtgtggcaa taacagattg gggtggttga  65100
gcctgaattc ctgatagctg cggagagata attgcagaaa ccgcatgctg tgggtggata  65160
tactgatact ggctgtattg ctggggaacg cccggtggga cgggtttata tagtccagcg  65220
ggtgcaactt gctgctgcgc ggttacggtt tgtatagctc tgagctgcga cacttcctgc  65280
tgtaaagaag aaactgctcc cattaaatct gcaatggttg tggacgcgcg ccccgctcta  65340
cgctccactg ggcgcggtga tcgttcacct ggatagtaaa taccctctat gtcatcacgt  65400
gtgttggcgt cccagtcgtg acggcgcttg cgtgtgtatc gccgctcttg ttgtggagac  65460
agtggaggcg aacactgaga gttttggacg gcttgcgagt cgctactttt ggcagcttta  65520
cggtctgcag ctagggctcc aacaagcgcc gtgatttgcg cttccaagtt agtgctgggg  65580
ggcacactcc agtatggagg tgcctgatac atcgatgttg gcaccatgga attgtaagcc  65640
ggttggatgt actgtgtagg cactgcgtgt gttgcggaag cttggccagc gtttattgga  65700
ggatgcgaag tgtgctggcc tacaacgagc tggttatact gcgccgcggg tactaaaatg  65760
tagtcaccag acactagcgg ggctccagca gcagacagag tttgcgggtt tgatgaagcc  65820
atcgcaccag ggtgtttggc gcgttcgcct atctgaccag cactgttgtc cgaggacggt  65880
agtgcggaac tgcctgagga agtgaaagcc tttgcgccaa gcgttacacg tgaataagat  65940
atgtcgcgaa ccctttcgcc gcttttataa ccgcaggtgc caaccagctc cgccccgcaa  66000
```

```
aagtcagctt tgttacagcc gttggtgatc ccgaagctcg cgctggcctg aaggtacgtg  66060
tgtccctcta tgccggcctc gcgccgtctt ctagccacca ggttccagcg gtttcgtaaa  66120
agcatgttat taacggcggt tgatagtaag actcgggtta gtgtatcttc tgatacgtgc  66180
catgttgcca tgtcacccaa tcgtgattgt gcctcgcggg cagtgattaa caattcctct  66240
cgcactgacg gagacaaccg cttaaaaggt gctaccgtat tttctggtgt ggcgtcgtaa  66300
gtaacgattg ttcccactct acgcccaatc acacacagag aaacgtgcgc aaatagggtt  66360
tcgtccggct cttcgtctgg acccaagcgt cgtgacgata gcgacgcaga tggcagatag  66420
ttgctcacta ggtacagtag ccgctcttgt tctgacaatc cttcggacat ttctccgaaa  66480
aaatctgggc ctgccgcagt tgccaaaacc gcacccaact gggggcagtt aacaattccc  66540
aaaaaaaatg ggccgcgtac atcatctact atggacaata cctcccctac cacacaccca  66600
ttgcggtggt cgatattaat gggtaaccta gatgctggtg gtagcgccgc cgcaactgtt  66660
tctctggtga gcgttaactc cccaccatca cccatatcat agagagctat ataccccgct  66720
acgtaaatag gaaggctcac aacattgctg tctgtagcgt acgcgtccat agtaaaattt  66780
gcagaggttt attataggaa agtacactcg gcatcagcat ctgcggctaa taaacactct  66840
agttcacagt ttaagaattt attgtagtga ctatgggcaa ggcattacat ggcggatgta  66900
aacgaaggaa tatacccaag acaaacaaag tacaacaggt cataatcact ggcaacatta  66960
aactgtccca aacgtttagt ttcctcgagt gatgccctca atctaggctt ttgcattaac  67020
agtccaaggc cccgttcgta ctggagagct acagcgtcgt gtgcggctag cacttcgttt  67080
ataggcgctg gcgcagtttt gcgtcggttc tctagctcta tgcctattag cctagtcagg  67140
tttgtttgat tgcgcccggt agacacatta actgcacggt gatgtgggtg attacgagct  67200
ccagtttggg cgtccaaaca aagggctgcc aaaccgggaa aaagctgggt tatctccacc  67260
tctgtgttag cgaggtatat tggagaaacg tagtgagagc ataaaaacgt aaagttattg  67320
ttgccgctgc ggctaaccat ggctgatgcg tcacccccta tcgcccctct agcattcccc  67380
agtgccacgg aaaggttggg tactattgct ccgagctgga aattatttcg caatttgtca  67440
gtataaacat tgccgttcca caacagacgg cgtagcaaca acagcgcggt gatggtgtta  67500
atcgttgagc gcagtagggt ttggtcttcc gttagaaata agttttgggc gcgcactaaa  67560
aatgcagccg ctgctttgtt aacatcgtct atgtatgccg tttggttcac atcaagttct  67620
ggtccaatag ctgtgttggt tgttcccaaa ctacctggga tagcaggcag tacctttagg  67680
cgtattagcg tttccaggac gctatgaccg ttaagcgcgc ctcgttcgta tctacctcct  67740
cccctggaa cgtgaaactg gtttttcgga agacgcgcac cattaaactc atacaccacc  67800
ttcccgatgg ctccatcctc aagggaggcc gatagagcct cgatgtatat gggcaactgt  67860
tcaattagtc ccgaaaagct cgtggggtac gagaagttgc tgtttaccgc acgatgagcc  67920
aaatggaggc ataacacggc agcctcaaag gcggaatatg gacggtttcc tatgtaaagc  67980
cgcccgcaag actggagagc taccactgct gtggacataa atgttttaga catgcgaccg  68040
tctctgtagt caatactgcg agtagccact ggccgttctg ttactaaacg gtcttgcagc  68100
gccctgtacc aggtgccaaa aaccactccg tttgaccctc ccgcggctcg ccccacaaac  68160
accgtagtta ataagtccac agctaggttt gtgtcaaact ccataggaac atcgtttttg  68220
gctatttgaa tttcactcaa cgattgggca acgttgttgt cgcgctggtc tgagtcactc  68280
gcgtttactt ggggcgttgc cgcatctgca ctttctgcag cacgcgcggc gtcttccagg  68340
```

-continued

```
gctgccaggg cgtcggccac tttagccact tgccgctcca aaggtctaat taaggcgtct  68400
acgtttgcgg agctgtattg actctgtgct tctagcgtgt ctatggcagc ggctgccgct  68460
cgatgtctgg ctgccacaag cttagtgggg tctgcccggg ggtttgagct ggctgtaaaa  68520
gttggggcgc tccagaagtt aagcggaaat ggtggggcaa taaattttcg cacatctgta  68580
ggtatagttg acctggcagt gtcgcataca tacagcgacc cgaagacata atccacatac  68640
tctgccatct cggctactac tataaggcct ttagcttcga tcttggtgta tacttgcgtg  68700
taggcgcgct aacaaaaaag gggcagcagt ctttaatgtc acgggctttt attttggggc  68760
aaatagggat gccacccagg caagggggtt tgcgagcgat atagtcgccg gttgatatcc  68820
cacagcggcg ttagtggtgt ttgcttgggc cgtcgccgaa aacaaactcg caacggcagc  68880
agtcgctgca ggtttagctt gcgttatagg ttgaatagac ccagtagtag ttttggctct  68940
aaaagctttg gaatttgttc ttcgcgtaac acatcgcctt ctagttgatc tctcagaaat  69000
gggaggggag tattccgcta ggcgtgatat agtgcaagat agcacagctg cgttgctata  69060
cactacctgt ggcgataaac gcgttaccct caacacccgc attcctcgtt gagctacaaa  69120
cactaacacc ggtgctagta aaatttcacc gcttcccgga ggcaaggttt tggctagcaa  69180
cctacatgag tcgtgaagct gtcgcatacc ccccttccgt tgtaaatttt tactagcggt  69240
gttcatattt tttgagaagc gacacgtttt tagttctatt aagatgcaga ccccctttggc  69300
gtcagagcca tgcccaaatt gcactgtaca tacacaatct gggcgccgct gtccgaggtt  69360
gacctcaaag gctagagaca cgcccatagc cgttttaaga gtttccgctg gcaccaattc  69420
actaaaaagg ggagcaagcc gcgctccgta cactccattc ttcttggcgc ttgccaaatc  69480
ttgaaccatt gcgttataga agcggttgtg gcaccgtata cccgctctga gtctgcttct  69540
agcggtgaga cgctgtttac gtttcatctc cacaggcagt aatggctgct tgcgtaccca  69600
cgggagaagc tccacgaagc gccagcggaa cgcccacccg gcggcaagta acaatagtta  69660
gaatttacct cgatggagtt tatggcatcg gtaagagcac gacgggacga gttatggcat  69720
cggctgctag cggaggaagt ccaactctat actttccaga gcctatggcg tactggcgga  69780
ctctttttga aacggacgta attagtggta tttacgacac ccaaaaccgg aaacagcagg  69840
gaaatttggc cgttgatgac gcggcattaa taactgcgca ttaccaaagc cgctttacca  69900
cgccctacct gatactccac gatcacactt gtacgttgtt tgggggaaac agcctacagc  69960
gtggaacaca accggacctg acccttgtgt ttgaccgcca cccggtcgcc tctaccgtat  70020
gctttccagc agcccgctac ctactcggtg acatgtcaat gtgcgcgcta atggctatgg  70080
ttgctaccct accaagagaa ccccagggtg gtaacattgt ggttaccacc ctaaatgtag  70140
aggagcatat acggagactg cgtacgcggg ctagaatagg agaacaaatt gacattacgc  70200
tgattgctac attgcgaaat gtgtacttta tgctagttaa tacatgtcac tttttgcgct  70260
ctgggcgagt ttggcgcgac ggttggggtg agctacccac ttcctgtggg gcttataagc  70320
atcgcgccac acagatggac gccttccaag agcgcgtttc accggagctg ggcgacactc  70380
tgtttgccct gtttaaaact caagaactgc tagacgatcg cggtgtaata ttggaagttc  70440
acgcttgggc gttggacgcg cttatgctaa aactgcgtaa cctgaatgtt ttcagtgccg  70500
atttaagtgg tacaccgcga caatgtgcag ctgttgtaga gtctttgctg ccacttatga  70560
gcagcacctt atcagatttt gattccgcct ctgctttaga gcgggcggca cgcaccttta  70620
acgcggagat gggcgtctga agctatatgt aatgtttgtt gtgccaatgc caaaattgtg  70680
aaataaagat tcatttgcca atatccatca tagcgccttg tgtgtttcgt gtgtaaactt  70740
```

```
ccagtttcta gtttggggat atataagccg ttgtgctctt aaatcattta gtacagcgcg  70800
gccgagatac tcgaggtatc cagtggttgt atattgggaa taaatactgc tgcgattatg  70860
tcacaaccgt atctaaaaat agctatctta gtggccgcta ctattgtgtc tgcgattccc  70920
gtttggacaa caccggtttc aacttcacca ccccaacaaa caaaattgca ctatgtggga  70980
aatggtacct gggtacacaa caatacattc aacgtaacca ggtatgacag gataaccatg  71040
gaaccagttt ataataacaa tttatcctct actacctttt ttgttgctat atcggagaga  71100
aattttcgca cggttaacac tccacttgga gcgtccgtat tttggatttt aaaaagcgct  71160
cttaatcctc ccaaacacca accctgtata gctaatgtgc cagaacccgg tgacccacgc  71220
ggaccgtgcg tcaactcaac tgtgagtcta ttttttaatg acaatttgga gccgttttta  71280
atgacaaaaa atcttttgga gtttgaagta ttgcccgaca actacataac cggatggacg  71340
tttgagcggt ctaaaactgt ggctacgaaa ggcaacccgg ttggagtggt tctctcccct  71400
ccccgaacaa gtccggatgt aaataacacc ataagagatg atggcacccc taaacagcac  71460
ttgagcatta tagacgaaca tactacgttc gtgctcgacc tgcaaaattt tacaaaaact  71520
ttaacttata taagcccatt tgctgcggtg tggccaataa cagcctttca tgccggaatt  71580
acagtaatgg ggtgtgacac aactcaggcg attgcgtacc tcggcaatgg gtttatgggt  71640
ttgcaaataa gctcggtaaa caatccaccg ctggagatga ttgttgcacc aaatgacgtc  71700
cgtgctcgga tagttaaccg ccttccccca agacgtcgac ttgagccacc cgggccatat  71760
gcaggaccta tctacaaggt gtacgtactc agtgatggaa atttttactt gggtcatggc  71820
atgagcaaga tttctaggga ggttgccgcg tacccagaag agagtttgga ctaccgctac  71880
cacttatcgc ttgccaacct tgatactctg gctatgttgg cagaactttc ttccggtaag  71940
agcaaggatg tgagctatta cttgtatcgc ataattgcga ggctggccgt agcaacgttt  72000
tcccttgcag aagttatacg cctgagtgac tatatgctcc ttcaagaggc catcgacgtg  72060
gatataaacc tccgcctaat tgtacctcta gtgatgaagt acgccgctgg gggaacggca  72120
gatagctcgt acacatcctc ggacgtagct atggaccaat tcgaggtggc tcaagcccag  72180
attgagaaga tagtagccga tataaatatc gaaaatgaat tgcgcaaacc tatgtacgag  72240
caccgctcat tattgaaaag cgtgtacgct tattctagaa agccgctacc aaacgcggta  72300
agctttgcta accggctcat cacggctatg tataaagaag caattaagga cagaattacg  72360
tggaactcta cgatgcgaga ggtgttattt tttgcggttg gtgctgctgc aggttcgcat  72420
gttatcctca cggatggccc agatctcggt ttacatgccc acaaagattc ttcgatgttt  72480
ctatctctta accgcaacat actcttgttg tgtacggcca tgtgtacggc gtcgcatgcc  72540
gtgtccgcag gagtaaaact agaggaagtt atggctggcc ttattgccgg gggtgtacaa  72600
tttagcctcc tagaagtatt tagtccatgt atggcgtctg ctcgatttga cctggccgaa  72660
gaagagcatg tgctagatct actgtccgtt atcccacctc gcctgtacac cgacttaaac  72720
actggcttgg aggacgacgg aaccaccatc cattcatacg gacggtctgc taacggaatt  72780
ttaaactctc gaatcgcata taactttgat gctgttcgtg tatttactcc agagttggcc  72840
tcatgcagca ctaaactacc aaaagttttg gtagtgctac ccttagcatc aaaccgaagc  72900
tacgttataa ctcgtactgc gcccaatata ggtttaactt actctcttga tggggtaaat  72960
atagcaaagc ctatagtcat cagttacatc acttatggaa attgtcaagt ttcgagagct  73020
acaatcaggt cagtttactt ggatcatccg ggccacaccc agtcgtgcgt atattgcggg  73080
```

```
agtgtgttta tgcggtatat ggcatccgga gcaattatgg atttgatata catagatgac  73140
aaagatgtag agttgcaact ggtagcaggg gaaaactcaa ctattccagc ctttaaccca  73200
aagctgtata cgcccagcat gaatgctctt ttaatgtttc caaacggaac agtaacccta  73260
atgtctgcat ttgcatccta ctcagctttt aaaattccca gtacttatct gtgggcttct  73320
attgggggtt tgttgctggc tattctgatt ttatatgtaa tcgttaaaat gttatgtggt  73380
ggtgtaatta ataatgacta tagtttgtta ttaaactctg agtaaacaca aacaatgtct  73440
agtgtgttgt attgcgtgta aacagtatac gagtgaacat ttatacgtaa aatggttaaa  73500
ttttatttc gctataaacg ggaatgcggc ggcgagggct gctgcggcgg cgagggctgc  73560
tgcggcggcg agggctgctg ggcggcgagg gctgctgcgg cggcgagggc tgctgcggcg  73620
gcgagggctg ctgcggcggc gagggctgct gcggcggcga gggctgctgc ggcggcgagg  73680
gctgctgcgg cggcgagggc tgctgcggcg gcgagggctg ctgcggcggc gagggctgct  73740
gcggcggcga gggctgctgc ggcggcgagg gctgctgcgg cggcgagggc tgctgcggcg  73800
gcgtaaatgc agctattcca caggctcccc gcttaaatag gaaaggtggg cgggcggttt  73860
actggtaaat gtagttacgt agcgttcgca cttggttaca ataattatta tatattatta  73920
gcaattggtg cgaacgggga attggtccaa tcaaatggtt taaaaacggc catgtgacat  73980
acaaaccaat cacaacacct agtattgatt acttatcaat aggttccaaa tcaataattt  74040
cgcctaatgc gggtttgtac tacctccagc tatcttccgt tgaaaattac aacggcatgg  74100
ggcggtcggg acaccaccat atataaatat ctcgcgcttg cattgtagac cgcaaactca  74160
cctttaatgt agtaaatttt acaacattaa aatgttattc gccttaataa aattacaata  74220
cagcgatgta acttcggagt ttttatgctc tgttaacatg cacagttaca ccaccacgct  74280
ttaatctctc gctgagtaag taatataagt agtatgcccc ctttcggctt aagtccaaat  74340
tatcaaatgc tgttattaaa gacacgttga gaactatggc caccggcaag ccgcttccca  74400
gcatgcgaca ggctgactgt gccgcccccc cgataccttc tttggcgtat agcttgttta  74460
gtacgcttgc aattttagct ttaatttcat ttgattcgtt gaaggaacta agccccaact  74520
caactctggt ggagtttgca gcaaactcgg caagtaggtt agcctctagc tccacaactt  74580
cagaaaaact accgtttact ggagtgttgg agtgggtata gcgaacgatt atctcgcata  74640
ggtctcctaa cattgcactt tcgcgtatta tttcatttac ggcatcggcc accaggtggg  74700
ggtctggtaa cggatcgcat gcgtcatgca ccgctccgat gtagctctcg accagctgtt  74760
ctagggatgc gtagcagttg attaggttcc acttgtttag aataaactgg cagagtacaa  74820
atcgttgtag cgtggtaatg cccagttgag taagctttcc cccaaaaaat cgcagttttc  74880
cctcatggcc gtatactgct aaaacggcat caacaatggt acttcgcgct tggttgaggt  74940
ggtcatccaa gcccggccat ggttcctcaa ccaagataat ttcatcgacc agtttgaata  75000
gtaactgtag tgattgtaac gatgctccac ttgctgattt gcttgatgag ttccagatgc  75060
tacagggttt tggaataagt cgcacctgca caaagtcgct caccactgtt tttctaagtg  75120
tgcgtttgga tccatttgtg gtgcctatgg ccattgttct cacggctctg ggagaggtga  75180
ctattacatc tgtgcggcta tgcctttcta actcgtcccg tagtgggggc ctggatacgg  75240
ggatgcgatc gaagagtcca gatacgagtg tatctagttc ttgtggcaac tcattcaaat  75300
atgcttgaac taaggtaaag catgccaggt tgggtgtgta gataaatcca gaagctgcgt  75360
ttgtaatagt tggaacggta aatagatgta gcgtcccatc ttgtggtata tctctccccg  75420
tagacacaat aagtccggat gtaaccttta gagaaaccat gcactcggcg agatatgggt  75480
```

```
cgtacacctc cagatcaaag ctcccgcata tatctctacc aaaagcctgg gtaccctgga  75540
ccaatacttc caagcgatca acaaatacgt cttcttccga gctaggcgcg ctctcatggc  75600
ggcccgttct gtgtaattcg ctgcgaacat aattggcgac aactctgtcg tttagcttta  75660
gaccccttag agttaaacca aactttgcaa tttctccact ttctggagct gcgtgcgatc  75720
ttggcactga gagtaaacat ccaccgtaaa taaaatacgc ccgatgacca caatcagtaa  75780
tgtagaaaac tactccgttg tgaattactg tgtcgctgta cttaaagtcc atagtttata  75840
ctacactgca ggcgtatgca cagcgataaa ggtgtatgtt gtgaacttaa aagcagctga  75900
gtataaacct tgtgaatggg cgttgctaga gacgctgcct ctatgcggtc gtggctgcaa  75960
atccacaatt cttttacagc aaactggttt tatattgggg atccgcttta aatatgagat  76020
acctagaaca ctaacagtaa gtggtctaag acggggacaa cccgtttatc acgcgggtca  76080
gcgcgtattt atataaactt tgcggttttt agttttaagg ggaccggttt gggacaaact  76140
aggggatgtc cctagctgtt tatgacattt tgtgattact gtttagtgtt tgggttcccg  76200
gaaatggcgc agttcgtggt aaatatataa acgttaaacg gcgtgtcacg atattgactt  76260
tttgaattat tcacgcttta tcatgggccg ttgccccgca tataaaattt acaacccta   76320
gcttgttata ctagtcctgg ctgtaccata tcctgctcac agactaccaa aatctctctg  76380
cattctttag ggctaaaaat gccacaaatg ggaaataccc gtttacataa accactcgag  76440
gacagcattc cactgattga aaacgatgaa aattcatccc aaactgaagt tgacctatat  76500
gactatgtgt ctatgtcatc ttacgggggc gatagtgact ttttaataag ctcggctggt  76560
ggcaacatag ccccagatag tcgcccgtca ttttcagtat gcgtgttcct gttttccatt  76620
tctgcacttg tggtaaaacc tgtttgctgt tttatatttc tcaaccacta cgttataacc  76680
ggaagttatg actttgcggt agctgggggga gtttgtacta tagtgtatta catgcggctt  76740
gcaataactg cctggtttat gtttcgcaac attcaagcag acatgctacc gctaaacact  76800
ttgcaacaat tttttattgg gtgtttggcc tttggtagaa ctgtcgcgtt tttggtggta  76860
gcatatacta ccttatttat acgctccgag ctgtttttca gcatgctagc acccaacgcc  76920
gagcgagagt atataactcc catcattgcc cacaagctta tgccacttat tagcgtccgc  76980
tctgccgttt gcttagtcat aatatctacc gccgtttacg cagcagacgc tatctgcgac  77040
acaattggat ttgcgatacc gcgcatgtgg atgtgtattt taatgagatc aacctccatg  77100
aagcgtaact agggggcctc ccactgaggc actaccggct tagcagctga ctaacacagt  77160
ataaaacgtg agaagaaatc agtctcatgc gccattagcg ctaggctagt tagcgtggag  77220
gaccggagcg ctaccgccag cagtttcatc cgcctggtta cgggtttgtt aacacctacc  77280
ggtgttttac cgctaccata atggaccggc gctctgaagc gtttaaaatt ccggttccag  77340
aagtaatcca tgccgggcaa attttatcaa ctatagaggt gtcatcacac cgcacgctgt  77400
ttgacttttt taagcagatt cgctctgacg acaatggctt atacgcagcg cagtttgacg  77460
tgctacttgg aacatattgc aacacgttaa cactggtgcg gtttttggag ctcggattat  77520
ccgtatcgtg tgtgtgtact aagttcccag agcttaatta cgttaacgat ggcacaattc  77580
aatttgaagt acaacagcca atgatagctc gggatggtcc ccacccagtg gatcagccta  77640
cccacaccta catgatgaag cacatagagc agcgatcctt gagcgcggct tttgctattg  77700
cagctgaggc tttgggtctg ataggaggca cttccctcga tggaactcag atctcgtcgt  77760
cgctgcgggt gagagctata caacagcttg ctagaaatgt gcaaacagtg ttggactctt  77820
```

ttgaacgagg cactgccgac cagcttttgc gcgttttgct ggagaaggct ccaccgctta 77880
cacttttggc tcctctgcaa atttaccgag acgagggccg cctggcgtct cgggtaaatc 77940
gcgccgttct cgtttcggag ctcaaacggc gggtaataga agatactttt tttttaacta 78000
agcacgagcg taacagaaag gagctggtgg tatcccgcct ggctgagctg gtaaattgta 78060
cagctccttc tgttgcggtt acgcgaatga cccactcaga cacaaaggga agaccagtgg 78120
atggtgtaat tgtcactact gctggtgtgc gccagcgctt attacagggc atcctaaccc 78180
tggaggatat ggccgcggac gttccggtaa cgtatggcga gatgatgatc agcggcacga 78240
acctggttac agcgctagtg atgggaaagg ccgtgagaaa cttagacgac gtggcccatc 78300
acttgttggg aatgcagcgc gatcaggtta ggtctaatga gcgcatgatt aaagactacg 78360
aagacgtacc cagcatggca cgggtgcgtg ccgacctagt tagtgtggga gaccgtttag 78420
ttttttgga gtccttggaa aagcgcgtgt atcaggcgac aaacgttccg taccctttgg 78480
ttggaaattt agacttgaca tttatcatgc cacttggaat cttcaaacct gccacagaca 78540
ggtactcgcg ccacgcagga agcttcacgc caaccccagg acagccagat ccccgaacct 78600
acccacccca gaccgtgtac ttctttaaca aagatggaaa tttggtacag atttcttttg 78660
atagcgccgc tggaacggtg tgccacagct cgtttttgga cgtagatgct gtgctggtgg 78720
ccatcaggag ggaccctcac gagctccact gtgcatttgg ggcttacgta accctacccc 78780
ccgcaggcag cttgctcgac cagatgagac ggtttttga gcgatggcat ctgctgatgc 78840
cagcgcgccc gcgttggacc gccgaggcgc taatgtcaat agatcagctt ctctccccct 78900
gcaacgcaaa cttacgccta gagcttcacc cagcatttga ttttttgtg gcccccgcag 78960
atgtggcact tccaggccca tttgacatgc caaacgtcat gcccacagtg gtggcaatgc 79020
ctcgtcttat caacggaaac attccacttc ccctctgccc cgtggaattt cgtgacagtc 79080
gcggctttga gcttagcgta gacagacaca ggctaaaccc ggctacggtt ttggcggtac 79140
gtggcacatt cagagacgcc aattacccta tggtgtttta cattctcgag gccgttattc 79200
atggcagcga acgcacattt tgtgctttgg ccagactcat aatgcagtgc atcgtcagct 79260
attggcgcaa cacccaccag gtggcgtttg ttaacaactt ttacatgctc atgtacatta 79320
acgcttacct cggaaatggc gaactgccag aagagtgtac ggctatttac cgcgacctcc 79380
tggagcatgt gcaggctctc agaagacttg tagttgagta tacagttcca ggggaagcag 79440
tgggtggaca gggacacgac gcgctaaaca acgtcctgct cgatccagct ttacttccac 79500
ccctgatttg ggactgtgac cctatcttgc acagggctga tatgggccga gctcgggcac 79560
aggatctatg ggtggatggg gtagactatg cagcaattcc ttgggtggag atggccgaag 79620
tagactttag aaacacaggc gggcgcttgg tccacaaccg acccatacgc ggggaaaaca 79680
agagaaaccc aatcgttcct catcacgacc cagaatggtc agtattatcg aagatatact 79740
actacgcagt ggtgcctgca ttttcacgcg gaaactgctg taccatggga atccgatatg 79800
accgcgtata cccgcttgtt cagaccgttg ttattcctga ccttggggca gaagaaattg 79860
cccccaccag ccccagcgac ccgcgccacc cgctcaatcc gcgccactta gttccaaaca 79920
cgctaaacat attatttcac aacgccagag tagcagtgga cgccgacgcc ctgcttcttc 79980
ttcaggaggt ggtcactaac atggcagagc gcacaactcc catattggct acaaccgctc 80040
cggacgcagg aacgtctacc gcagtaacac aagagatgcg cacttttgat ggaaccctcc 80100
atcacggcat tttaatgatg gcttaccagc gcaacgacga aacgctttta gagggtacct 80160
tcttttaccc cgccccagtc aatgctcttt ttgcctgccc agatcaccta ggggcattac 80220

```
cgggtcttaa tgcagaagta ttggaagccg ccagagacgt gcctccagtt cctcactttt  80280
ttggagggaa ttactacgcg acggttagac aacctgtggc gcagcacgcc atacagagcc  80340
gcgtggatga gaacacgcta acatattcgc ttatggctgg gtacttcaaa ctgggtccca  80400
tagccctatc ccatcaattt gccactgggt ttcacccagg gattgcattt accgttgtac  80460
ggcaagacag gttccttacg gaaaacatcc tctttgcgga gaaggcgtca gagtcatact  80520
ttatgggcca gctacaggtt aaccgccacg aggctgttgg gggggttaac tttgtactaa  80580
ctcaaccgcg agccaacgtt gacctgggag tggggtttac agctgcttac gagccgcgcg  80640
ctgccactcc cgtaacagac atgggaaatt tgcctcagaa tctgtatcta accagaggta  80700
cgatcccaat gcttgacgga gacgcagacg cgtatttgcg gcgggttgtt aacaccggaa  80760
accgcctagg accccaaggt ccccgcccta tctttggtca gctgatgcca gctacacctg  80820
cgggcgtagc tcacggtcaa gcggcggtat gtgaatttat cgttacaccg gtgtcggcag  80880
accttaatta ttttaggcga ccctgcaacc ccagagggag gagcgctgga cctgtatatg  80940
cctgtgacgg tgaggccgat gccgtggatg ttatgtacga ccacacacag ggtgatcccg  81000
cttaccccaa ccgtgctacc gttaaccctt gggcttctca gcgaaactca tatggtgaca  81060
gattgtataa cggcaagtat aacatgaacg gggcatctcc tgtgtacagt ccctgtttca  81120
agtttttcac gcctacagaa gtagacgcca aggggcgtaa tatgacacag ctaatagccg  81180
acgtgggtgc tagtgtggcc ccgagtacgt ccaacacaga aatccagttt aaacgccccc  81240
atggatcgtc agacttggtg gaagacccat gttcgttgtt tcaagaagcg tatcctctac  81300
tcagctccac tgatacagca ttgctacgca cgcctcacgt tggcgaaatt ggcgcagatg  81360
aaggacattt tgcccagtac ctaattcgcg acgaatcccc cctgaaaggc tgttttccac  81420
gaatttaggt tgtgcccgcc tacaactttt cacttgcaaa ctcaataaaa cgcacagttt  81480
gtatattcag ttgtcagttt gctctactcg agcgtcggcg ctttgtctag ccctcttagt  81540
gggtattgtt accggctggg gttttattgg cgttgttatt ggggagattt tagttgatag  81600
aaagcatacc gaggttttgg gggtgtcgct taatttcggt gtctgtaaac gtaaaaagag  81660
atggctagcg ctgcatttga gatcgacata ttgcttccag gagacctgtc tccttccgat  81720
ttgtcggcgc tgcaaaaatg cgagggtaag attgtttttt taactgccct gcgtcgtcgc  81780
gtcatgcttt ccagtgttac cctcgcgtcg tactacgtta acggcgcacc cccagacacg  81840
ctatccctga tggcggcgtt tcgtaggcgt tttccagcta taatacagcg cgtgttaccc  81900
aacaaaatga tagcagtggc cctgggcgtt tctgttcttc ctcctggaac gttcatacaa  81960
aacacaggcc cgtttgactt aaccaacggc gactctgtgt gtgcgcttcc cccaatatta  82020
gacgtggagg acaaactgcg tctcggatct gtgggcgagg aaatactatt cccgctaact  82080
gttccgctcg cccaggctcg agaactcatc gcgcggctgg tagctcgtgc ggtgcaggcc  82140
ctcactccaa acgcccaggg tcatcgcgga gcggatgtaa tgttttacaa cggaaggaaa  82200
tacaacgtaa ccccagattt cagacaccga gacgcggtca acggagtggc gaggtcgctg  82260
gtcctcaaca tgatttttgc aatgaacgag ggctccctag tgctcctttc gctgatcccc  82320
aatctgctca cattgggtac ccaagacgga tttgtaaacg ccatcattca gattggtagc  82380
gccacacgcg aggttggcca gcttatccac cagcagcccg taccccagcc gcaagatggg  82440
gctcgccgct tttgtgtata cgacgcttta atgtcgtgga tcggagttgc atctcgtctg  82500
ggtgacgttg tcgggggaaa acctctggtg aggatctgta cgtttgaagg cccggctact  82560
```

-continued atttccagag gagaaaaggc cccggttatt caaacgctgc tgtaacttaa taccccaaaa 82620
ctatctaata aataaaaact gagactgtta tattcatttc agtgtgttta ataagaattg 82680
tgaacataac ttattctata tctcattgcg tggaaagact ggaaaacgca ttggtggtag 82740
gtggaaggct cgccatataa acagccatca ctagggcaac caacatgtca tcagacgcgc 82800
cgtttcgctt accggtaaac actctggttt ctgaggtacc ggtaatcacc tcggttaagt 82860
ttttcatctg ggtcagcaaa tactccaccg ggtctgtttg aaggcgcacc gtatttgata 82920
tgagctcctg cgaggcaagt accaatcctg agttgaatgc tttaataaaa tggtcaaacg 82980
cccccgtttt ttgtttttgt agtaaaaaaa acggataggc aacggaactt cccgggggtg 83040
tacagtgata aaataacaca gtccccggca tatgcaccac gtccgcctgt cgtagcgtgt 83100
tgagttccag ttgaatgttt gttgctattg ctaccgcagc gtcttggcta ctgttaccct 83160
cgacagctat tctaacagag tcaaaggggc ggctgtgaat agcaaaaacc tttgctaggc 83220
attgagcaac acacctagct atgagctcag ccgagctacc cgttagggcg cttagaaaaa 83280
agtgctccaa gccaaacaca atccagtttg agcgatagcg gccaactaca gccacgccgg 83340
ttcctgaagc catagcattt gtagtaaacg caggatcaac gtagacgtaa aggttgttgg 83400 acataaatatc ttgattagcg acagtagaag gtcgatacaa caaaaaacgg tcctgagcag 83460
tttttgtaaa aactggttca tctctatgtg ctcccgaaat gtttccacca cctattattt 83520
cttgcataaa tgaatccggt aaaaatagct ctgccgtgtt acgcatggct ccatccattg 83580
ttataaaaac cggtttgttt aaaatgtaac atgagcacga agtagcgttt gtgtgcgcct 83640
ttacgcgctc catatgttcg tcgcagatat aggttaccac gttcaaaagc tcgtctgccg 83700
ctcctttgag gttatataaa aagctggtac tggcctttcc cgtgttggtg gaggacacga 83760
aaatgatctt gcagttggtt tgattaagga atcctataat cgtttgtaca gcctcggggc 83820
gtataaaatt ggcctcatca acaaacagta ggttaaagtc ttggccgcga ataccctgga 83880
acagagggaa taaaaaagag aacagattgt tagaggtttc acttaagcct ggccctcgac 83940
gcgagttgca gcaattttgt tttttaacca gctatatacc tagttctata tacaatccga 84000
gggcattgac ggcgcaacaa taaaacacta aaaactatgg atgcgcatat agccaacgaa 84060
actaagcatc tgatgacaca cggtaatcgc aacacactag cgatggtaca cgtaattatt 84120
ccagatgagt gtctaaaaaa ggctgggatt gagccggcga ggctttcaga tcgacataga 84180
gctagtccgt ctacgactcc cgcgtttaga gtgtttaccc agactcgata tcatgccact 84240
ggaaaatgtt cgttatggcg caccattttt gccggatatg tgcaacgagg ggccattaca 84300
agcgcgctgg tgcctactat tccttcagac cacccccggc tatttcaatc aaccccggat 84360
tcgggtggat tattcgtatc tctagaaatc gaatgtgacg cagatggccg ctttgatgcc 84420
tttactatag ttgcactgag aattgacatt accgacgact cgcgtactac agaaattttg 84480
tttacctatg atgagctgtt acccccaggc accagatacg gggcagattc cgcgcgtata 84540
gcactcttgt gccgccaatt tgtggcttat gttaacagtc attctaatgt ttcagatagc 84600
gctattaaag cggcttcgca catagaagct acgtttgctg aagatttaaa gtctactggc 84660
tgtcatcaat tatcgcaggg atcacgcata aatcctaccg agtacctatt ttcgggcggg 84720
ggctttgaca acaaccaagt tttggcgcgg cttgaggagg acgataaaga aataatgtcc 84780
cttattcgca gggcgtctga ggtaattgca aagcgtaacc cggttcgggt gctaaacacc 84840
caggatcgta acggtgcctc tttaaggcga aaatgcatag catctggcct caaacaaggg 84900
gctattggag cacatgcacc ggtatcttcc acgcgcgacg gagctagtca tagtagccaa 84960

```
gagggaactg ctttactctt gggccttgaa ccccctgact ctggaaggtt tgttaacagc  85020
ggctctcggc gccatctacc tcagcaaggg ccaaaaagcc ccgtgggtaa agactgttcg  85080
tcgggggcaa tagacgacgt tttattgctc acccccgaaa actcaacccc cctcacccca  85140
ctagactggc tggatgtggg ccacgcagca gttgccgggg gagatacacc cgtagacgtg  85200
tggcgccgaa ggcctatatc tctggtggct cgaaagcact acggaacctg cgaaacattt  85260
gttgttgtgt cgtatgaaaa ttctaccgca tggggggta ggagggctag agatggacac  85320
ctgactgggt ccatcaaccc cgctgtgcta caggcgtgtg ttgccgtagg cgtagaccac  85380
cctagaaatt tgccacccga aacgcgtgct gcgcttatag cacagtttcc aatgcttcgt  85440
atccccttg gtgacactcc accgcctgtg gccgcgtttg atgcggctgc ggaattggct  85500
ctaatagaac atttccgcaa agcgtgtgtt tctgcccttt tggccgcaat ctcagaacgc  85560
ctgcgcgtag aacctcgaat gtcacagcta attgagtatg acattccaaa caataaccgc  85620
gactgcatca taagcgttgc acagcgagct cctgagttgc tggaagcggt ggcccttgct  85680
attcaaaatg tttccatagc tgagttttgt aatagcgctt taatgcttgc ggctctttcg  85740
catttaaaca ttttatcaaa aaacaatcac ggacgaatac cctatcacaa atcctggctt  85800
ccaagcttgg ctgggggacc agatgcgttt attttcgact attatagctc gggtggggaa  85860
gtaattaaag tttcccacgt tccactggct atattagttt ctgcaactcg gaccggccaa  85920
cattcgtgta agtttgctcg gggtgcgccg ggagtatctg ccaaaacgta cgagcgatat  85980
cttcctgggg agtgttacgc gtacatatgt gtgggcctaa acagatcgtt tgacgctata  86040
gtagttttac ccggtggatt cgcttgtagg gcaaatgcct cgagaaaact cgcgtggcca  86100
gctcatctca tagagccgat attagagcgc tactgctgga caattccgtc ctactgagat  86160
taaacgctaa aaattatggc tgccgactta aatagctact cgagtatatg ggaggggtcc  86220
tcgttgtccc ccaaccgaca actcaccata gaagccgcta attgtttaac agaggcgctc  86280
acagaagata ttgcagtgct acgccttatt cgcagcgacc cacgcgtcaa aatttttatg  86340
gcggtgagtg ttcttactcc caggctggcg cggtttgccc caccccaatc taaactaaca  86400
cacactgcca agtgtgccgt gataatgata tacctaactc gcccgaaggc cctggctcta  86460
caacccaagc agtttcacgt gctagtaacc tttagcaaga gcagcgtata ctctctggta  86520
atgagagtga aaacaaagcc gtttcctata agcccacaga gattttgtgg ggtgtttcaa  86580
gaccctgaac caatcgggct accgtccgac gtgcccaacc ctgccacaga aaatattccc  86640
actgaaatta acgaccgttt ggacgtaagt aattttgcaa ctcagacgca gcccccaaag  86700
gacaagtacg actgttgcgt tctggcaccg ggtgtttggt ggtataaggc gcaaaaagct  86760
atatactttt tgcagatgga cgaagctctg ttggctctgt gcccagctgg gtggaaggcc  86820
agaggtttgg gaattattct cgggcgtttg cttaaccacc aggaaggctg ttctacatgt  86880
cgctttactg aacactcgga tccgctcaac gcaaccgcgg actctgtggc tacacccgaa  86940
tcgtgtttat gctgggctcc atgtttgtgg cgtaagtcac gccagcgaga gttaaaggtg  87000
gagggggatc gctatttatt tcgcgttctc tttatggacg ccgtggagcg agtgcgtcta  87060
acgggattgc gacgcagccc aaaaatcaca gctgatctcg cagaccttgt cgtgggtata  87120
gggtcacatg gacaacaaat tccagttaat agcgctggat ggaaactggt ggcgctcgat  87180
gctaacatta gtaaacttat cgtttgtgga tgctactctc tacgctacct ctgtccttcg  87240
actgactgca aaacccaaca gttatcaacg agcgaggacg cataacaagc tacggaccaa  87300
```

```
gtaaaacccg gccggtgttt ctcccattga aactgctatt tttaccatcg caaataaaca  87360
tttcaaaaac cccttgtctc cctgcggttt gttataacca ataatacgcg ctaccggagt  87420
tttataaaac cacttacgtt ggtgttgtgg ctcgaggcga atacgatagt gctttttgat  87480
ccatccggaa atgagaagga tatattttca cctttaacgt ggtcgacagg agagttgcca  87540
aaccattggc gaagcctggc gcctatctcg tcaaaaaccg gttctgtagc tttgcgtatg  87600
tgggccgtgt atcctatttt gattcccttg aaagtagcta gagctagcgc tataaggggc  87660
accaaaaacc aggttttccc atgtcttcgc ggaaccaaaa agacggtcgc gcgctgccga  87720
aagtggcgga tggtggcgtc cgaaaactcg ggagtattaa acaccatttt tagaaacgcc  87780
cctattcggt ctgcgtggtc ccccaagata acggcagcta taaagtaagt agcgtgcatg  87840
agaatcattt tttggaaaag ctctagtgtt ccacgctgct ttccgtaggt ggggacatcc  87900
acctttatgc gcttgcttgt ttgttggccg tccccgtcta ggtcagctcc gttaaaagag  87960
gtgtcaacca ggcgactgaa gcgcgccaca aagttggcga cttggtgaaa ggcgtccgaa  88020
gaacgaagag agtcaaaggt gttcataata ctgtagtagg cgtttcggca cgagcgagct  88080
tcagcgtcat tatattcaac aaaagaaata gtttttagtg cctgttttac ttttgggtct  88140
acataagctt ccactgagga gggatccaat cgttctttgc tttctccacc acgccatttt  88200
gacaggctcc taaatagtaa tctcctagcc accgaagcaa atatttgcgc tgtttcgcag  88260
cagtcgtgca acgttccgac cccaggtaca acagtttggt gacgctgggg agttggaatc  88320
gcaaagttaa gaaaggccgt ctttacgtca tcttctcctc cggtttgagc ttccgctgcc  88380
ctatttttag caccactgcg agattgaacc tcttttcgga gagtttcaaa atactgtata  88440
gtctccctgc tcaacgcttt gccaaacatt tttgcgtaca cctcccccag ccgccggtat  88500
gagcttctca acacagtcta ggcgcaggag gctgcagttg gaagaagcct accaacgtga  88560
aatgattttt aaaatgcgta ccctagattt ggtgcgcgag ggcgttgaca aacgcaaccc  88620
tgcctttgtc cgtgcattta cgtcagcaaa ggaggcaagt ttggacttga atagatacat  88680
gcaggctcat tctagggtgg ggcgagtgga acaaaacgcc agggcgctcg cgcagcgcgt  88740
ggaggcacaa gccgctgttg gtgaaatact tgacagacat cgcaggtttt tgcataaaga  88800
ttttatagat aagtttgact cactagagga ctctctagta gaaagagaag agcgcttggg  88860
tgatgttcta tcagatataa actgtgacgg tggcagcggt gaagcaggcg agtcggagga  88920
atggctcggt cacgaggacg aagctctgtt gatgagatgg atgttggagg aagcaccacg  88980
agtgagtacg aaaattgcga tggaccctca ttctccccgc ttaacatgtc ctgtgccaaa  89040
aaaagcacca aaaaacgctc gctgcgaagc tcgcggattt ggggtggaaa atcatccgac  89100
tcagagcaca ctccattgct caccagaaac agttgcggac caacgggtaa cactagacga  89160
aaacatgcgg gaatatcaaa ccacaaacgt ggagcatcac ttaaccacga aaatggggac  89220
aaatcgttcc aatcaggaca caactgcccc cgcattagag cgtcagcggt tagatgtggt  89280
gcagcaacgc gaaaaatcgt caggattacc gaagaaggcg cctcacggca agacaatatc  89340
tggcccggcc agtcaggaat ggctgggtgg cattcccccc ctaagcgacg aagaactcca  89400
agtcgacatg gggattccaa ccatgaacgg tcccatctat ccggacaacc ttcacagagc  89460
gtagttagag ttggaggtcg cttgctcacg caaactccac tccgaaaaac tataatttta  89520
caaccaaagc ttgtacgcaa agtgtttatg cctacattta ctgtaaaccc cggtatgcac  89580
tataggcgcg tatctttagg ggaaacacca aaatttggag gtgccggaag ttatggcgaa  89640
gttcaaattt ttaaacaaaa tggctagcc atcaagacgt cttctagccg ctcttgtttt  89700
```

```
gaacatgagc tggcagtgag tcttttaacc ggagagtgct cgctacgtgc gcaatctacc  89760
ctaggtatag ggggaattat ttgccttatg gccttttctc ttccgtctaa acaaatggtt  89820
tttccggcct atgatgcaga cttaaacgca tacgggtata gactatcacg caatggtcca  89880
ccctccgtgc tggttaccga gtcaatagaa cgggcgttca tcggtctcgg gcgcgcgctg  89940
gtatatctta acactagctg cggcctaacc catttggacg ttaaaggtgg taacatattt  90000
gttaaccatt ctcattttgt tataagcgac tgtgtaatag gagacttaag tttgatgaca  90060
ctgaatacta actctatggc gatgcgtgca gagtttgaaa ttgatactgg agaagaggaa  90120
attaaaacac tccgcctacc caaaagtgcg tcacagatga catttagctt tgtggttggc  90180
catggacata accagcccct gagcgtgatt gcggacttta ttaacaacag cggactcgcc  90240
aaaaatactg gcccaataaa acacgacgtt gggctagcag ttgacctgta tgcacttggg  90300
caggcgctac ttgatctcct acttgttggt tgcatctcgc cctgcctgtc ggttcctata  90360
cttagaaccg caacctacta ctactattca aaccggcttt ctgtggacta cgcactagac  90420
cttctggcat accgctgctc tttatacccg gcgattttcc caaccacccc tctaacaacg  90480
atatacggca ttccctggga ccaggtcgag ggtgtttttg aaagtattgc aggagcacat  90540
caccgcgagg cttttagagc tcacctggat aggtaccgcc taacacacag gcggcttttc  90600
gcgtcaataa gaataccatc cgcatttacc agcgtactcg agctcgtttc tctcctgtgt  90660
cattccaacg aaaaggctcg cctgtcgatc cctctgttat ggactcctca cccgtaacat  90720
acagcggagc acctccgtat aagctgcgtc gcctcaacac atcgtaccca tacgcctcta  90780
agctacgcga gcgcgacagt ttaacagttg aaacattttc cggatacata aaccaggaga  90840
gtatttccga ggaagaagtt tacgagacta tggctactac cgctgtcttg tctacccgga  90900
tgtacctacc atcagtttta cccaacggga tagccaccat gacgtttttg gatcatttga  90960
agaaaagcct cccacttccc catagcgata agcgattaaa cccaatcttt tatcgtcttg  91020
cctacatacg cgacctggtg ggacaaatgg agattgaggg catagtcgag cgtggaaccg  91080
cttcacgcct actaggtgcc cgtaagccag caggatttgt ggcgggaact tacacacacg  91140
ctcgagattt gtccaagaca atgtctatag caaacattcg ggatgccgtg ctagctatag  91200
aggcgcaaac ccgcgaccag agcgaaagcc aactgtgggc actacttcgg cgtggcttag  91260
ctacagcgtc taccatgaaa tggggggcgc tcggaccaca gtatcacccg cagtggtgtg  91320
agcttagtac caattctcgc ggaatcccaa acaatccggc gctccagttt ggtcaaacca  91380
acgaacgaac ggcgaggtct ttaatctctg ctctttatgt agctcgttcc gaagccgcca  91440
ccccagatct gctgatggac ccaggatgtg gacaatgctt catgtttgac gagtctgcta  91500
gtgttcccgg cgacgcctat gcatgtggct tactcataga cgccagaaca ggtgttgtgg  91560
gggcatcttt ggatatgctt gtgtgtgacc gggactccaa cggggtactc tctccacact  91620
ctacccaaac tacattggat ttttttgaaa ttaagtgcag agctaagtat ctatttgacc  91680
ccgatttatt tagccccgta gctacggcct atgccaactt gttaaaacat cgtaccgcag  91740
tatgcttgcg caaatttctg cggtctatta aaaaccccgc agtagagtac tttgcttcca  91800
atcgtgtgcc gggtgcaaca gaagcgctga ttacatgtaa ctcctcgtgg aaaccacgtg  91860
aggtaaatga gactaacagg cgctgtggtg actttgataa agatcatctt gctttaaacc  91920
tggacgcgtc atcagacgtt tggctattta gtgagccgga ccttgagcta caaactatta  91980
ctccagctcg ctgggatact ggagagttgg ctctgtcagt tccggtattc gccaacccga  92040
```

```
gacacccaaa ctttaaacaa atacttgttc aggcatacgt gttgtctggt cattttccaa  92100
accataaact tcggccgttt ttggtaacgt ttattggccg ccatcgcaag aaatgtgaag  92160
aaggaaaaac gttcacaatt tgtgatcgcc cggaggggag cccatacaac ttgaacgagg  92220
ttgttcactc cagctgcgct attcccattc tcctgatcgt gactccggtg attgtggacc  92280
gcgagggttg ctgggaagac attgaaattg agagtctcac cgcgtttaac aaaacttcgg  92340
acgcaatatg ggacaacgac tctcgtgtgg atgttttaga accaaccagc ttgtaaccca  92400
cagcggtgag atagtgtctc taaacgctga cacatttgag gagtttagca tggatgagtt  92460
cgacattccc cccgcccccc cgaggccagt cttcaagcaa cccagccctt acaaacaacc  92520
aaaccccgcc aaagttcagc gaaacctttc ttcaaaacga cgagacccat attaaataaa  92580
aaagaattgt acggcatata aacgtgtaac gtgttttatt gtttaatagt atagcactgt  92640
ttaattacag acagttctgt aaaaaactag tacgtttgtg ttaacggtaa tctctgcgcg  92700
agtttctatt caaatcgtgg tgggggtcgt catagtattc tgtctcaaat tcattgctaa  92760
caacgtcgta aattggctct tctgagtccg tctctgagtc ttcattcaag agcatgcccc  92820
tggactcggc aacgttcaaa ggttttgtag ttctgcgggg tcctctcacc ctgttgacat  92880
attttcgcgc ctttgacgac accgttttta cgcgcccgta gaattctgta ttacgctttt  92940
tgtgaaacat aattgctctt actagtcgca cgactagcat gattatggaa attacggcca  93000
taattcccac cactgcttta gaagcagtgg ccagatttgg agcctggaca gaaaccatcg  93060
tatgaaagtg aacaaagtaa ctgtgggtag ccactgccag cgtagagcta gccaccaaaa  93120
cagcgagcgc tggtcctatt aggacatgca catagtggga caccacaagt tcgacgatta  93180
tcaaaaacaa tagcccgagg gccacaaaca cacccacggc tactgttacc gtttgccaca  93240
aagtgatgtg aaagctgttg gcgagtatta cccctagcat tagggacagt ataggcaggg  93300
aaattccaag catgcccagg cttaggttgg tcataaccgc gcgtccgtgg cccgccattc  93360
gatgtagcac tggcatgttg gtctttaaga tgcgaaggtt gctagagtac tggtcgcttg  93420
aggttccgag tccgctaaaa ctcaggcaaa aaaatacaag cgcaacaaaa tggactatgt  93480
aagctgccgc tgccaaaacc acttgcttgt gtgaaagtag caaaattaca acctgtaaga  93540
gccacgtagt cagcgttccc aacacgagag tcacatggga cgcaatgagt gtggtagtgg  93600
gccgggagca tccagcaacc gctgtgcact ctttaccccg agcgaatttg cgtaatagaa  93660
ctgccgagat tatgaggtat aatgatatgg ccatcagtac gattgtagag tagtaaagaa  93720
atgcaaccag cgacgtggtc tctaaaaaca gggttggtgc caccccacca actatttttt  93780
gcatccacac cccgttaacc acgctgtggt tctcctgtgt gtagtctacc agagacccat  93840
aaaaacacgg atatccggtt ttttgaagag acgccgtcac aagagttata aaaagcactg  93900
aggttgtaag tgcgaaacag aacacttgca caagccacat cttccagtta atgccttcaa  93960
ttggaccggt ccccatagtt cccgacaacg gcagcaaagg ctcctcgatg acagcagcgc  94020
cacgtcgtgc catggctggc tttagtgatg caacgcttgg tggtccgaaa gaaagtttag  94080
cgttctcagc ggtggaaaac agctatactt ccagtgtttc tctggccaag atgttatatg  94140
ggggagactt ggaagagtgg gtgcgtcaca agcgtccagg tgtgagtctg gaaatccaat  94200
cgcgagctcc cgtttgcttt ccccacgcccc acaatccgtc tagcaggcgc gtaactgttg  94260
taagagctcc tatgggttcg ggcaagacaa cggcgctact aaaatggctc agcgaggcgc  94320
tggacgcgcc tgatattagc gctctcgtcg tttcgtgccg gagaagcttc actcgcacct  94380
tatctaaacg atttaatgac gctaaattgc ctgggtttgc tacgtatttt acgtccacaa  94440
```

```
actataccat ggccggggag ccttttcgtc gcctactggt tcagattgaa agcttgcacc  94500
gcgtcgatga taaccttctc aacaattacg acattttagt actagacgaa gtaatgtcca  94560
caatagggca gctctactca ccaacaatgg ttcaccttaa caaggttgat gctcttttaa  94620
ccaggttact aaaaacttgc ccccgtgtaa tagccatgga cgctacagca aacgcgcagc  94680
tagtggactt cctagcatct gcgcgcggtg agcgcagcgt tcacgtaatt ataaactcat  94740
ttgccgcgcc tggattttcg cagcgccatg gaatcctgct acggacccta gggacggacg  94800
tattgcgggc agccctagga tttgtttgtg ttgaagatga aaacggagct aaagttatgg  94860
aggcagactc cagaccaatt tcggccagac ttcgcgaagt tagctctaca ggttttttttg  94920
gtcgcttaat gcataggctc atcgaggggc acaacgtgtg tgttttttct tctacagttt  94980
ccttttcaga aattgtcgcc aggttttgct cacattttac agactctata ttagtgttaa  95040
actctttacg acccagcgaa gatgttgcgt tttggggggg agtaagagta ctcatataca  95100
ccacggtggt tacagtgggc ttgagttttg atactgcaca ttttcacagc atgtttgctt  95160
atgttaagcc aatgagtcac ggaccagaca tggtgtctgt atatcagtct ctcgggcgag  95220
ttagagagct catcgacaac gaactgtttg tttacgtgga tagctccggg gcccgcgctg  95280
agccaatttt tactcctatg ctacttaacc acgtggtaag ccgagagggt ggatggcctg  95340
cagagttttc tcaagttaca aacgcactct gttctcagtt taaggctcgc tgtggacctg  95400
cctatagaac tgaatctaca cgtggactca ctctgtttgt tcggtttaag tataagcatt  95460
ttttcgagcg atgcacactg gcaagtgttg gagacagcat aaacatttta tataccttat  95520
tggagtccaa ccgcatgctg gtatctatag aagggtgcca atttcccctg accgccgctt  95580
gtttttgcag ctttttacaa gatctgcgac ttgacgcata cgccgccaga aaggagttaa  95640
agcagttaag gatatccgcc agtcctgcga caacaccgac tgaagttttt gaaaacgacg  95700
atgttgctat gtttattcaa aagtacttgc gccacggtgt tactcacaat gacatattag  95760
accttttggt agaccttaac agtcccatag ttagggagca gtttgttaat gtggccgttt  95820
tgggtgcctg cttgcgccta ccagcagcac tagaaagccc cgaagttttt gcgggggttt  95880
acaaacatta cgcttccgga gttgtgccgg tgattagtga cgctggagca cttgagagtg  95940
tatcaataac accagacgtt aacgttctag cgcgctggga tttatataaa agctgcacgc  96000
gtcatgcccg cgatatagct tgggacccgt cccgcggggg gtccgggctg gatatgtctg  96060
aagatttcat tacaaacact ttgagcgctg actctaaccg atttcaaagt ttgctggtgg  96120
aaatagcaaa gtgtaacgtg acaccgttag agatgctagc tgcgggggct gtgcgtggtg  96180
ttaccaccgc gctatcaggc aaacctaaaa ctagagtgcc gctatcacaa gcagagcatg  96240
ctgtttccct gtttaaggtg ttatgggagg atgtgtttgg ggctagactc accaagagca  96300
cacaaacctt tcctggaggt gtgcgcgtca aaaacttacg taaaaacgag atagtggctc  96360
ttttagagtc agtaaaggta aaccactcag aatacaaaac gcacagagag ttatatgcac  96420
tgctaatgtg caacaggaag ttgtttgctg gacccagata taagctaagg gcgccaaagt  96480
ggagcagaaa catctgtttc ttagaattgg acactactgg tacctgcaaa accccacttg  96540
acgccgcgct agcagatata gcccctagcg cctggccaca ggtctgcggt gctgttgact  96600
ttggcgccct gtgagactaa accccatggg ggaaaacgtg gaatggttta atggatatgt  96660
atgtgccaca agtatctact ctttatggac agatccacac cagcctggga atctccaagc  96720
gcttgtctac ttgctatgtc ggcgcgtgga caactataca gcagagtttt gtcacgttgt  96780
```

```
agtctctgga gaacttctaa ggcatggagc ccgcaaccca tctttggtaa cacctgcacg  96840
tgtagccagt gccgcaaaaa ccgcagcggt acctgggtgt tggccgttgg cccctctggg  96900
agatgctatg ttgtggaaat cggtgtacgg tagcgtagct tcagcgctta aactaactct  96960
gggaagtttt gctttttata aacccatgat gtttggagtt aatacgcaaa ctggactttt  97020
ggttaccatc aaacccgccg catctgaggg tgttcgtggt ggagaccccg tctctccgcg  97080
ggcagcactc gtaaacgcat ctgtggaagt agacttagac cccactggta tcgaagcgag  97140
tgctgctagc gtcacaggat catccctcgc tagagccaga ctctgcgcgc ttaaagatgg  97200
atatttctc acaaagcaag acatcgccct agaagttgag atcaccacga aggaggtttc  97260
attttataga aaatatgact ctgtgcagca gccagcaaac aaacgccgtg gggacatggt  97320
agatctattt attgtacatg aaagaactct taggctaatg ggatctaagc acatgagcgt  97380
taaagtttta gtaccacgga cgtttgactg ttttgtggct agctcccagg cgttgtcggg  97440
tctagcagct atggctttgt acaagcagtg gcacgctact ctattttctt tagagcgctc  97500
agaaactgta gtgcaaattt ttgcttatct tggcccagaa ttaaacccgt gtggagagga  97560
cgcagactac tgttgctttg ttggatttcc cgggcttcca accctcaagg ctggtcttaa  97620
caccgcggat gcagtgcgcg aagctctcga cgcatataaa ctgtctgacg gtttatggcc  97680
tgctctgggt atgagcgcgt ttcacttttt acacccctgg gaaccagaag acaaatggcc  97740
aggtgaaacc gccgcaaaac ggttggagag tgtagccccc atactacaaa ttgaaagcgc  97800
agatgtttgg ggagcaggcc gggtaacgtg cattttagag tctgacgctg taatgcaggg  97860
accatggttt gcaaaatttg atttttcagc attttttccc acgctttatc tgttgctgtt  97920
tccaactaat gagcgcttag cccaggtagt tataaaaaga gctcgcggtc aaaaccccgc  97980
cctaaagccc gctctggtat catttttttgg tgggttgcag cacattaacc ccatggccta  98040
taggctaatt atagctatat ctaacgaaat cagtaggcgg ttagagcacg aagttaacca  98100
gatgggtttt gccatatgta cgtatgttaa agatggcttt tggggggcag ctggaaatat  98160
gctagtagac tcggtatcct actccgatgc tctggtttac gctgaagcgc ttagaagcgc  98220
tgctcaaggc gcagcgctta gttacgtgtc agagctgggg ctttcgttac cagatggagt  98280
tgacctgcgt ttgcggttgg agggtttgtt tactgatgcc atttcgtggt ctacccactg  98340
ttactggcta tacaaccgca taacaaatat tgaagacttt gtaggctttc ccaccaaaag  98400
tgaagctagc agagcagcaa aggctagctt atcggctctg ctcccgcgtg ttgcggcggt  98460
tgcagactct ggagacttgg atatgctcca tcagctcgtg aaagagtcgt gtgagcagct  98520
tgttgcagaa gcgtttgcca agcggaacga cccaaagttt tggagtacta agacagagat  98580
agattcgtct acgcaactcc ccacagcagt ttacaggagt ggatgcttgc tcgaccaaga  98640
ccgtgggcag agggacattg tactgacgcg tcgaagtgat tgcgaatccg cattgcctgt  98700
accctggatg ctttttccac caccgctggt attggggcgc atagactgta tggtatatct  98760
cacgtccatt tttaaaactt acctgggcat gctaaaccga gcgatatcag ctttatgtga  98820
cgcggataaa cccgtaaatg tagagttcca aattacagat tatgcgtttt tatttactta  98880
aataaaaacc aaaaacgttt catttttttt cagtttattt gcgtataata caccacccag  98940
gctagtcgta taacacgtat attgattcgg gaaccggctt ttcgttggtt gaggtccacc  99000
aactatagat agtatccgct attgtttttg tacacagcgg agagttcaga atagcctttt  99060
tacagcgcat tactcccagg gggcagggtt tatcgggttg gttgacaaac gcagccctgt  99120
aaccggcgct gtaaatagcg tctaatacag ccggagtgtt tgatttatgt ccgagtaaca  99180
```

```
tcttagccat catgtagttg gggagcactc gggtctggtc aaacgggttg tggttagtcg  99240
ctgacatcag cgtgttaagc acccacgttg cgcctatata catcaatctt cgcatcttta  99300
aaagcggggt gatggttttg gagatgttgc gcagtatgcc ctcaacttgt acaaaaagcg  99360
atgaagtagc tcgttttgga gagcagtttt ccagatacat ttggattata catagggtga  99420
agtctataag gttggttggg agatacagta caagtctgtg agataatatt acaggtgcca  99480
ctcccagcac gtttactcgg tcttcgagag gagttactat aaaaagagaa aatcccttaa  99540
aggcggacag gttcaagcat gagttcatgt acgtttcaca cgaaacctcg gcgtcttctt  99600
ggccgtccag ggttagcatt agtttgccag acgggtccac tcttatgtta gtgattgacg  99660
tggtcgtgaa ggaagggggc agcccgggaa cctctctgac ttctgtcacg aatcgaggag  99720
ttgcgtgcca aaccagatcg tcgactatag ctgttgctaa atcgtctccg tttgtaatag  99780
cctccaccat ttcgtccacg gtagcgctgt gggctaaggg atctatctcg tcccgcataa  99840
tagcgctcat tgtcaggttg ctcttcttca gatggggtat cgtctccggg aacagacgtc  99900
ttccaattag cagaatttag agccgcaatt gagttcctaa ctttcgccac aaaaagcgta  99960
gataactctg tcagataagc ttcgagcctg gttttttga acactgccac acacagctcc 100020
tcctccgagc ggtacgcctc ttggtgtgta attaaaaatc ccaggtgacg cgcacgaaga 100080
atagaaaaaa agtatggcgc aagcaaaagg gatattgagc tgttagagta cgaaactgac 100140
atttcttgac cttggttgtt agtgattcgg ttcattttga agcagcgtag taactcttga 100200
tcccacaaac gcgataggcg ctccacgtca gcagcataag ctggaatata cctagactga 100260
aagctattgg caacatagcc gtcatccccc attaaatttc ttatgtcgat aacttcatgc 100320
ccgagttctc cggctttggc gcccccatga gcggtgcagg atcccacact aggtggtggg 100380
gtgttcccgt ctgcggccgc ttgtgttaca cgcagtaatt gttcgcggag gtgggttaat 100440
tcgctttctc tgtcctgtag ctgatttagc agcccgccgt ttccagcccg taaatcttct 100500
atagttttga acaggttgtt aacgtatccc tctagcattc catttatgcc attaatcaca 100560
gaggtgcgaa aggcttcctg cacgggcata ttaccccct ggcgggtctt tccgctctgc 100620
ccaaatccgg gcatagacgt gtctatctga gcgctgctga ggatattggt actcgtttcg 100680
tctaaatacg atctgactgt ttcagttatg tcacctatat gtcgcatgct tttcatgtta 100740
actatgagtt taaccagcct agaggcggcg gagctagaat gcatttcttc cccctctccc 100800
atgagcttgt ccacggcttt ggacgcccat cccggtccct gggattcttc ctttttcctg 100860
ccaactagaa tcttaacggg cacagtgttc agcagttggc atagtttagc gtgctcgcgt 100920
agggcgtggc agttacacac ttcgccgcaa atccgctgaa gtggagagtc aaacagtacg 100980
gtgccatctt tccatatagg ctgccataac accaaacact ctccccgcct accggtggtt 101040
gagtctatag ccacgacctc tctgcgtttg tagtggtaaa atattttcac cctgtcgtag 101100
tccataatgg ccacgctggc ggtacacctc gccagttcaa ccacagcctc caacccctcg 101160
cgcaagagac tgttggccac atacagttta cctgccaggt ctcgctcgtc tacacagctc 101220
tccagagagg gtacgtcagt tggcagctta cgccacaact ttgggtgtac ggttgcgccc 101280
ggagcgcgct taagcctctg taggggtatt agccccaaac acgctatcca gtctatgtac 101340
tttgcaaagc tggcggtgcc atccggctcg ctggcagaaa aacacgcggt tatactgcga 101400
acaaagtcta atagcgacat ttgtagcgtg cgatgccagg ttgcaaaaat ttgttctgct 101460
acgcgtaccg cttccccctc gctaaacatt ccgtaggtcg ctgctatttc ttccgcgctt 101520
```

```
accccacgac tgtctaggtg ggtttgccaa tcctttgcga ggtcctcgta tcgcgtagct 101580
ctaagcgtat tggtgagaat agttgtttgt atctgtctga ttgctgcctc tgttgaccta 101640
attgcgttgt acactccttg gccttctgtg tatccgagct cccccatgag gatttccttg 101700
aatagcattg ttttgggggt tggatgaata agaacccaac ccccttcagt agatatttgc 101760
tcctcttctg cttgattctg aaggccagtt gcagactcaa agcgcactgg gttttttcgc 101820
tctcttttg gggctttagc ttcagcataa cggaggcgtt tttgcttggg ttcgatggag 101880
gcccccgaca tttttttaga acaccgcgaa actgggaacg aacgccgcga gggctcagag 101940
gagaaaataa cgccgtctac ctcctccgaa gattttaacc cacagctctt cccaaacgag 102000
gtatatttga actttacgtc tatgcacgga atccagcccg tggtgactcg tatcagagag 102060
ctgtctagaa aaactgtttc tccagctatg gtgccgccgc tggaatggtt tgaaaagatg 102120
ccaaaactgg aaacgcccct agatatagag ccgttacatc taccctttc cgtttacctc 102180
attagcggga acgccggctc cgggaaaagc acgtgtattc aaacgctaaa cgaaaccatg 102240
gattgcgtca ttactggcgc tactcgcgtg gctgcacaaa atgtgtacac gaagctgtct 102300
tctgcttttg ctactcgcca catcaacacg atttttcaag agtttggatt tcggggaaac 102360
cacgtgcagg cgcagctggg caaataccaa tacgcgtgct cttctagccc gcctcctata 102420
gaagagctgc agaagcgcga catagtttac tattgggagg tgctagttga cataacacgc 102480
cgcctttttg agtctactac atcacgcggt gagtttgaaa atatcagagc actggagcgc 102540
ttgctgggac gcacccccgg atctttaaca aggctcgcct tttgcataaa cggctcgctg 102600
ccagcattta ctagaactaa tattattatt atagacgaag ttggactatt gggtcgccat 102660
ctactaacgg ttgttgtgta ctgctggtgg atgttaaacg ctgcctataa gtcgccgcag 102720
tacgctgagg gaaggattcc tgtggttgtg tgtgtggggt ctccaaccca aacggattcg 102780
ctagagtctc gctttgagca taaaaactta aagtgtcacg ttaggtctag tgagaacgta 102840
ctaactcata ttatcaccaa caaaacaatt agggaatacg tttctctgtc aactaattgg 102900
gcaattttta taaataacaa gcgatgccag gagtacgaat ttggtgaact aatgaaagtt 102960
ctcgaatatg gactcccaat aacagacgag cacatgcgcc tagtagacaa ctttgttgta 103020
ccagaggcct tcattaacaa cccggctaac cttcccggtt ggactcgact ttactcatcg 103080
cacaaggagg taagcgcgta catggccaag ttgcacgcgc acctaaaagt ttcgggagaa 103140
aaacaatttg tagtgttcac gctgccagca tatacgtttg taaaaaccgc cgcctttgac 103200
gaatataaga agataactaa acaaccatct ttagcgttgg ataagtggct aactgctaac 103260
gctagccggg ttagcaacta ctctcagagc agagaccagg acgctggaag aactcagtgc 103320
gagtattact cagatcacgg cgtcgtggtt gctcgaacgg acgtgacgta cgtgttaaac 103380
agccaggttt cggtaactac gcgcatgcgc aagtttgttt ttgggtttag tgggacgttt 103440
gagtcgtttg acgccgtgct caaggatgac gcgtttatta aaacccaagg agaaacgtcc 103500
atagagtatg catatcgctt tttgtccaca ttgcttttca gcggcatgat aaacttttac 103560
aactttttaa agcgcccggg tctaaacgaa gggaagatta ccgaagcata taggcgcatg 103620
gcagctttaa ccgcaaagct agttcctggc acgtctgttt tagaaagcgc atgcgataat 103680
ccaagcggtg caccgctaaa ctttagaggg ttaacagccc ccccgggcca gactgtggat 103740
agcgctaaca gctgggatga cgacgacgtg gtgtttgcag cccttaacga aggcgccata 103800
gacatgctgt attgtaatta tgagtttgtc aggcccgaaa ctacacaaga ggtatactcg 103860
cagtttctaa tgctaaagac catgtttatg ggagatacgc ccattttcac ggacctgttt 103920
```

ggtgatgaat ttaaatcttc cccatttgac gcgtttgtag acaatataag ctataagggg 103980
tgtgaaattt ttgtggggag catgcgcggg ggcgtttctt ctatagctct tcagacagac 104040
agctacacgc ttatggggta tacgagcgcc ccggtttacc cgtttgttga ggaactggct 104100
cgcagaaaac ttcatgaggg catcgcagag ctttttggtg caatgaacat gcctcgcatg 104160
gtgctgcgag accaacacgg gtttatgtcg gttctaaacg ttaaccttag cgagtttgta 104220
gagtcagtgg acgacaccga gttgaacatg gccaccgctg tggactacgg ccttagctct 104280
aagctcgcca tgactattgc cagatcacag gggctgagtt tggataaagt ggcgatatgc 104340
tttccccgca acaacctgag gattaacagc gtctatgttg ccatgtcacg cactgtgtca 104400
tcaaagtttt tacggatgaa cctaaacccg ctaagagaac gtcacgagcg cgacactgtc 104460
ataagccagc atatattagc agccctgagg gacagagacg tccagattgt gtattgaaag 104520
ctgccacgca atagtcggag atttaacgcg cgcaggtttt acgccaatgg agtcttgtag 104580
ccccccggtt acgtttatta cttatgcgct gtatggaata aaaacttctc ctgcttggac 104640
tcttcccaac tttgaacagg ttatttctag ctgcggctgg ggatacagac tgatcgccgt 104700
tgggtcagag tctagatgcg atgttatgcc aaaaggcagc tttgtgatac aacatggcgc 104760
ctctataaca gcgctggtgc tggattgtgg cgtggagttc tgctcgtacg cgtttacgca 104820
tgccgatagc accagagttc cactaaccac cgaagacggg tctgtgttgg tggttccatt 104880
ttgtggctgg gtatgtgttg gtagggatag atgtttgcga agcctgtccg gtggggtact 104940
cacaatcagc tgggatgtga gccagacggc gtacatcagc gttgccgttt atcgtccatc 105000
caccgtacag tgccatgccc tgacctgtac caacgtggaa actaccggaa gttcaaacgc 105060
ggccattact gacggctctg actcagagcc gtcagtattt gcaaaccagg aagctgacaa 105120
tacccaagat caggatggcg gtccagattt tctggaaact attctaatgg aatcagatct 105180
atatggtgcc aacggaccag ccctaatgga gccgtgcttt accggcctct ctgacgactc 105240
gctgccttaa caaacaaacc tgtttctatg ttttaaaccc ccccatatgt ttaaatgaaa 105300
accaaaataa aagtttatat aaacaaataa acgtttattt gttttttata atgtttttta 105360
catatgcctc agcgtgtttc ttcttggcct tgggtgtcct tgctgctgtg ggagccttgc 105420
tgatgtagac tgtgttatag attttcgcct gtggtattga ctttcgctgc ggtgaccgtg 105480
gctattgctg cgctgagtat agctcgagct gctggaactg tgcccctcac tgcgcgaatt 105540
gcgcccctcg ccgcgcgacc gttgagacga gcgtagcgta ttagacgctg aagcgttaac 105600
tagcggttct tgcctgctga tagattttct tcgctgagcg gccatggcaa gtgctactag 105660
cgttccagaa ggcctatcgg ggcgatctcg atgcttgtcg cccccggcca caacgtgtgt 105720
gtctttgcta gaaacagagt ttcgcctaga caaagatctg tgtcggggtc tctcttctgc 105780
ctccggttga gatataacag aatccgtccg tactggtgtt gttgcggcgg caagcttagc 105840
ggcagctcgg ctgttccttt cgagaaacct gcgatagtcg tccgcggtag cagcgcgtcc 105900
tcgcccaaac acgtccatgc ttctcacggc tggtcgggct atgcagagta gaagagctgc 105960
gccgaaacac tcacttggct tgcgcgttag cttctataac gttatccctg tggaggtaca 106020
ctttatccac agcggaaaat tcgtaaatgt acacgggaac caccggatgt gtacgtccgt 106080
ccgacgatcg cgtgtaatac tttctgggtt ttcgcgcttg gattaccgac tggagctggt 106140
ctctaatctg cttggcgtga gctctgcgac acagaacaaa catttgcaag cttttattgc 106200
tgcgcaccac gcgctcagac gggcattggc gccttttgcg acgcgtggcg ctcgcgctag 106260

```
aaaacgaaga ggtttttgta catgcaatgg taaactttgc cagagtcacg cgcaggtcct 106320
ttctgatagt gtccgtgagc tggcggcggc cgagttcatc aattgaagat accataaaca 106380
tggtgtcaaa tccaacgtag ttagagtttt ccccgtcggg ggtggggccc ccgaaggatt 106440
ctaaggataa gtcaggtacg caaagcgggg ttgtgggagc ggtggtggtg catgtcgagc 106500
tggtcagcgc cggtggccta agttcggtaa gcgagtcgcc tactgttccg ttgacaacct 106560
cgaccggcca tccccaccca ctcagcacgg ttaatgcgga ctccatttgc ggtagcggtt 106620
aggaaccggt ctggacctgc ggagggcttg cttatgtagc cacgggatat gggtgggcgt 106680
tgttttcacc gtaaattact caatcagcca gtttatggga ctttttcctg ctttagcgag 106740
atacgcatta gcctccaaaa agtgtgggca atccctgaaa tttacacgcg agagaggcga 106800
ggggtgtccg tatgtgagca ctaggtggtg ttgtctgctt ggagagcaaa acttttgggc 106860
atgagcaccc cacagcatga acacgaggcc ctgtgacgtt gcacatagcc ggtcgataac 106920
agcacgaact aacctgtgcc atccaagagt agcgtgggat cctggctgtc cgcgcgtaac 106980
cgtcagtgtg gtgttgatga gaagcacacc ctgactggcc catttatcca aaaatccatg 107040
tgtcggaggc ctaaatgccg ggtacgattt ctggacggcg gagtatatgt tgcgcaagtt 107100
tgggggtaca ggtactccct tttgaacgct aaatgctagc ccatgcgcct gaccgggtgc 107160
atggtacgga tcctggccca cgataaccac acgaaccttt tctgggggcg caaaccgagt 107220
ccaggcaaaa atgtcttcct ttttgggaaa cacctcttcc ctggcacatc gcagcttata 107280
ctcacccaga agaagtttga cgtactgttg ttgcatttct ttttctagaa taggcctcca 107340
agagggcgct atgttaaatt ctagctcaat ctcttcccat gagctttgga ggttgttggt 107400
caaaagtggg tgtgtagaaa caccggtgtt aataagagag actccaggtg gaagtccaca 107460
tggccgcttt cgcttttgtg ggggagcccc agattcacat tcctttggtg attccttaca 107520
caccgtttgg ctggctttgc tggtgggtat tggcagtctt tgttgttttt cgaccggctt 107580
agtctcgatt atgtctgcgg tggtagatag ttttgtttta agatcacaag cgctgctcat 107640
tctgaagttt cttgaatttc tgcgtagtat gaagctggta tgcagctatc ttttactcct 107700
tcagctattt ctttagactc tggcgttgat aaaaaaaaag gccccgcaaa acagcccagc 107760
ggaggagggc ccaatatctc gtctggagag gcctgagatt gagtaagaga ctcatctaag 107820
gcaagaagga gcatctcttt aaagtcttgg ggaatgtttc cgtttgtgac gtcttcagcc 107880
aaaccctgaa tgacggcaaa tggattaacc caaacaggtt tgggtggtat gtcaacccac 107940
aaaatggctt ctggaggtgt gcagtgagcc ttcaccataa tccctagcgt tttgtttagt 108000
aagtttttaa cattgggggg tgtaaatagt tggcctttca ttataggccc actaccgcag 108060
ctagcttcta aaatacgctt gggttcaccc gatgaccacg taaactccag cttatttgac 108120
ttcgctagct tggtagctac aagccatgtt atcatataga ttagttcaag cttaatccaa 108180
cagaacatcg gccgccccat tcttttaaaa gactctaaac taagtggctg tttagctttc 108240
gtacatcggt ttatgtacag atttttgcga gacacaccca attgggagtg atacatttgt 108300
ttacgttaat ataaacacat attaacatac tatagtttat tctcgcctca gagtgagatg 108360
agggttaaaa aacgatctgt gtggcacacc tatagggata aaaatcatac ccgcaaacta 108420
tttggtggaa caactgatgt gaacttttaa cgctagggct aacgctaacg ctagggctaa 108480
cgctaacgct agggctaacg ctaacgctag ggctaacgct aacgctaggg ctaacgctaa 108540
cgctagggct aacgctaacg ctagggctaa cgctaacgct agggctaacg ctaacgctag 108600
ggctaacgct aacgctaggg ctaacgctaa cgctagggct aacgctaacg ctagggctaa 108660
```

```
cgctaacgct agggctaacg ctaacgctag ggctaacgct aacgctaggg ctaacgctaa 108720
cgctagggct aacgctaacg ctagggctaa cgctaacgct agggctaacg acaggaagtt 108780
gtcataattg cgcgctatag ctgccatttt gaaaaatttg tactgtcatt gtttttgaca 108840
ttatgatgtc atctttgtgg gacacaatca gccattttta aaccacgcct tttgacaacg 108900
cccataaagc tgttagatgt acccattgaa agtggtaata cccgcccatg gtggtctagg 108960
ttggggggtt tttatattag aaaaaacaag gcggtatttt ggcagcgggt agcatattgg 109020
taaaaggtaa gtgattttta atattaaaca caccattaac ctatgcggaa gtcagttaaa 109080
aagggggccg attggtgtat atttggaatg gttcataaaa aatgtatggg ggcatagtca 109140
gcagagtcgc tttattttta atggaaagcc accacatcgg gttggcgtga acgtgtaccc 109200
aattaagaaa attggatgtt gccaaactgt aaaaaaaaac aatatattcc aaatatccaa 109260
gcattaatag aggagattgg actagcacca aatgtggtgt acatttttta atttaagttt 109320
aatgtaaaca tttactttgc taggggtcat aaaattggga agtgttacat tttatatctt 109380
tagtgaatgt atattagcgt ttcatttatt aattttaaat gggtgggaat cccgtgtgtt 109440
tggtattggg gagttgggaa tgcgttaata acccaataag gggtgtttgc taagggtggc 109500
ctttgtatga taagagtaaa acattctcta gctagccact aggggataca tattaatacc 109560
gcaggaagcc tcatattgta atagcttaac aattcatttt tccttccaaa aatatttagg 109620
atatcctgcg tgctatccac gatggattta aatgtgccag gtaaactaag caaatatttt 109680
actaaatggt atagttgcag tattcgggtg tatatatgtt ttatgaaggt tacctaaaat 109740
cattagcgct atttttaact attgcatcat cgtgttaaaa ggcgctgttt gggaaaagga 109800
gatttctgca ggtgcagtgg cttgctaaag cttaaaatct tgcagcttta ggaatcttct 109860
ttttcaaacg gaactataat cgacattata atttatacta atgttatgaa cctcttatat 109920
ttcccccttt gcttgtttgt attaattatt tacaccaccc ccctcctttg ctagggttaa 109980
catttttgtg ttaaatattt ataattgctg gtattaactt tttaaaaaca ttataaaact 110040
ttttatttaa aaatagattt atttacaaga tgtaggttat cttttacaca ggtcatataa 110100
ggtcattggt ttcttcgata tctgtaacag ttgtggggac atgtcctctc ttcgtgtgtg 110160
gaaggccgcg actgaaatat gcgctgaaga ctgcgaactc gttggctccc ctgtctaagt 110220
aatgagttag ggacaacgg gtctgggtat ggcacaggtg gtacactctg tcgtcgtggt 110280
ctcagcaaaa cattaccacg tctcctggta atgctacctt ctgttggtct ttgcacagtg 110340
tgtatgttgc atccactaaa gctttcagag tctgcagatc cgtgttctgc atgtatagct 110400
gcagtggtag gttccataaa cagacgatta gtattttgtg agccagattc tgaggcttcg 110460
ccgctagagc gtcttcgtgg ggcaagggct ctaaaccttt gtacaaactc ccgcaggttg 110520
tatccggacg gcgctagctg gtctccgctt gataacacaa caggttgttg ctgtgtctga 110580
acgggtaacg aggcttgcca atgcaaacag cgtcttcctg ggattgaacg gttttgctgt 110640
tgggtagcag gtacttcgtc ttcagcatta tgctctggtt ggggagtgca atccaatgtg 110700
ttagtatgct cagaagttag gtccactgtg ggtatttcac cctcgctgtc caaagttagg 110760
tctataatag cccccacggc ttcccgaccg gaaaggttaa cctccgacgg attttcttgt 110820
ctggccgggc caccagtggc ggctggcaca gctgctggcc ttctaccccg tcccccccgt 110880
cttccccgtc ttccacgtct accccttcta gtgggtgcgt taggccttgg gtgcacgggt 110940
ctggggtttt ctgggcgaaa tgttgtattt ggcatgtttt ctgagtcaga gtcgttgctg 111000
```

```
gtgtctcctg ggtcagttag gttgtttgga tcaacctctg tgtcgctgtc tgtttcgttt 111060
tcagaggaag agctcgacga ggaatcgatg tattcaacac ctcttccgtg agaaagtgta 111120
gagataggcc tcgatgcaac gcacaactct gcctggataa taagttcagt aacaaaggaa 111180
gctgtgtcgt ccaaaaacat cggccaaaac tggcgagtga gctcttcctc gttgcagccg 111240
tgatcgcaca gtgtatccat aacaatgttt cgcattacca gcgccagctc cggggtatca 111300
aacagttggt ctagtttttc acaaagccag tccaccaaag gctgtaatcg aggggatcca 111360
gcagtaccat tagcgttaag ggtacaaat gccattggtc cattccatgc agatatattt 111420
tccggagcat cgcctctatc agcatcccaa aattggccct caaagctatc ctcgtcttcg 111480
tcgctgtcat agtcaaactc aacgctcacc ttagtttctt taaactcgct gtcactctcg 111540
atagtatgta ccacggagtt gacaggtacc ttgcagagag gacaggttgg gttttgtcga 111600
atccagcgcg taatacacac gtagcagaaa gcatgcaagc atggaagcgc catagagtag 111660
ttgctggggt cttctaggca gattggacat cgctcagcat caacagccgc catggttgca 111720
agaagtttga agtttccaaa tgaaaaggct gtatcagcta ttaactcaag ctttgggccg 111780
ttcatatatc tagattaaga accacgtgat attgcacgcc catctatggc atttatccaa 111840
tcccacccct ccgaaaaaac attttttaat gcatgccaca ccggccttga aaacggttta 111900
accttatcga acatttgtaa aatagttagc atgtgtaata atgggggcgt gtttgttaag 111960
agcttgtagc taatttagag ctatttttca tagcgtgtgt actacgctgc tatttaaaat 112020
taatgttgtg tgtattgggc cggcttagta ttccataccc caatattgct tggtatctaa 112080
ttttactcac cgtattttag gtgggctaca agttttggca gaaacgatag aatggcttat 112140
tacaacaata tacacgtggg tggtactgtg ctataccaat gttctgggta tagtgtaaat 112200
aaaaagatcg tagtgggggt aggactcaaa aacagaattt ccaatttagg ccaatataaa 112260
ccaaaggtgg gtgggtttat tactgcgtat agtttcctca ttttgtcaag gtccccaaaa 112320
ccacaccgat accacttaaa atatcacatt atagtgttta tagttcactt agccacttag 112380
tttccaaagt ataattattg ccgtttgggt cacgggcgtt taccttgccc gcgcccgaga 112440
gagaggccgg cccccaccgc ccataacgcg ggccctcatt caaatagggg gcgtggcttt 112500
ttgggggggg cttaaagtgg gtgtgaccgg aagcggaagt gacgcaagcg gaaggggagg 112560
agcaggaagg ggaggagcag gacccactaa cccgcccact aacccgccca ctaacccgcc 112620
cactaacccg cccactaacc cgcccactaa cccgcccact aacccgccca ctaacccgcc 112680
cactaacccg cccactaacc cgcccactaa cccgcccact aacccgccca ctaacccgcc 112740
cactaacccg cccactaacc cgcccactaa cccgcccact aacccgccca ctaacccgcc 112800
cactaacccg cccactaacc cgcccactaa cccgcccact aacccgccca ctaacccgcc 112860
cactaacccg cccactaacc cgcccactaa cccgcccact aacccgccca ctaacacaaa 112920
ccacaccgga attaataatt aaaaacatgt tttattaatg taattttgtg aagcaagcaa 112980
cagggggcgc gtttggggat ggattggggt ggagtttgcg ttgtgacggg cgaacacata 113040
gttgtggatg tgctgatttt tgttttggtg tgtccatagg gtggagctgt tgtttaggtg 113100
agataggggt tgcaccagtc ttctccgtcc tcctcgtccg ataccacctc tatcttgatg 113160
ggggcgcgtc ggatcaactg cgctgccggg ctcaccccag ggtgatctgc aaccagctcc 113220
acgtcccccg gtccgtcgat ctcaagctca tcgtcggact cgggaaggca cagctccagc 113280
gcgcccatgt ggaggaccga ggtcgagcgc tgaccgaacc ccggctccca ctcaacccga 113340
ggggctcggc ggcgaggagc ctccgtgatg ggcatcacca ggggttcagc ctcggcgtcg 113400
```

```
ggctccagca gcgcgaccct gcagaactcg ctcagcagtt ctgggatcag cagctcggcg 113460
ggctccacgg ccccggctcc gcgccgtccg caggcgaggt acaccgggcg cagccatgcc 113520
ccaaggcccc atcggttggc cgcgcggtgg ctctgggctg cgccctcctc aaagtctggg 113580
tcgtggaacc cgagcccctc ggcctgggct ctcatgtcct tgcagccgtc gtagtctggc 113640
agaacccgct ggcggtactc cctaggtggc agtggaacgc gggtgcgctc tccggcccgg 113700
gtgtccaccg tgtaggccac gttggccgcc cgacacagct tcaggggctc cgagttcggg 113760
tagaggcgcg caaacgcggc ctcggccctc gcgaacagtc cgggcccgaa gagggtgctg 113820
gaagtgagga ccgcgcggct gaggtggcgc tcccggggcc agcgaacggc gcaggcgacc 113880
cgaggggtga gggtggcccg catgtagatg tggtactggc tgatggcggg accgtcctgg 113940
ggccagtcct ctagggagac cgcgtccagc actaggagct tgcgtctggc ggagcccagg 114000
cgaaggcaca agtactcgat gcagcctgta aaggccaagt cccccgtgga gaggagcagg 114060
actccctggg cgtttagggc agacacgtcg gggggcccag tccagttgcc agcccaggcg 114120
tgggaccgct ttgtgagtac ccggttcccc agggccgcca gcagcgccga gagccccccc 114180
ttgatgtcgg accagagggg ctcccggcgc gagccgccgg gtcgggtggt tgggagtcca 114240
cccagcaggt cctcgtccgg tagcggggag tagagcacca ccaccttcac gtcttcgggg 114300
tcggggatct ggttcatcca ggcagcccgg cggcggagcg gtccgctggc agccagctct 114360
ccaaagcgcg cgccctccct ggccggaggc ccgttgcagc gggctgcgat ggtagccagg 114420
gcctgggggt cgaaggtaag cgcggggcgc caggcctcgg ggaacagcgg gtggtctatc 114480
agctcagcca cgagctctgg gggacagtaa gcagcgcggg cagagtcccc ggggggtggc 114540
gtgtggcagt ctccatgggg aacgcgtctg aagcctcccc ggcggtgtgg cccctcgggc 114600
ggcatgggcc ccaaagctcg aggggcctga gtacccaccc tgcgctttgg ggcaggaggg 114660
ctctctaccg gagcgaccgg gtcgtatcct ccgcgggacc ccgggagctc ccccgccgcc 114720
ggctccaggg gctcggagcg ccgcttcccg ctcttgcccc tggggcgccc gttgacggga 114780
cggtcgttcg gggaggcgta gggtgccggt ccgccccctc cctgcgagga gaccggcatc 114840
tcctggccga ggatagcctg ggaggcagcc ggtggggagc gagccttctg ccccgagggg 114900
cgagcctggg tctgggtggc ccgggagcag gttgtcggcc ccccgctgct ctggtgctgc 114960
ggggaagaag actgagagtg agacgtggcc ggcaccacga gaggcttccc gggaacagtg 115020
ggccacaagg cggggatgcg ggaggtctgg cttccctcgg aggaggagag ggactgctgc 115080
tgcccaacgt cgccgccgac agacgatgaa gactgtgacc gaggaggcgc aagcaggccc 115140
acggcttccc ccaacatgcc cccggccaga ctgggtatgc taaacacggc ctgggtgatg 115200
gtccaggccg aggcccgggc ccgggctccc tccgcgttgt agcgcaccag gggtgcgacg 115260
gttctggcca caaccagaac cgcgcggacc gcgaggcgca gctcgtcggg gcccaggcgg 115320
tggatagggt cagagtcccc gagtagcctg gcacgctcga ccaggtccct gagttcgtag 115380
agggcgcagg cagcagtctc gagcccagcg gggttggagc acagcgcttc gggagggcag 115440
gcgggagagg ggatctcgct tgggtcaagc ccggggacag cggacgctcc gccgcggagg 115500
cgaagtaggg cttcgaaaac ggcctggcag gccagtacgc agacgtctcc gagttccctg 115560
agcctgaagg cggtaggctt gggggttctg gtaccaggac ccgcggccgc cgtcttgcgc 115620
cgtggcccga gggccgcgca caccctggtg tactcctcgc ggaccctagc agatgtggcc 115680
gggggatccg gctgttgaga ggcagcctgt gcttgggccg ggtagctagc cgtgaccccg 115740
```

gccgccgagt gggagtcctg ccgcccggcg tcgtcgcgcg ggtaggccat gtccgcgtac 115800
gcccgtctga ggctctggag tatgaagctc ttttgcgtgc ggtcgtagcg gcggctcatg 115860
gccaccgagg ctgccgcgtg cggaagggcc catagagcat tcccggccgc catggcgtcc 115920
ccgatgtggg gcagggggtt agcaacgctc cccgtgatga aggacccatg tccgcgggga 115980
gcgtgtatga acttctggca gaactgggcc aggttctggt cggccccgcc gagcttggag 116040
ttttgcagcc aagacatggc ctcgcggttc tcaaacacca tgcgcaccag agcgttgtac 116100
tgcttggtgg agtcccccat ctcgggcaca aatacaggta cggcggtctg ggcttcggcg 116160
tagcgcgagg cggccagaac tatttcgggg tcatcccaga gcccgtcccg cgagtccccg 116220
gttcccccat agcgcaccct ccccggtggt ggggcgtccg acccgggcca tgggtctccg 116280
gatggtgtga gcagcggctc gcgctggcag gttccgagcc ctggggcctg agaggagcag 116340
ttcatgtcca acaggtccca cgcgcatccc gggagggcct cttcggcccc ggttgtggcg 116400
gcggtctggg gtatgggtct tgggtggcag cgcttgcgct tagaggcccc ggccaacgca 116460
gacttgggcc gctggtcctt gggagctctg tgtgggctct gccctggagg agacattctc 116520
gggtcgggct tctccagcgt cttggccaga ttggcgtccc taaccccctc caggtactct 116580
aaaatgcgag ctcccggggc gaggggcccg cccgggttac tcggggtggg agcgccggtt 116640
gaagccgcaa aagcgccgac ggggctttgg tgccccttct ctgagcgtcc gctctttggg 116700
gtgtacgatc caggggctat acgatccccg ctaatctgcc caggggaccc ggtggccggt 116760
tgggtttttg cggcgctcgg cgagggatgg gggcgaggag ttttctcttc gcccccatca 116820
tcgctgtcac tgtcttcgga ggaagacgaa gacgagctgc tcgccccggc accatcggct 116880
tggtcttccg tcgatgagga ggacgaggac gacgatgata tggagatgct ccggcccctt 116940
ggcgccggcc tcccctcggg ggaggccgag ggtggaaact cggccccggg agaccccggg 117000
caggtctcgg tgtcgctccc ggtgccctgg ttataggcac ctccgcccga tgatccggtg 117060
tccctgcgac cggcccctgt agccgcggac gagtgaacca tcttcagcat ctcggcgagc 117120
cccggagcgg ggttatgagc gggcgatgcc ggcactgctg ctctggccgg agaccgcttt 117180
gccttcccgc cgcggggctc gggggccggg gaaggcggcg ggatgactac cgccggggtg 117240
gccaagggcg cgtcgtccac cccaaacatc ccctggcttc cgtacagcag atccggggcg 117300
gccggggtat ggaacccctc ttcggccgcg ctggctgcgc ggatgaggtt gtcctcgtcc 117360
aggttgttgc tctcgatgaa gtcgtagagg tccggagcaa aatcgctgcg ctggctggcc 117420
atggctcgct ctctcccggg ttttagagga gaacgggtga ggtgcgcgct cgaaccgagg 117480
ttagacgctg ctggagctct ctaccctgaa aaggcaaggg cggacaaaat gcttggttgg 117540
agcggcgcct aatggtaaaa gggaacgcgg gccatggcct ctcccagctg gggtggtagc 117600
tccgccccac tagaaaccca aaagccagca ccctaagctc ggccgggcag acgcaggccg 117660
agtatgcccg cagagtgatg cctcaagcgg cagagccgga gtagcgccgt agttttggct 117720
cgagaacagc gaaggagaag agagcagata agtatgaagc caagttggta agccgtcccc 117780
cgggagctct tacctccaca agccgagaag ggagcaccaa aagcgggcaa gcctgccaag 117840
agtaaatcga tgtcctttga ggagatggtt ggtctagttg agctgagagg ctctctagtc 117900
tgcgatgcta cgatgagtga gcaacaggtg ctatatacta caacgatggg gtttgtacct 117960
cccccaatgg gaggggccaa cccacaaagg ccgtttggat tggctggctg cgatgggcgg 118020
tgggcgtgta tccgttccaa ccaatgatac actagtgtac aattttcatt tacatgcgcc 118080
taacgccttc ccctagctct acccaatggc aattggtatg tcatttttaa tttgcatgtg 118140
tttcctccca gggaagcgcg tcgcaccaac aggaggtagc cgagcacatc tcatatgcat 118200
aaagatggac gccaactgcc gccatgacac ttccgtgcat atatcatttg catgcatctc 118260
ctccccggta gagcgtcgca ccaactaggg tccgtatctc acatctcata tgcataaaga 118320
ggaaggcgct gtggtgccac gacacttcct ggtaaatatc atctgcatac aaatgagcct 118380
gggaggagca cggggagttg tatgcgaaat taattttaat aaaaatggcg cgtgcgttat 118440
ttcccaagga agcggaaatg gcgcacctgc aaagggaggg ggcaatgggc ggtgggcggt 118500
aactcatttg ttttgtaatt tcctgtgaat ctcattaaag tttaaccaat taaaacacgt 118560
atcgtttttt gtgtatgaaa tgggcgggat actatctacg tggaccaatt tgcatattat 118620
atgaaaacta accgcatgat ggcgctattt tttaaacact cgatttacat gcacttttat 118680
atacgccctt gtggtggcgc agttacacgt taacaggtgc agtttataca gataaccacc 118740
atgtggtgct ctagatcgca gtccatcgta acgacattct atgacgctat acactcagta 118800
caacccacgc cccctctacg taacacattt cccaccctat attcaaataa gtatgtgggt 118860
tgggtctatt aagatcaatg ggaggggggta ccggggggaa atatacacgc ccattttcac 118920
ctcccgcccc caccccatcc aatttgattt ctgtttatcg gccaactaaa aagtaaaacc 118980
gtagaaccgt gtaagcggtt aagcgcttta cgttttacta caggtgtgag aatgtagtag 119040
aaaaataaga ttcaaccacc catcagtaac tccacgacat acatcttgcg ggtctgccat 119100
ttataattaa acgaccccccc cttagttttt ttttattgct aatgcgtaaa cctgccccat 119160
gcccccagta caaacaaggg gggggggca ctaaaaattt ttgcgcgaaa aaaaaaacgt 119220
gggtgatata cggcgggtat ggatatgggg gggggcaata aaagttttta cgatataaac 119280
ggcaacgtac ggtttacggt gtgcgtgtgg ggggggcgca ctaaaatacg gttactaacg 119340
caccccagcg tatggcgaga gtggttgggt aggttgctag ctggcacagt gccatgcgcg 119400
ctcccgagat attacgtaac ccggataaga agtgcgaaca tgtagtgttc gcactttgtt 119460
acaataagta ttataactta ttagtgattg gtgcgaacgg cacctatacc caatcaggat 119520
tgagtataaa aaccacgtgc catgtttcca attttgtccg ataatcgata acctattatt 119580
aaagaaggcg tggtgaagta catgtatacg ccttctggaa ggcgtggaac atgggactag 119640
tgtatatatt agccagcgcc tcaccatgtg aagggacaca cgcagctcca aaactcaagc 119700
cgtttgatac gcatccactg caaaacctat cgaggtaggt gtggcgtacc gtcgtggggg 119760
tggtcgtggg ggtggtcgtg gggtggtcg tgggggtggt cgtgggggtg gtcgtggggg 119820
tggtcgtggg ggtggtcgtg gggtggtcg tgggggtggt cgtgggggtg gtcgtggggg 119880
tggtcgtggg ggtggtcgtg gggtggtcg tgggggtggt cgtgggggtg gtcgtggggg 119940
tggtcgtgac catttttctc attcgcttat aggctcgagc gccaatcgcg acccccgcct 120000
cgttttggcc gaacaaaacg ccccgtgtct actcgatttg cgccaagcga gcccagaccg 120060
cagcaaccat gccacacggc cagccatgtg gggcgtgcga cggatcctgc cgcatgtcac 120120
agcggggggc gccgtccacc agccccatca taccctccct gtccccctca tctggtggga 120180
acccatcccc acgctccagc cagcgcatag actccgtgcg cgtgcccgcc aggcttcccg 120240
gcggctctga ccatccggaa tacggcctgc cgctctcgcc gaggtcgctg cgcccgtacc 120300
tgtctcgggg gccgggagcg ttctgcgctc cgccgtggcg cccagacgta aaccgcctcg 120360
ccggggacgt caatcgcttg tttaggggta tatctacttc atctattcac gtaacagaag 120420
actcgcgcgt cctgcgcagg gtgctgttgg acttttacgc tatggggtac acgcatgcac 120480

```
gccctaccct agaatgttgg caggcccttt tgcagctgat gccggagcag agccttccgc 120540
tgcgggccac gctgcgtgcc ataaactcgg aagacaagta cgagcagagg tttcttgatc 120600
cgcccagcaa gccacccaaa accctctttg gggaagagtg cgaagttagc ggcgacgagt 120660
ctccgtcaga ggaggaagag gctagcggaa atagcaccat ttcagagttt agtcccgagg 120720
aagagagcgc cagcagcgac tttgaaagct tttcggacga ggaagacgac tcttgttgca 120780
cgggaaagtg gtctagcagc gaaagcgata gcgaggcaga tgtccccacc aaccctccca 120840
ccacacgtgc ccgcgctgct caaaagcgcc gcgggcgccc tgtccccaaa ggcgggcgcc 120900
cggccaaaag cgctcgccgg tgattaaaag cacacgcaac caaaaccgca taggtagtta 120960
ccgtttttag tagccctatt agttcccacc ataacccccca acacgccgca gttaattcat 121020
atgtagcatc aatgcgcgtc tatccccgct tataaccaaa taaatcgttg actaaccttc 121080
atcgagcaca atctcgtgtt tgtcgcgtgc atgcagcaaa cggtgggtgg tattggggtt 121140
gggcgagcgc tatacagaag atctccccccg ccgtcgtaac acgcgttccc cgttaaacgt 121200
gcaagccgtg tgcgtacgcc caacggtgcc cctttatcgc cgtatgaata tgtgaagagc 121260
gataacagca cccacgcaaa cgggccggcc ggggtgagat gtgtgccgga aggcatgatg 121320
gaagaacaat aggatagagg cacgggcggg gctatggcac atgcgattcc ccgccccgcc 121380
gaggaaatac ccctggtacc cggccgcgcc cggtcagtgc gcctaggctc cacgctcccg 121440
agagttatgg actgcgcgta cggttccccc atggcggtag acgggggtgt gagaaccggg 121500
ggagactgcg gaggcggtga ggggctgtac cccaccagca cggacacggc cgcgcacgcg 121560
gtgtcgcttc cccgctcagt gggcgaattc gcgtcagcgg tgcgcgctat gtccgcggat 121620
gccgctgacg cgctcaggag aggagcgggg cctcccccccg aaatctggcc gcgcgcgtac 121680
cgcatgttct gcgaactatt cggccgatat gcggtcagcc ccatgcccgt tttccactcg 121740
gcggacccgc tacgccgcgc ggtggggagg tacctggtag acctaggcgc cgcgccggtg 121800
gagacccacg ctgagctcag cacccgcctc cttttttgcg cccactggtg ctgcctgggg 121860
cacgcgttcg gctgttcccg ccaggccatg tacgagcgcg agtgcgcacg gtttttcgaa 121920
gcgagactcg ggatcgggga gacccccccca gccgactcgg agcgctactg ggtggcgctg 121980
ctggacatgg cgggggccga tccggagcta tttccccgac acgccgccgc cgccgcgtac 122040
ctgcgtaccc gaggccgaaa gctcccgctc cccctgcccc cacaggcggg ttccgcgacg 122100
gtatcggtgg ccagtcaatc aataaacttt taaactttct atattgcata aaccaaagcg 122160
ttcaagtacc tccccacctc cccacctccc cacctcccca cctccccacc tccccacctc 122220
cccacctccc cacctcccca cctccccacc tccccacctc cccacctccc cacctcccca 122280
cctccccacc tccccacctc cccacctccc cacctcccca cctccgatag ggggtgggaa 122340
acaagctacc cgggccatcg aacaaacgcg cagaggctgg ggttctctac tatgaggttt 122400
tattgactgg cgggtgcggg acagcagggt gggaaatcgt ggcggtagag gcgatggccg 122460
cgtccgcggg ttcgcgtcac tgaaatacgc gcgcgaggaa cgccccgacg atcccggata 122520
tcgcgcacag gacagcgacg agcacgacgc cggcgaccgt gagggccacg cgtcgccgcc 122580
tgtgtcgccg cgcctgccgc cggccgaccc tctggatgaa caggctggcg ttaaacagca 122640
acgaccaggt tgtctgagtt tttatcaacc gaatttccat tttttggctg ttgggcatct 122700
ctgggatgtg catctaaaac ttgatcaccg atgcttgatt gttgagcatt tctggtatgc 122760
tgttttggtt caccctgaag atctaggcgt aaaaaggttg tgtttatttc ctgaaacgca 122820
tcttctgtaa cgtttgactg gaactcccat ccatgtttta gtacatagcg cctagatggt 122880
```

atgggcaatt tctttggacc agtccagttt gacatttcct cttctagcca ttttggaacc 122940
tcagcaaatg cttcttcaag cagatcactc ggatcgacgc tgtaagcatc ttttgtgtct 123000
gctctgatgt agtaaagtgt ttctgatggt tgattttctc cctcgtagta ctcttctgga 123060
tataaaaatg gcaatcggac aaatgttcca tcgtccagct gcttgtaaaa tcgcttttca 123120
aactttggag gtggtagggc cttaaagctg agcacttcgc catcaacttt actttcaact 123180
ggaacacggc caggcatctc actcggtcca actggaaagt agccttcggg tacctttgca 123240
aagtacccct cgttcatttc ttcgcgacaa cgtctgaagt atggccgccc aagcatatac 123300
ttatatgggt taaagagata tttgcgcggt tcttgagaag cgccgtcctt ggcgttggac 123360
tcgctcacag ttgcagatga aaaggtgggt gccaaaacta gatgcggtgg attagcgttg 123420
cggcggcgag caagattaca gcgaaaaact tcggtgcctg cagtggcggc tgtaagcatg 123480
tcggagctca tgtctaaaga tagacgtgaa gtttgtaagt aaaaatctca caggaaacca 123540
cacttggcaa agcgcagtga ctagcaaaga gcttccccaa ccttttaacg tctggctgtt 123600
ctatcaaaca cacccccctag taggcgtgat ttccacgtca tttctgtggg tttccgggca 123660
gctgcacgag gagataggt gctaggtggt attgtagagt tggcttgcat cgacgtgcta 123720
acgcgctgca agtttttgcc ttttgatggc tgtggagtaa aacacatctt atcgtttagg 123780
ctggctgtag actcttggca aaacaggcca ttataagttt ttttagaacg tcttttagtt 123840
tttgttctgt tagttatttg tggacataaa ttctcttgta aacgcatagg gtctacaacc 123900
gcataaatta accgcttaaa atttggcggg ggagatacaa aagatgattt atgttgtaat 123960
aaactgcgcg cgctctcagg gtggtcttgt ccgggtaaaa ccttttgttt tagtagatgc 124020
ttataatcca cggttgtcaa cggtattgtt tcgaatagtt ttccgcacac gaagctgggc 124080
tgccaagatt tattaaactc atcttcgatc tccacataca caattcgctt ggggcccggt 124140
atgaggttga acacaggcct gcataaatct gcagctccca aaacccatag gtggtatggc 124200
ctattgatga taatgctgga gttgaggtag ttgtagccgg atagtacaga aagccactct 124260
atactaatgc caattctatc ctcttgataa atcacgccat ttctttctag ggctatagca 124320
gtagcccccc tagttctcac tataggcctg catgcttttg gcagggctaa gagactcgaa 124380
gaaaatttgt acaggtcagc agaacgcacc actattggta ttcctagagg ttctgaggct 124440
aatacaaaac atagtcgtcc caaaaactcc cacagttttc catctacgtc gatagaactg 124500
tcgggcaaag ctttatgcct gtcaaccacc atgacaactg taattaaaac cacacccatg 124560
ttattagcaa atgggtgtgt taaaccaacc caataaattt cagcagagct gctctagcta 124620
cacactttgt tgtgaaaaag acttgctgtg ttacgggatt cgtagcttta taagcacacg 124680
cccacagcat cggcatggaa aataaacaat acgaccacct attgtccgac tggctatccg 124740
gtaatattag cgaggcatct gaatcgatgg atacgacacc cccactacag ctttctgtac 124800
atcctcaaaa tccaagctgt ggggggcag ccgctaatga ggacctgtac tcagacataa 124860
gcgatggcga ccttgaatgt agtgactgcg atagtgcatc tgagagcgat gaagacgatg 124920
acgatgggct aatgccccca aaagaaaagg cgaaggaagt ggctgcttca tttgggttca 124980
aggtcattaa aacgctaact cctggctcag aggggcgtgt tatggttgca acaaaggagg 125040
gccagccaga ccaggtcgta ttgaagattg gccaaaaggg aactacgctc atcgaagcca 125100
tgatgctaag aaacgtaaac cacccatgcg tgattaaaat gaaggacacc ctagtgtctg 125160
gtggaataac ttgcatggta ctacctcact acaattcgga tctgtacaca tttttgactc 125220
ggcgatcaac gcgtatacct attgatcagg cattgattat agaacgacag attctagagg 125280
ggctgcggta ccttcacgca cagcggatca tacacagaga tgttaagact gaaaatattt 125340
ttataaacag cgtcgatcaa gtgtgcatag cagactttgg agcagcacaa tttccggttg 125400
tggaccccat ggaccttggt ttggctggta ccgtggaaac taacgctccg gaagttttgg 125460
ccagagcaaa atacaattcg aaggtagaca tatggagcgc cggaatagtt ctgtttgaaa 125520
tgctcgcata tccatcaact ctatttgagg acccgccgag taccccacaa gagtatgtaa 125580
aaagctgtca ttctcaacta ctgagaataa tatcaaagct aaagataaac cctgaggagt 125640
ttccacggga accagagtct aggctcgtgc gcggatacat cgaatacgcc agcctagagc 125700
gtaagccaca tacgcgctat ccttgcttcc agcgcgtgaa cctacacatt gacggggaat 125760
ttttgatcca taaaatgcta gcgttcaatg ctgcgatgcg cccatccgca gaagagttgt 125820
tgtcctaccc aatgtttatg aatctgtagg atgactaaca gatttggggt ggagacggcg 125880
tgggcgatac tgtataaagt tgtactactt accagcccag tcagtgtgct gtagtgccac 125940
cacctgtaaa gctgtgataa gctgcagtta tgttggctgt gggagcaact ctgtgtttac 126000
tgagtttcct aactggcgct actggacggc tagctcctga cgacctctgc tatgcagaac 126060
cccgcaaaac cggtcccatg ccccgctcaa aacctaaaca ccaacccccta ctatttgaag 126120 ccccaaaggt tgctcttacg gcagagtcaa agggttgtca actaatattg ttagaccctc 126180
caatagacat gggctatcgc ttagaggaca agataaacgc ttccattgct tggtttttttg 126240 actttggtaa ttgtcgaatg cccatcgcat acagagagta ctatgattgc gttggcaacg 126300
caatcccatc tccagaaaca tgtgatggtt actcatttac acttgttaaa acagagggtg 126360
tagttgagtt taccatcgta aacatgagct tactgttgca gcctggaata tacgacagtg 126420
gaagttttat atacagcgcc cttctagata tggatgtatt gactggacgc gtaattttga 126480
acgtggagaa cgacactaac tatccatgcg gaatgactca cggcctcact gcttatggca 126540
acatcaacgt agatgaaacc acgcacacaa ccccacatcc acgtgctgtc gggtgttttc 126600
cagaactcat taacttcgat gcatgggaaa acgttacatt cgaagaaatg ggataccag 126660 acccaaactc atttcttgat gatgagagtg attacccgaa tacaatggac tgttactcgt 126720
gggatttata cacatatccc aaaagcctga agcaggcaga ggggccccaa accttgttaa 126780
taggtgcagt tggactcaga atactcgcgc aagcatggaa gtttgttgaa aatgaaacct 126840
acagcagcat acgcgcagat gctaaggagt tgatgttaca cagccagtcc tgtacagctg 126900
attcgtcgca agaaagcaca tctatgaaga ataaccctat ttattcagag gggagcctca 126960
tgctaaacgt tcagcacgat gacagcatcc acacggaagg gatgaagaat aaccctgttt 127020
attcagagag cctcatgcta aacgtccagc acgatgacag catccacacc gggggtgtgt 127080
tgcatggcct ccaagactgc gacaaccagc tcaaaactgt gtatatttgc ctagctctta 127140
ttggactcgg cacatgtgcc atgataggac taatagttta catttttgtg ctaaggtcaa 127200
aaatatcttc ccacaattta tcgcgctcac aaaatgtaaa acatagaaac tatcatcgac 127260
ttgagtacgt tgcataatac atgtcaaata aaagttaaaa attaaacatt gttgtctgta 127320
ataactgagt gtggttttaa aaatactaaa tcgcggcaat gttgcaaacg gtcctctaca 127380
aaagagaggg ttgatggtat atatgaaata gtcccccctt catgagtttc gcgtagaggt 127440
ctaacttaac agcgatgggg ttcatctatg ttagcagaat actgctatgc ctggcagttg 127500
gtatttatgc catagggggca acaaccgcgg aaactactac cgctagctcg tcaacttctg 127560
gaagtaccca gtccgcgtct agcgaaacta atagtagtag ttcccccacc acgggcccca 127620
ctaccacatc ttcccaaaca tcctcttcta actctaccca aacaccttca acgtctcaaa 127680
cacccactac tagctcgtct accgtttcca caactactac ttcaaactca acaaacgaaa 127740
gttctactgc gacggctaca tcaactgcaa ctccaacatc cacagaagct tctacgtcaa 127800
caactacatc aacctcggtg tccgaatcac caacatcaac cacagctacc acagctgcta 127860
ctaccacaac tgaatccacc acaactgaat ccaccacagc tgctactacc acagctgcta 127920
ctaccacagc tgctactacc acagctgcta ctaccacagc tgctactacc acagctgcta 127980
ctaccacagc tgctactacc acagctgcta ctaccacagc tgctactacc acagctgcta 128040
ctaccacagc tgctactacc acagctgcta ctaccacagc tgctactacc acagctgcta 128100
ctaccacagc tgctactacc acagctgcta ctaccacagc tgctactacc acagctgcta 128160
ctaccacagc tgctactacc acagctgcta ctaccacagc tgctactacc acagctgcta 128220
cgccaacaga gtcaagcgag gcatcttcca cattagcggc caccacagct gacaccacag 128280
ctgacaccac agctgacacc acagctgaca ccacagctga caccacagct gacaccacag 128340
ctgacaccac agctgacacc acaactactt cagggtccac cgcagctaac acaacctcta 128400
ccacatcggc cactgtaaca atagctccaa caacatttac gactaagtat accacaaatt 128460
cttcgtctac cgggaaaata aacacctcca aaaatacacc aaaaccccca caatatacta 128520
cagcttccac ggagaaacca actaaggcga attctttaac agcggcgaac gcaacgggct 128580
tatccaccaa acccccaact ttattcacgc ccacacaaac aagcccaaca cctagcgaaa 128640
cgtctgtggg taccagagag tacttggcaa tcacctatgg aaaaactaca tatacaactc 128700
ccactaatgc cctaagttca actaatgttt ggcctgccag agataatagt tcaactcaac 128760
aaacaaccca acatgactac atagtaacta cccaaaaact tacgggacat ttacaccagc 128820
acaagggccg cgcaaatggt aaaaacgtca ataataagtc tcacccatca gtgcgaccag 128880
ataggttaac gccacacacg gattaccact attactacga tgataccgat tacccacagg 128940
acggttcatt tgagcgtgta accccacccc cacaaggcca accaaacata gagctgggtg 129000
tggctacgct tagaaaaaac tttttggtgg caacgtgtac cgtggaggct actatgggct 129060
tgtcattttt ttggaaaatt ggcaacgcca gcgttgacgc gtttagcagg ggaacaacgc 129120
atacgcgagt gatgcgcaat gggtcacctg tttatgcgct aatatctacg ctaaaaattc 129180
cgtgggttaa tgtgattcca ttaaccgaga ttacttgcgc tgcgtgtaaa gacaatttta 129240
ttggcaatga agctgatctc acctcgtgca ccgttaaatc aaccacaata ccatgtccag 129300
gccaacaacg cacccatatt ttcttttcta tgaaggggga cagagctgtt tgtattacat 129360
cagaacttgc gtccccacca actataacat ggtcggttgg atcaaacagg ttgcacaaca 129420
atggatttac gcaaacgtgg tatgaaatac aacctggagt gtgtggaata ttgcgtagcg 129480
aggtccacat tagccgcccg tcttggcgcg ttggtgcccc aacgcgcgat tatctttgcg 129540
aagccacagt atcagatgca aagacgagtg attacaaggt tttacctaac gcttactcga 129600
cttccaactt cgctttagtg gctgcgacca cgctaacagt aacaatttta tgtttgctgt 129660
gctgcttgta ctgtatgtta acacgccccc gggcgtccgt atattaactc aaaaattatc 129720
tctttggctt tacaacccgt ggtagcgtgt gtagaagcgc gccgctactt tagtgggttt 129780
tttttaataa acgcggtatg tctaccttca agcctatgat gaacggatgt ttggtgtttg 129840
cggctattat aacgctcttg agttttatgc tatctctggg aacatgcgaa aattacaggc 129900
gtgtggttcg ggggaaccaa aatcagcgac ccgagtttcc accaccccga tacaacttta 129960
caattgtgac aacatacaat gaaacgtcgc taccatcacc gtttattaac gaccaagtaa 130020
aaattgttga cgttcgaacc gtggctgcta cacgcccatg tgaaatgata gcgctgattg 130080
caaaaacaaa cgtagactca attataaaag agctagatgc tgcccacaaa acatattccg 130140
caagactgac ttggtttaaa attacgccaa catgcgcaac gccaatccat gatgttgttt 130200
atatgaaatg caatccaaag ttattatttg gaatgtgtga tgagcgatca aatatattat 130260
ggctcaatag tttgattaca actgctgcgg agacagacga cgaacttgga cttgtattgg 130320
cctcccctgc ccatagctac tctggactgt ataggcgcgt tatacaaatt gatggaaggc 130380
gaatttatac agacttttcc gtaacaattc cgagcagcca ttgtccgctt tcttttgagc 130440
agaactttgg taatcctgat cgctgtaaaa ctcctgagca atactcgcgg ggtgaagtat 130500
atacaagtcg ttttctcagt gaattcaact acagacaagg tgtacattta gcatgggtaa 130560
aacactggtt tgtgcaagat ggtggaaacc ttccagtaca gttttacgaa gcccaggcgt 130620
ttgcaagacc agtaccaccg gataatcacc caggatttga ttcggtcgaa tcggaaataa 130680
cacaaaataa aacaaaccca aagcaagaac aggcaagtcc aaaacccaat ccaccattta 130740
agtggcccag tataaaacaa ttggccccaa gaatcgatga ggtggataat gccaaagaaa 130800
tcaccacaaa aaaaccacca gcgtctaata gcaactctac gtttattgga gttgttattg 130860
gtttgggtgt tgttggcttg atatcagttg gagcaatttt atacgtttgt tggcgtcgaa 130920
gaaagtcaca gaacaagtct ggaaaaaatg gctcacctag cctacgctct acctttaagg 130980
atgtcaaata tactcagctt ccgtaaacag tgttgcgtaa catgctggga ggtacccacg 131040
gccttaaagc tacgctgttt ggagataaaa cgcacaactt acatcaaacg cgacacagca 131100
agtagtcgct atggccaaac atactgtatt gtttactgct tcgatattac tagctatatc 131160
tatgtgtgca accgcaatta tatatcgcgg agaacatatg agcatgtacc tcaacgccag 131220
ttcagagttt gcagtgtacc caaaagacaa gtctctagta gttgttggac acatgctgtt 131280
tctagatgga caacgactcc caactaccaa ctatagtgga cttatcgagt tgattcatca 131340
caactactct aggggctgct actctgtcat tcaaacaata tcgtatgaat catgcccgcg 131400
tgtggccaat aatgctttca gatcttgcct tcacaaaact tctaatcaca accaggacta 131460
ctttcatgtg aacacctctg tagaaactaa cgttctctta aacattaccc ggccacagcc 131520
cgcagattcc ggggcgtata tcctccgcgt aaaactcaac cacgctccca cggcagatgt 131580
ttttggtgtt tcggccttcg tttatgattt acaatctaac acagttccag agccagttcc 131640
aaccgctaaa gaacccagta atgtgtttac acggacacct gcccctgcac ctgctaacac 131700
ctctaccaaa actggctcca acacaacatc gtctcaatcg acgtggttgt atactccgac 131760
tcctcgccca gccttggaaa cacacctcac tacagcaccg gctaacgaaa ctgtagttag 131820
tggtgatacc gccatgctct gtcatgggtt tcggccatca accgcagtac caacaatata 131880
catgcatcta ttaggactta ctggcaacct acccgaagat gttttgctaa tagaggactc 131940
ggagattctt cgtacaccac cccccaaacc gcaaaccact tcttccagaa ctgagggtga 132000
tgactttaag caaacaaact caacttcccc aaaatcgcgc aataagattg ttgcgatggt 132060
ggttattcca accgcgtgtg tgttaatgtt gttgctggtg gttgttggtg caatcatcaa 132120
cggtgccgtg cgcaaacatt ttctgagctg cgcaagccgc agaatctacc gctcaagaca 132180
aggtggagtt tcatcgtcag agtggagccg gttggcgtgt gggcccacct tagcagcctc 132240
atcagaatcg ctggctgatg atacaacggc ctcgccacca tcccacaagc ctacagaaaa 132300
acctacaccg gaaagcgatc ctcttctaga acagttgaac cgtaaactgg aggccataaa 132360
agaggaagac taataatggg gggttttaaa gtttatgtat tattgtttct atatattaaa 132420
aattgttgaa atataaatat cttatgtaat gtttacatta ttcgtgattg ggacggtctt 132480
aggggaggtg gtgcaactag ggtttaaagc cctgaatgtt ctggagtgaa cccacagttc 132540
tcctctttgg cgtcaaagca atcagacgtc caatctaaag tagaacgtca caatggagct 132600
gttagactcc cgccgtgctt ttttcttttt tgtactaata acagtactcg atgcgtgggg 132660
agttcaacgg gttgaactca ccgagggggc atgggccatg atcgacggaa gagacgtttt 132720
aaccccaact aacacgacca ctagggttac aaaggcctgg acatttttgg aaaccccacc 132780
gggatgtgct ggtgatataa cagtcaagac tgtgtgcgta agcgctagtc tgtgcgaaga 132840
taacattata ataggaaatc actgtaacct actaaccggg gagcatggca ttgcgcttgc 132900
agagtttaac gtagttaacg gatcgctaca aaggaccaaa gatgtgtact ttgttaatgg 132960
aacagttttt cctattctgg cagaaacccg cagcgtgtta caaattcaga gggcaacccc 133020
atccatagct ggagtttata ctcttcatgt ttccatgaac ggacaaataa aacactctgt 133080
tgtattgctc accgtaaaga aaccaccaac actaccacgc gtacatgtca agacgcctcc 133140
acccatacta gttccccagg ttacaccaga ggcacataca gatttcatag tgcgcggata 133200
ccactcgcgc gtatatgctg tgggtgagtc ctttgacctg tctgtgcacc tagaatccca 133260
catacaggag tctagcttta acgctgaaat ccaatggtac tatatgaata cgtcatcgtc 133320
atcatgcgat ttgtttcgag tttttgaaac atgcattttt cacccaaccg ctatggcctg 133380
cctgcacccc gaacaacacg cctgctgctt tacatctccc gtcagggcta cgaagattct 133440
tcatcgagta tatggtaact gcagcaatcg tggatccaca tggccttctc ggtgccatag 133500
tactttgttg ggcgataggc cacattttat ccaaccggca ccaaacaggg tagacttgtt 133560
attcaaagat atacccgaat cagcgaccgg gttgtatgtg tttgtgttat tgtacaacgg 133620
acatccggag gcgtggacgt atacgttgct ttctacagca aatcacttta tgaacgtgct 133680
tacggaccga acacgcccac ggctaggaga gcacttttat acggaccacg ggcaccagct 133740
tttcactcct catccatctg aggcaacaac tcaagagttg ggagcttgga ccagacacta 133800
cctcgctttt ttgttgatca taatctgcac ctgtgccgcg ctgctaattg ccttggtggt 133860
gtggggctgc attctataca tccgaagcaa ccgcaagccg tatgaagtac taaacccgtt 133920
tgaaacggtt tacacaagcg ttcccagcaa cgatccaacc gacgaagtct tggtatttga 133980
gcgtctggct tcagactccg acgactcctt cgactcaagt tcagacgaag aattggaact 134040
accacaacct ccaccagccg cacaacttca gccgtatagt tcactagaaa gtgcagacgc 134100
gtcgagaggc cggtcgggtt tcaaggtctg gttccgcgat acaccagagg cgtctccgga 134160
gccgcttcat agaccaaccc cacccgtcgg accggactac agcaaggtcg cgtcaaagct 134220
caggtctatc ctaaaatgaa tttcaacaac aaagataccg cttgcgcagg aaatgtgtgc 134280
tatgctgaag gactacgcaa tcgtaagtag tccggttcga aacagcacct tcgaagagta 134340
tctcgactca cttaataatt acgaccgccg tttgagagct gactcaactt cagattcgga 134400
ctctgagtgt aaaacccccct ctgaagacga ttcaaatatc aaagagttta caaaaattat 134460
ggatctaaaa ccaccatctc cagaacccga gccagcggca gcagaagagc cggttagcac 134520
cgccgtttac atcttaaacg agtgggtggc cccaatgctt ggacattttc tcgcaatgta 134580
tgtgtatgat ttgcttttta attaaaccaa agattgtcac cacaatattt agttgtttgt 134640
tttatatgca agcgctaaac ccaacactaa agggttatat attatcccgg gggacttttg 134700

```
cagtaatata tattttgctg ccagtgttca ctggtgctca gtgcgcccaa ccagcacagc 134760
ccgttttaat ctctatacgc tctgtctatt ttccttaccc cgctccgtaa cacctcactt 134820
tctctcatac taccgccttt ttcacgctac tccaacagct cctacaactt acagttacca 134880
ccacaccatc gcccttaacc accaagccac atgggtgagc ctgaacctgt ggtagcgttg 134940
actgaagacg ctccactgtc cgtgtacaac cccaactaca ggagtgataa cgcactcata 135000
gccgatggtg attccagccc cattgggggg gattgttgtc cggcagaggc ggtggctgcc 135060
gctgaggagg tagctacggc tgctttggct tctgaagaaa tctacgagat gcatatcaaa 135120
tcctgcattt cttccaccac atgcggtgac cataataact caatcggcgt aacatcgggg 135180
cttactgttt gcgcggctga gtgtcacccc ccgtccccag aggccgtagg tattgaggat 135240
gtggtggttg tgcaaactgc ggctaccact aatggcccct cagatacagt acccgccagt 135300
gctgcggcct cagtgattag cgatgataac ggctgtgtac cgctgctagg gtcacgcctg 135360
gaactagaaa actatgactt ggagtctggc tgctactaca gcgaaagcga caacgaaacc 135420
gccagcctgt tcatccagag ggtcggccgg cggcaggcgc ggcgacacag gcggcgacgc 135480
gtggccctca cggtcgccgg cgtcgtgctc gtcgctgtcc tgtgcgcgat atccgggatc 135540
gtcggggcgt tcctcgcgcg cgtatttcag tgacgcgaac ccgcggacgc ggccatcgcc 135600
tctaccgcca cgatttccca ccctgctgtc ccgcacccgc cagtcaataa aacctcatag 135660
tagagaaccc cagcctctgc gcgtttgttc gatggcccgg gtagcttgtt tcccaccccc 135720
tatcggaggt ggggaggtgg ggaggtgggg aggtggggag gtggggaggt ggggaggtgg 135780
ggaggtgggg aggtggggag gtggggaggt ggggaggtgg ggaggtgggg aggtggggag 135840
gtggggaggt ggggaggtgg ggaggtgggg aggtggggag gtacttgaac gctttggttt 135900
atgcaatata gaaagtttaa aagtttattg attgactggc caccgatacc gtcgcggaac 135960
ccgcctgtgg gggcaggggg agcgggagct ttcggcctcg ggtacgcagg tacgcggcgg 136020
cggcggcgtg tcggggaaat agctccggat cggcccccgc catgtccagc agcgccaccc 136080
agtagcgctc cgagtcggct ggggggggtct ccccgatccc gagtctcgct tcgaaaaacc 136140
gtgcgcactc gcgctcgtac atggcctggc gggaacagcc gaacgcgtgc cccaggcagc 136200
accagtgggc gcaaaaaagg aggcgggtgc tgagctcagc gtgggtctcc accggcgcgg 136260
cgcctaggtc taccaggtac ctccccaccg cgcggcgtag cgggtccgcc gagtggaaaa 136320
cgggcatggg gctgaccgca tatcggccga atagttcgca gaacatgcgg tacgcgcgcg 136380
gccagatttc ggggggaggc cccgctcctc tcctgagcgc gtcagcggca tccgcggaca 136440
tagcgcgcac cgctgacgcg aattcgccca ctgagcgggg aagcgacacc gcgtgcgcgg 136500
ccgtgtccgt gctggtgggg tacagcccct caccgcctcc gcagtctccc ccggttctca 136560
cacccccgtc taccgccatg ggggaaccgt acgcgcagtc cataactctc gggagcgtgg 136620
agcctaggcg cactgaccgg gcgcggccgg gtaccagggg tatttcctcg gcggggcggg 136680
gaatcgcatg tgccatagcc ccgcccgtgc ctctatccta ttgttcttcc atcatgcctt 136740
ccggcacaca tctcaccccg gccggcccgt ttgcgtgggt gctgttatcg ctcttcacat 136800
attcatacgg cgataaaggg gcaccgttgg gcgtacgcac acggcttgca cgtttaacgg 136860
ggaacgcgtg ttacgacggc gggggagatc ttctgtatag cgctcgccca accccaatac 136920
cacccaccgt ttgctgcatg cacgcgacaa acacgagatt gtgctcgatg aaggttagtc 136980
aacgatttat ttggttataa gcggggatag acgcgcattg atgctacata tgaattaact 137040
gcggcgtgtt gggggttatg gtgggaacta atagggctac taaaaacggt aactacctat 137100
```

gcggttttgg ttgcgtgtgc ttttaatcac cggcgagcgc ttttggccgg gcgcccgcct 137160
ttggggacag ggcgcccgcg gcgcttttga gcagcgcggg cacgtgtggt gggagggttg 137220
gtggggacat ctgcctcgct atcgctttcg ctgctagacc actttcccgt gcaacaagag 137280
tcgtcttcct cgtccgaaaa gctttcaaag tcgctgctgg cgctctcttc ctcgggacta 137340
aactctgaaa tggtgctatt tccgctagcc tcttcctcct ctgacggaga ctcgtcgccg 137400
ctaacttcgc actcttcccc aaagagggtt ttgggtggct tgctgggcgg atcaagaaac 137460
ctctgctcgt acttgtcttc cgagtttatg gcacgcagcg tggcccgcag cggaaggctc 137520
tgctccggca tcagctgcaa aagggcctgc caacattcta gggtagggcg tgcatgcgtg 137580
taccccatag cgtaaaagtc caacagcacc ctgcgcagga cgcgcgagtc ttctgttacg 137640
tgaatagatg aagtagatat acccctaaac aagcgattga cgtccccggc gaggcggttt 137700
acgtctgggc gccacggcgg agcgcagaac gctcccggcc cccgagacag gtacgggcgc 137760
agcgacctcg gcgagagcgg caggccgtat tccggatggt cagagccgcc gggaagcctg 137820
gcgggcacgc gcacggagtc tatgcgctgg ctggagcgtg gggatgggtt cccaccagat 137880
gagggggaca gggagggtat gatggggctg gtggacggcg ccccccgctg tgacatgcgg 137940
caggatccgt cgcacgcccc acatggctgg ccgtgtggca tggttgctgc ggtctgggct 138000
cgcttggcgc aaatcgagta gacacggggc gttttgttcg gccaaaacga ggcgggggtc 138060
gcgattggcg ctcgagccta taagcgaatg agaaaaatgg tcacgaccac ccccacgacc 138120
acccccacga ccaccccac gaccaccccc acgaccaccc ccacgaccac ccccacgacc 138180
acccccacga ccaccccac gaccaccccc acgaccaccc ccacgaccac ccccacgacc 138240
acccccacga ccaccccac gaccaccccc acgaccaccc ccacgaccac ccccacgacg 138300
gtacgccaca cctacctcga taggttttgc agtggatgcg tatcaaacgg cttgagtttt 138360
ggagctgcgt gtgtcccttc acatggtgag gcgctggcta atatatacac tagtcccatg 138420
ttccacgcct tccagaaggc gtatacatgt acttcaccac gccttcttta ataataggtt 138480
atcgattatc ggacaaaatt ggaaacatgg cacgtggttt ttatactcaa tcctgattgg 138540
gtataggtgc cgttcgcacc aatcactaat aagttataat acttattgta acaaagtgcg 138600
aacactacat gttcgcactt cttatccggg ttacgtaata tctcgggagc gcgcatggca 138660
ctgtgccagc tagcaaccta cccaaccact ctcgccatac gctggggtgc gttagtaacc 138720
gtattttagt gcgccccccc cacacgcaca ccgtaaaccg tacgttgccg tttatatcgt 138780
aaaaactttt attgcccccc cccatatcca tacccgccgt atatcaccca cgtttttttt 138840
ttcgcgcaaa aatttttagt gccccccccc ccttgtttgt actgggggca tggggcaggt 138900
ttacgcatta gcaataaaaa aaaactaagg gggggtcgtt taattataaa tggcagaccc 138960
gcaagatgta tgtcgtggag ttactgatgg gtggttgaat cttatttttc tactacattc 139020
tcacacctgt agtaaaacgt aaagcgctta accgcttaca cggttctacg gttttacttt 139080
ttagttggcc gataaacaga aatcaaattg gatggggtgg gggcgggagg tgaaaatggg 139140
cgtgtatatt tccccccggt accccctccc attgatctta atagacccaa cccacatact 139200
tatttgaata tagggtggga aatgtgttac gtagaggggg cgtgggttgt actgagtgta 139260
tagcgtcata gaatgtcgtt acgatggact gcgatctaga gcaccacatg gtggttatct 139320
gtataaactg cacctgttaa cgtgtaactg cgccaccaca agggcgtata taaaagtgca 139380
tgtaaatcga gtgtttaaaa aatagcgcca tcatgcggtt agttttcata taatatgcaa 139440

```
attggtccac gtagatagta tcccgcccat ttcatacaca aaaaacgata cgtgttttaa 139500
ttggttaaac tttaatgaga ttcacaggaa attacaaaac aaatgagtta ccgcccaccg 139560
cccattgccc cctccctttg caggtgcgcc atttccgctt ccttgggaaa taacgcacgc 139620
gccatttta ttaaaattaa tttcgcatac aactccccgt gctcctccca ggctcatttg 139680
tatgcagatg atatttacca ggaagtgtcg tggcaccaca gcgccttcct ctttatgcat 139740
atgagatgtg agatacggac cctagttggt gcgacgctct accggggagg agatgcatgc 139800
aaatgatata tgcacggaag tgtcatggcg gcagttggcg tccatcttta tgcatatgag 139860
atgtgctcgg ctacctcctg ttggtgcgac gcgcttccct gggaggaaac acatgcaaat 139920
taaaaatgac ataccaattg ccattgggta gagctagggg aaggcgttag gcgcatgtaa 139980
atgaaaattg tacactagtg tatcattggt tggaacggat acacgcccac cgcccatcgc 140040
agccagccaa tccaaacggc ctttgtgggt tggcccctcc cattggggga ggtacaaacc 140100
ccatcgttgt agtatatagc acctgttgct cactcatcgt agcatcgcag actagagagc 140160
ctctcagctc aactagacca accatctcct caaaggacat cgatttactc ttggcaggct 140220
tgcccgcttt tggtgctccc ttctcggctt gtggaggtaa gagctcccgg gggacggctt 140280
accaacttgg cttcatactt atctgctctc ttctccttcg ctgttctcga gccaaaacta 140340
cggcgctact ccggctctgc cgcttgaggc atcactctgc gggcatactc ggcctgcgtc 140400
tgcccggccg agcttagggt gctggctttt gggtttctag tggggcggag ctaccacccc 140460
agctgggaga ggccatggcc cgcgttccct tttaccatta ggcgccgctc caaccaagca 140520
ttttgtccgc ccttgccttt tcagggtaga gagctccagc agcgtctaac ctcggttcga 140580
gcgcgcacct cacccgttct cctctaaaac ccgggagaga gcgagccatg gccagccagc 140640
gcagcgattt tgctccggac ctctacgact tcatcgagag caacaacctg gacgaggaca 140700
acctcatccg cgcagccagc gcggccgaag aggggttcca taccccggcc gccccggatc 140760
tgctgtacgg aagccagggg atgtttgggg tggacgacgc gcccttggcc accccggcgg 140820
tagtcatccc gccgccttcc ccggcccccg agccccgcgg cgggaaggca aagcggtctc 140880
cggccagagc agcagtgccg gcatcgcccg ctcataaccc cgctccgggg ctcgccgaga 140940
tgctgaagat ggttcactcg tccgcggcta caggggccgg tcgcagggac accggatcat 141000
cgggcggagg tgcctataac cagggcaccg ggagcgacac cgagacctgc ccggggtctc 141060
ccggggccga gtttccaccc tcggcctccc ccgaggggag gccggcgcca aggggccgga 141120
gcatctccat atcatcgtcg tcctcgtcct cctcatcgac ggaagaccaa gccgatggtg 141180
ccggggcgag cagctcgtct tcgtcttcct ccgaagacag tgacagcgat gatgggggcg 141240
aagagaaaac tcctcgcccc catccctcgc cgagcgccgc aaaaacccaa ccggccaccg 141300
ggtcccctgg gcagattagc ggggatcgta tagcccctgg atcgtacacc ccaaagagcg 141360
gacgctcaga gaaggggcac caaagccccg tcggcgcttt tgcggcttca accggcgctc 141420
ccaccccgag taacccgggc gggcccctcg ccccgggagc tcgcatttta gagtacctgg 141480
agggggttag ggacgccaat ctggccaaga cgctggagaa gcccgacccg agaatgtctc 141540
ctccagggca gagcccacac agagctccca aggaccagcg gcccaagtct gcgttggccg 141600
gggcctctaa gcgcaagcgc tgccacccaa gacccatacc ccagaccgcc gccacaaccg 141660
gggccgaaga ggccctcccg ggatgcgcgt gggacctgtt ggacatgaac tgctcctctc 141720
aggccccagg gctcggaacc tgccagcgcg agccgctgct cacaccatcc ggagacccat 141780
ggcccgggtc ggacgcccca ccaccgggga gggtgcgcta tgggggaacc ggggactcgc 141840
```

gggacgggct ctgggatgac cccgaaatag ttctggccgc ctcgcgctac gccgaagccc 141900
agaccgccgt acctgtattt gtgcccgaga tgggggactc caccaagcag tacaacgctc 141960
tggtgcgcat ggtgtttgag aaccgcgagg ccatgtcttg gctgcaaaac tccaagctcg 142020
gcggggccga ccagaacctg gcccagttct gccagaagtt catacacgct ccccgcggac 142080
atgggtcctt catcacgggg agcgttgcta accccctgcc ccacatcggg gacgccatgg 142140
cggccgggaa tgctctatgg gcccttccgc acgcggcagc ctcggtggcc atgagccgcc 142200
gctacgaccg cacgcaaaag agcttcatac tccagagcct cagacgggcg tacgcggaca 142260
tggcctaccc gcgcgacgac gccgggcggc aggactccca ctcggcggcc ggggtcacgg 142320
ctagctaccc ggcccaagca caggctgcct ctcaacagcc ggatccccg gccacatctg 142380
ctagggtccg cgaggagtac accagggtgt gcgcggccct cgggccacgg cgcaagacgg 142440
cggccgcggg tcctggtacc agaaccccca agcctaccgc cttcaggctc agggaactcg 142500
gagacgtctg cgtactggcc tgccaggccg ttttcgaagc cctacttcgc ctccgcggcg 142560
gagcgtccgc tgtccccggg cttgacccaa gcgagatccc ctctcccgcc tgccctcccg 142620
aagcgctgtg ctccaacccc gctgggctcg agactgctgc ctgcgccctc tacgaactca 142680
gggacctggt cgagcgtgcc aggctactcg gggactctga ccctatccac cgcctgggcc 142740
ccgacgagct gcgcctcgcg gtccgcgcgg ttctggttgt ggccagaacc gtcgcacccc 142800
tggtgcgcta caacgcggag ggagcccggg cccgggcctc ggcctggacc atcacccagg 142860
ccgtgtttag catacccagt ctggccgggg gcatgttggg ggaagccgtg ggcctgcttg 142920
cgcctcctcg gtcacagtct tcatcgtctg tcggcggcga cgttgggcag cagcagtccc 142980
tctcctcctc cgagggaagc cagacctccc gcatccccgc cttgtggccc actgttcccg 143040
ggaagcctct cgtggtgccg gccacgtctc actctcagtc ttcttccccg cagcaccaga 143100
gcagcggggg gccgacaacc tgctcccggg ccacccagac ccaggctcgc ccctcggggc 143160
agaaggctcg ctccccaccg gctgcctccc aggctatcct cggccaggag atgccggtct 143220
cctcgcaggg agggggcgga ccggcaccct acgcctcccc gaacgaccgt cccgtcaacg 143280
ggcgccccag gggcaagagc gggaagcggc gctccgagcc cctggagccg gcggcggggg 143340
agctcccggg gtcccgcgga ggatacgacc cggtcgctcc ggtagagagc cctcctgccc 143400
caaagcgcag ggtgggtact caggcccctc gagctttggg gcccatgccg cccgaggggc 143460
cacaccgccg gggaggcttc agacgcgttc cccatggaga ctgccacacg ccaccccccg 143520
gggactctgc ccgcgctgct tactgtcccc cagagctcgt ggctgagctg atagaccacc 143580
cgctgttccc cgaggcctgg cgcccccgcgc ttaccttcga cccccaggcc ctggctacca 143640
tcgcagcccg ctgcaacggg cctccggcca gggagggcgc gcgctttgga gagctggctg 143700
ccagcggacc gctccgccgc cgggctgcct ggatgaacca gatccccgac cccgaagacg 143760
tgaaggtggt ggtgctctac tccccgctac cggacgagga cctgctgggt ggactcccaa 143820
ccacccgacc cggcggctcg cgccgggagc ccctctggtc cgacatcaag gggggggctct 143880
cggcgctgct ggcggccctg gggaaccggg tactcacaaa gcggtcccac gcctgggctg 143940
gcaactggac tgggcccccc gacgtgtctg ccctaaacgc ccagggagtc ctgctcctct 144000
ccacggggga cttggccttt acaggctgca tcgagtactt gtgccttcgc ctgggctccg 144060
ccagacgcaa gctcctagtg ctggacgcgg tctccctaga ggactggccc caggacggtc 144120
ccgccatcag ccagtaccac atctacatgc gggccaccct cacccctcgg gtcgcctgcg 144180

```
ccgttcgctg gccccgggag cgccacctca gccgcgcggt cctcacttcc agcaccctct 144240

tcgggcccgg actgttcgcg agggccgagg ccgcgtttgc gcgcctctac ccgaactcgg 144300

agcccctgaa gctgtgtcgg gcggccaacg tggcctacac ggtggacacc cgggccggag 144360

agcgcacccg cgttccactg ccacctaggg agtaccgcca gcgggttctg ccagactacg 144420

acggctgcaa ggacatgaga gcccaggccg aggggctcgg gttccacgac ccagactttg 144480

aggagggcgc agcccagagc caccgcgcgg ccaaccgatg gggccttggg gcatggctgc 144540

gcccggtgta cctcgcctgc ggacggcgcg gagccggggc cgtggagccc gccgagctgc 144600

tgatcccaga actgctgagc gagttctgca gggtcgcgct gctggagccc gacgccgagg 144660

ctgaacccct ggtgatgccc atcacggagg ctcctcgccg ccgagcccct cgggttgagt 144720

gggagccggg gttcggtcag cgctcgacct cggtcctcca catgggcgcg ctggagctgt 144780

gccttcccga gtccgacgat gagcttgaga tcgacggacc gggggacgtg gagctggttg 144840

cagatcaccc tggggtgagc ccggcagcgc agttgatccg acgcgccccc atcaagatag 144900

aggtggtatc ggacgaggag gacggagaag actggtgcaa cccctatctc acctaaacaa 144960

cagctccacc ctatggacac accaaaacaa aaatcagcac atccacaact atgtgttcgc 145020

ccgtcacaac gcaaactcca ccccaatcca tccccaaacg cgccccctgt tgcttgcttc 145080

acaaaattac attaataaaa catgttttta attattaatt ccggtgtggt ttgtgttagt 145140

gggcgggtta gtgggcgggt tagtgggcgg gttagtgggc gggttagtgg gcgggttagt 145200

gggcgggtta gtgggcgggt tagtgggcgg gttagtgggc gggttagtgg gcgggttagt 145260

gggcgggtta gtgggcgggt tagtgggcgg gttagtgggc gggttagtgg gcgggttagt 145320

gggcgggtta gtgggcgggt tagtgggcgg gttagtgggc gggttagtgg gcgggttagt 145380

gggcgggtta gtgggcgggt tagtgggcgg gttagtgggc gggttagtgg gcgggttagt 145440

gggcgggtta gtgggcgggt tagtgggtcc tgctcctccc cttcctgctc ctccccttcc 145500

gcttgcgtca cttccgcttc cggtcacacc cactttaagc ccccccaaa aagccacgcc 145560

ccctatttga atgagggccc gcgttatggg cggtggg                         145597
```

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 3

```
gcctctagat taacggtaat ctctgcgc                                   28
```

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 4

```
aaggatccat ggcacgacgt ggcg                                       24
```

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
aatctgcagg tagctacggc ctatg 25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
aagaattccc gcaatacgtc cgtcc 25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
ccggatccct accagagacc cataa 25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
aagaattccc gcaatacgtc cgtcc 25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
aatctgcagg tagctacggc ctatg 25

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
ttaagtcgac atttgaatag aaactcg 27

GM-NEGATIVE EHV-MUTANTS WITHOUT HETEROLOGOUS ELEMENTS

SEQUENCE LISTING

This application contains a sequence listing in accordance with 37 C.F.R. 1.821-1.825. The sequence listing accompanying this application which has been submitted electronically in ASCII format is hereby incorporated by reference in its entirety. Said ASCII copy, created on Jul. 25, 2014, is names 01-1372-US-5 SL.txt and is 387,567 bytes in size.

BACKGROUND OF THE INVENTION

The present invention relates to the field of animal health and in particular of Equine Herpes Viruses (EHV) wherein the gene encoding the protein gM is absent, and which is free of heterologous elements. Further aspects of the invention relate to pharmaceutical compositions comprising said viruses, uses thereof, and methods for the prophylaxis and treatment of EHV infections. The invention also relates to pharmaceutical compositions comprising the combination of EHV-1 and EHV-4 viruses wherein the gene encoding the protein gM is absent and which is free of heterologous elements.

Equine herpesvirus 1 (EHV-1), a member of the Alphaherpesvirinae, is the major cause of virus-induced abortion in equines and causes respiratory and neurological disease. Equine herpesvirus 4 (EHV-4) can also induce respiratory symptoms, abortions or neurological disorder. The entire DNA sequence of both species (EHV-1: Strain Ab4p; EHV-4: Strain NS80567) has been determined (Telford, E. A. R. et al., 1992; Telford, E. A. R. et al., 1998). However, only few genes and gene products have been characterized in regard to their relevance for the virulence and immunogenic properties of EHV.

Herpesvirus glycoproteins are crucially involved in the early stages of infection, in the release of virions from cells, and in the direct cell-to-cell spread of virions by fusion of neighboring cells. To date, 11 herpes simplex virus type 1 (HSV-1)-encoded glycoproteins have been identified and have been designated gB, gC, gD, gE, gG, gH, gI, gJ, gK, gL, and gM. HSV-1 mutants lacking gC, gE, gG, gI, gJ, and gM are viable, indicating that these genes are dispensable for replication in cultured cells. Comparison of the HSV-1 and equine herpesvirus 1 nucleotide sequences revealed that all of the known HSV-1 glycoproteins are conserved in EHV-1. According to the current nomenclature, these glycoproteins are designated by the names of their HSV-1 homologs. It is known that EHV-1 gC, gE and gI are not essential for growth in cell culture, whereas gB and gD are essential for virus growth in cultured cells. The contributions of other EHV-1 glycoproteins to replication in cultured cells are not known (Flowers, C. C. et al., 1992). Transcriptional and protein analyses have shown that the glycoproteins gB, gC, gD, gG, gH, and gK are expressed in EHV-1-infected cells. Glycoprotein gM (encoded by gene UL10 [Baines, J. D. et al., 1991; Baines, J. D. et al.,1993]) is the only reported nonessential glycoprotein which is conserved in all herpesviral subfamilies and has been described for human and murine cytomegalovirus and the Gammaherpesvirinae members EHV-2, herpesvirus saimiri, and Epstein-Barr virus. Like many herpesvirus glycoproteins, HSV-1 gM is present in virions and membranes of infected cells. HSV-1 mutants solely lacking gM grew to titers in cell culture systems reduced approximately 10-fold relative to those of wild-type virus and showed a reduced virulence in a murine model (Baines, J. D. et al., 1991; MacLean, C. A. et al., 1993). The EHV-1 gM homolog (gp21/22a; referred to as EHV-1 gM from now on) was first described by Allen and Yeargan (Allen, G. P. et al, 1987) and was shown to be a major constituent of the virus envelope. Further investigations revealed that gene 52, the gene homologous to HSV-1 UL10, encodes the 450-amino-acid EHV-1 gM polypeptide (Pilling, A. et al., 1994; Telford, E. A. R. et al., 1992). EHV-1 gM represents a multiple hydrophobic protein which contains eight predicted transmembrane domains and has been reported to be present in infected cells and in purified virions as an Mr 45,000 protein (Pilling, A. et al., 1994; Telford, E. A. R. et al., 1992).

For control of EHV-1 infections, two different approaches were followed. First, modified live vaccines (MLVs) have been developed, including the strain RacH (Mayr, A. et al., 1968; Hübert, P. H. et al., 1996), which is widely used in Europe and the United States. Second, inactivated vaccines and subunit vaccines based on recombinant expressed viral glycoproteins such as the glycoproteins (g) B, C, D, and H, which induced partial protection against subsequent challenge EHV-1 infection in a murine model. Subunit vaccines comprising said glycoproteins e.g. gB, gC, gD, and gH only poorly protect against reinfection (Awan et al., 1990, Osterrieder et al., 1995, Tewari et al., 1994, Stokes et al, 1996).

The following U.S. patent applications are also incorporated by reference herein: U.S. patent application Ser. No. 09/789,495, filed Feb. 16, 2001, U.S. patent application Ser. No. 10/105,828, filed Mar. 25, 2002, and U.S. patent application Ser. No. 09/812,720, filed Mar. 20, 2001.

The technical problem underlying this invention was to provide improved vaccines which protect better against EHV infection than prior art vaccines.

BRIEF DESCRIPTION OF THE DRAWINGS

This figure shows the map of viruses and plasmids used for the construction of HΔgM-w. "First-generation" HΔgM virus has previously been constructed by either inserting the *Escherichia coli* lacZ (HΔgM-lacZ) or the green fluorescent protein (GFP) expression cassette (HΔgM-GFP). The BamHI map of EHV-1 strain RacH is shown (A) and the BamHI-HindIII fragment containing the gM-ORF is magnified showing the genomic organization of the region (B). The gM-negative virus, HΔgM-GFP carries a GFP-expression cassette, replacing the major part of the EHV-1 gM gene. The GFP-specific probe, that was used in Southern blots, is depicted (C). Plasmid pBH3.1 carries the EHV-1 BamHI-HindIII fragment of interest and was used to construct plasmid pXuBaxA. After cotransfection of DNA of HΔgM-GFP with plasmid pXuBaxA resulted HΔgM-w (D). Restriction sites: BamHI-B, HindIII-H, SphI-S, HincII-Hc, ApaI-A, PstI-P

DNA of RacH, HΔgM-GFP and of HΔgM-w was cleaved with BamHI, HindIII or PstI and analyzed with a GFP-specific probe (GFP) or the EHV-1 BamHI-HindIII fragment of pBH3.1 (pBH3.1). DNA-hybrids were detected by chemoluminescence using CSPD. Molecular weight marker sizes (Biolabs) are given in kbp on the left margin. The arrow points to a barely visible specific hybrid.

Figure 3:
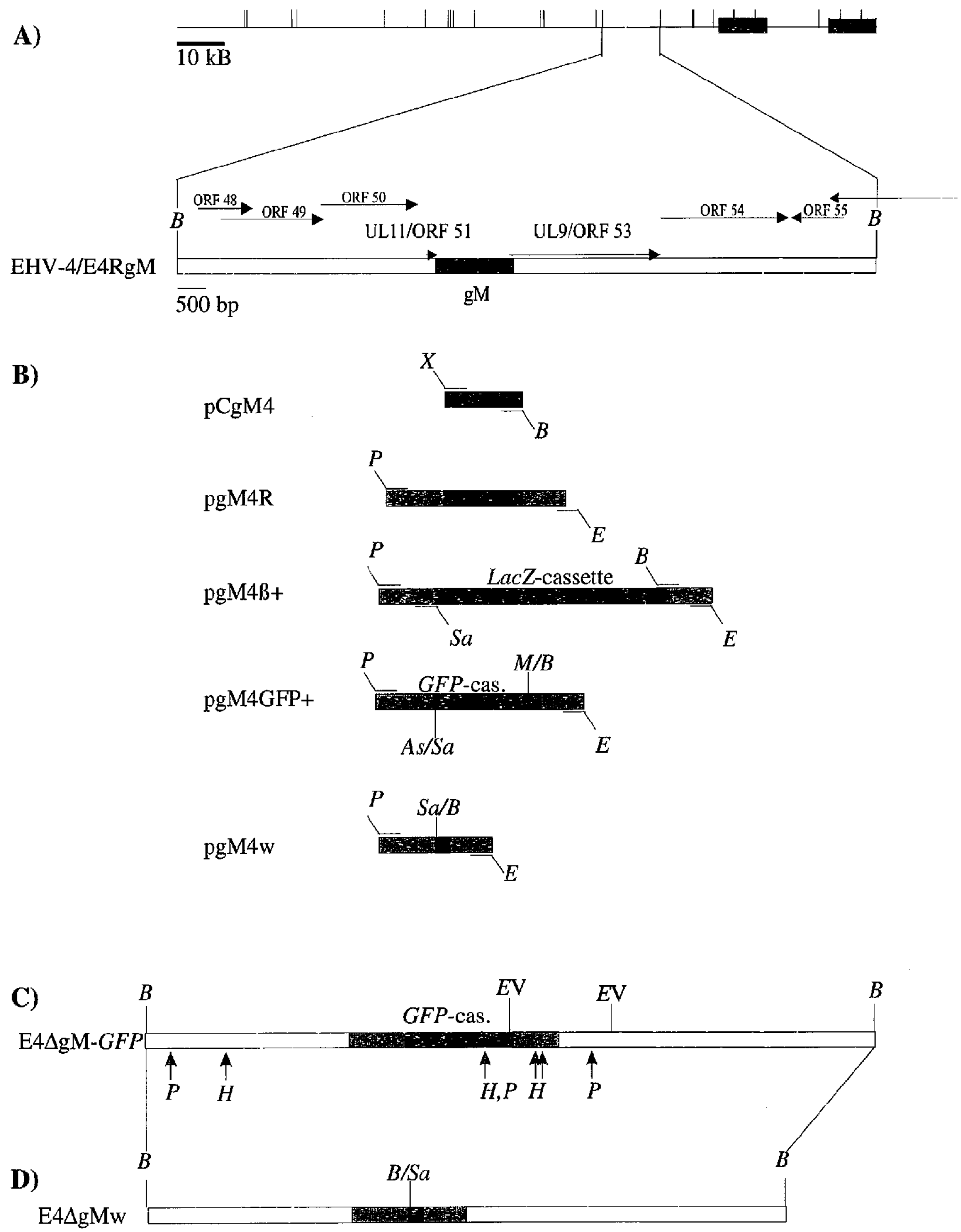

FIG. 3: Generation of a gM negative EHV-4 virus without foreign sequences (E4ΔgM-w).

In this figure, a BamHI map of EHV-4 strain NS80567 is depicted. The enlarged BamHI-e fragment encompasses the gM- and neighboring ORFs (A). Plasmid constructs and priming sites are depicted (B). Plasmid pgM4GFP+ was used for the generation of E4ΔgM-GFP, the GFP-positive and gM negative EHV-4 (B, C). Recombination of DNA of E4ΔgM-GFP with either plasmid pgM4R (B), containing 3.109 bp of EHV-4 sequences including the gM-ORF, resulted in E4RgM, the gM-repaired EHV-4 (A), or with plasmid pgM4w (B) resulted in E4ΔgM-w, the GFP- and gM-negative EHV-4 (D). Restriction sites: BamHI-B, PstI-P, EcoRI-E, SalI-Sa, MluI-M, AsnI-As, EcoRV-EV FIG. 4: Southern blot of a gM-deleted EHV-4 virus without foreign sequences (E4ΔgM-w).

DNA of EHV-4, E4RgM, E4ΔgM-w and E4ΔgM-GFP were cleaved with PstI, EcoRV or HindIII as indicated and DNA-fragments blotted onto nylon membranes. Parallel membranes were either hybridized with GFP-specific sequences or with a probe, named gM3.1, containing the EHV-4 specific sequences taken out of plasmid pgM4R (FIG. 3). DNA hybrids were detected by chemoluminescence using CSPD. Molecular weight marker sizes (Biolabs) are given in kbp.

Figure 5:
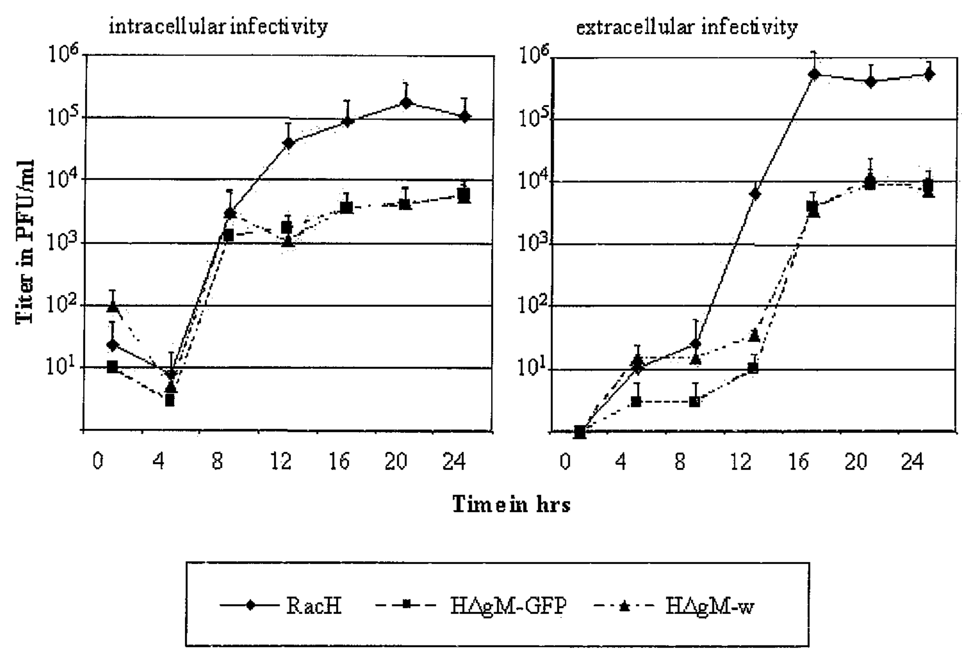

FIG. 5: Growth characteristics of the gM deleted EHV-4 virus, E4ΔgM-w.

Cells were infected with an MOI of 2 of the different viruses, as listed in the box. Kinetics of virus growth are depicted as virus titers determined in supernatants of infected cells (extracellular activity) or within infected cells (intracellular activity) relative to the time point indicated. Shown are the means of two individual experiments, standard deviations are given as error bars.

Figure 6A:
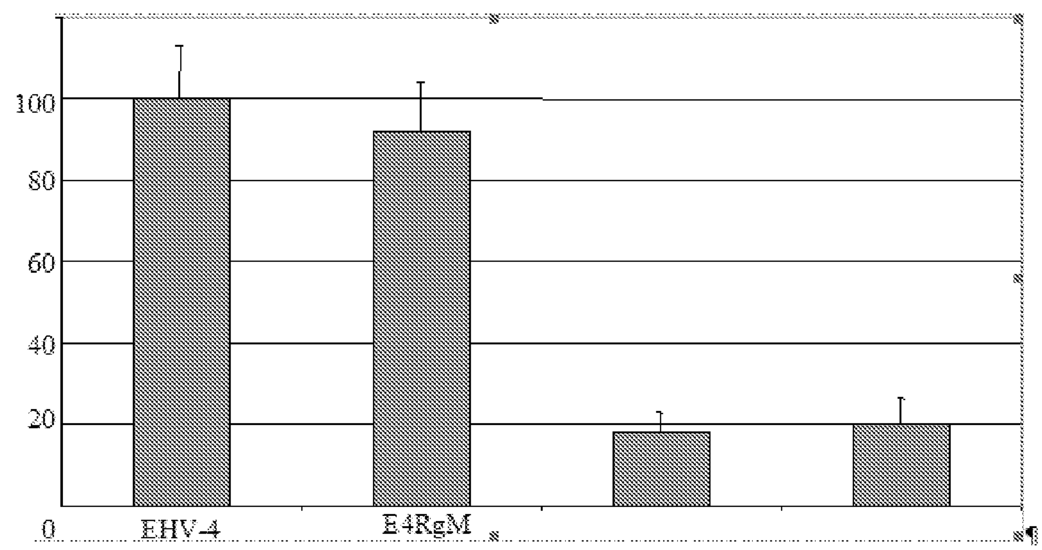

FIG. 6A: Plaque sizes of E4ΔgM-w. Vero or Vero-gM cells in 6-well plates were infected with 50 PFU of either EHV-4, E4RgM, E4ΔgM-GFP or E4ΔgM-w. Maximal diameters of 150 respective plaques were determined and average plaque sizes are given in %, relative to sizes of wildtype plaques, that were set 100%. Standard deviations are given as error bars.

Figure 6B:
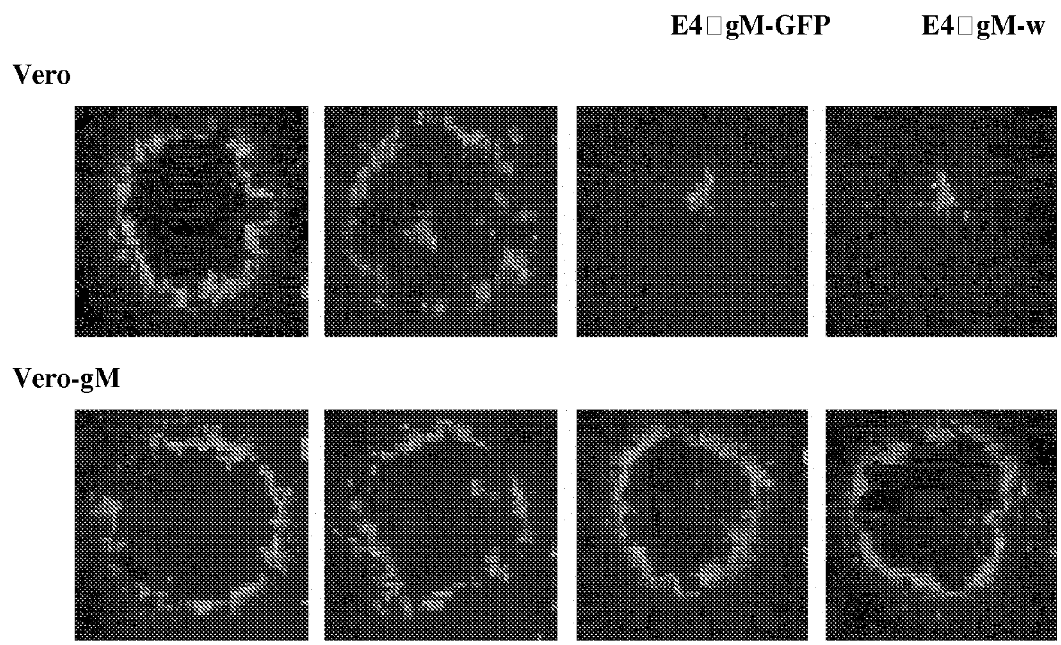

FIG. 6B illustrates the plaques that were stained by indirect immunofluorescence (anti-gD Mab 20C4, 1:1000) at day 4 p.i. and analyzed in an Axioscope (x100, Zeiss, Germany). Pictures were scanned and digitally processed.

FIG. 7: EHV-4 virus penetration into Vero cells.

Penetration of EHV-4, E4RgM, E4ΔgM-w and E4ΔgM-GFP produced on non complementing Vero cells (A) or on complementing Vero-gM cells (B) into Vero cells. At given time points the penetration efficiency was determined as the percentage of the number of plaques present after citrate treatment relative to that of plaques present after control treatment. Means of two independent experiments are given. Standard deviations are depicted as error bars.

FIG. 8: PCR primer sequences (SEQ ID NOS 3-10, respectively, in order of appearance) and location of amplificates within the EHV-4 genome.

Sequences representing restriction enzyme recognition sites are printed in bold and the respective enzymes are listed. PCR products were inserted into the given vectors, resulting in plasmids pCgM4, pgM4R pgM4Del1 or pgM4Del2, as indicated. The location of a fragment within the EHV-4 genome is given relative to the sequence determined by Telford et al. (1998) (SEQ ID NO:2).

Figure 9:
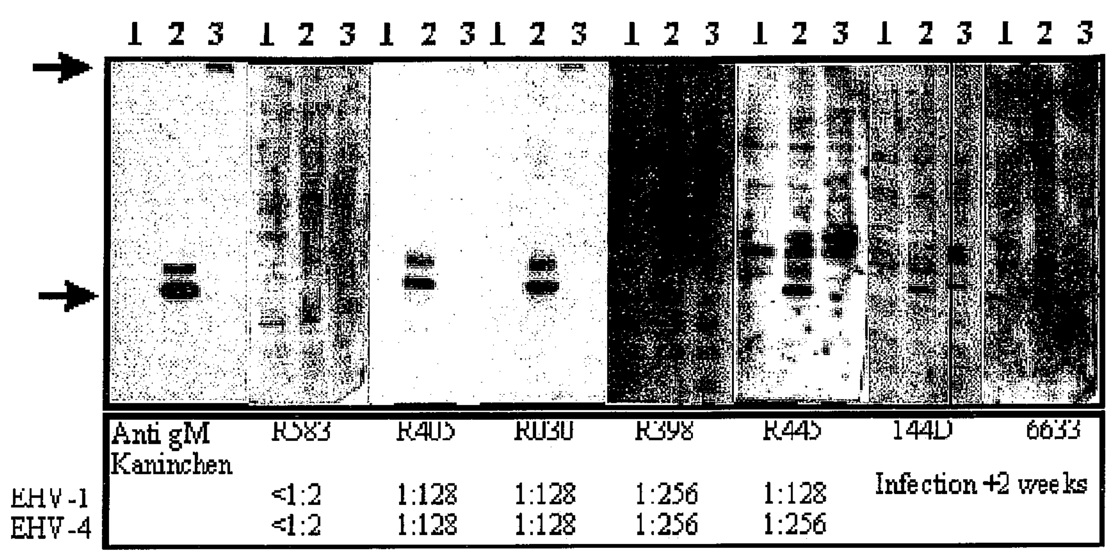

FIG. 9: Western Blot analysis of horse sera.

Lysates of EHV-1 gM expressing cell line ccgM and Rk13 cells were either heated for 2 min at 56° C. (1,2) or for 5 min at 95° C. (3) (gM is highly hydrophobic and known to aggregate upon boiling, so that it does not enter the separating gel anymore). Identical blots were incubated with various horse sera (1:3000) or the anti-gM rabbit serum. Arrows point to gM specific reactivity in boiled and unboiled samples. Neutralizing test titers (NT) are given for sera, that were obtained from the virological diagnostic unit.

FIG. 10:

(A) Comparison of EHV-1 gM to EHV-4 gM using an anti-EHV-1 gM polyclonal antibody. Cells were infected with the indicated viruses (MOI of 0.5-1) and cell lysates were prepared at the stated time points p.i. EHV-1 or -4 virions were purified by repeated centrifugation through a sucrose cushion (30%) and resuspended in PBS. Samples were mixed with buffer containing 5% 2-mercaptoethanol and then either heated to 99° C. for 5 min or left at 4° C. Proteins were separated by SDS-10% PAGE and blotted onto nitrocellulose filters. Antibody binding was visualized using anti-rabbit immunoglobulin G (IgG) peroxidase conjugate (Sigma) followed by ECLTM detection (Pharmacia-Amersham).

(B) Virions were purified of Edmin337 cells infected with EHV-4, E4ΔgM-w, E4ΔgM-GFP or E4RgM and subjected to Western blot analysis as described in (A). gB reactivity of virions was then compared to gM reactivity using anti EHV-1 gB monoclonal antibody 3F6 or the anti EHV-1 gM polyclonal antibody.

DESCRIPTION OF THE INVENTION

Definitions of Terms Used in the Description

Before the embodiments of the present invention it must be noted that as used herein and in the appended claims, the singular forms “a”, “an”, and “the” include plural reference unless the context clearly dictates otherwise. Thus, for example, reference to “an EHV virus” includes a plurality of such EHV viruses comprising also all subspecies like EHV1, 4 and others, reference to the “cell” is a reference to one or more cells and equivalents thereof known to those skilled in the art, and so forth. Unless defined otherwise, all technical and scientific terms used herein have the same meanings as commonly understood by one of ordinary skill in the art to which this invention belongs.

Although any methods and materials similar or equivalent to those described herein can be used in the practice or testing of the present invention, the preferred methods, devices, and materials are now described. All publications, patents and patent applications mentioned herein are incorporated herein by reference for the purpose of describing and disclosing the cell lines, vectors, and methodologies as reported which might be used in connection with the invention. Nothing herein is to be construed as an admission that the invention is not entitled to antedate such disclosure by virtue of prior invention.

The term “EHV” as used herein refers to all equine herpes viruses such as species EHV-1 and EHV-4 within the family Alphaherpesvirinae. The terms EH-virus, EH virus EHV virus, EHV-virus and EHV all relate to equine herpes viruses.

Virulence: “virulence” as used herein relates to an EH-virus capable of propagating in the target host species (i.e. horses) with the potential to induce subclinical and clinical disease characterized by respiratory symptoms, abortions or neurological disorders. Examples of virulent EHV are wild-type viruses inducing strong clinical symptoms. Examples of virulence factors are hemolysins (lysing red blood cells) or adhesins (proteins by which the pathogen can adhere to the host and initiate colonisation or invasion). More specifically, “virulence” here means that the gM gene product, a major constituent of the virus envelope, enables the virus to penetrate the host and is involved in cell-to-cell spread.

Attenuation: “An attenuated EH-virus” as used herein is relates to infectious EHV which do not cause EHV-associated subclinical or clinical disease. In particular according to the invention, such attenuated EH-viruses are EHV which can replicate and do not express gM.

A "functional variant" of the EH-virus according to the invention is EHV virus which possesses a biological activity (either functional or structural) that is substantially similar to the EHV according to the invention. The term "functional variant" also includes "a fragment", "a functional variant", "variant based on the degenerative nucleic acid code" or "chemical derivative". Such a "functional variant" e.g. may carry one or several nucleic acid substitutions, deletions or insertions. Said substitutions, deletions or insertions may account for 10% of the entire sequence. Said functional variant at least partially retains its biological activity, e.g. function as an infectious clone or a vaccine strain, or even exhibits improved biological activity.

A "variant based on the degenerative nature of the genetic code" is a variant resulting from the fact that a certain amino acid may be encoded by several different nucleotide triplets. Said variant at least partially retains its biological activity, or even exhibits improved biological activity.

A "fusion molecule" may be the DNA molecule or infectious EHV virus according to the invention fused to e.g. a reporter such as a radiolabel, a chemical molecule such as a fluorescent label or any other molecule known in the art.

As used herein, a "chemical derivative" according to the invention is a DNA molecule or infectious EHV clone according to the invention chemically modified or containing additional chemical moieties not normally part of the molecule. Such moieties may improve the molecule's solubility, absorption, biological half-life etc.

A molecule is "substantially similar" to another molecule if both molecules have substantially similar nucleotide sequences or biological activity. Thus, provided that two molecules possess a similar activity, they are considered variants as that term is used herein if the nucleotide sequence is not identical, and two molecules which have a similar nucleotide sequence are considered variants as that term is used herein even if their biological activity is not identical.

The term "vaccine" as used herein refers to a pharmaceutical composition comprising at least one immunologically active component that induces an immunological response in an animal and possibly but not necessarily one or more additional components that enhance the immunological activity of said active component. A vaccine may additionally comprise further components typical to pharmaceutical compositions. The immunologically active component of a vaccine may comprise complete virus particles in either their original form or as attenuated particles in a so called modified live vaccine (MLV) or particles inactivated by appropriate methods in a so called killed vaccine (KV). In another form the immunologically active component of a vaccine may comprise appropriate elements of said organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian or other species plus optionally subsequent isolation and purification procedures, or by induction of said synthetic processes in the animal needing a vaccine by direct incorporation of genetic material using suitable pharmaceutical compositions (polynucleotide vaccination). A vaccine may comprise one or simultaneously more than one of the elements described above.

The term "vaccine" as understood herein is a vaccine for veterinary use comprising antigenic substances and is administered for the purpose of inducing a specific and active immunity against a disease provoked by EHV. The EHV vaccine according to the invention confers active immunity that may be transferred passively via maternal antibodies against the immunogens it contains and sometimes also against antigenically related organisms.

Additional components to enhance the immune response are constituents commonly referred to as adjuvants, like e.g. aluminumhydroxide, mineral or other oils or ancillary molecules added to the vaccine or generated by the body after the respective induction by such additional components, like but not restricted to interferons, interleukins or growth factors.

A "vaccine composition" or "pharmaceutical composition" essentially consists of one or more ingredients capable of modifying physiological e g immunological functions of the organism it is administered to, or of organisms living in or on the organism. The terms include, but are not restricted to antibiotics or antiparasitics, as well as other constituents commonly used to achieve certain other objectives like, but not limited to, processing traits, sterility, stability, feasibility to administer the composition via enteral or parenteral routes such as oral, intranasal, intravenous, intramuscular, subcutaneous, intradermal or other suitable route, tolerance after administration, controlled release properties.

Disclosure of the Invention

The invention overcomes the difficulties and prejudice in the art that an equine herpes virus cannot be generated free of foreign sequences. The solution to the above technical problem is achieved by the description and the embodiments characterized in the claims. By using the methods according to the invention, EH-viruses of superior quality for use in vaccines are provided. The central coding sequence for the protein gM is eliminated in a way that the remaining gM carboxyterminal sequences are in a different reading frame than the aminoterminal sequences. The neighboring gene for the essential protein UL9 homolog (gene 53), its orientation and overlap with the gene coding for the protein gM requires that a minimal nucleotide sequence of the gene for gM must remain to allow the expression of gene 53 and thereby retain virus viability. Therefore, an EHV according to the invention relates to EHVs that are characterized in that the gene coding for the protein gM is deleted in a way that the expression of the gene coding for the UL9 homolog (gene 53) is not affected. The term "not affected" does not relate to certain quantity or qualitative properties of UL9 but simply means that the expression of the gene is not affected as long as said protein is expressed by the virus and present in an essentially sufficient amount for the viability of the virus.

The long lasting need in the art for a vaccine comprising recombinant equine herpesvirus 4 is satisfied by the present invention which overcomes major difficulties in the art. The EHV-1 and EHV-4 viruses according to the invention may advantageously be used, for example, in a vaccine.

Hence, in a first important embodiment, the invention relates to a recombinant Equine Herpes Virus (EHV) wherein the gene encoding protein gM, and therefore gM itself, is absent, characterized in that it is free of heterologous elements. "Free of heterologous elements" means that no foreign sequence, i.e. no non-EHV sequence, such as a lacZ- or GFP-encoding cassette, is present in the coding sequence for said virus according to the invention (a so-called "white clone"). Thus, the EHV according to the invention is entirely encoded by EHV sequences. The EHV according to the invention is free of bacterial elements or nucleic acids encoding said bacterial elements. Furthermore, almost the entire coding sequence for the gM protein and therefore the encoded above-mentioned gM protein is eliminated. Thus, preferably, said EHV according to the invention is characterized in that the protein gM is absent due to deletion of the gene coding for the protein gM. However, as set out supra, "the gene encoding protein gM is absent" also requires that a minimum gM sequence remains so that at least the overlapping gene 53 sequence is still present, while the remaining gM sequences may be deleted (see infra). This may all be accomplished by molecular biology techniques (see infra) so that recombinant EHV are generated.

The use of lacZ as a marker for successful deletion of the gM gene of EHV-1 or 4 did not lead to successful generation of viruses according to the invention (see Examples 1, 2). The inventors therefore developed an inventive method to obtain said virus. An EH-virus was constructed in which the gM gene was deleted by insertion of a cassette containing the GFP marker. This approach surprisingly allowed the differentiation between input virus (green fluorescent plaques) and new recombinant plaques (non-fluorescent plaques).

Preferred is an EHV obtainable by a method comprising the steps of:

a) isolating a wild-type EHV;
b) establishing a plasmid encoding the EHV gM gene, optionally with flanking sequences;
c) generating a complementing cell line expressing gM or parts thereof;
d) establishing an EH virus carrying a GFP-encoding cassette insert in its gM coding sequence by co-transfecting the complementing cell line of step b) with EHV-nucleic acid and a plasmid encoding gM which is interrupted by a GFP-encoding cassette insert;
e) deleting the GFP-encoding cassette; and
f) selecting for the EHV clones wherein the GFP-encoding cassette is successfully deleted.
g) "lacZ" is known to the artisan as the gene encoding β-galactosidase. According to the invention, "GFP" relates to green fluorescent protein (GFP) produced by the bioluminescent jellyfish (Chalfie et al., 1994).

"Complementing cell line" refers to a cell line, into which a gene normally not present in the cell line genome is introduced and expressed constitutively. Useful cell lines include, but are not limited to rabbit kidney cell line Rk13, cell line cc (Seyboldt et al., 2000) or the Vero cell lines (ATCC catalogue #CRL-1586), such as clone 1008, as also disclosed in Examples 1 and 2, and any other cell line known to the artisan. Usually it can be selected for cell clones expressing this additional protein. This cell line expresses the gene which is deleted in the virus, complementing this deficiency, and enables the growth of the virus after gene deletion.

Standard molecular biology methods of use of restriction enzymes, ligation, PCR, transfection etc. are known in the art (see e.g. Sambrook et al. (1989). Molecular Cloning: A Laboratory Manual, 2nd ed., Cold Spring Harbor Laboratory Press, Cold Spring Harbor, N.Y.)

Preferably, such EHV according to the invention is characterized in that it is EHV-1. More preferred, the EHV-1 according to the invention is characterized in that 850-1100 bp of the 1332 bp gM open reading frame are deleted. Even more preferred, the EHV-4 according to the invention is characterized in that 900-1000 bp of the gM open reading frame are deleted. More preferred also, the EHV-1 according to the invention is characterized in that 960-970 bp of the gM open reading frame are deleted (960, 961, 962, 963, 964, 965, 966, 967, 968, 969 or 970 bp). Most preferred, the EHV-1 according to the invention is characterized in that 962 bp of the gM open reading frame are deleted.

More preferred, the EHV-1 according to the invention is characterized in that the coding sequence for gM is deleted except for 150-200 base pairs (bp) of the coding sequence encoding the C-terminal portion of gM and 150-250 bp of the coding sequence encoding the N-terminal portion of gM. In this more preferred embodiment, the coding sequence of gM is deleted, only nucleotides 93118-93267 to 93118-93317 of the sequence encoding the C-terminal portion of gM and nucleotides 94223-94472 to 94323-94472 of the coding sequence encoding the N-terminal portion of gM remain. Thus, more preferred is an EHV-1 according to the invention characterized in that nucleotides 93268-93318 to 94222-94322 (encoding the core portion of gM) are deleted (numbering according to Telford, 1992, SEQ ID NO:1). Within the given ranges, any number of nucleotides may be deleted. Thus, according to the invention, the deletions may start no lower than nucleotide position 93268, but has to begin at position 93318. The deletion may end as early as position 94222, but no later than position 94322. Thus, a preferred EHV-1 according to the invention is characterized in that nucleotides 93268 to 94322 of the gM coding sequence as corresponding to SEQ ID NO:1 are deleted. Any combination is within the scope of the invention, such as 93272 to 94312, 93300 to 94300 and so forth.

Even more preferred, the EHV-1 according to the invention is characterized in that the coding sequence for gM is deleted except for 160-190 bp of the coding sequence encoding the C-terminal portion of gM and 190-220 bp of the coding sequence encoding the N-terminal portion of gM. In this more preferred embodiment, the coding sequence of gM is deleted, only nucleotides 93118-93277 to 93118-93307 of the sequence encoding the C-terminal portion of gM and nucleotides 94253-94472 to 94283-94472 of the coding sequence encoding the N-terminal portion of gM remain. Thus, more preferred is an EHV-1 according to the invention characterized in that nucleotides 93278-93308 to 94252-94282 (encoding the core portion of gM) are deleted (numbering according to SEQ ID NO:1).

More preferred also, the EHV-1 according to the invention is characterized in that the coding sequence for gM is deleted except for 180 to 190 (180, 181, 182, 183, 184, 185, 186, 187, 188, 189, 190) bp of the coding sequence encoding the C-terminal portion of gM coding sequence and 200 to 210 (200, 201, 202, 203, 204, 205, 206, 207, 208, 209 or 210) bp of the coding sequence encoding the N-terminal portion of gM. In this more preferred embodiment, the coding sequence of gM is deleted, only nucleotides 93118-93297 to 93118-93307 (93297, 93298, 93299, 93300, 93301, 93302, 93303, 93304, 93305, 93306, 93307) of the sequence encoding the C-terminal portion of gM and nucleotides 94263-94472 to 94273-94472 (94263, 94264, 94265, 94266, 94267, 94268, 94269, 94270, 94271, 94272, 94273) of the coding sequence encoding the N-terminal portion of gM remain. Thus, more preferred is an EHV-1 according to the invention characterized in that nucleotides 94298-94308 to 94262-94272 (encoding the core portion of gM) are deleted (numbering according to SEQ ID NO:1). This means, that any nucleotides inside the above-mentioned remaining nucleotides may be deleted according to the invention, e.g. nucleotides 94299-94263 or 94299-94264 or 94300-94272 or any combination thereof.

Most preferred, the EHV-1 according to the invention is characterized in that the coding sequence for gM is deleted except for 184 bp of the coding sequence encoding the C-terminal portion of gM coding sequence and 209 bp of the coding sequence encoding the N-terminal portion of gM. In this most preferred embodiment, the coding sequence of gM is deleted, only nucleotides 93118-93301 of the sequence encoding the C-terminal portion of gM and nucleotides 94264-94472 of the coding sequence encoding the N-terminal portion of gM remain. Thus, most preferred is an EHV-1 according to the invention characterized in that nucleotides 94263 to 93302 (encoding the core portion of gM) are deleted (numbering according to SEQ ID NO:1). In this most preferred embodiment, 962 nucleotides of the sequence encoding gM are deleted. This is exemplified in a non-limiting manner in Example 1.

Also more preferred is an EHV-1 characterized in that gM is deleted and it is free of heterologous elements and it is a recombinant variant based on a strain selected from the group of AB69 (ATCC VR2581), EHV-1 Ts-mutant ECACC V99061001, KyA, KyD, Ab1, Ab4, RacH, RacL11 or RacM of EHV-1 and no heterologous elements such as GFP- or lacZ-elements are present. Also more preferred, an EHV-1 according to the invention is characterized in that gM is deleted and it is free of heterologous elements such as GFP- or lacZ-elements and it is a recombinant variant based on strain RacH of EHV-1. Most preferred, an EHV-1 according to the invention is characterized in that gM is deleted and it is free of heterologous elements such as GFP- or lacZ-elements and it is the RacH-based recombinant variant isolate HΔgM-w as disclosed in Example 1. Said EHV-1 HΔgM-w according to the invention was deposited at the "Centre for Applied Microbiology and Research (CAMR) and European Collection of Cell Cultures (ECACC)", Salisbury, Wiltshire SP4 0JG, UK, as patent deposit according to the Budapest Treaty. The date of deposit was Oct. 16, 2002, the preliminary identification reference is H-delta-gM-w, and the accession number given by the international depository authority ECACC/CAMR is 02101663. Also preferred are EHV-1 having all of the identifying characteristics of said deposited EHV-1.

All before-mentioned EHV-1 have superior properties over viruses with heterologous elements such as GFP. Said EHV-1 according to the invention have an advantageously higher extracellular infectivity than those still comprising heterologous elements. This is exemplified in FIG. 5 (e.g. between 4 and 12 hours).

Until the present invention was made, no one in the art was able to generate a recombinant EHV-4 virus which may be used as a vaccine. EHV-1 and EHV-4 are homologous and cross-reactive to some degree. However, there was a long need in the art for attenuated EHV-4 viruses as EHV-1 does not appear to provide sufficient protection against EHV-4 infection. Thus, preferably, an EHV according to the invention is characterized in that it is EHV-4. More preferred, the EHV-4 according to the invention is characterized in that 900-1150 bp of the 1332 bp gM open reading frame are deleted. Even more preferred, the EHV-4 according to the invention is characterized in that 1000-1150 bp of the gM open reading frame are deleted. More preferred also, the EHV-1 according to the invention is characterized in that 1110-1115 bp of the gM open reading frame are deleted (1110, 1111, 1112, 1113, 1114 or 1115 bp). Most preferred, the EHV-1 according to the invention is characterized in that 1110 bp of the gM open reading frame are deleted.

More preferred, the EHV-4 according to the invention is characterized in that the coding sequence for gM is deleted except for 0-50 base pairs (bp) of the coding sequence encoding the C-terminal portion of gM and 150-250 bp of the coding sequence encoding the N-terminal portion of gM. In this more preferred embodiment, the coding sequence of gM is deleted, only nucleotides 92681-92680 to 92681-92730 of the sequence encoding the C-terminal portion of gM and nucleotides 93766-94033 to 93866-94033 of the coding sequence encoding the N-terminal portion of gM remain. Thus, more preferred is an EHV-4 according to the invention characterized in that nucleotides 92681-92731 to 93765-93865 (encoding the core portion of gM) are deleted (numbering according to SEQ ID NO:2). Within the given ranges, any number of nucleotides may be deleted. Thus, according to the invention, the deletions may start no lower than nucleotide position 92681, but has to begin at position 92731. The deletion may end as early as position 93765, but no later than position 93865. Thus, preferably, an EHV-4 according to the invention is characterized in that nucleotides 92681 to 93865 of the gM coding sequence as corresponding to Telford positions (1998) (SEQ ID NO:2) are deleted. Any combination is within the scope of the invention, such as 92672 to 93801, 92700 to 93800 and so forth.

Even more preferred, the EHV-4 according to the invention is characterized in that the coding sequence for gM is deleted except for 10-40 bp of the coding sequence encoding the C-terminal portion of gM and 190-220 bp of the coding sequence encoding the N-terminal portion of gM. In this more preferred embodiment, the coding sequence of gM is deleted, only nucleotides 92681-92690 to 92681-92720 of the sequence encoding the C-terminal portion of gM and nucleotides 93806-94033 to 93836-94033 of the coding sequence encoding the N-terminal portion of gM remain. Thus, more preferred is an EHV-4 according to the invention characterized in that nucleotides 92691-92721 to 93805-93835 (encoding the core portion of gM) are deleted (numbering according to SEQ ID NO:2).

More preferred also, the EHV-4 according to the invention is characterized in that the coding sequence for gM is deleted except for 30 to 40 (30, 31, 32, 33, 34, 35, 36, 37, 38, 39 or 40) bp of the coding sequence encoding the C-terminal portion of gM coding sequence and 200 to 210 (200, 201, 202, 203, 204, 205, 206, 207, 208, 209 or 210) bp of the coding sequence encoding the N-terminal portion of gM. In this more preferred embodiment, the coding sequence of gM is deleted, only nucleotides 92681-92710 to 92681-92720 (92710, 92711, 92712, 92713, 92714, 92715, 92716, 92717, 92718, 92719, 92720) of the sequence encoding the C-terminal portion of gM and nucleotides 93816-94033 to 93826-94033 (93824, 93825, 93826, 93827, 93828, 93829, 93830, 93831, 93832, 93833, 93834) of the coding sequence encoding the N-terminal portion of gM remain. Thus, more preferred is an EHV-4 according to the invention characterized in that nucleotides 92711-92721 to 93823-93833 (encoding the core portion of gM) are deleted (numbering according to SEQ ID NO:2). This means, that any nucleotides inside the above-mentioned remaining nucleotides may be deleted according to the invention, e.g. nucleotides 94299-94257 or 94299-94256 or 94300-94257 or any combination thereof.

Most preferred, the EHV-4 according to the invention is characterized in that the coding sequence for gM is deleted except for 34 bp of the coding sequence encoding the C-terminal portion of gM coding sequence and 209 bp of the coding sequence encoding the N-terminal portion of gM. In this most preferred embodiment, the coding sequence of gM is deleted, only nucleotides 92681-92714 of the sequence encoding the C-terminal portion of gM and nucleotides 93825-94033 of the coding sequence encoding the N-terminal portion of gM remain. Thus, most preferred is an EHV-4 according to the invention characterized in that nucleotides 92715 to 93824 (encoding the core portion of gM) are deleted (numbering according to SEQ ID NO:2). In this most preferred embodiment, 1110 nucleotides of the sequence encoding gM are deleted. This is exemplified in a non-limiting manner in Example 2.

Also more preferred, an EHV-4 according to the invention is characterized in that gM is deleted and it is free of heterologous elements such as GFP- or lacZ-elements and it is a recombinant variant based on strain MSV Lot 071398 of EHV-4. Most preferred, an EHV-4 according to the invention is characterized in that gM is deleted and it is free of heterologous elements such as GFP- or lacZ-elements and it is based on strain MSV Lot 071398 and isolate E4ΔgM-4 as disclosed in Example 2. Said EHV-1 HΔgM-w according to the invention was deposited at the "Centre for Applied Microbiology and Research (CAMR) and European Collection of Cell Cultures (ECACC)", Salisbury, Wiltshire SP4 0JG, UK, as patent deposit according to the Budapest Treaty. The date of deposit was Jan. 14, 2003, the preliminary identification reference is EHV-4, and the accession number given by the international depositary authority ECACC/CAMR is 03011401. Also preferred are EHV-4 having all of the identifying characteristics of said deposited EHV-4.

All before-mentioned EHV-4 have superior properties over viruses known in the prior art as there are no recombinant EHV-4 available in the art. Furthermore, said EHV-4 according to the invention have an advantageously higher extracellular infectivity than those still comprising heterologous elements such as GFP. This is exemplified in FIG. 10 (e.g. at 24 hours).

Another important element of the invention is a nucleic acid coding for an EHV as disclosed supra. The artisan can easily determine the corresponding sequence by standard molecular biology methods known in the art.

There was a particular difficulty in the art to obtain the EHV according to the invention. The present inventors constructed gM negative EHV viruses by introducing a marker gene (lacZ) into the gM gene. When it was attempted to remove this cassette, in both EHV-1 and EHV-4 mutants produced by lacZ insertion, all clones phenotypically lacZ negative still contained the lacZ cassette. The inventors therefore developed an inventive method to obtain said viruses. An EH virus was constructed in which the gM gene was deleted by insertion of a cassette containing the GFP marker. This approach surprisingly allowed the differentiation between input virus (green fluorescent plaques) and new recombinant plaques (non-fluorescent plaques). Also, a Vero cell line (based on Vero cell clone 1008) constitutively expressing EHV4-gM was generated by the present inventors to overcome the difficulties in the art. Said cell line was generated by transfection of the appropriate gM gene and subsequent selection for gM-expressing Vero cells. Only said cells enabled the inventors to replicate EHV4 gM negative virus. Said gM-complementing Vero cell line according to the invention was deposited at the "Centre for Applied Microbiology and Research (CAMR) and European Collection of Cell Cultures (ECACC)", Salisbury, Wiltshire SP4 0JG, UK, as patent deposit according to the Budapest Treaty. The date of deposit was Jan. 28, 2003, the preliminary identification reference is VERO GM, and the accession number given by the international depositary authority ECACC/CAMR is 03012801. Also preferred are cell lines having all of the identifying characteristics of said deposited VERO GM cell line.

Preferred is a method for obtaining a recombinant EHV, comprising the steps of:

a) isolating a wild-type EHV;
b) establishing a plasmid encoding the EHV gM gene, optionally with flanking sequences;
c) generating a complementing cell line expressing gM or parts thereof;
d) establishing an EH virus carrying a GFP-encoding cassette insert in its gM coding sequence by co-transfecting the complementing cell line of step b) with EHV-nucleic acid and a plasmid encoding gM which is interrupted by a GFP-encoding cassette insert;
e) deleting the GFP-encoding cassette; and
f) selecting for the EHV clones wherein the GFP-encoding cassette is successfully deleted.

Said above-captioned cells are an important embodiment of the present invention. Thus, the invention relates to a cell line for use in a method according to the invention, characterized in that the gene encoding the protein gM is transfected into said cell line and said cell line expresses gM. The invention preferably relates to a cell line according to the invention, characterized in that it is a cell line selected from the group of Vero cells (Vero-gM cells), RK-13, and cc (cc-gM).

As disclosed supra for EHV-1, the use of lacZ as a marker instead of GFP in EHV-4 also did not lead to successful generation of viruses according to the invention (see in a non-limiting manner in Example 2). "LacZ-positive" cells generally stained less intense on Vero cells than on Rk13 cells and were thus harder to identify, and the EHV-4 system replicated slower than EHV-1 and thus gave less time between plaque identification and isolation of viable virus progeny. Therefore, the use of GFP represented the only way to obtain said EHV-4 virus. The procedure was carried out as described supra for EHV-1 and surprisingly also led to the successful identification of EHV-4 gM deleted virus by virtue of identifying fluorescent plaques.

The isolation of wild-type EHV is accomplished by collecting lung tissue at necropsy from animals suspected to have been diseased by EHV, and isolating EHV on tissue cells as known in the art. The EHV 1 complete genome sequence has been published by Telford et al. (1992) (SEQ ID NO;1). Likewise, the complete genome sequence for EHV-4 has been published by Telford et al. (1998) (SEQ ID NO:2). The PCR amplification of DNA sequences by use of specific primers binding to complementary strands of target DNA flanking the DNA stretch of interest represents a standard molecular biology method. Methods for ligating appropriate DNA sequences into plasmids suitable for the constructions intended, for DNA transfection into eukaryotic cells, for Southern Blot and Western Blot analyses, for site-directed excision of DNA fragments via restriction enzymes and for selection of cell lines expressing the desired heterologous gene or plasmids harboring the desired gene or virus in which a certain gene is deleted are known to the skilled person. Standard molecular biology methods such as above mentioned techniques are known to the skilled person and can also be found e.g. in Sambrook et al. (1989) Molecular Cloning: A Laboratory Manual, 2nd ed., Cold Spring Harbor Laboratory Press, Cold Spring Harbor, N.Y. and Bertram, S. and Gassen, H. G. Gentechnische Methoden, G. Fischer Verlag, Stuttgart, New York, 1991).

"Deletion" means the removal of one or several nucleotides or amino acids.

Another important embodiment of the invention is a pharmaceutical composition or vaccine comprising an EHV according to the invention, optionally in combination with a pharmaceutically acceptable carrier or excipient.

Also an important part of the present invention is a pharmaceutical composition comprising a nucleic acid according to the invention as disclosed supra.

Preferably, a vaccine according to the invention refers to a vaccine as defined above. The term "live vaccine" refers to a vaccine comprising a particle capable of replication, in particular, a replication active viral component.

Preferably, a vaccine according to the invention comprises a gM-deleted EHV-1 according to the invention as disclosed supra combined with a gM-deleted EHV-4 according to the invention as disclosed supra or optionally any other antigenetic group and optionally a pharmaceutically acceptable carrier or excipient. Said vaccine may be administered as a combined vaccine at the same point in time. Most preferably, said attenuated EHV-1 according to the invention may be administered first followed by administration of an attenuated EHV-4 according to the invention three to four weeks later. Most preferably also, said attenuated EHV-1 according to the invention may be administered in combination with an attenuated EHV-4 according to the invention in a typical vaccination scheme where two or three basic vaccinations are given. A typical vaccination scheme of such a vaccine is two vaccinations four weeks apart (basic vaccination), followed by regular boosts every six months. However, any of said vaccines according to the invention as disclosed supra may also be administered at different intervals, e.g. every three months.

The artisan may choose to divide the administration into two or more applications, which may be applied shortly after each other, or at some other predetermined interval range. Preferably, such interval may be: 1° immunization, 2° immunization approx. 4 weeks thereafter and optionally 3° immunization 5-6 months thereafter. Depending on the desired duration and effectiveness of the treatment, vaccines may be administered once or several times, also intermittently. The vaccines according to the invention may be administered to a mare prior to breeding and again during its pregnancy to prevent EHV-associated abortions. Other horses can be vaccinated, e.g. once a year. Foals may be vaccinated shortly after birth.

The vaccines of the present invention may be applied by different routes of application known to the expert, notably intravenous injection or direct injection into target tissues. For systemic application, the intravenous, intravascular, intramuscular, intraarterial, intraperitoneal, oral, or intramucosal (e.g. nasal or respiratory spray or injection) routes are preferred. A more local application can be effected subcutaneously, intracutaneously, intrapulmonarily or directly in or near the tissue to be treated (connective-, bone-, muscle-, nerve-, epithelial tissue). A vaccine composition according to the invention can also be administered via an implant or orally. Most preferred is the intramuscular administration.

For preparing suitable vaccine preparations for the applications described above, the expert may use known injectable, physiologically acceptable sterile solutions. For preparing a ready-to-use solution for parenteral injection or infusion, aqueous isotonic solutions, such as e.g. saline or corresponding plasma protein solutions are readily available. The vaccine preparations may be present as lyophylisates or dry preparations, which can be reconstituted with a known injectable solution directly before use under sterile conditions, e.g. as a kit of parts. The final preparation of the vaccine preparations of the present invention are prepared for injection, infusion or perfusion by mixing purified virus according to the invention with a sterile physiologically acceptable solution, that may be supplemented with known carrier substances or/and excipient.

The applied dose of each EH-virus according to the invention present in the vaccine formulation preferably may be between 104 and 108 TCID50/per animal, between 105 and 107 TCID50/per animal, most preferably 106 TCID50/per animal.

The invention further relates to the use of EHV according to the invention in the manufacture of a medicament for the prophylaxis and/or treatment of EHV-associated conditions.

The invention further relates to the use of a nucleic acid according to the invention in the manufacture of a medicament for the prophylaxis and/or treatment of EHV-associated conditions.

The invention further relates to a method for the prophylaxis and/or treatment of an animal characterized in that a pharmaceutical composition according to the invention is applied to said animal and the therapeutic success is monitored.

The invention preferably relates to a method of treating an EHV-infected equine animal with a gM-deleted EHV according to the invention as described supra, wherein the said attenuated EHV or the vaccine composition as disclosed supra is administered to the equine animal in need thereof at a suitable dose as known to the skilled person and the reduction of EHV symptoms such as viremia and leukopenia and/or coughing and/or pyrexia and/or nasal discharge and/or diarrhea and/or depression and/or abortion is monitored. Said treatment preferably may be repeated. Thus, the invention relates to a method for the prophylaxis and/or treatment of an animal characterized in that a pharmaceutical composition according to the invention is applied to said animal and the therapeutic success is monitored. The treatment may be carried out as disclosed for the vaccine composition supra.

The invention preferably relates to a method of detecting antibodies against specific structures of infecting EHV-1 or EHV-4 and to a method of differentiating wild-type infections from the presence of gM deleted EHV-1 or EHV-4 as described above by an immunological method Immunological methods are known to the expert in the field and include, but are not limited to ELISAs (enzyme-linked immuno-sorbent assay) or Sandwich-ELISAs, dot-blots, immunoblots, radioimmunoassays (Radioimmunoassay RIA), diffusion-based Ouchterlony tests, rocket immunofluorescent assays or Western-blots. Examples for immunological methods are e.g. described in: An Introduction to Radioimmunoassay and Related Techniques, Elsevier Science Publishers, Amsterdam. The Netherlands (1986); Bullock et al., Techniques in Immunocytochemistry, Academic Press, Orlando, Fla. Vol. 1 (1982), Vol. 2 (1983), Vol. 3 (1985); Tijssen, Practice and Theory of Enzyme Immunoassays: Laboratory Techniques in Biochemistry and Molecular Biology, Elsevier Science Publishers, Amsterdam, The Netherlands (1985).

Said ELISA may use, but not be confined to the use of immobilized gM gene product or a part of gM gene product or any other EH virus 1 or EH virus 4 gene product on a plastic surface suitable for ELISA analysis.

An ELISA according to the present invention comprises, but is not limited to the steps of a) immobilizing a gM gene product or a fragment thereof onto a plastic support
b) rinsing the plastic surface with an appropriate washing buffer (e.g., PBS-Tween)
c) adding the samples to selected wells and incubating the ELISA plate according to standardized methods
d) washing the wells of the ELISA plate and adding a suitable antibody coupled to an enzyme such as HRP (horse radish peroxidase)
e) detecting bound antibody/HRP conjugate by adding a suitable substrate, followed by photometric read-out of optical density of individual wells. Suitable antibodies, e.g. rabbit anti horse Ig, are known in the field.

EXAMPLES

The following examples serve to further illustrate the present invention; but the same should not be construed as limiting the scope of the invention disclosed herein.

Example 1 gM Deleted EHV-1 Isolates

The gM negative EHV-1 were constructed by either inserting the *Escherichia coli* lacZ (HΔgM-lacZ) or the green fluorescent protein (GFP) expression cassette (HΔgM-GFP) thereby replacing 74.5% of gM-gene sequences. The expression of a marker protein facilitates the identification and subsequent purification of a recombinant virus. To avoid the presence of any "non-EHV-1" sequences within the vaccine virus, it was decided to remove the marker gene sequences and construct another, second generation gM-negative EHV-1, a "white" HΔgM (HΔgM-w).

Figure 1:
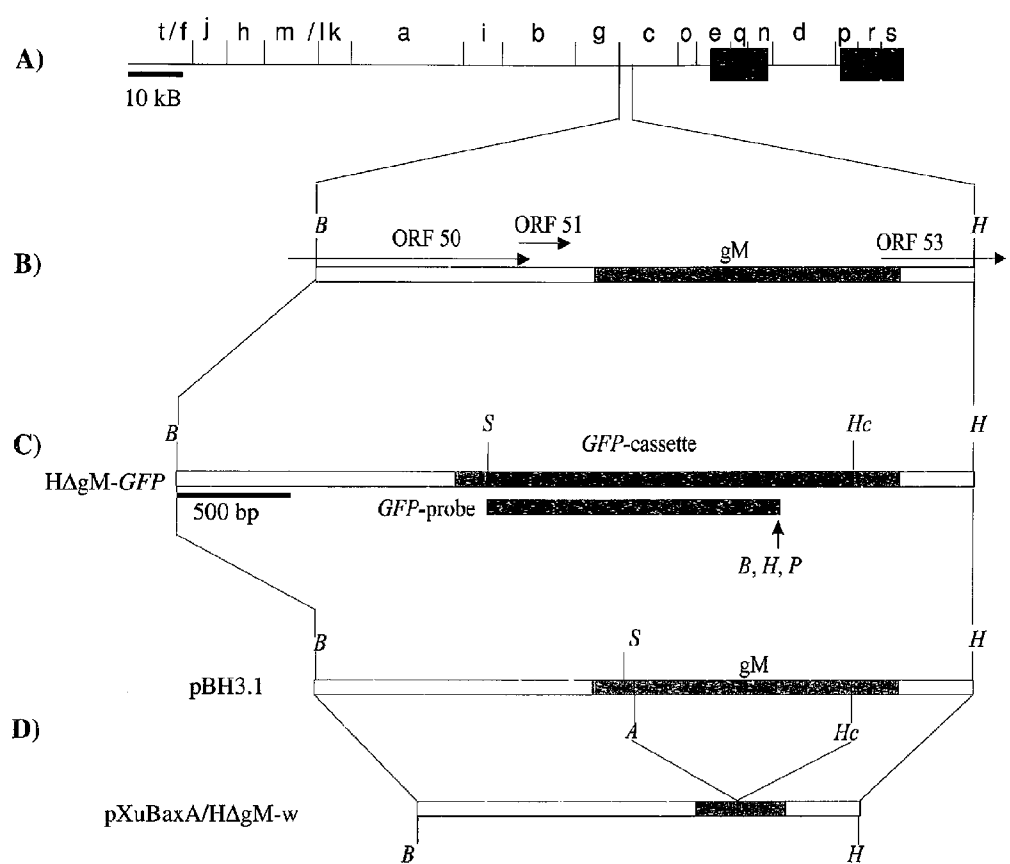
FIG. 1: Generation of a gM negative EHV-1 RacH virus without foreign sequences (HΔgM-w)

To this end, plasmid pXuBaxA was constructed (FIG. 1). At first recombination of pXuBaxA-sequences into the lacZ-marked virus HΔgM-lacZ was attempted. In a first step, DNA transfections mediated by the calcium phosphate method were optimized, such, that several white plaques resulted after plating of 100-1000 PFU of transfection supernatants. Consequently, several plaques were chosen for purification of progeny virus and subjected to four to five rounds of isolation of single plaques.

Multiple, independently isolated, phenotypically lacZ-negative virus populations were genotypically analyzed by Southern blotting and turned out to still carry sequences of the lacZ-cassette. Difficulties in isolating truly lacZ-negative virus populations due to "lacZ-silencing" had been anticipated and therefore a great number of phenotypically lacZ-negative virus populations were purified and analyzed without success. Therefore, the strategy of generating a "white" gM-negative RacH virus was changed by switching to cotransfections with the gM negative EHV-1, that had been constructed by insertion of a GFP cassette. Using the GFP-expressing virus facilitated the distinction between input virus (green fluorescent plaques) and new recombinant viruses (non fluorescent plaques) and thus increased the efficiency of isolating phenotypically GFP-negative plaques. Changing the "input" gM-negative RacH was not supposed to influence the genotype of the expected recombinant virus as (i) both the first generation HΔgM viruses are, apart from the marker, genetically identical and as (ii) the final genotype in the region of interest is determined by the recombination plasmid (pXuBaxA).

For construction of plasmid pXuBaxA (construct necessary to obtain the "white" gM negative EHV-1) the 962 bp ApaI-HincII fragment within the 1352 bp open reading frame of EHV-1 gM was removed of plasmid pBH3.1 (FIG. 1, section D). Plasmid pBH3.1 carries the EHV-1 BamHI-HindIII fragment surrounding the gM gene (Seyboldt et al., 2000). To prevent expression of any truncated gM-product, restriction endonucleases ApaI and HincII have been chosen such that after blunt end adjusting and ligation the remaining C-terminal gM sequences (183 bp) were not in frame with the remaining N-terminal sequences (208 bp).

EHV-1 gM expressing cell line ccgM (Seyboldt at al., 2000; obtained from Dr. N. Osterrieder) was maintained in minimal essential medium supplemented with 5-10% fetal calf serum (Biochrom, γ-irradiated). Homologous recombination into EHV-1 was achieved by calcium phosphate mediated co-transfection of ccgM-cells with 5-10 μg of plasmid pXuBaxA (FIG. 1, section D) and 2 μg of DNA of HΔgM-lacZ or HΔgM-GFP, respectively.

Figure 2:
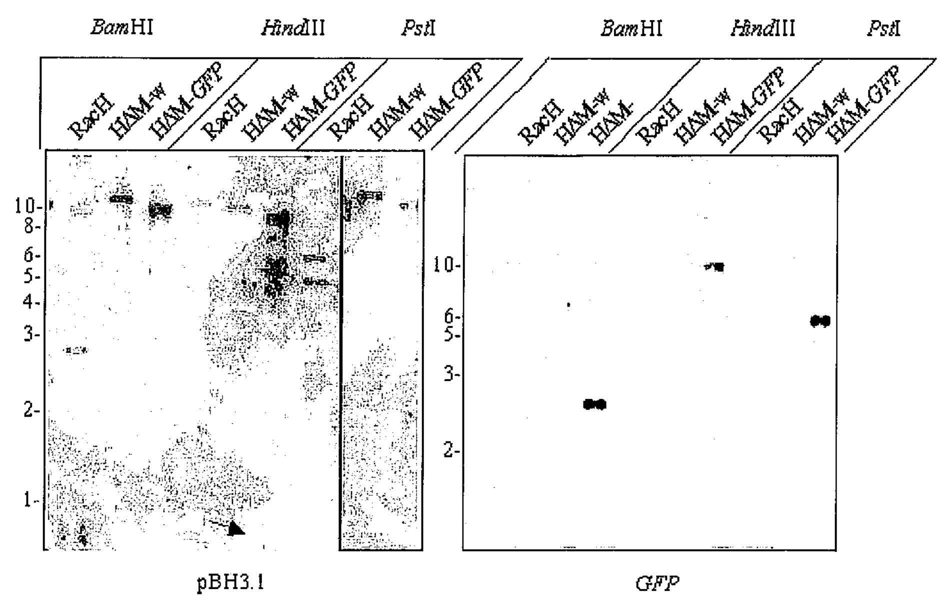
FIG. 2: Southern blot of gM-deleted EHV-1 virus without foreign sequences (HΔgM-w).

Subsequent analysis of DNA of HΔgM-GFP with a digoxigenin labeled probe specific for the BamHI-HindIII fragment of plasmid pBH3.1 (FIG. 2) revealed (i) a 2.757 bp and a 9.043 bp fragment on BamHI, (ii) a 10.006 bp and a 825 bp fragment on HindIII, (iii) and to a 5.415 bp and a 4.474 bp fragment on PstI digested DNA.

The restriction enzymes used (BamHI, HindIII, PstI) do cut within sequences of the GFP-marker cassette, thereby altering the fragment pattern relative to the respective GFP-marker cassette free DNA.

The GFP-probe bound to the respective first fragments (i-iii) and did not detect GFP-specific sequences on DNA of RacH or of HΔgM-w.

On DNA of RacH the expected BamHI (11.166 bp), HindIII (10.199 bp) and PstI (9.257 bp) fragments were detected, which decreased in size after removal of 962 bp of gM-sequences accordingly (to: 10.204 bp, 9.237 bp and 8.279 bp; FIG. 3, section B).

Single-step growth kinetics of gM-negative viruses (HΔgM-w or HΔgM-GFP), which had been constructed as described in the legend to FIG. 1, and RacH were performed. Rk13 cells in 24 well plates were infected at an MOI of 2 of the respective viruses. Supernatants and infected cell pellets were harvested separately at various times p.i. (0, 4, 8, 12, 16, 20, 24 h p.i.). Supernatants were cleared of cellular debris by low speed centrifugation and cells were subjected to freeze-thawing before cell-associated infectivity was assayed. All virus titers were determined individually on Rk13 or ccgM cells, respectively, in 24 well plates. The results (data not shown) can be summarized as follows: Cell-associated infectivity of both HΔgM-viruses was reduced between factor 1.6 (4 h p.i.) and 45 (20 h p.i.) on Rk13 cells when compared to titers of cells infected with RacH (intracellular infectivity). Extracellular virus titers of both the HΔgM viruses were maximally reduced by 186 (HΔgM-w) or 650 (HΔgM-GFP) fold (12 h p.i.) compared to those of RacH (extracellular infectivity), supporting a role of gM in virus egress of RacH also.

Example 2 gM Deleted EHV-4 Isolates

To parallel the construction of gM-negative EHV-1, lacZ selection was chosen for selection of EHV-4. To allow the isolation of a gM-negative EHV-4, a Vero cell line constitutively expressing EHV-4 gM was constructed. Vero cell clone C1008 (ATCC number: CRL-1586 was maintained in minimal essential medium supplemented with 5-10% fetal calf serum (Biochrom, γ-irradiated). Recombinant cell line Vero-gM was generated by Effectene™ (Qiagen) mediated transfection of 1 μg of plasmid pCgM4 (FIG. 3, section B) and 0.1 μg of plasmid pSV2neo (conferring resistance to G418; Neubauer et al., 1997) into Vero cells. Cell clones were first selected for resistance to G418 (Calbiochem), then for transcomplementation of a gM negative EHV-4. G418 was added to the medium of every 5th passage of recombinant cell lines (500 μg/ml). All cells were regularly analyzed for Mycoplasma by PCR and for Bovine Viral Diarrhea Virus (BVDV) antigen by FACS analysis. The selected cell clone was called Vero-gM and used in the following experiments.

EHV-4 DNA was cotransfected with plasmid pgM4β (FIG. 3, section B) into Vero-gM cells. The recombination resulted in several "lacZ-positive" plaques, that were isolated and replated. But then the purification of a deletion mutant in EHV-4 turned out to be more difficult and slower than in EHV-1 as: (i) "lacZ-positive" plaques generally stained less intense on Vero cells than on Rk13 cells and were thus harder to identify, and as (ii) the EHV-4 system replicated slower than EHV-1 and thus gave less time between plaque identification and isolation of viable virus progeny.

Figure 4:
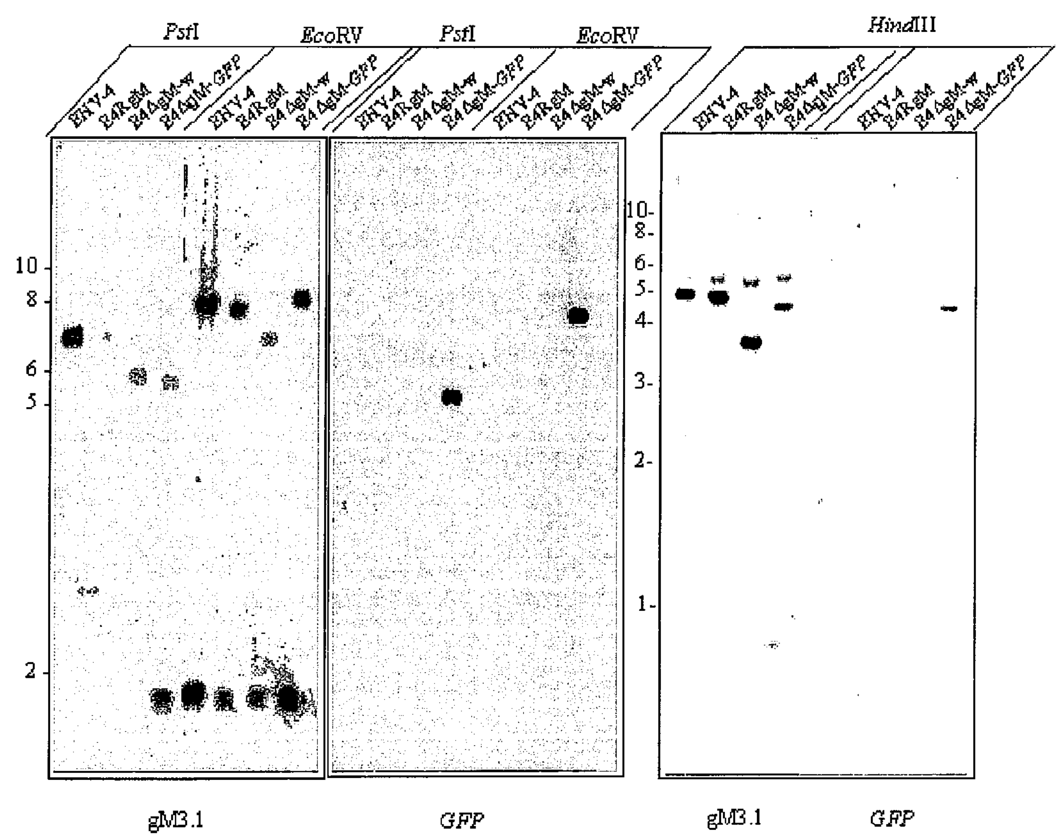

All lacZ-positive plaques, that were isolated, were lost over the first round of purification, which made it imperative to search for another solution. It was therefore attempted to use the GFP-marker for EHV-4 also. In a first step, plasmid pgM4GFP+ (FIG. 3, section B) was constructed and used for recombination into EHV-4 DNA. Resulting GFP-positive plaques were purified by three rounds of isolating single plaques on cell line Vero-gM. A homogenous GFP-positive virus population was chosen and viral DNA subjected to Southern blot analysis (FIG. 4). DNA of the resulting virus, E4 gM-GFP (FIG. 3, section C), was then cotransfected with either plasmid pgM4R or pgM4w (FIG. 3, section B). Plasmid pgM4R was used for the construction of an gM-repaired EHV-4, called E4RgM (FIG. 3, section A). Plasmid pgM4w was the basis to generate the simultaneously gM- and marker gene-negative EHV-4, E4 gM-w (FIG. 3, section D). E4RgM and E4 gM-w virus populations were isolated for a GFP-negative phenotype, purified on Vero or on Vero-gM cells and finally analyzed by Southern blot (FIG. 4). To express EHV-4 gM in eukaryotic cells plasmid pCgM4 was generated (FIG. 3, section B). The complete ORF of EHV-4 gM was amplified by PCR using primers given in FIG. 8 and the Taq polymerase (MBI-Fermentas). The resulting PCR-product was inserted into vector pcDNAI/Amp (Invitrogene).

Plasmid pgM4R resulted after PCR-amplification of nucleotides 91.699 to 94.808 (Telford et al., 1998) (SEQ ID NO:2) of EHV-4 and insertion of the amplification product into vector pGEM3Zf+ (Promega) (FIG. 3, section B and FIG. 8). This plasmid was used for the construction of the gM-repaired EHV-4, E4RgM (FIG. 3, section A).

To construct plasmid pgM4β+ (FIG. 3, section B), that was designed to initially delete 1110 bp of the 1352 bp EHV-4 gM, a multistep strategy was chosen. In a first step, both the flanking sequences necessary for DNA recombination were amplified independently by PCR using the PFU polymerase (Stratagene). Restriction sites necessary for stepwise cloning were added by primer sequences (FIG. 8). PCR products were inserted into vector pTZ18R (Pharmacia), resulting in plasmids pgM4Del1 and pgM4Del2 (FIG. 8).

In a next step the 3.9 kbp *E-coli* lacZ expression cassette was released from plasmid ptt264A+ (Osterrieder et al., 1996) by SalI and BamHI digest and was inserted into plasmid pgM4Del1 resulting in plasmid pgM4Del1β+. Then, EHV-4 specific sequences, taken out of pgM4Del2, were introduced into pgM4Del1+ using PstI and SalI, such that the marker gene cassette was flanked by EHV-4 specific sequences in the resulting plasmid pgM4β+ (FIG. 3, section B).

Plasmid pgM4β+ was then digested with SalI and BamHI, again releasing the lacZ-cassette, the resulting 5'-overhangs were filled in with the Klenow polymerase and the construct resulting from religation was called pgM4w (FIG. 3, section B). Again a frame shift between the N-terminal 208 nt and the remaining C-terminal 33 nt of the gM-sequence was designed.

To generate plasmid pgM4GFP+ (FIG. 3, section B), the lacZ-cassette was taken out of pgM4β+ (FIG. 3, section B) using the SalI and BamHI sites and replaced by the GFP-cassette (including CMV-promoter and SV40-polyA), that had been removed of vector pEGFP-C1 (Clontech) via AsnI and MluI digest. Restriction enzyme generated overhangs were blunt end adjusted by the Klenow polymerase.

Correct amplification of all PCR products was confirmed by cycle sequencing (MWG Biotech) and comparison to the published sequence of EHV-4 strain NS80567 (Telford et al., 1998) (SEQ ID N0:2).

Recombination into EHV-4 was done by using the cell line Vero-gM and either plasmid pgM4β+ or pgM4GFP+ (FIG. 3, section B) was cotransfected with EHV-4 DNA to generate a first generation gM-negative EHV-4 (FIG. 3, section C). Plasmid pgM4w (FIG. 3, section B) in combination with DNA of the gM-negative EHV-4 resulted in E4ΔgM-w (FIG. 3, section D). Finally, the gM-repaired EHV-4, E4RgM (FIG. 3, section A), was isolated after co-transfection of plasmid pgM4R (FIG. 3, section B) with DNA of E4ΔgM-GFP into Vero-cells.

DNA of EHV-4, E4RgM, E4ΔgM-w and E4ΔgM-GFP were cleaved with PstI, EcoRV or HindIII and DNA-fragments blotted onto nylon membranes. Parallel membranes were either hybridized with GFP-specific sequences (identically to FIG. 2) or with a probe, named gM3.1, containing the EHV-4 specific sequences taken out of plasmid pgM4R (FIG. 3, section B).

Digestion results obtained (FIG. 4) were as follows:

(i) On DNA of E4ΔgM-GFP the GFP-probe recognized fragments at 5.531 bp, when PstI cleaved, at 8.383 bp after EcoRV-digest and at 4.528 bp after HindIII digest. Identical fragments plus fragments at 1.792 bp (PstI), 1.801 bp (EcoRV) and 826 plus 5.487 bp (HindIII) reacted with probe gM3.1.

(ii) Neither parental EHV-4, nor the repaired virus E4RgM or E4ΔgM-w carried any GFP specific sequences.

(iii) The gM3.1 reactive DNA-fragments in EHV-4 and E4RgM were detected at 6.806 bp (PstI), at 7.874 bp plus 1.801 bp (EcoRV) and at 4.837 plus 5.487 bp (HindIII), respectively.

(iv) The gM- and GFP-cassette negative virus E4ΔgM-w, did not hybridize with GFP-sequences, but with the respective EHV-4 specific sequences (gM3.1). The latter probe detected fragments, lacking 1110 bp of gM sequences, when compared to wild type virus, i.e. at 5.696 bp (PstI), at 6.764 bp plus 1.801 bp (EcoRV) and at 3.727 bp plus 5.487 bp (HindIII), respectively.

On HindIII cleaved DNA of all of these viruses another gM3.1 probe specific fragment exists at 126 bp (FIG. 2), but this fragment is to small to be shown in this Southern blot.

Figure 7A:
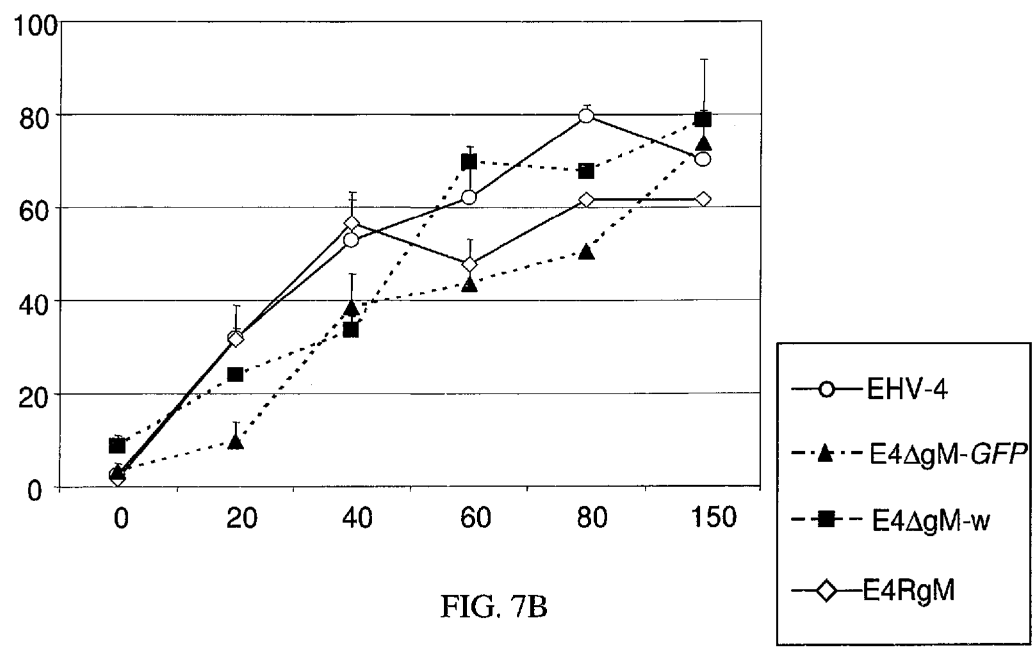

Viruses E4ΔgM-GFP and E4ΔgM-w lost their capacity to express gM and in addition E4ΔgM-w lost the marker gene sequence.

a) Virus growth on culture cells. Virus growth properties of the various mutant viruses as detailed above were compared on Vero and on Vero-gM cells. Cells seeded in 24 well plates were infected at an MOI of 1-2 and extracellular (extracellular infectivity) and intracellular (intracellular infectivity) virus titers were determined at different time points p.i. (FIG. 5). While growth properties of the rescuant E4RgM virus corresponded well to those of EHV-4, there was a surprising inhibition in the production of E4ΔgM-w and E4ΔgM-GFP extracellular virus titers on non-complementing cells. Within this series of experiments (mean of two independent experiments) extracellular infectivity could never be detected before 24 h p.i. Even at 30 hours p.i. only very low titers were extracellularly observed (maximum of 1.5 plaques/ml at the lowest dilution 10-1), although cells showed severe cytopathic effect. Differences in intracellular infectivity, however, never reached 100 fold and peaked at 24 hours p.i. (84 fold between EHV-4 and E4ΔgM-w). The delay in detecting intracellular infectivity was only one time point (12 h versus 15 h. p.i.). Taken together it could be surprisingly demonstrated that deletion of gM-sequences of the EHV-4 background massively influenced virus replication in vitro, but that expression of gM is not essential for replication. Especially extracellular infectious virus decreased and the ability to directly infect adjacent cells was diminished—as reflected by plaque sizes.

b) Plaque size. Diameters of 150 plaques after infection of Vero or Vero-gM cells with EHV-4, E4RgM, E4ΔgM-w or E4ΔgM-GFP were measured and average plaque sizes were determined relative to sizes of wildtype plaques, that were set 100%. It was clearly demonstrated, that the gM negative viruses were able to infect and replicate in Vero cells, but that the maximal plaque diameters were markedly reduced, to less than 20% of wildtype plaque diameters (FIG. 6). Infection with the parental or the rescuant virus resulted in wild-type-like appearance of plaques, indicating that the observed phenotype was indeed induced by the gM-deletion. This was additionally corroborated by the fact, that plaque formation of E4ΔgM-w and E4ΔgM-GFP was fully restored on cell line Vero-gM (Data not shown).

c) Penetration experiments. In this experiment, the influence of the EHV-4 gM on entry kinetics of EHV-4 was assessed. 100 PFU of the different viruses, parental EHV-4, the gM repaired virus E4RgM, as well as the gM-deletion mutants and E4ΔgM-GFP (see FIG. 3), were allowed to adsorb at 4° C. to Vero cells in 6-well plates. After 90 min, the respective inocula were replaced by fresh medium and penetration was initiated by shifting the incubation temperature to 37° C. At different times after the temperature shift—starting immediately (=0 min)—extracellular infectivity was pH-inactivated by treating cells with a citrate buffer (pH 3.0). Parallel samples were washed accordingly, but the citrate buffer was replaced by PBS, such that at every time point the "adsorbed infectivity" could be compared to the "penetrated infectivity". Numbers of plaques were determined after incubating cells for four days under a methocell overlay.

d) Several sets of experiments were performed: In FIG. 7A results are depicted for genotypically and phenotypically gM-negative viruses after propagation on non complementing Vero cells, whereas FIG. 7B represents kinetics of phenotypically complemented E4ΔgM-w and E4ΔgM-GFP, as viruses had been grown on gM-expressing Vero-gM cells.

A mean of 52.8% (56.7%) of the infectious parental EHV-4 (E4RgM) was protected from extracellular acid treatment at 40 min after initiating penetration (FIG. 7A, open circles) whereas only 33.7% (E4ΔgM-w—closed rectangles) and 38.5% (E4ΔgM-GFP—closed triangles) of gM negative viruses were protected, yet. At later time points of entry kinetics, the different graphs start to variously overlap and a maximal penetration efficiency between 61.7% and 78.9% is reached after 150 min of penetration time, indicating that a certain assay variability may account for the slight differences observed.

Figure 7B:
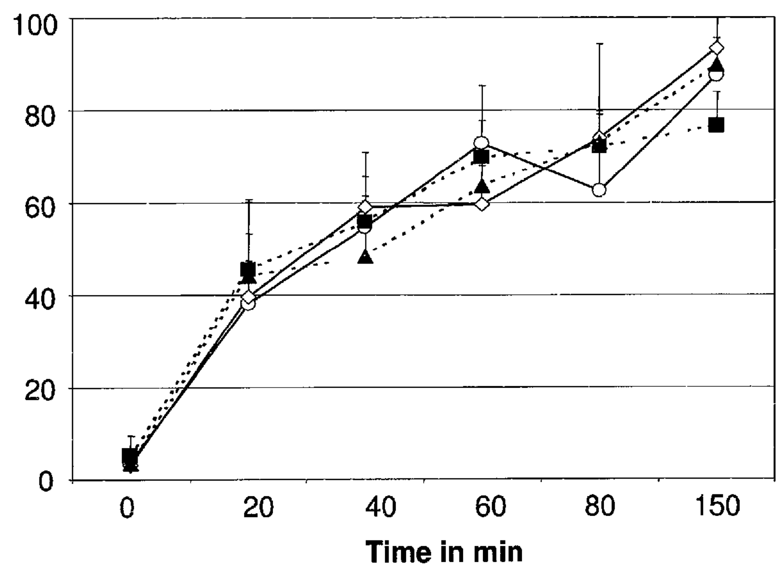

When gM negative viruses had been prepared on complementing Vero-gM cells no difference at all was observed in their penetration efficiency (FIG. 7). As opposed to a delay in entry kinetics of gM-negative EHV-1 of about 20% (strain RacL11; Osterrieder et al., 1996) to up to 40% (strain KyA; Seyboldt et al., 2000), the effect of deleting gM of EHV-4 has to be noted with reservation. Nevertheless the following conclusions can be drawn: (i) A difference was observed in kinetics of phenotypically complemented to non complemented gM-negative viruses (FIGS. 7A and 7B), but (ii) the influence of deleting gM on EHV-4 penetration is virtually undetectable.

Example 3

Analysis of Horse Sera for Anti gM Antibodies Using a gM Specific Serological Test To state whether gM can be used as a serological marker for distinction of wild type infection versus vaccination with a gM-negative vaccine, several assumptions had to be tested. Primarily it needed to be assessed whether sera of field virus infected horses contain gM-specific antibodies. For initial analysis a Western blot test was chosen, as this system allowed to identify a specific reaction against background reactivity. When using highly neutralizing sera (EHV-1 and/or -4 neutralizing titers between 1:128 and 256), it was established (data not shown) that lysates of EHV-1 gM expressing cell line ccgM allowed the detection of a specific signal by horse sera and that a dilution of sera to 1:3000 seemed to work best.

Consequently, sera of all 12 foals (6 vaccinates and 6 controls) that had participated in an EHV-1 gM vaccine trial were analyzed for gM reactivity in Western blot. Of each individual horse three different sera were tested: Taken before entering the trial (Pre), 4 weeks after the second vaccination (V2) and two weeks after challenge infection (C), respectively.

In summary by Western blot analyses (FIG. 9) it was shown that (i) sera of horses, exhibiting EHV-1 neutralization activity, all tested positive for gM, that (ii) gM reactivity was never detected in any of the samples analyzed before known contact to EHV-1 or after vaccination with the gM-negative EHV-1 and that (iii) after infection of vaccine trial horses with the gM-positive challenge virus, gM was clearly detectable in 10 out of 12 cases. Finally (iv) it was observed that anti EHV-1 antibody titers and the intensity of gM reactivity seemed not to be directly correlated.

Due to the high background reactivity of horse sera, the establishment of serological tests is difficult. Based on indirect immunofluorescence (IIF) data obtained in horse sera, it was confirmed that either an indirect or a blocking test system will have to be established or highly purified gM-polypeptides need to be used in an ELISA test. To this end, an ELISA was established as follows. Either purified gM polypeptides or the complete gM was immobilized onto the solid support of a 96 well plate which was coated to ensure good attachment of the capturing protein. For the assay, unspecific binding sites were be blocked by either dry milk or similar substances to prevent unspecific binding. Following this, the plastic surface was rinsed with an appropriate washing buffer (e.g., PBS-Tween) to remove excess blocking agent. Then the test samples were added to selected wells and the ELISA plate was incubated at 37° C. according to standardized methods, allowing antibodies in the test sample to bind to the immobilized capturing protein. In the next step, the wells of the ELISA plate were washed thoroughly by several times rinsing with washing buffer, followed by the addition of a suitable anti-horse antibody coupled to an enzyme such as HRP (horse radish peroxidase). The detection of bound antibody/HRP conjugate was finally performed by adding a suitable substrate, followed by photometric read-out of optical density of individual wells. The value obtained was be compared to positive and negative controls run in the same assay.

Example 4

Identification of EHV-4 gM

Figure 10:
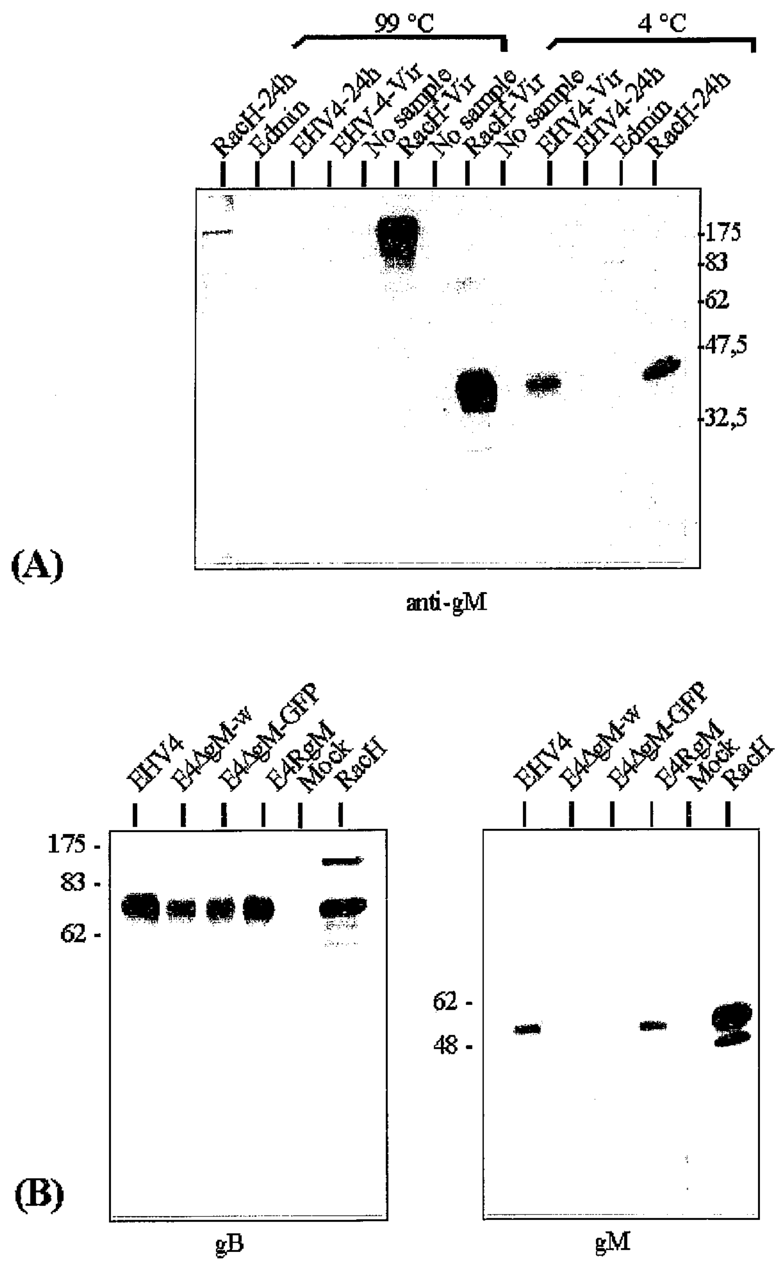

Although the predicted amino acid sequence of EHV-4 gM is calculated to be 86.7% identical to that of EHV-1 gM (Telford et al., 1998), anti EHV-1 gM Mab 13B2 (Allen and Yeargan, 1987) specifically reacts in Western blot with the type-specific protein only (Crabb et al., 1991). To nevertheless identify the EHV-4 homolog in this study, other anti-EHV-1 gM antibodies (Seyboldt et al., 2000; Day, 1999) were tested on purified EHV-4 virions, on lysates of cells infected with EHV-4 or on lysates of Vero-gM cells. The latter being a recombinant cell line developed to synthesize EHV-4 gM under control of the IE-HCMV promoter. The reactivity of all anti-EHV-1 gM monoclonal antibodies against EHV-4 gM was below the detection limit in Western blot, whereas parallel EHV-1 samples were always readily reactive (data not shown). Only the polyclonal antiserum, that had been generated in rabbits against a His-tagged EHV-1 gM derived polypeptide (amino acid 376-450; Seyboldt et al., 2000), reacted strong enough with the heterologous gM to allow the identification of EHV-4 gM (FIG. 10, section A). Using this antibody a specific reactivity at an Mr of about 50,000 to 55,000 was observed in purified EHV-4 virions. According to its predicted hydrophobic properties the detected gM-protein aggregated upon boiling. In contrast the form of gM expressed in recombinant Vero-gM cells mainly run at an Mr of about 46,000 to 48,000, indicating that the gM-proteins of EHV-4 are processed similarly as has been shown for EHV-1 (Osterrieder et al., 1997; Rudolph and Osterrieder, 2002).

Several experiments were conducted to analyze the phenotype of the gM-deletion in EHV-4. To compare expression of other glycoproteins, lysates of Vero cells infected with EHV-4, E4RgM, E4ΔgM-w or E4ΔgM-GFP were subjected to Western blot analysis. It is demonstrated that the deletion of gM did not influence the production of the late proteins gB or gD, indicating that early steps in virus replication were not substantially affected by the deletion.

In another experiment it could be demonstrated by analysis of virion preparations of wildtype, repaired or both gM-deleted EHV-4, that no gM reactivity at all was detectable within gM-negative viruses, whereas the protein was readily reactive in control virions. The presence of virions in the respective preparation was shown in a parallel blot probing against gB (FIG. 10, section B).

REFERENCES

The following references, to the extent that they provide exemplary procedural or other details supplementary to those set forth herein, are specifically incorporated herein by reference.

Allen, G. P., Yeargan, M., Costa, L. R. R. and Cross, R., 1995. Major histocompatibility complex class I-restricted cytotoxic T-lymphocyte responses in horses infected with equine herpesvirus 1. J. Virol. 69, 606-612.

Allen, G. P. and Yeargan, M. R., 1987. Use of λgt11 and monoclonal antibodies to map the genes for the six major glycoproteins of equine herpesvirus1. J. Virol. 61, 2454-2461.

Awan, A. R., Chong, Y.-C. and Field, H. J., 1990. The pathogenesis of equine herpesvirus type 1 in the mouse: A new model for studying host responses to the infection. J. Gen. Virol. 71, 1131-1140.

Baines, J. D. and Roizman, B., 1991. The open reading frames UL3, UL4, UL10 and UL16 are dispensable for the replication of herpes simplex virus 1 in cell culture. J. Virol. 65, 938-944.

Baines, J. D. and Roizman, B., 1993. The UL10 gene of herpes simplex virus 1 encodes a novel viral glycoprotein, gM, which is present in the virion and in the plasma membrane of infected cells. J. Virol. 67, 1441-1452.

Chalfie M, Tu Y, Euskirchen G, Ward W W, Prasher D C, 1994. Green fluorescent protein as a marker for gene expression. Science 263, 802-805.

Crabb, B. S.; Allen, G. P., Studdert, M. J., 1991. Characterization of the major glycoproteins of equine herpesviruses 4 and 1 and asinine herpesvirus 3 using monoclonal antibodies. J. Gen. Virol. 72, 2075-82.

Day, L. 1999. Characterization of selected glycoproteins of equine herpesvirus-1: immune responses in the murine model. Ph.D. thesis. University of Leeds, Leeds, United Kingdom.

Flowers, C. C. and O'Callaghan, D. J., 1992. The equine herpesvirus type 1 (EHV-1) homolog of herpes simplex virus type 1 US9 and the nature of a major deletion within the unique short segment of the EHV-1 KyA strain genome. Virology 190, 307-315.

Hübert, P. H., Birkenmaier, S., Rziha, H. J. and Osterrieder, N., 1996. Alterations in the equine herpesvirus type-1 (EHV-1) strain RacH during attenuation. J. Vet. Med. B 43, 1-14.

Kyhse-Andersen, J., 1984. Electroblotting of multiple gels: a simple apparatus without tank for rapid transfer of proteins from polyacrylamide gels to nitrocellulose. J. Biochem. Biophys. Methods 10, 203-210.

Laemmli, U. K., 1970. Cleavage of structural proteins during the assembly of the head of bacteriophage T4. Nature 227, 680-685.

MacLean, C. A., Robertson, L. M. and Jamieson, F. E., 1993. Characterization of the UL10 gene product of herpes simplex virus type 1 and investigation of its role in vivo. J. Gen. Virol. 74, 975-983.

Malik, A. K., Martinez, R., Muncy, L., Carmichael, E. P. and Weller, S. K., 1992. Genetic analysis of the herpes simplex virus type 1 UL9 gene: isolation of a LacZ insertion mutant and expression in eukaryotic cells. Virology 190(2), 702-715.

Mayr, A., Pette, J., Petzoldt, K. and Wagener, K., 1968. Untersuchungen zur Entwicklung eines Lebendimpfstoffes gegen die Rhinopneumonitis (Stutenabort) der Pferde. J. Vet. Med. B 15, 406-418.

Neubauer, A., Beer, M., Brandmüller, C., Kaaden, O.-R. and Osterrieder, N., 1997. Equine herpesvirus 1 mutants devoid of glycoprotein B or M are apathogenic for mice but induce protection against challenge infection. Virology 239, 36-45.

Osterrieder, N., Wagner, R., Brandmüller, C., Schmidt, P., Wolf, H. and Kaaden, O.-R., 1995. Protection against EHV-1 challenge infection in the murine model after vaccination with various formulations of recombinant glycoprotein gp14 (gB). Virology 208, 500-510.

Osterrieder, N., Neubauer, A., Brandmüller, C., Braun, B., Kaaden, O.-R. and Baines, J. D., 1996. The equine herpesvirus 1 glycoprotein gp21/22a, the herpes simplex virus type 1 gM homolog, is involved in virus penetration and cell-to-cell spread of virions. Journal of virology, June 1996, p. 4110-4115.

Osterrieder, N.; Neubauer, A.; Fakler, B.; Brandmüller, C.; Seyboldt, C.; Kaaden, O. R.; Baines, J. D., 1997. Synthesis and processing of the equine herpesvirus 1 glykoprotein M. Virology 232, 230-239.

Pilling, A., Davison, A. J., Telford, E. A. R. and Meredith, D. M., 1994. The equine herpesvirus type 1 glycoprotein homologous to herpes simplex virus type 1 glycoprotein M is a major constituent of the virus particle. J. Gen. Virol. 75, 439-442.

Rudolph, J.; Seyboldt, C.; Granzow, H.; Osterrieder, N., 2002. The gene 10 (UL49.5) product of equine herpesvirus 1 is necessary and sufficient for functional processing of glycoprotein M. J. Virology 76, 2952-2963.

Sambrook, J., Fritsch, D. F. and Maniatis, T., 1989. Molecular Cloning: A laboratory manual. 2nd ed. Cold Spring Harbor Laboratory Press, Cold Spring Harbor, N.Y.

Seyboldt, C., 2000. Structural and functional analysis of the equine herpesvirus type 1 glycoprotein M. Doctoral thesis, Ludwig-Maximilians-University, Munich, Germany.

Seyboldt, C.; Granzow, H.; Osterrieder, N. 2000. Equine herpesvirus 1 (EHV-1) Glycoprotein M: Effect of deletions of transmembrane domains. Virology 278, 477-489.

Stokes, A., Alber, D. G., Greensill, J., Amellal, B., Carvalho, R., Taylor, L. A., Doel, T. R., Killington, R. A., Halliburton, I. W. and Meredith, D. M., 1996. The expression of the proteins of equine herpesvirus 1 which share homology with herpes simplex virus 1 glycoproteins H and L. Virus Res. 40, 91-107.

Telford, E. A. R., Watson, M. S., McBride, K. and Davison, A. J., 1992. The DNA sequence of equine herpesvirus-1. Virology 189, 304-316.

Telford, E. A. R., Watson, M. S., Perry, J., Cullinane, A. A. and Davison, A. J., 1998. The DNA sequence of equine herpesvirus-4. Journal of Gen. Virol. 79, 1197-1203.

Tewari, D., Whalley, J. M., Love, D. N. and Field, H. J., 1994. Characterisation of immune responses to baculovirus expressed equine herpesvirus type 1 glycoproteins D and H in a murine model. J. Gen. Virol. 75, 1735-1741.

What is claimed is:

1. A recombinant Equine Herpes Virus type 4(EHV-4), wherein 900-1150 bp of the gM open reading frame are deleted, wherein said EHV-4 is free of heterologous elements.

2. A recombinant Equine Herpes Virus type 4 (EHV-4) wherein the entire gM coding sequence is deleted except for 0-50 bp of the coding sequence for the C-terminal portion and except for 150-250 bp of the coding sequence for the N-terminal portion, and wherein said EHV-4 s free of heterologous elements.

3. The EHV-4 according to claim 2, wherein the entire gM coding sequence is deleted except for 34 bp of the coding sequence for the C-terminal portion and except for 209 bp of the coding sequence for the N-terminal portion.

4. A recombinant Equine Herpes Virus type 4 (EHV-4) wherein nucleotides 92681-92731 to 93765-93865 of the gM coding sequence as corresponding to SEQ ID NO:2 are deleted, and wherein said EHV-4 is free of heterologous elements.

5. The EHV-4 according to claim 4, wherein nucleotides 92681 to 93865 of the gM coding sequence as corresponding to SEQ ID NO:2 are deleted.

6. The EHV-4 according to claim 4, wherein nucleotides 92715 to 93824 of the gM coding sequence as corresponding to SEQ ID NO:2 are deleted.

7. The EHV-4 according to claim 1, wherein said EHV-4 is based on MSV Lot 071398 and isolate E4ΔgM-w and that it is the EHV-4 which was deposited at the ECACC/CAMR on Jan. 14, 2003 with the accession number 03011401.

* * * * *